(12) United States Patent
Medendorp, Jr. et al.

(10) Patent No.: US 11,020,502 B1
(45) Date of Patent: Jun. 1, 2021

(54) ULTRAVIOLET (UV) LIGHT EMISSION DEVICE, AND RELATED METHODS OF USE, PARTICULARLY SUITED FOR DECONTAMINATION

(71) Applicant: UV Innovators, LLC, Cary, NC (US)

(72) Inventors: Nicholas William Medendorp, Jr., Raleigh, NC (US); Stephen Michael Grenon, Durham, NC (US); Scott Eric Liddle, Raleigh, NC (US); Anthony Barret Smith, Durham, NC (US); Robert Alexander Stevenson, Morrisville, NC (US); Jeffery Michael Rosino, Apex, NC (US); Nathan Thomas Luck, Cary, NC (US)

(73) Assignee: UV INNOVATORS, LLC, Cary, NC (US)

( * ) Notice: Subject to any disclaimer, the term of this patent is extended or adjusted under 35 U.S.C. 154(b) by 0 days.

(21) Appl. No.: 17/139,342

(22) Filed: Dec. 31, 2020

Related U.S. Application Data

(60) Provisional application No. 63/019,231, filed on May 1, 2020, provisional application No. 63/079,193, filed on Sep. 16, 2020.

(51) Int. Cl.
  *A61L 2/10* (2006.01)
  *A61L 2/24* (2006.01)
  *A61L 9/20* (2006.01)

(52) U.S. Cl.
  CPC ........ *A61L 2/10* (2013.01); *A61L 2/24* (2013.01); *A61L 9/20* (2013.01); *A61L 2202/11* (2013.01); *A61L 2202/14* (2013.01); *A61L 2202/16* (2013.01)

(58) Field of Classification Search
  USPC ............................................. 422/24
  See application file for complete search history.

(56) References Cited

U.S. PATENT DOCUMENTS

| | | |
|---|---|---|
| 1,118,006 A | 11/1914 | Henri et al. |
| 1,132,265 A | 3/1915 | Henri et al. |
| 1,145,140 A | 7/1915 | Henri et al. |
| 1,151,267 A | 8/1915 | Henri et al. |
| 1,266,803 A | 5/1918 | Henri et al. |
| 2,058,826 A | 10/1936 | Reece |
| 2,201,548 A | 5/1940 | Treinis |
| 2,253,251 A | 8/1941 | Selig |
| 2,298,124 A | 10/1942 | Hartman |
| 2,553,711 A | 5/1951 | Jackson |
| 2,732,501 A | 1/1956 | Blaeker |
| 2,935,611 A | 5/1960 | Myers |
| 2,977,647 A | 4/1961 | Vassiliades et al. |
| 3,185,839 A | 5/1965 | Glasson et al. |
| 3,433,946 A | 3/1969 | Harwick |
| 3,683,638 A | 8/1972 | Devon |
| 4,008,045 A | 2/1977 | Free |
| 4,063,890 A | 12/1977 | Baron |
| 4,141,686 A | 2/1979 | Lewis |
| 4,255,663 A | 3/1981 | Lewis |
| 4,469,835 A | 9/1984 | Laurin |
| 4,535,247 A | 8/1985 | Kurtz |
| 4,786,812 A * | 11/1988 | Humphreys .............. A61L 9/20 250/455.11 |
| 4,806,770 A | 2/1989 | Hylton et al. |
| 4,816,145 A | 3/1989 | Goudy, Jr. |
| 4,910,942 A | 3/1990 | Dunn et al. |
| 4,952,369 A | 8/1990 | Belilos |
| 4,963,750 A | 10/1990 | Wilson |
| 4,973,847 A | 11/1990 | Lackey et al. |
| 5,053,033 A | 10/1991 | Clarke |
| 5,133,932 A | 7/1992 | Gunn et al. |
| 5,150,705 A | 9/1992 | Stinson |
| 5,213,759 A | 5/1993 | Castberg et al. |
| 5,326,542 A | 7/1994 | Sizer et al. |
| 5,372,781 A | 12/1994 | Hallett et al. |
| 5,433,920 A | 7/1995 | Sizer et al. |
| 5,503,559 A | 4/1996 | Vari |
| 5,587,069 A | 12/1996 | Downey, Jr. |

(Continued)

FOREIGN PATENT DOCUMENTS

| CN | 201481833 U | 5/2010 |
|---|---|---|
| CN | 102772812 A | 11/2012 |

(Continued)

OTHER PUBLICATIONS

Boeing, "Boeing Licenses Ultraviolet Wand to Healthe, Inc. to Counter COVID-19," PRNewswire, Seattle, Sep. 22, 2020, https://investors.boeing.com/investors/investor-news/press-release-details/2020/Boeing-Licenses-Ultraviolet-Wand-to-Healthe-Inc.-to-Counter-COVID-19/defaultaspx, 2 pages.

Healthe, "Healthe® WAND PRO," Specification Sheet 111620, Version 7, Nov. 2020, available at https://healtheinc.com/app/media/2020/11/Healthe_WandPro_SpecSheet_v7.pdf, 2 pages.

Alphawire, "EcoCable® Mini;" Lit No. EcoC-Mini-1409, 2014, 13 pages.

Apem, "Q8 Series: Ø8 mm panel mount LED indicators," IND-Q8-2001, 2001, 7 pages.

(Continued)

*Primary Examiner* — Phillip A Johnston
(74) *Attorney, Agent, or Firm* — Withrow & Terranova PLLC

(57) ABSTRACT

Ultraviolet (UV) light emission devices and related methods of use. The UV light emission devices disclosed herein are particularly suited for use in disinfecting surfaces and air. The UV light emission devices disclosed herein can be provided in the form factor of a handheld device that is easily held and manipulated by a human user. The human user can manipulate the handheld UV light emission device to decontaminate surfaces, air, and other areas by orienting the handheld UV light emission device so that the UV light emitted from its light source is directed to the area of interest to be decontaminated.

30 Claims, 54 Drawing Sheets

(56) References Cited

U.S. PATENT DOCUMENTS

| | | | |
|---|---|---|---|
| 5,624,573 A | 4/1997 | Wiesmann | |
| 5,626,768 A | 5/1997 | Ressler et al. | |
| 5,637,877 A | 6/1997 | Sinofsky | |
| 5,707,594 A | 1/1998 | Austin | |
| 5,742,063 A | 4/1998 | Scroggins et al. | |
| 5,744,094 A | 4/1998 | Castberg et al. | |
| 5,780,860 A | 7/1998 | Gadgil et al. | |
| 5,817,276 A | 10/1998 | Fencl et al. | |
| 5,852,879 A | 12/1998 | Schumaier | |
| 5,874,741 A | 2/1999 | Matschke | |
| 5,920,075 A | 7/1999 | Whitehead | |
| 5,928,607 A | 7/1999 | Frisk | |
| 5,935,431 A | 8/1999 | Korin | |
| 5,961,920 A | 10/1999 | Soremark | |
| 5,997,812 A | 12/1999 | Burnham et al. | |
| 6,006,659 A | 12/1999 | Rosenthal | |
| 6,030,578 A | 2/2000 | McDonald | |
| 6,039,928 A | 3/2000 | Roberts | |
| 6,087,764 A | 7/2000 | Matei | |
| 6,162,406 A | 12/2000 | Michael | |
| 6,200,307 B1 | 3/2001 | Kasinkas et al. | |
| 6,231,820 B1 | 5/2001 | Wedekamp | |
| 6,245,293 B1 | 6/2001 | Fencl et al. | |
| 6,254,625 B1 | 7/2001 | Rosenthal et al. | |
| 6,258,370 B1 | 7/2001 | Behrends et al. | |
| 6,258,736 B1 | 7/2001 | Massholder | |
| 6,267,924 B1 | 7/2001 | Fencl et al. | |
| 6,269,680 B1 | 8/2001 | Prieve et al. | |
| 6,280,615 B1 | 8/2001 | Phillips et al. | |
| 6,283,986 B1 | 9/2001 | Johnson | |
| 6,301,359 B1 | 10/2001 | Roberts | |
| 6,313,470 B1 | 11/2001 | Fencl et al. | |
| 6,344,176 B1 | 2/2002 | Metzger | |
| 6,365,113 B1 | 4/2002 | Roberts | |
| 6,398,970 B1 | 6/2002 | Justel et al. | |
| 6,403,030 B1 | 6/2002 | Horton, III | |
| 6,447,720 B1 | 9/2002 | Horton, III et al. | |
| 6,447,721 B1 | 9/2002 | Horton, III et al. | |
| 6,458,331 B1 | 10/2002 | Roberts | |
| 6,468,433 B1 | 10/2002 | Tribelski | |
| 6,469,308 B1 | 10/2002 | Reed | |
| 6,475,433 B2 | 11/2002 | McGeorge et al. | |
| 6,490,351 B1 | 12/2002 | Roberts | |
| 6,500,267 B1 | 12/2002 | Fencl et al. | |
| 6,524,529 B1 | 2/2003 | Horton, III | |
| 6,565,803 B1 | 5/2003 | Bolton et al. | |
| 6,627,000 B2 | 9/2003 | Fencl et al. | |
| 6,655,577 B2 | 12/2003 | Mihaylov et al. | |
| 6,656,424 B1 | 12/2003 | Deal | |
| 6,660,227 B2 | 12/2003 | Lopez Ordaz | |
| 6,669,838 B1 | 12/2003 | Baarman | |
| 6,707,254 B1 | 3/2004 | Moisan et al. | |
| 6,730,113 B2 * | 5/2004 | Eckhardt | A61L 2/10 128/898 |
| 6,730,265 B2 | 5/2004 | Horton, III | |
| 6,737,020 B1 | 5/2004 | Horton, III et al. | |
| 6,753,537 B2 | 6/2004 | Woo | |
| 6,766,097 B2 | 7/2004 | Horton, III | |
| 6,773,584 B2 | 8/2004 | Saccomanno | |
| 6,776,824 B2 * | 8/2004 | Wen | A47L 5/24 55/485 |
| 6,784,440 B2 | 8/2004 | Fink et al. | |
| 6,803,587 B2 | 10/2004 | Gadgil et al. | |
| 6,861,658 B2 | 3/2005 | Fiset | |
| 6,911,177 B2 | 6/2005 | Deal | |
| 6,911,657 B2 | 6/2005 | Waluszko | |
| 6,916,452 B1 | 7/2005 | Rix et al. | |
| 6,924,495 B1 | 8/2005 | Brickley | |
| 6,953,940 B2 * | 10/2005 | Leighley | A61L 2/10 250/455.11 |
| 6,974,958 B2 | 12/2005 | Gadgil et al. | |
| 7,002,161 B2 | 2/2006 | Greene | |
| 7,084,389 B2 | 8/2006 | Spector | |
| 7,169,311 B2 | 1/2007 | Saccomanno | |
| 7,173,255 B2 | 2/2007 | Snowball | |
| 7,175,806 B2 | 2/2007 | Deal et al. | |
| 7,175,807 B1 | 2/2007 | Jones | |
| 7,201,767 B2 | 4/2007 | Bhullar | |
| 7,211,813 B2 | 5/2007 | Jensen | |
| 7,217,933 B2 | 5/2007 | Gadgil et al. | |
| 7,234,586 B1 | 6/2007 | Newman | |
| 7,316,200 B2 | 1/2008 | Bosma et al. | |
| 7,319,230 B2 | 1/2008 | Skaggs | |
| 7,323,065 B2 | 1/2008 | Fencl et al. | |
| 7,326,387 B2 | 2/2008 | Arts et al. | |
| 7,372,044 B2 | 5/2008 | Ross | |
| 7,416,588 B2 | 8/2008 | Burrows et al. | |
| 7,445,441 B2 | 11/2008 | West et al. | |
| 7,465,942 B2 | 12/2008 | Holden | |
| 7,476,885 B2 | 1/2009 | Garcia et al. | |
| 7,476,888 B2 | 1/2009 | Fiset | |
| 7,498,004 B2 | 3/2009 | Saccomanno | |
| 7,507,980 B2 | 3/2009 | Garcia et al. | |
| 7,511,283 B2 | 3/2009 | Chor | |
| 7,560,706 B1 | 7/2009 | Castelluccio | |
| 7,598,501 B2 | 10/2009 | Jones | |
| 7,642,522 B2 | 1/2010 | Egberts | |
| 7,646,000 B2 | 1/2010 | Shih | |
| 7,665,181 B2 | 2/2010 | Gebhard et al. | |
| 7,683,344 B2 | 3/2010 | Tribelsky et al. | |
| 7,691,343 B2 | 4/2010 | Ueberall | |
| 7,692,159 B2 | 4/2010 | Lane et al. | |
| 7,695,673 B2 | 4/2010 | Moisan et al. | |
| 7,695,675 B2 | 4/2010 | Kaiser et al. | |
| 7,791,044 B1 | 9/2010 | Taylor et al. | |
| 7,829,016 B2 | 11/2010 | Deal et al. | |
| 7,836,548 B2 | 11/2010 | Cho | |
| 7,884,336 B2 | 2/2011 | Gibson | |
| 7,888,656 B2 | 2/2011 | Freedgood | |
| 7,982,199 B2 | 7/2011 | Deshays | |
| 7,989,779 B1 | 8/2011 | Ray et al. | |
| 7,994,489 B2 | 8/2011 | Fiset | |
| 8,029,739 B2 | 10/2011 | Field et al. | |
| 8,058,629 B2 | 11/2011 | Long | |
| 8,067,750 B2 | 11/2011 | Deal | |
| 8,083,512 B2 | 12/2011 | Adriansens | |
| 8,084,752 B2 | 12/2011 | Ranta et al. | |
| 8,101,135 B2 | 1/2012 | Lee et al. | |
| 8,105,532 B2 | 1/2012 | Harmon et al. | |
| 8,110,819 B2 | 2/2012 | Boyarsky et al. | |
| 8,114,346 B2 | 2/2012 | Hyde et al. | |
| 8,125,333 B2 | 2/2012 | Ressler et al. | |
| 8,142,713 B2 | 3/2012 | Gordon | |
| 8,143,596 B2 | 3/2012 | Yerby | |
| 8,161,596 B2 | 4/2012 | Cheung et al. | |
| 8,164,073 B2 | 4/2012 | Mohr | |
| RE43,332 E | 5/2012 | Tribelsky et al. | |
| 8,168,963 B2 | 5/2012 | Ratcliffe | |
| 8,173,066 B2 | 5/2012 | Mohr et al. | |
| 8,203,124 B2 | 6/2012 | Havens et al. | |
| 8,236,239 B2 | 8/2012 | Bernstein | |
| 8,246,839 B2 | 8/2012 | Ueberall | |
| 8,252,099 B2 | 8/2012 | Worrilow | |
| 8,252,100 B2 | 8/2012 | Worrilow | |
| 8,269,190 B2 | 9/2012 | Dornblaser et al. | |
| 8,278,628 B2 | 10/2012 | Hamilton | |
| 8,283,639 B2 | 10/2012 | Lane et al. | |
| 8,296,493 B1 | 10/2012 | Engelhardt et al. | |
| 8,297,435 B2 | 10/2012 | Lathem | |
| 8,318,090 B2 | 11/2012 | Gordon | |
| 8,330,121 B2 | 12/2012 | Douglas | |
| 8,337,770 B2 | 12/2012 | Wind | |
| 8,357,330 B1 | 1/2013 | Erdlen et al. | |
| 8,357,914 B1 | 1/2013 | Caldwell | |
| 8,366,654 B2 | 2/2013 | Iranitalab | |
| 8,378,324 B2 | 2/2013 | Gardner, III | |
| 8,381,728 B2 | 2/2013 | Rao et al. | |
| 8,399,853 B2 | 3/2013 | Roiniotis | |
| 8,399,854 B1 | 3/2013 | Crawford | |
| 8,404,273 B2 | 3/2013 | Baumgart et al. | |
| 8,421,032 B2 | 4/2013 | Dornseifer | |
| 8,431,075 B2 | 4/2013 | Davis | |
| 8,431,910 B1 | 4/2013 | Perry | |
| 8,458,922 B2 | 6/2013 | Parisi et al. | |

(56) References Cited

U.S. PATENT DOCUMENTS

| | | |
|---|---|---|
| 8,460,353 B2 | 6/2013 | Beran et al. |
| 8,466,433 B2 | 6/2013 | Ullman |
| 8,470,239 B1 | 6/2013 | Kerr |
| 8,481,985 B2 | 7/2013 | Neister |
| 8,506,897 B2 | 8/2013 | Davis |
| 8,512,631 B2 | 8/2013 | Kerr |
| 8,518,017 B2 | 8/2013 | Caluori |
| 8,519,356 B2 | 8/2013 | Boyle |
| 8,525,126 B2 | 9/2013 | Lee et al. |
| 8,525,128 B2 | 9/2013 | Mohr |
| 8,536,541 B2 | 9/2013 | Taylor et al. |
| 8,557,188 B2 | 10/2013 | Lo |
| 8,569,715 B1 | 10/2013 | Tantillo |
| 8,575,567 B2 | 11/2013 | Lyslo et al. |
| 8,372,128 B2 | 12/2013 | Reuben |
| 8,597,569 B2 | 12/2013 | Gruen et al. |
| 8,606,981 B2 | 12/2013 | Engelhardt et al. |
| 8,614,425 B2 | 12/2013 | Conradt et al. |
| 8,617,464 B2 | 12/2013 | Kerr |
| 8,624,202 B2 | 1/2014 | Gil |
| 8,631,533 B1 | 1/2014 | Gulian et al. |
| 8,633,454 B2 | 1/2014 | Durkin |
| 8,653,481 B2 | 2/2014 | Packman et al. |
| 8,662,705 B2 | 3/2014 | Roberts |
| 8,685,318 B2 | 4/2014 | Collard et al. |
| 8,698,100 B2 | 4/2014 | Schumacher |
| 8,710,460 B2 | 4/2014 | Dayton |
| 8,742,366 B2 | 6/2014 | Snowball |
| 8,747,764 B1 | 6/2014 | Burchman et al. |
| 8,747,770 B2 | 6/2014 | Davis |
| 8,753,575 B2 | 6/2014 | Neister |
| 8,754,385 B1 | 6/2014 | Gutman |
| 8,757,160 B2 | 6/2014 | Rao et al. |
| 8,779,385 B2 | 7/2014 | Noori |
| 8,791,441 B1 | 7/2014 | Lichtblau |
| 8,809,807 B2 | 8/2014 | Nelson et al. |
| 8,834,788 B2 | 9/2014 | Fogg et al. |
| 8,845,928 B2 | 9/2014 | Bernstein |
| 8,845,961 B2 | 9/2014 | Bernstein |
| 8,847,174 B2 | 9/2014 | Domenig et al. |
| 8,859,994 B2 | 10/2014 | Deal |
| 8,877,124 B2 | 11/2014 | Bergman |
| 8,890,087 B2 | 11/2014 | Ben-David et al. |
| 8,895,938 B2 | 11/2014 | Ullman |
| 8,895,939 B2 | 11/2014 | Lyslo et al. |
| 8,895,940 B2 | 11/2014 | Moskowitz et al. |
| 8,907,304 B2 | 12/2014 | Kreitenberg |
| 8,911,664 B1 | 12/2014 | Cavanaugh |
| 8,911,677 B2 | 12/2014 | Gerstner et al. |
| 8,921,813 B2 | 12/2014 | Palmer et al. |
| 8,928,234 B2 | 1/2015 | Kim et al. |
| 8,941,078 B2 | 1/2015 | Tantillo |
| 8,951,468 B1 | 2/2015 | Perry |
| 8,961,872 B2 | 2/2015 | Fehr et al. |
| 8,975,605 B2 | 3/2015 | Neister |
| 8,977,796 B2 | 3/2015 | Engelhardt et al. |
| 8,999,237 B2 | 4/2015 | Tumanov |
| 8,999,238 B2 | 4/2015 | Kreitenberg |
| 9,006,683 B2 | 4/2015 | Wen |
| 9,023,274 B2 | 5/2015 | Garner et al. |
| 9,024,277 B2 | 5/2015 | Domenig et al. |
| 9,034,251 B1 | 5/2015 | Gutman |
| 9,034,254 B2 | 5/2015 | Kim et al. |
| 9,044,521 B2 | 6/2015 | Farren |
| 9,045,358 B2 | 6/2015 | Greuel |
| 9,056,147 B2 | 6/2015 | Ma |
| 9,095,633 B1 | 8/2015 | Dayton |
| 9,101,260 B2 | 8/2015 | Desu-Kalyanam |
| 9,114,183 B2 | 8/2015 | Campagna |
| 9,114,184 B2 | 8/2015 | Messina et al. |
| 9,144,618 B2 | 9/2015 | Kreitenberg |
| 9,149,548 B2 | 10/2015 | Davis |
| 9,149,549 B2 | 10/2015 | Kreitenberg |
| 9,162,000 B2 | 10/2015 | Ullman |
| 9,168,321 B2 | 10/2015 | Oestergaard et al. |
| 9,186,802 B2 | 11/2015 | Parisi et al. |
| 9,198,990 B2 | 12/2015 | Fletcher |
| 9,205,162 B2 | 12/2015 | Deal et al. |
| 9,211,352 B2 | 12/2015 | Kassel et al. |
| 9,226,985 B2 | 1/2016 | Dam |
| 9,233,182 B2 | 1/2016 | Arlemark |
| 9,254,342 B2 | 2/2016 | Engelhardt et al. |
| 9,265,174 B2 | 2/2016 | Shostak et al. |
| 9,265,849 B2 | 2/2016 | Kerr |
| 9,265,850 B2 | 2/2016 | Davis et al. |
| 9,272,058 B1 | 3/2016 | Montgomery |
| 9,272,059 B2 | 3/2016 | Lyslo et al. |
| 9,289,523 B2 | 3/2016 | Lee |
| 9,289,527 B1 | 3/2016 | Lichtblau |
| 9,295,286 B2 | 3/2016 | Shin |
| 9,295,741 B2 | 3/2016 | Yerby |
| 9,295,742 B2 | 3/2016 | Rasooly et al. |
| 9,320,818 B2 | 4/2016 | Vardiel et al. |
| 9,345,796 B2 | 5/2016 | Stewart |
| 9,345,798 B2 | 5/2016 | Trapani |
| 9,352,469 B2 | 5/2016 | Stewart |
| 9,358,313 B2 | 6/2016 | Deal |
| 9,364,573 B2 | 6/2016 | Deshays et al. |
| 9,381,265 B2 | 7/2016 | Hamilton |
| 9,387,268 B2 | 7/2016 | Farren |
| 9,402,985 B2 | 8/2016 | Caluori |
| 9,408,929 B2 | 8/2016 | Ma |
| 9,415,125 B2 | 8/2016 | Chen et al. |
| 9,415,126 B2 | 8/2016 | Dobrinsky et al. |
| 9,439,996 B2 | 9/2016 | Gross |
| 9,463,258 B2 | 10/2016 | Kassel et al. |
| 9,468,695 B2 | 10/2016 | Liao et al. |
| 9,486,548 B2 | 11/2016 | Aurongzeb et al. |
| 9,492,574 B2 | 11/2016 | Rasooly et al. |
| 9,492,577 B1 | 11/2016 | Dayton |
| 9,498,550 B2 | 11/2016 | Kneissl et al. |
| 9,498,551 B2 | 11/2016 | Yanke |
| 9,511,159 B2 | 12/2016 | Kreiner et al. |
| 9,511,163 B2 | 12/2016 | Larsen |
| 9,522,200 B2 | 12/2016 | Boisvert |
| 9,526,387 B1 | 12/2016 | Li et al. |
| 9,550,006 B2 | 1/2017 | Boodaghians et al. |
| 9,555,144 B2 | 1/2017 | Garner et al. |
| 9,592,312 B2 | 3/2017 | Lyslo et al. |
| 9,597,420 B2 | 3/2017 | Maxik et al. |
| 9,603,956 B2 | 3/2017 | Newham |
| 9,603,960 B2 | 3/2017 | Dobrinsky et al. |
| 9,623,130 B2 | 4/2017 | Tumanov |
| 9,623,131 B2 | 4/2017 | Taboada et al. |
| 9,623,133 B2 | 4/2017 | Childress et al. |
| 9,623,138 B2 | 4/2017 | Pagan et al. |
| 9,630,859 B2 | 4/2017 | Chen |
| 9,662,410 B2 | 5/2017 | Mackin |
| 9,666,424 B1 | 5/2017 | Veloz et al. |
| 9,675,720 B2 | 6/2017 | Roma et al. |
| 9,676,008 B1 | 6/2017 | Huang |
| 9,682,161 B2 | 6/2017 | Farren et al. |
| 9,687,575 B2 | 6/2017 | Farren |
| 9,687,577 B2 | 6/2017 | Dobrinsky et al. |
| 9,687,646 B2 | 6/2017 | Sobue et al. |
| 9,700,642 B2 | 7/2017 | Neister |
| 9,707,306 B2 | 7/2017 | Farren |
| 9,717,325 B2 | 8/2017 | Mongan et al. |
| 9,718,302 B2 | 8/2017 | Young et al. |
| 9,724,441 B2 | 8/2017 | Shur et al. |
| 9,724,442 B1 | 8/2017 | Munn |
| 9,750,831 B2 | 9/2017 | Barreau et al. |
| 9,770,522 B2 | 9/2017 | Taskinen et al. |
| 9,782,505 B2 | 10/2017 | Lyslo et al. |
| 9,787,113 B2 | 10/2017 | Kim et al. |
| 9,789,215 B1 | 10/2017 | Collins et al. |
| 9,795,701 B2 | 10/2017 | Dayton |
| 9,801,966 B2 | 10/2017 | Garrett |
| 9,802,019 B2 | 10/2017 | Arcilla et al. |
| 9,803,909 B2 | 10/2017 | Son et al. |
| 9,814,794 B2 | 11/2017 | Dayton |
| 9,827,339 B2 | 11/2017 | Nunn et al. |
| 9,827,340 B2 | 11/2017 | Cheng et al. |
| 9,833,525 B2 | 12/2017 | Schumacher |

(56) References Cited

U.S. PATENT DOCUMENTS

| | | |
|---|---|---|
| 9,834,456 B2 | 12/2017 | Collins et al. |
| 9,839,210 B2 | 12/2017 | Stewart |
| 9,839,707 B2 | 12/2017 | Won |
| 9,855,350 B1 | 1/2018 | Dahlquist |
| 9,855,351 B2 | 1/2018 | Kim |
| 9,855,353 B1 | 1/2018 | Stacy |
| 9,856,152 B2 | 1/2018 | Bokermann et al. |
| 9,868,651 B2 | 1/2018 | Matlack et al. |
| 9,889,217 B2 | 2/2018 | Franc |
| 9,889,219 B2 | 2/2018 | Dayton |
| 9,901,652 B2 | 2/2018 | Cole et al. |
| 9,907,870 B2 | 3/2018 | Boodaghians et al. |
| 9,907,871 B2 | 3/2018 | Kreiner et al. |
| 9,912,790 B2 | 3/2018 | Kim et al. |
| 9,919,067 B2 | 3/2018 | Nevin |
| 9,925,390 B2 | 3/2018 | Yehezkel |
| 9,943,617 B1 | 4/2018 | Burchman et al. |
| 9,943,618 B2 | 4/2018 | Liao et al. |
| 9,950,088 B2 | 4/2018 | Garner et al. |
| 9,956,307 B2 | 5/2018 | Burapachaisri et al. |
| 9,968,697 B1 | 5/2018 | Phillips |
| 9,974,873 B2 | 5/2018 | Cole |
| 9,974,875 B2 | 5/2018 | Davis |
| 10,010,633 B2 | 7/2018 | Trapani |
| 10,010,635 B2 | 7/2018 | Jeong et al. |
| 10,022,467 B2 | 7/2018 | Chang |
| 10,024,559 B2 | 7/2018 | Gwak et al. |
| 10,029,926 B2 | 7/2018 | Lichi et al. |
| 10,039,853 B1 | 8/2018 | Munn |
| 10,046,073 B2 | 8/2018 | Farren et al. |
| 10,046,076 B1 | 8/2018 | Collins et al. |
| 10,046,175 B2 | 8/2018 | Gerber |
| 10,053,251 B2 | 8/2018 | Clusserath |
| 10,064,966 B2 | 9/2018 | Kassel et al. |
| 10,064,968 B2 | 9/2018 | Statham et al. |
| 10,071,262 B2 | 9/2018 | Randers-Pehrson et al. |
| 10,076,582 B1 | 9/2018 | Liao et al. |
| 10,086,097 B2 | 10/2018 | Dayton |
| 10,092,664 B2 | 10/2018 | Dayton |
| 10,092,665 B2 | 10/2018 | Lyslo et al. |
| 10,092,669 B2 | 10/2018 | Marshall |
| 10,117,958 B2 | 11/2018 | Dombrowsky et al. |
| 10,130,726 B2 | 11/2018 | Pujol et al. |
| 10,137,213 B2 | 11/2018 | St. Louis et al. |
| 10,139,305 B2 | 11/2018 | Salg |
| 10,151,084 B2 | 12/2018 | Koll et al. |
| 10,159,761 B2 | 12/2018 | Kreitenberg |
| 10,166,308 B2 | 1/2019 | Engelhardt et al. |
| 10,166,309 B2 | 1/2019 | Liao et al. |
| 10,183,084 B2 | 1/2019 | Cahan et al. |
| 10,183,085 B2 | 1/2019 | Dobrinsky et al. |
| 10,183,086 B2 | 1/2019 | Ullman |
| 10,186,884 B2 | 1/2019 | Kim et al. |
| 10,195,298 B2 | 2/2019 | Kreitenberg |
| 10,195,299 B2 | 2/2019 | Baker et al. |
| 10,201,626 B1 | 2/2019 | Rapp |
| 10,206,548 B1 | 2/2019 | Hall et al. |
| 10,207,015 B2 | 2/2019 | Dayton |
| 10,220,106 B2 | 3/2019 | Kim et al. |
| 10,226,541 B2 | 3/2019 | Trapani |
| 10,226,542 B2 | 3/2019 | Messina et al. |
| 10,228,622 B2 | 3/2019 | Kimsey-Lin |
| 10,232,067 B2 | 3/2019 | Kim et al. |
| 10,238,763 B2 | 3/2019 | Kreiner et al. |
| 10,245,339 B2 | 4/2019 | Shin et al. |
| 10,245,340 B2 | 4/2019 | Stibich et al. |
| 10,245,341 B2 | 4/2019 | Stibich et al. |
| 10,255,466 B2 | 4/2019 | Jinadatha |
| 10,258,706 B2 | 4/2019 | Henniges et al. |
| 10,265,428 B1 | 4/2019 | Gross et al. |
| 10,265,429 B2 | 4/2019 | Kreiner et al. |
| 10,265,430 B2 | 4/2019 | Liao et al. |
| 10,265,432 B2 | 4/2019 | Paranhos et al. |
| 10,265,540 B2 | 4/2019 | Yehezkel |
| 10,271,932 B2 | 4/2019 | Caluori |
| 10,272,166 B2 | 4/2019 | Mackin |
| 10,272,167 B2 | 4/2019 | Starkweather et al. |
| 10,272,168 B2 | 4/2019 | Shur et al. |
| 10,279,057 B2 | 5/2019 | Ma |
| 10,279,059 B2 | 5/2019 | Bettles et al. |
| 10,286,094 B2 | 5/2019 | Dobrinsky et al. |
| 10,293,066 B2 | 5/2019 | Dayton |
| 10,301,806 B2 | 5/2019 | Childress et al. |
| 10,307,495 B2 | 6/2019 | Mori et al. |
| 10,307,501 B2 | 6/2019 | Dayton |
| 10,307,504 B2 | 6/2019 | Munn |
| 10,314,928 B2 | 6/2019 | Dobrinsky et al. |
| 10,328,166 B2 | 6/2019 | Georgeson |
| 10,328,168 B1 | 6/2019 | Veloz et al. |
| 10,335,505 B2 | 7/2019 | Gil et al. |
| 10,342,884 B2 | 7/2019 | Betties et al. |
| 10,351,443 B2 | 7/2019 | Bokermann et al. |
| 10,354,857 B2 | 7/2019 | Chen et al. |
| 10,363,327 B2 | 7/2019 | Liao et al. |
| 10,363,328 B2 | 7/2019 | Yanke |
| 10,363,329 B2 | 7/2019 | Childress et al. |
| 10,363,330 B2 | 7/2019 | Bettles et al. |
| 10,369,243 B2 | 8/2019 | Dayton |
| 10,369,379 B2 | 8/2019 | Randers-Pehrson et al. |
| 10,376,604 B2 | 8/2019 | Romo et al. |
| 10,383,963 B2 | 8/2019 | Toita et al. |
| 10,383,964 B2 | 8/2019 | Shatalov et al. |
| 10,383,965 B2 | 8/2019 | Dombrowsky |
| 10,391,189 B2 | 8/2019 | Stibich et al. |
| 10,401,012 B2 | 9/2019 | Owen et al. |
| 10,406,253 B2 | 9/2019 | Kreitenberg |
| 10,406,254 B2 | 9/2019 | Garner et al. |
| 10,413,622 B2 | 9/2019 | Mackin |
| 10,426,852 B2 | 10/2019 | Dobrinsky et al. |
| 10,426,973 B2 | 10/2019 | Williamson et al. |
| 10,427,954 B2 | 10/2019 | Vardiel et al. |
| 10,429,014 B2 * | 10/2019 | Jenks ................ G01N 21/91 |
| 10,439,408 B1 | 10/2019 | Bastiyali |
| 10,441,670 B2 | 10/2019 | Shur et al. |
| 10,441,671 B2 | 10/2019 | Sobhy et al. |
| 10,449,263 B2 | 10/2019 | Joshi |
| 10,451,298 B2 | 10/2019 | Matschke et al. |
| 10,456,489 B2 | 10/2019 | Dayton |
| 10,456,496 B2 | 10/2019 | Munn |
| 10,463,759 B2 | 11/2019 | Munn |
| 10,478,515 B2 | 11/2019 | Shur et al. |
| 10,485,887 B2 | 11/2019 | Ramanand et al. |
| 10,493,176 B2 | 12/2019 | McCormick et al. |
| 10,494,273 B2 | 12/2019 | Vardiel et al. |
| 10,500,294 B2 | 12/2019 | Paul et al. |
| 10,500,296 B2 | 12/2019 | Kreitenberg |
| 10,507,311 B2 | 12/2019 | Quisenberry |
| 10,512,703 B2 | 12/2019 | Dayton |
| 10,512,704 B2 | 12/2019 | Dytioco et al. |
| 10,517,976 B2 | 12/2019 | Shur et al. |
| 10,525,153 B2 | 1/2020 | Kim et al. |
| 10,525,155 B2 | 1/2020 | Lee et al. |
| 10,532,119 B2 | 1/2020 | Dombrowsky et al. |
| 10,543,289 B2 | 1/2020 | Taboada et al. |
| 10,549,000 B2 | 2/2020 | Yellen et al. |
| 10,550,011 B2 | 2/2020 | Jung et al. |
| 10,556,025 B2 | 2/2020 | Ufkes |
| 10,556,026 B2 | 2/2020 | Bilenko et al. |
| 10,556,027 B2 | 2/2020 | Kreiner et al. |
| 10,561,750 B2 | 2/2020 | Mintie et al. |
| 10,568,981 B2 | 2/2020 | Lyslo et al. |
| 10,576,174 B2 | 3/2020 | Shur et al. |
| 10,583,212 B2 | 3/2020 | Ufkes |
| 10,583,213 B2 | 3/2020 | Stibich et al. |
| 10,585,218 B2 | 3/2020 | Ufkes et al. |
| 10,588,993 B2 | 3/2020 | Quilici |
| 10,596,280 B2 | 3/2020 | Henderson et al. |
| 10,596,281 B1 | 3/2020 | Tchon et al. |
| 10,596,282 B2 | 3/2020 | Gil et al. |
| 10,596,288 B2 | 3/2020 | Betties et al. |
| 10,597,311 B2 | 3/2020 | Mayrand |
| 10,603,391 B2 | 3/2020 | Mishkin et al. |
| 10,603,394 B2 | 3/2020 | Farren et al. |
| 2001/0042842 A1 | 11/2001 | Leighley et al. |

(56) References Cited

U.S. PATENT DOCUMENTS

| | | |
|---|---|---|
| 2001/0048891 A1 | 12/2001 | McGeorge et al. |
| 2002/0043504 A1 | 4/2002 | Chen et al. |
| 2002/0045848 A1 | 4/2002 | Jaafar et al. |
| 2002/0063954 A1 | 5/2002 | Horton, III |
| 2002/0083535 A1 | 7/2002 | Fraden |
| 2002/0085947 A1 | 7/2002 | Deal |
| 2002/0098109 A1 | 7/2002 | Nelson et al. |
| 2002/0117631 A1 | 8/2002 | Gadgil et al. |
| 2002/0146343 A1 | 10/2002 | Jenkins et al. |
| 2002/0162969 A1 | 11/2002 | Reed |
| 2002/0162970 A1 | 11/2002 | Sasges |
| 2003/0019505 A1 | 1/2003 | Scheir et al. |
| 2003/0021723 A1 | 1/2003 | Lopez Ordaz |
| 2003/0034459 A1 | 2/2003 | Bonin |
| 2003/0086817 A1 | 5/2003 | Horton, III |
| 2003/0086818 A1 | 5/2003 | Holley, Jr. et al. |
| 2003/0086831 A1 | 5/2003 | Horton, III |
| 2003/0086848 A1 | 5/2003 | Saccomanno |
| 2003/0089670 A1 | 5/2003 | Saccomanno |
| 2003/0103866 A1 | 6/2003 | Wang et al. |
| 2003/0127506 A1 | 7/2003 | Braun, Jr. |
| 2003/0168507 A1 | 9/2003 | Mihaylov et al. |
| 2003/0223904 A1 | 12/2003 | Lakhdar Bacha |
| 2004/0009091 A1 | 1/2004 | Deal et al. |
| 2004/0013777 A1 | 1/2004 | Hallstadius |
| 2004/0016887 A1 | 1/2004 | Fink et al. |
| 2004/0045806 A1 | 3/2004 | Neff et al. |
| 2004/0047776 A1 | 3/2004 | Thomsen |
| 2004/0055620 A1 | 3/2004 | Fencl et al. |
| 2004/0056201 A1 | 3/2004 | Fink et al. |
| 2004/0084630 A1 | 5/2004 | Waluszko |
| 2004/0089815 A1 | 5/2004 | Woo |
| 2004/0120844 A1 | 6/2004 | Tribelsky et al. |
| 2004/0120850 A1 | 6/2004 | Kaiser |
| 2004/0129894 A1 | 7/2004 | Coulombe et al. |
| 2004/0140347 A1 | 7/2004 | Mihaylov et al. |
| 2004/0146426 A1 | 7/2004 | Biering et al. |
| 2004/0146437 A1 | 7/2004 | Arts et al. |
| 2004/0158302 A1 | 8/2004 | Chornenky et al. |
| 2004/0175288 A1 | 9/2004 | Horton, III |
| 2004/0183461 A1 | 9/2004 | Robert et al. |
| 2004/0219056 A1 | 11/2004 | Tribelsky et al. |
| 2004/0222163 A1 | 11/2004 | Saccomanno |
| 2004/0232359 A1 | 11/2004 | Fiset |
| 2005/0013729 A1 | 1/2005 | Brown-Skrobot et al. |
| 2005/0022844 A1 | 2/2005 | Field et al. |
| 2005/0061241 A1 | 3/2005 | West et al. |
| 2005/0061743 A1 | 3/2005 | Buttner |
| 2005/0077482 A1 | 4/2005 | Poppi et al. |
| 2005/0092931 A1 | 5/2005 | Gadgil et al. |
| 2005/0101854 A1 | 5/2005 | Larson et al. |
| 2005/0156119 A1 | 7/2005 | Greene |
| 2005/0158206 A1 | 7/2005 | Moisan et al. |
| 2005/0163648 A1 | 7/2005 | Liang |
| 2005/0163652 A1 | 7/2005 | Metzger et al. |
| 2005/0163653 A1 | 7/2005 | Crawford et al. |
| 2005/0163668 A1 | 7/2005 | Crawford et al. |
| 2005/0175512 A1 | 8/2005 | Yuen |
| 2005/0178984 A1 | 8/2005 | Brickley |
| 2005/0187596 A1 | 8/2005 | Fiset |
| 2005/0220665 A1 | 10/2005 | Ding |
| 2005/0223998 A1 | 10/2005 | Bosma et al. |
| 2005/0230320 A1 | 10/2005 | Evans |
| 2005/0230638 A1 | 10/2005 | Ancona et al. |
| 2005/0230639 A1 | 10/2005 | Ancona et al. |
| 2005/0253086 A1 | 11/2005 | Snowball |
| 2005/0256553 A1 | 11/2005 | Strisower |
| 2006/0011556 A1 | 1/2006 | Ueberall |
| 2006/0011856 A1 | 1/2006 | Skaggs |
| 2006/0017025 A1 | 1/2006 | Jensen |
| 2006/0079948 A1 | 4/2006 | Dawson |
| 2006/0104859 A1 | 5/2006 | Tribelsky |
| 2006/0151715 A1 | 7/2006 | Greene |
| 2006/0185116 A1 | 8/2006 | Lee et al. |
| 2006/0186358 A1 | 8/2006 | Couvillion |
| 2006/0188389 A1 | 8/2006 | Levy |
| 2006/0192136 A1 | 8/2006 | Gadgil et al. |
| 2006/0213791 A1 | 9/2006 | Holden |
| 2006/0216193 A1 | 9/2006 | Johnson et al. |
| 2006/0255291 A1 | 11/2006 | Harris |
| 2006/0263275 A1 | 11/2006 | Lobach |
| 2007/0009377 A1 | 1/2007 | Goodrich et al. |
| 2007/0012340 A1 | 1/2007 | Jones et al. |
| 2007/0023710 A1 | 2/2007 | Tom et al. |
| 2007/0031281 A1 | 2/2007 | Stevens |
| 2007/0057197 A1 | 3/2007 | Chor |
| 2007/0075268 A1 | 4/2007 | Harris |
| 2007/0145292 A1 | 6/2007 | Jones |
| 2007/0164232 A1 | 7/2007 | Rolleri et al. |
| 2007/0164233 A1 | 7/2007 | Mohr |
| 2007/0194255 A1 | 8/2007 | Garcia et al. |
| 2007/0258851 A1 | 11/2007 | Fogg et al. |
| 2007/0260231 A1 | 11/2007 | Rose et al. |
| 2007/0272877 A1 | 11/2007 | Tribelsky et al. |
| 2007/0274879 A1 | 11/2007 | Millikin |
| 2007/0276455 A1 | 11/2007 | Fiset |
| 2008/0035864 A1 | 2/2008 | Fiset |
| 2008/0048541 A1 | 2/2008 | Sumrall et al. |
| 2008/0052872 A1 | 3/2008 | Cho |
| 2008/0056933 A1 | 3/2008 | Moore et al. |
| 2008/0061252 A1 | 3/2008 | Garcia et al. |
| 2008/0065175 A1 | 3/2008 | Redmond et al. |
| 2008/0067417 A1 | 3/2008 | Lane et al. |
| 2008/0067418 A1 | 3/2008 | Ross |
| 2008/0067419 A1 | 3/2008 | Shih |
| 2008/0073287 A1 | 3/2008 | Kolber et al. |
| 2008/0073595 A1 | 3/2008 | Thiruppathi |
| 2008/0075629 A1 | 3/2008 | Deal et al. |
| 2008/0077122 A1 | 3/2008 | Boyden et al. |
| 2008/0077123 A1 | 3/2008 | Boyden et al. |
| 2008/0077145 A1 | 3/2008 | Boyden et al. |
| 2008/0093210 A1 | 4/2008 | Edwards |
| 2008/0131329 A1 | 6/2008 | Lin et al. |
| 2008/0131330 A1 | 6/2008 | Lyon et al. |
| 2008/0159908 A1 | 7/2008 | Redmond |
| 2008/0199353 A1 | 8/2008 | Mlodzinski et al. |
| 2008/0199354 A1 | 8/2008 | Gordon |
| 2008/0203891 A1 | 8/2008 | Gaertner et al. |
| 2008/0210884 A1 | 9/2008 | Egberts |
| 2008/0213128 A1 | 9/2008 | Rudy et al. |
| 2008/0213129 A1 | 9/2008 | van der Pol et al. |
| 2008/0219883 A1 | 9/2008 | Thur et al. |
| 2008/0224066 A1 | 9/2008 | Nolen et al. |
| 2008/0253941 A1 | 10/2008 | Wichers et al. |
| 2008/0257355 A1 | 10/2008 | Rao et al. |
| 2008/0265179 A1 | 10/2008 | Havens et al. |
| 2008/0271282 A1 | 11/2008 | Gebhard et al. |
| 2008/0283769 A1 | 11/2008 | Deshays |
| 2008/0286145 A1 | 11/2008 | Ratcliffe |
| 2008/0286146 A1 | 11/2008 | Schroll et al. |
| 2008/0289649 A1 | 11/2008 | Woytkiw |
| 2008/0295271 A1 | 12/2008 | Perunicic |
| 2008/0306454 A1 | 12/2008 | Sikora |
| 2008/0308748 A1 | 12/2008 | Burrows |
| 2009/0000639 A1 | 1/2009 | Tribelsky et al. |
| 2009/0004050 A1 | 2/2009 | Lee et al. |
| 2009/0032527 A1 | 2/2009 | Lee et al. |
| 2009/0056044 A1 | 3/2009 | Rizoiu et al. |
| 2009/0068071 A1 | 3/2009 | Hamilton |
| 2009/0112297 A1 | 4/2009 | Fiset |
| 2009/0117001 A1 | 5/2009 | Hyde et al. |
| 2009/0123331 A1 | 5/2009 | Ross |
| 2009/0126145 A1 | 5/2009 | D'Agostino et al. |
| 2009/0130169 A1 | 5/2009 | Bernstein |
| 2009/0148358 A1 | 6/2009 | Wind |
| 2009/0155121 A1 | 6/2009 | Mohr et al. |
| 2009/0169425 A1 | 7/2009 | Park et al. |
| 2009/0169442 A1 | 7/2009 | Levy et al. |
| 2009/0179547 A1 | 7/2009 | Auday et al. |
| 2009/0184268 A1 | 7/2009 | Garcia et al. |
| 2009/0191100 A1 | 7/2009 | Deal |
| 2009/0196802 A1 | 8/2009 | Streppel |
| 2009/0205664 A1 | 8/2009 | Lyon |
| 2009/0218512 A1 | 9/2009 | Ranta et al. |

(56) References Cited

U.S. PATENT DOCUMENTS

| | | |
|---|---|---|
| 2009/0242075 A1 | 10/2009 | Busick et al. |
| 2009/0252646 A1 | 10/2009 | Holden et al. |
| 2009/0256085 A1 | 10/2009 | Thiruppathi |
| 2009/0257910 A1 | 10/2009 | Segal |
| 2009/0257912 A1 | 10/2009 | Lane et al. |
| 2009/0274576 A1 | 11/2009 | Ressler |
| 2009/0280028 A1 | 11/2009 | Muggli et al. |
| 2009/0285727 A1 | 11/2009 | Levy |
| 2009/0289015 A1 | 11/2009 | Levy |
| 2009/0294692 A1 | 12/2009 | Bourke, Jr. et al. |
| 2009/0304553 A1 | 12/2009 | Gordon |
| 2009/0311149 A1 | 12/2009 | Freedgood |
| 2009/0314956 A1 | 12/2009 | Long |
| 2009/0317309 A1 | 12/2009 | Lee et al. |
| 2009/0317506 A1 | 12/2009 | Adriansens |
| 2010/0003175 A1 | 1/2010 | Gibson |
| 2010/0007492 A1 | 1/2010 | Ressler et al. |
| 2010/0012147 A1 | 1/2010 | Lu |
| 2010/0028201 A1 | 2/2010 | Neister |
| 2010/0072399 A1 | 3/2010 | Street et al. |
| 2010/0076531 A1 | 3/2010 | Beran et al. |
| 2010/0104471 A1 | 4/2010 | Harmon et al. |
| 2010/0127189 A1 | 5/2010 | Boyarsky et al. |
| 2010/0143188 A1 | 6/2010 | Roiniotis |
| 2010/0168823 A1 | 7/2010 | Strisower |
| 2010/0186187 A1 | 7/2010 | Cheung et al. |
| 2010/0187437 A1 | 7/2010 | Ueberall |
| 2010/0193709 A1 | 8/2010 | Dalton |
| 2010/0212335 A1 | 8/2010 | Lukitobudi |
| 2010/0222852 A1 | 9/2010 | Vasily et al. |
| 2010/0237254 A1 | 9/2010 | Mason et al. |
| 2010/0253207 A1 | 10/2010 | Joulaud et al. |
| 2010/0266445 A1 | 10/2010 | Campagna |
| 2010/0314553 A1 | 12/2010 | Yerby |
| 2010/0320405 A1 | 12/2010 | Gardner, III |
| 2010/0326484 A1 | 12/2010 | Wu |
| 2011/0008205 A1 | 1/2011 | Mangiardi |
| 2011/0020175 A1 | 1/2011 | Collard et al. |
| 2011/0040236 A1 | 2/2011 | Isaacs et al. |
| 2011/0044848 A1 | 2/2011 | Wright |
| 2011/0054574 A1 | 3/2011 | Felix |
| 2011/0060272 A1 | 3/2011 | Iranitalab |
| 2011/0076196 A1 | 3/2011 | Chittka et al. |
| 2011/0081274 A1 | 4/2011 | Packman et al. |
| 2011/0099831 A1 | 5/2011 | Parisi et al. |
| 2011/0100865 A1 | 5/2011 | Brink et al. |
| 2011/0104004 A1 | 5/2011 | Bobbitt |
| 2011/0108143 A1 | 5/2011 | Caluori |
| 2011/0112232 A1 | 5/2011 | Krishna et al. |
| 2011/0138905 A1 | 6/2011 | Kim et al. |
| 2011/0139999 A1 | 6/2011 | Clark et al. |
| 2011/0158862 A1 | 6/2011 | Kim et al. |
| 2011/0162155 A1 | 7/2011 | Wai |
| 2011/0171080 A1 | 7/2011 | La |
| 2011/0213339 A1 | 9/2011 | Bak |
| 2011/0215261 A1 | 9/2011 | Lyslo et al. |
| 2011/0240883 A1 | 10/2011 | Ullman |
| 2011/0243789 A1 | 10/2011 | Roberts |
| 2011/0256019 A1 | 10/2011 | Gruen et al. |
| 2011/0272595 A1 | 11/2011 | Neister |
| 2011/0274581 A1 | 11/2011 | Davis |
| 2011/0274582 A1 | 11/2011 | Davis |
| 2011/0286882 A1 | 11/2011 | Wu |
| 2011/0291995 A1 | 12/2011 | Shr et al. |
| 2011/0305597 A1 | 12/2011 | Farren |
| 2011/0308917 A1 | 12/2011 | Lathem |
| 2012/0006995 A1 | 1/2012 | Greuel |
| 2012/0012136 A1 | 1/2012 | Nguyen et al. |
| 2012/0022619 A1 | 1/2012 | Fiset |
| 2012/0045363 A1 | 2/2012 | Gil |
| 2012/0061592 A1 | 3/2012 | Dornblaser et al. |
| 2012/0068088 A1 | 3/2012 | Durkin |
| 2012/0074334 A1 | 3/2012 | Milligan |
| 2012/0085926 A1 | 4/2012 | Ingram et al. |
| 2012/0093684 A1 | 4/2012 | Martin et al. |
| 2012/0097862 A1 | 4/2012 | Snowball |
| 2012/0107184 A1 | 5/2012 | Asiyanbola et al. |
| 2012/0116294 A1 | 5/2012 | Boenig et al. |
| 2012/0121457 A1 | 5/2012 | Farren |
| 2012/0126134 A1 | 5/2012 | Deal et al. |
| 2012/0134879 A1 | 5/2012 | Tarifi |
| 2012/0141322 A1 | 6/2012 | Fogg |
| 2012/0161031 A1 | 6/2012 | NeCamp |
| 2012/0165716 A1 | 6/2012 | Reuben |
| 2012/0168647 A1 | 7/2012 | Davis |
| 2012/0181447 A1 | 7/2012 | Yerby |
| 2012/0196011 A1 | 8/2012 | Felix |
| 2012/0227586 A1 | 9/2012 | Chan et al. |
| 2012/0227745 A1 | 9/2012 | Arcilla et al. |
| 2012/0228517 A1 | 9/2012 | Mohr |
| 2012/0230867 A1 | 9/2012 | Kerr |
| 2012/0240968 A1 | 9/2012 | Schumacher |
| 2012/0241644 A1 | 9/2012 | Ben-David et al. |
| 2012/0246863 A1 | 10/2012 | Douglas |
| 2012/0261590 A1 | 10/2012 | Boyle |
| 2012/0261593 A1 | 10/2012 | Noori |
| 2012/0156094 A1 | 11/2012 | Gordon |
| 2012/0280147 A1 | 11/2012 | Douglas |
| 2012/0282135 A1 | 11/2012 | Trapani |
| 2012/0305787 A1 | 12/2012 | Henson |
| 2012/0305804 A1 | 12/2012 | Goldman |
| 2012/0313006 A1 | 12/2012 | Chiu |
| 2012/0315186 A1 | 12/2012 | Davis |
| 2012/0319311 A1 | 12/2012 | Nutter et al. |
| 2012/0328474 A1 | 12/2012 | Campagna |
| 2013/0001435 A1 | 1/2013 | Engelhardt et al. |
| 2013/0004367 A1 | 1/2013 | Roberts |
| 2013/0015753 A1 | 1/2013 | Son et al. |
| 2013/0022495 A1 | 1/2013 | Allen, IV et al. |
| 2013/0026389 A1 | 1/2013 | Lee et al. |
| 2013/0037047 A1 | 2/2013 | Saiger |
| 2013/0045132 A1 | 2/2013 | Tumanov |
| 2013/0048876 A1 | 2/2013 | Crawford |
| 2013/0052079 A1 | 2/2013 | Bernstein |
| 2013/0062534 A1 | 3/2013 | Cole |
| 2013/0064733 A1 | 3/2013 | Gerstner et al. |
| 2013/0078142 A1 | 3/2013 | Gordon |
| 2013/0115146 A1 | 5/2013 | Hamilton |
| 2013/0126760 A1 | 5/2013 | Klein et al. |
| 2013/0129567 A1 | 5/2013 | Gray |
| 2013/0152921 A1 | 6/2013 | Rao et al. |
| 2013/0167854 A1 | 7/2013 | Shin |
| 2013/0175458 A1 | 7/2013 | Kerr |
| 2013/0175460 A1 | 7/2013 | Farren |
| 2013/0177474 A1 | 7/2013 | Kerr |
| 2013/0181141 A1 | 7/2013 | Brueck et al. |
| 2013/0195716 A1 | 8/2013 | Fehr et al. |
| 2013/0207002 A1 | 8/2013 | Greuel et al. |
| 2013/0214174 A1 | 8/2013 | Domenig et al. |
| 2013/0224071 A1 | 8/2013 | Bernstein |
| 2013/0234041 A1 | 9/2013 | Deal |
| 2013/0243646 A1 | 9/2013 | Kearns et al. |
| 2013/0243647 A1 | 9/2013 | Garner et al. |
| 2013/0259742 A1 | 10/2013 | Kerr |
| 2013/0269206 A1 | 10/2013 | Parisi et al. |
| 2013/0277574 A1 | 10/2013 | Dayton |
| 2013/0280125 A1 | 10/2013 | Kim et al. |
| 2013/0281921 A1 | 10/2013 | Sobue et al. |
| 2013/0294969 A1 | 11/2013 | Chen et al. |
| 2013/0299019 A1 | 11/2013 | Caluori |
| 2013/0299032 A1 | 11/2013 | Caluori |
| 2013/0303877 A1 | 11/2013 | Strisower |
| 2013/0303996 A1 | 11/2013 | Rasooly et al. |
| 2013/0323119 A1 | 12/2013 | Alwan |
| 2013/0323120 A1 | 12/2013 | Ma |
| 2013/0340460 A1 | 12/2013 | Andros et al. |
| 2014/0001109 A1 | 1/2014 | Lee et al. |
| 2014/0001374 A1 | 1/2014 | Ullman |
| 2014/0014228 A1 | 1/2014 | Kolber et al. |
| 2014/0034849 A1 | 2/2014 | Lyslo et al. |
| 2014/0044590 A1 | 2/2014 | Trapani |
| 2014/0050612 A1 | 2/2014 | Kneissl et al. |
| 2014/0056757 A1 | 2/2014 | Chen et al. |
| 2014/0059796 A1 | 3/2014 | Boodaghians et al. |

(56) References Cited

U.S. PATENT DOCUMENTS

| | | |
|---|---|---|
| 2014/0084185 A1 | 3/2014 | Palmer et al. |
| 2014/0091236 A1 | 4/2014 | Jhawar et al. |
| 2014/0107409 A1 | 4/2014 | Bailey et al. |
| 2014/0116961 A1 | 5/2014 | Bokermann et al. |
| 2014/0117250 A1 | 5/2014 | Vardiel et al. |
| 2014/0127077 A1 | 5/2014 | Rock |
| 2014/0140888 A1 | 5/2014 | Neister |
| 2014/0140893 A1 | 5/2014 | Kohler |
| 2014/0158909 A1 | 6/2014 | Hamilton |
| 2014/0158910 A1 | 6/2014 | Fletcher |
| 2014/0161663 A1 | 6/2014 | Farren et al. |
| 2014/0166900 A1 | 6/2014 | Nelson et al. |
| 2014/0175280 A1 | 6/2014 | Tantillo |
| 2014/0203188 A1 | 7/2014 | Yerby |
| 2014/0207215 A1 | 7/2014 | Fiset |
| 2014/0212332 A1 | 7/2014 | Bergman |
| 2014/0217306 A1 | 8/2014 | Ferran et al. |
| 2014/0217307 A1 | 8/2014 | Messina et al. |
| 2014/0222120 A1 | 8/2014 | Fiset |
| 2014/0227132 A1 | 8/2014 | Neister |
| 2014/0241941 A1 | 8/2014 | Kreitenberg |
| 2014/0245866 A1 | 9/2014 | Hadlock et al. |
| 2014/0248179 A1 | 9/2014 | Engelhardt et al. |
| 2014/0252247 A1 | 9/2014 | Moskowitz et al. |
| 2014/0263091 A1 | 9/2014 | Carter, III et al. |
| 2014/0271348 A1 | 9/2014 | Deal et al. |
| 2014/0271352 A1 | 9/2014 | Stewart |
| 2014/0271353 A1 | 9/2014 | Oestergaard et al. |
| 2014/0284499 A1 | 9/2014 | Schumacher |
| 2014/0291552 A1 | 10/2014 | Schumacher |
| 2014/0300581 A1 | 10/2014 | Aurongzeb et al. |
| 2014/0328985 A1 | 11/2014 | Snowball |
| 2014/0330452 A1 | 11/2014 | Stewart |
| 2014/0334974 A1 | 11/2014 | Rasooly et al. |
| 2014/0341777 A1 | 11/2014 | Deshays et al. |
| 2014/0346370 A1 | 11/2014 | Dobrinsky et al. |
| 2014/0356229 A1 | 12/2014 | Farren |
| 2014/0363335 A1 | 12/2014 | Dam |
| 2014/0368103 A1 | 12/2014 | Son et al. |
| 2014/0371710 A1 | 12/2014 | Williamson |
| 2014/0378792 A1 | 12/2014 | Krimsky et al. |
| 2015/0004056 A1 | 1/2015 | Fogg et al. |
| 2015/0008336 A1 | 1/2015 | Rubinchikov et al. |
| 2015/0017059 A1 | 1/2015 | Arlemark |
| 2015/0017061 A1 | 1/2015 | Robison |
| 2015/0028228 A1 | 1/2015 | Almasy et al. |
| 2015/0041679 A1 | 2/2015 | Deal |
| 2015/0056096 A1 | 2/2015 | Hoover |
| 2015/0057650 A1* | 2/2015 | Grosser .............. A61L 9/20 606/27 |
| 2015/0064064 A1 | 3/2015 | Kim et al. |
| 2015/0064065 A1 | 3/2015 | Kreitenberg |
| 2015/0069263 A1 | 3/2015 | Moyal |
| 2015/0069266 A1 | 3/2015 | Domenig et al. |
| 2015/0069269 A1 | 3/2015 | Lyslo et al. |
| 2015/0069270 A1 | 3/2015 | Shur et al. |
| 2015/0073396 A1 | 3/2015 | Randers-Pehrson et al. |
| 2015/0076363 A1 | 3/2015 | Wen |
| 2015/0076369 A1 | 3/2015 | Ullman |
| 2015/0086420 A1 | 3/2015 | Trapani |
| 2015/0090903 A1 | 4/2015 | Cole |
| 2015/0090904 A1 | 4/2015 | Cole |
| 2015/0102235 A1 | 4/2015 | Lee |
| 2015/0114911 A1 | 4/2015 | Helmore |
| 2015/0115170 A1 | 4/2015 | Shostak et al. |
| 2015/0137762 A1 | 5/2015 | Kim et al. |
| 2015/0148734 A1 | 5/2015 | Fewkes et al. |
| 2015/0148776 A1 | 5/2015 | Sobue et al. |
| 2015/0151016 A1 | 6/2015 | Boisvert |
| 2015/0165078 A1 | 6/2015 | Nevin |
| 2015/0174276 A1 | 6/2015 | Tumanov |
| 2015/0182648 A1 | 7/2015 | Engelhardt et al. |
| 2015/0190537 A1 | 7/2015 | Kerr |
| 2015/0190538 A1 | 7/2015 | Olvera et al. |
| 2015/0196674 A1 | 7/2015 | Newham |
| 2015/0199487 A1 | 7/2015 | Grauds et al. |
| 2015/0209457 A1 | 7/2015 | Bonutti et al. |
| 2015/0209458 A1 | 7/2015 | Kreitenberg |
| 2015/0209459 A1 | 7/2015 | Kreitenberg |
| 2015/0209460 A1 | 7/2015 | Kreitenberg |
| 2015/0217012 A1 | 8/2015 | Garner et al. |
| 2015/0231288 A1 | 8/2015 | Campagna |
| 2015/0246152 A1 | 9/2015 | Gross |
| 2015/0251921 A1 | 9/2015 | Sobanksi et al. |
| 2015/0258234 A1 | 9/2015 | Larsen |
| 2015/0265346 A9 | 9/2015 | Randers-Pehrson et al. |
| 2015/0265735 A1 | 9/2015 | Ma |
| 2015/0290346 A1 | 10/2015 | Kassel et al. |
| 2015/0297766 A9 | 10/2015 | Cole |
| 2015/0306263 A1 | 10/2015 | Yanke |
| 2015/0306341 A1 | 10/2015 | Hoefler |
| 2015/0313354 A1 | 11/2015 | Mongan et al. |
| 2015/0328348 A1 | 11/2015 | Colayco |
| 2015/0338336 A1 | 11/2015 | Dobrinsky et al. |
| 2015/0343102 A1 | 12/2015 | Romo et al. |
| 2015/0343104 A1 | 12/2015 | Maxik et al. |
| 2015/0352348 A1 | 12/2015 | Murphy-Shutorian et al. |
| 2015/0359915 A1 | 12/2015 | Farren et al. |
| 2015/0367008 A1 | 12/2015 | Roma et al. |
| 2016/0000950 A1 | 1/2016 | Won |
| 2016/0000951 A1 | 1/2016 | Kreiner et al. |
| 2016/0008498 A1 | 1/2016 | Boysset et al. |
| 2016/0074547 A1 | 1/2016 | Kreiner et al. |
| 2016/0030612 A1 | 2/2016 | Kim et al. |
| 2016/0030613 A1 | 2/2016 | Paul et al. |
| 2016/0036952 A1 | 2/2016 | Kim et al. |
| 2016/0045633 A1 | 2/2016 | Pagan et al. |
| 2016/0074545 A1 | 3/2016 | Kim |
| 2016/0074546 A1 | 3/2016 | Rizzone |
| 2016/0082138 A1 | 3/2016 | Kermode et al. |
| 2016/0082281 A1 | 3/2016 | Gerber et al. |
| 2016/0083271 A1 | 3/2016 | Chen |
| 2016/0083272 A1 | 3/2016 | Rajagopalan et al. |
| 2016/0089206 A1 | 3/2016 | Lee et al. |
| 2016/0089459 A1 | 3/2016 | Boodaghians et al. |
| 2016/0089460 A1 | 3/2016 | Jeong et al. |
| 2016/0089461 A1 | 3/2016 | Kassel et al. |
| 2016/0101201 A1 | 4/2016 | Franc et al. |
| 2016/0101202 A1 | 4/2016 | Gil et al. |
| 2016/0106872 A1 | 4/2016 | Martinez |
| 2016/0107000 A1 | 4/2016 | Randers-Pehrson et al. |
| 2016/0114067 A1 | 4/2016 | Dobrinsky et al. |
| 2016/0121007 A1 | 5/2016 | Dayton |
| 2016/0121008 A1 | 5/2016 | Taboada et al. |
| 2016/0129141 A1 | 5/2016 | Barreau et al. |
| 2016/0136312 A1 | 5/2016 | Park et al. |
| 2016/0136314 A1 | 5/2016 | Kreitenberg |
| 2016/0151524 A1 | 6/2016 | Lyslo et al. |
| 2016/0151645 A1 | 6/2016 | Williamson |
| 2016/0158395 A1 | 6/2016 | Hughes et al. |
| 2016/0175896 A1 | 6/2016 | Montgomery |
| 2016/0176727 A1 | 6/2016 | Younis |
| 2016/0184467 A1 | 6/2016 | Cheng et al. |
| 2016/0206766 A1 | 7/2016 | Yerby |
| 2016/0220716 A1 | 8/2016 | Childress et al. |
| 2016/0228591 A1 | 8/2016 | Engelhardt et al. |
| 2016/0249436 A1 | 8/2016 | Inskeep |
| 2016/0250362 A1 | 9/2016 | Mackin |
| 2016/0251238 A1 | 9/2016 | Matlack et al. |
| 2016/0262369 A1 | 9/2016 | Stewart |
| 2016/0263261 A1 | 9/2016 | Trapani |
| 2016/0271280 A1 | 9/2016 | Liao et al. |
| 2016/0271282 A1 | 9/2016 | Trapani |
| 2016/0271803 A1 | 9/2016 | Stewart |
| 2016/0278895 A1 | 9/2016 | Caluori |
| 2016/0289272 A1 | 10/2016 | Otterlei et al. |
| 2016/0296649 A1 | 10/2016 | Ramanand et al. |
| 2016/0296650 A1 | 10/2016 | Liao et al. |
| 2016/0303265 A1 | 10/2016 | Coles |
| 2016/0317268 A1 | 11/2016 | Dietzel et al. |
| 2016/0317685 A1 | 11/2016 | Pujol et al. |
| 2016/0317686 A1 | 11/2016 | Dayton |
| 2016/0317687 A1 | 11/2016 | Dayton |
| 2016/0339127 A1 | 11/2016 | Ma |

(56) References Cited

U.S. PATENT DOCUMENTS

| | | |
|---|---|---|
| 2016/0339133 A1 | 11/2016 | Lichtblau |
| 2016/0339138 A1 | 11/2016 | Nagao et al. |
| 2016/0339262 A1 | 11/2016 | Fiset |
| 2016/0375165 A1 | 12/2016 | Cole et al. |
| 2016/0375166 A1 | 12/2016 | Kreitenberg |
| 2016/0376046 A1 | 12/2016 | Clusserath |
| 2017/0007215 A1 | 1/2017 | Podoly |
| 2017/0014537 A1 | 1/2017 | Nunn et al. |
| 2017/0028088 A9 | 2/2017 | Maxik et al. |
| 2017/0029292 A1 | 2/2017 | Rajagopalan et al. |
| 2017/0035918 A1 | 2/2017 | Kassel et al. |
| 2017/0035920 A1 | 2/2017 | Boodaghians et al. |
| 2017/0035923 A1 | 2/2017 | Yanke |
| 2017/0056540 A1 | 3/2017 | Dayton |
| 2017/0072077 A1 | 3/2017 | Baker et al. |
| 2017/0080116 A1 | 3/2017 | Kreiner et al. |
| 2017/0080251 A1 | 3/2017 | Yehezkel |
| 2017/0086560 A1 | 3/2017 | Pires et al. |
| 2017/0087262 A1 | 3/2017 | Toita et al. |
| 2017/0100498 A1 | 4/2017 | Sobhy et al. |
| 2017/0100500 A1 | 4/2017 | Garner et al. |
| 2017/0112953 A1 | 4/2017 | Dayton |
| 2017/0112954 A1 | 4/2017 | Dayton |
| 2017/0136136 A1 | 5/2017 | Li et al. |
| 2017/0143859 A1 | 5/2017 | Lyslo et al. |
| 2017/0157276 A1 | 6/2017 | Dobrinsky et al. |
| 2017/0157279 A1 | 6/2017 | Dayton |
| 2017/0174536 A1 | 6/2017 | Robison et al. |
| 2017/0182194 A1 | 6/2017 | Shin et al. |
| 2017/0182305 A1 | 6/2017 | Kermode et al. |
| 2017/0182332 A1 | 6/2017 | Fiset |
| 2017/0190397 A1 | 7/2017 | Salters et al. |
| 2017/0197002 A1 | 7/2017 | Dobrinsky et al. |
| 2017/0197493 A1 | 7/2017 | Paranhos et al. |
| 2017/0202988 A1 | 7/2017 | Clark |
| 2017/0209607 A1 | 7/2017 | Safraoui |
| 2017/0209608 A1 | 7/2017 | Cameron |
| 2017/0216466 A1 | 8/2017 | Dujowich et al. |
| 2017/0216468 A1 | 8/2017 | Roma et al. |
| 2017/0224853 A1 | 8/2017 | Jay |
| 2017/0224854 A1 | 8/2017 | Mackin |
| 2017/0224855 A1 | 8/2017 | Mackin |
| 2017/0224858 A1 | 8/2017 | Stibich |
| 2017/0232123 A1 | 8/2017 | Burapachaisri et al. |
| 2017/0246332 A1 | 8/2017 | Marshall |
| 2017/0253497 A1 | 9/2017 | Mayrand |
| 2017/0274223 A1 | 9/2017 | Reidenberg et al. |
| 2017/0284011 A1 | 10/2017 | Jeong et al. |
| 2017/0290932 A1 | 10/2017 | Mori et al. |
| 2017/0290933 A1 | 10/2017 | Collins et al. |
| 2017/0290935 A1 | 10/2017 | Boodaghians et al. |
| 2017/0290937 A1 | 10/2017 | Dobrinsky et al. |
| 2017/0296686 A1 | 10/2017 | Cole |
| 2017/0299289 A1 | 10/2017 | Brats et al. |
| 2017/0304472 A1 | 10/2017 | Neister et al. |
| 2017/0304473 A1 | 10/2017 | Farren et al. |
| 2017/0307234 A1 | 10/2017 | Matschke et al. |
| 2017/0314243 A1 | 11/2017 | Kali et al. |
| 2017/0333170 A1 | 11/2017 | Caluori |
| 2017/0333580 A1 | 11/2017 | Cahan et al. |
| 2017/0333582 A1 | 11/2017 | Davis |
| 2017/0333583 A1 | 11/2017 | Shur et al. |
| 2017/0333618 A1 | 11/2017 | Krohn et al. |
| 2017/0340153 A1 | 11/2017 | Wise-Jarvis |
| 2017/0340760 A1 | 11/2017 | Starkweather et al. |
| 2017/0340762 A1 | 11/2017 | Ullman |
| 2017/0348446 A1 | 12/2017 | Golden, Sr. |
| 2017/0360977 A1 | 12/2017 | Stibich et al. |
| 2017/0368213 A1 | 12/2017 | Mintie et al. |
| 2017/0368216 A1 | 12/2017 | Regalado et al. |
| 2017/0368220 A1 | 12/2017 | Joshi |
| 2017/0373516 A1 | 12/2017 | Kim et al. |
| 2018/0008735 A1 | 1/2018 | Almeida |
| 2018/0008736 A1 | 1/2018 | Lyslo et al. |
| 2018/0043043 A1 | 2/2018 | Spector |
| 2018/0044204 A1 | 2/2018 | Lichi et al. |
| 2018/0051447 A1 | 2/2018 | Hills et al. |
| 2018/0055959 A1 | 3/2018 | Lin et al. |
| 2018/0055960 A1 | 3/2018 | Reiber et al. |
| 2018/0055961 A1 | 3/2018 | Noad |
| 2018/0055964 A1 | 3/2018 | Dayton |
| 2018/0064833 A1 | 3/2018 | Childress et al. |
| 2018/0071414 A1 | 3/2018 | Dujowich et al. |
| 2018/0071417 A1 | 3/2018 | Taboada et al. |
| 2018/0085481 A1 | 3/2018 | Schumacher |
| 2018/0093001 A1 | 4/2018 | Georgeson |
| 2018/0110893 A1 | 4/2018 | Chang |
| 2018/0117194 A1 | 5/2018 | Dobrinksky et al. |
| 2018/0134584 A1 | 5/2018 | Kolch et al. |
| 2018/0140727 A1 | 5/2018 | Roma et al. |
| 2018/0154028 A1 | 6/2018 | Offutt et al. |
| 2018/0154029 A1 | 6/2018 | Shr et al. |
| 2018/0154032 A1 | 6/2018 | Dombrowsky et al. |
| 2018/0161468 A1 | 6/2018 | Dayton |
| 2018/0161594 A1 | 6/2018 | Yehezkel |
| 2018/0169279 A1 | 6/2018 | Randers-Pehrson et al. |
| 2018/0182607 A1 | 6/2018 | Chen et al. |
| 2018/0370821 A1 | 6/2018 | Kishi et al. |
| 2018/0185534 A1 | 7/2018 | Dombrowsky et al. |
| 2018/0185535 A1 | 7/2018 | Dombrowsky et al. |
| 2018/0193500 A1 | 7/2018 | Safavi et al. |
| 2018/0193501 A1 | 7/2018 | Ufkes |
| 2018/0193502 A1 | 7/2018 | Ufkes |
| 2018/0193504 A1 | 7/2018 | Kreiner et al. |
| 2018/0200396 A1 | 7/2018 | Messina et al. |
| 2018/0207302 A1 | 7/2018 | Vasilenko |
| 2018/0209613 A1 | 7/2018 | Callahan |
| 2018/0214585 A1 | 8/2018 | Piper |
| 2018/0214592 A1 | 8/2018 | Garner et al. |
| 2018/0214595 A1 | 8/2018 | Munn |
| 2018/0215634 A1 | 8/2018 | Jung et al. |
| 2018/0221519 A1 | 8/2018 | Nguyen |
| 2018/0221521 A1 | 8/2018 | Shur et al. |
| 2018/0224584 A1 | 8/2018 | Shur et al. |
| 2018/0236113 A1 | 8/2018 | Gross et al. |
| 2018/0236114 A1 | 8/2018 | Davis |
| 2018/0236116 A1 | 8/2018 | Burapachaisri et al. |
| 2018/0243582 A1 | 8/2018 | Kaneda et al. |
| 2018/0250428 A1 | 9/2018 | Canfield |
| 2018/0250429 A1 | 9/2018 | Rock |
| 2018/0250723 A1 | 9/2018 | Schomer |
| 2018/0256764 A1 | 9/2018 | Kreitenberg |
| 2018/0259256 A1 | 9/2018 | Kim et al. |
| 2018/0264150 A1 | 9/2018 | Shur et al. |
| 2018/0264151 A1 | 9/2018 | Shur et al. |
| 2018/0265382 A1 | 9/2018 | Schuentz |
| 2018/0272014 A1 | 9/2018 | Dombrowsky |
| 2018/0272016 A1 | 9/2018 | Hunt |
| 2018/0272017 A1 | 9/2018 | Stibich et al. |
| 2018/0289845 A1 | 10/2018 | Chan |
| 2018/0289847 A1 | 10/2018 | McCormick et al. |
| 2018/0289940 A1 | 10/2018 | Spotnitz et al. |
| 2018/0296709 A1 | 10/2018 | Mishkin et al. |
| 2018/0304225 A1 | 10/2018 | Bourke, Jr. |
| 2018/0326105 A1 | 11/2018 | Crosby |
| 2018/0333510 A1 | 11/2018 | Lee et al. |
| 2018/0339075 A1 | 11/2018 | Kennedy et al. |
| 2018/0343847 A1 | 12/2018 | Ervin |
| 2018/0343898 A1 | 12/2018 | Alzeer et al. |
| 2018/0353017 A1 | 12/2018 | Miranda et al. |
| 2018/0353629 A9 | 12/2018 | Neister et al. |
| 2018/0353631 A1 | 12/2018 | Grinstead et al. |
| 2018/0361001 A1 | 12/2018 | Liao et al. |
| 2018/0361008 A1 | 12/2018 | Munn |
| 2018/0369435 A1 | 12/2018 | Dhiman et al. |
| 2018/0369439 A1 | 12/2018 | Brockschmidt et al. |
| 2018/0369440 A1 | 12/2018 | Dytioco et al. |
| 2018/0373157 A1 | 12/2018 | Kimsey-Lin |
| 2019/0001007 A1 | 1/2019 | Lyslo et al. |
| 2019/0016610 A1 | 1/2019 | Hoehne |
| 2019/0022260 A1 | 1/2019 | Cole |
| 2019/0022261 A1 | 1/2019 | Dayton |
| 2019/0022263 A1 | 1/2019 | Quilici |
| 2019/0030195 A1 | 1/2019 | Haiti et al. |

(56) References Cited

U.S. PATENT DOCUMENTS

| | | |
|---|---|---|
| 2019/0031536 A1 | 1/2019 | Vardiel et al. |
| 2019/0038914 A1 | 2/2019 | Igarashi et al. |
| 2019/0046676 A1 | 2/2019 | Dayton |
| 2019/0053674 A1 | 2/2019 | Hall et al. |
| 2019/0054201 A1 | 2/2019 | Zhang et al. |
| 2019/0060495 A1 | 2/2019 | Gil et al. |
| 2019/0060496 A1 | 2/2019 | Tillotson |
| 2019/0070325 A1 | 3/2019 | Preminger et al. |
| 2019/0076558 A1 | 3/2019 | Zhang-Miske et al. |
| 2019/0076569 A1 | 3/2019 | Peterson |
| 2019/0083672 A1 | 3/2019 | Munn |
| 2019/0083673 A1 | 3/2019 | Munn |
| 2019/0091358 A1 | 3/2019 | Liao et al. |
| 2019/0091738 A1 | 3/2019 | Chen |
| 2019/0099507 A1 | 4/2019 | Garrett |
| 2019/0099508 A1 | 4/2019 | Garrett |
| 2019/0099613 A1 | 4/2019 | Estes et al. |
| 2019/0105415 A1 | 4/2019 | Gross et al. |
| 2019/0110746 A1 | 4/2019 | Dau et al. |
| 2019/0111168 A1 | 4/2019 | Baumler et al. |
| 2019/0111169 A1 | 4/2019 | Flaherty et al. |
| 2019/0117802 A1 | 4/2019 | Hishinuma et al. |
| 2019/0117806 A1 | 4/2019 | Cahan et al. |
| 2019/0117813 A9 | 4/2019 | Dayton |
| 2019/0126058 A1 | 5/2019 | McCarthy |
| 2019/0134242 A1 | 5/2019 | Bonutti et al. |
| 2019/0134249 A1 | 5/2019 | Taboada et al. |
| 2019/0134595 A1 | 5/2019 | Bourke, Jr. et al. |
| 2019/0142981 A1 | 5/2019 | Kim et al. |
| 2019/0142986 A1 | 5/2019 | Zhang et al. |
| 2019/0160190 A1 | 5/2019 | Kreitenberg |
| 2019/0160192 A1 | 5/2019 | Fudakowski |
| 2019/0160305 A1 | 5/2019 | Randers-Pehrson et al. |
| 2019/0162471 A1 | 5/2019 | Stewart |
| 2019/0167230 A1 | 6/2019 | Cho et al. |
| 2019/0167792 A1 | 6/2019 | Sowemimo-Coker et al. |
| 2019/0167827 A1 | 6/2019 | Gaska et al. |
| 2019/0171111 A1 | 6/2019 | Kimsey-Lin |
| 2019/0172336 A1 | 6/2019 | Haidegger et al. |
| 2019/0175780 A1 | 6/2019 | Munn |
| 2019/0184044 A1 | 6/2019 | Yellen et al. |
| 2019/0192708 A1 | 6/2019 | Igarashi |
| 2019/0192709 A1 | 6/2019 | Igarashi |
| 2019/0192844 A1 | 6/2019 | Wegener et al. |
| 2019/0201563 A1 | 7/2019 | Swaney et al. |
| 2019/0201570 A1 | 7/2019 | Dobrinsky et al. |
| 2019/0209722 A1 | 7/2019 | Stibich et al. |
| 2019/0214244 A1 | 7/2019 | Park et al. |
| 2019/0216958 A1 | 7/2019 | Kreitenberg et al. |
| 2019/0216964 A1 | 7/2019 | Kreiner et al. |
| 2019/0219506 A1 | 7/2019 | Gould et al. |
| 2019/0223585 A1 | 7/2019 | Wigand et al. |
| 2019/0224352 A1 | 7/2019 | Rasooly et al. |
| 2019/0231912 A1 | 8/2019 | Dobrinsky |
| 2019/0240363 A1 | 8/2019 | Kreiner et al. |
| 2019/0240365 A1 | 8/2019 | Dombrowsky et al. |
| 2019/0254903 A1 | 8/2019 | Hag |
| 2019/0255201 A1 | 8/2019 | Rosen et al. |
| 2019/0262484 A1 | 8/2019 | Georgeson |
| 2019/0262485 A1 | 8/2019 | Ramanand et al. |
| 2019/0262487 A1 | 8/2019 | Gil et al. |
| 2019/0262489 A1 | 8/2019 | Yanai et al. |
| 2019/0262493 A1 | 8/2019 | Collins et al. |
| 2019/0269810 A1 | 9/2019 | Brehm |
| 2019/0270630 A1 | 9/2019 | Dahan et al. |
| 2019/0274421 A1 | 9/2019 | Cosolito |
| 2019/0282718 A1 | 9/2019 | Cole |
| 2019/0290791 A1 | 9/2019 | Baker et al. |
| 2019/0290794 A1 | 9/2019 | Brockschmidt |
| 2019/0298869 A1 | 10/2019 | Poulsen |
| 2019/0298871 A1 | 10/2019 | Dobrinsky |
| 2019/0298875 A1 | 10/2019 | Childress et al. |
| 2019/0309248 A1 | 10/2019 | Alibek et al. |
| 2019/0313785 A1 | 10/2019 | Jimenez et al. |
| 2019/0321503 A1 | 10/2019 | Warnell |
| 2019/0321504 A1 | 10/2019 | Dayton |
| 2019/0321506 A1 | 10/2019 | Zhang et al. |
| 2019/0328915 A1 | 10/2019 | Paul et al. |
| 2019/0328919 A1 | 10/2019 | Saad et al. |
| 2019/0328920 A1 | 10/2019 | Stibich et al. |
| 2019/0336627 A1 | 11/2019 | Lucio |
| 2019/0336628 A1 | 11/2019 | Dombrowsky |
| 2019/0336632 A1 | 11/2019 | Dombrowsky et al. |
| 2019/0336714 A1 | 11/2019 | Vazales et al. |
| 2019/0345701 A1 | 11/2019 | Koll et al. |
| 2019/0351084 A1 | 11/2019 | Garner et al. |
| 2019/0351085 A1 | 11/2019 | Dayton |
| 2019/0351086 A1 | 11/2019 | Dayton |
| 2019/0365938 A1 | 12/2019 | Romo et al. |
| 2019/0374075 A1 | 12/2019 | Barnett et al. |
| 2019/0374664 A1 | 12/2019 | Kay et al. |
| 2019/0374665 A1 | 12/2019 | Jo et al. |
| 2019/0381336 A1 | 12/2019 | Randers-Pehrson et al. |
| 2019/0382597 A1 | 12/2019 | Gross |
| 2019/0388572 A1 | 12/2019 | Cole et al. |
| 2019/0388706 A1 | 12/2019 | Randers-Pehrson et al. |
| 2020/0030469 A1 | 1/2020 | Neister et al. |
| 2020/0030472 A1 | 1/2020 | Kim et al. |
| 2020/0054893 A1 | 2/2020 | Yoon et al. |
| 2020/0061223 A1 | 2/2020 | Hallack |
| 2020/0070214 A1 | 3/2020 | Mangiardi |
| 2020/0073199 A1 | 3/2020 | Lin et al. |
| 2020/0075972 A1 | 3/2020 | Jorgenson et al. |
| 2020/0078480 A1 | 3/2020 | Starkweather et al. |
| 2020/0078483 A1 | 3/2020 | Eidman |
| 2020/0085983 A1 | 3/2020 | Ramanand et al. |
| 2020/0093945 A1 | 3/2020 | Jeong |
| 2020/0215210 A1 | 7/2020 | Rosen et al. |
| 2020/0215214 A1 | 7/2020 | Rosen et al. |
| 2020/0215215 A1 | 7/2020 | Randers-Pehrson et al. |
| 2020/0246632 A1 | 8/2020 | Naito |
| 2020/0360554 A1 | 11/2020 | Sakaguchi et al. |
| 2020/0384144 A1 | 12/2020 | Sakaguchi et al. |

FOREIGN PATENT DOCUMENTS

| | | |
|---|---|---|
| CN | 202961251 U | 6/2013 |
| CN | 204972697 U | 1/2016 |
| CN | 205011421 U | 2/2016 |
| CN | 205181844 U | 4/2016 |
| CN | 207304076 U | 5/2018 |
| CN | 209490289 U | 10/2019 |
| EP | 70087 B1 | 1/1986 |
| EP | 582739 A1 | 2/1994 |
| EP | 552189 B1 | 3/1995 |
| EP | 1027082 A1 | 8/2000 |
| EP | 1042006 B1 | 8/2001 |
| EP | 919246 B1 | 4/2002 |
| EP | 818206 B1 | 10/2002 |
| EP | 916937 B1 | 1/2005 |
| EP | 1453375 B1 | 5/2005 |
| EP | 1721684 A3 | 7/2008 |
| EP | 2127684 A1 | 12/2009 |
| EP | 1962905 B1 | 2/2010 |
| EP | 2303338 A1 | 4/2011 |
| EP | 2198886 B1 | 6/2011 |
| EP | 2303338 A4 | 8/2011 |
| EP | 2391421 A1 | 12/2011 |
| EP | 2288578 B1 | 2/2012 |
| EP | 2391421 A4 | 6/2012 |
| EP | 1523341 B1 | 9/2012 |
| EP | 2175892 B1 | 9/2012 |
| EP | 1866627 B1 | 9/2013 |
| EP | 2683442 A1 | 1/2014 |
| EP | 2729175 A1 | 5/2014 |
| EP | 2683442 A4 | 8/2014 |
| EP | 2780043 A1 | 9/2014 |
| EP | 2953655 A1 | 12/2015 |
| EP | 2968633 A1 | 1/2016 |
| EP | 2996727 A1 | 3/2016 |
| EP | 2999553 A1 | 3/2016 |
| EP | 3003986 A1 | 4/2016 |
| EP | 3016607 A1 | 5/2016 |
| EP | 3129069 A1 | 2/2017 |

(56) References Cited

FOREIGN PATENT DOCUMENTS

| | | |
|---|---|---|
| EP | 1887297 B1 | 4/2017 |
| EP | 3148594 A1 | 4/2017 |
| EP | 3150562 A1 | 4/2017 |
| EP | 3160661 A1 | 5/2017 |
| EP | 3162327 A2 | 5/2017 |
| EP | 3164160 A2 | 5/2017 |
| EP | 3162327 A3 | 7/2017 |
| EP | 3195900 A1 | 7/2017 |
| EP | 3206721 A1 | 8/2017 |
| EP | 3234653 A1 | 10/2017 |
| EP | 2709958 B1 | 12/2017 |
| EP | 3256172 A1 | 12/2017 |
| EP | 3302328 A1 | 4/2018 |
| EP | 3328444 A1 | 6/2018 |
| EP | 3335573 A1 | 6/2018 |
| EP | 3338812 A1 | 6/2018 |
| EP | 3373973 A1 | 9/2018 |
| EP | 3421053 A1 | 1/2019 |
| EP | 3436394 A1 | 2/2019 |
| EP | 3442313 A1 | 2/2019 |
| EP | 3466451 A1 | 4/2019 |
| EP | 3473150 A1 | 4/2019 |
| EP | 2654806 B1 | 5/2019 |
| EP | 3082919 B1 | 5/2019 |
| EP | 3495325 A1 | 6/2019 |
| EP | 3111961 B1 | 7/2019 |
| EP | 3111962 B1 | 7/2019 |
| EP | 3326693 B1 | 8/2019 |
| EP | 2582401 B1 | 9/2019 |
| EP | 3253453 B1 | 9/2019 |
| EP | 3520912 A3 | 9/2019 |
| EP | 3560067 A1 | 10/2019 |
| EP | 3003375 B1 | 11/2019 |
| EP | 3193634 B1 | 11/2019 |
| EP | 3316915 B1 | 11/2019 |
| EP | 3562435 A1 | 11/2019 |
| EP | 3581624 A1 | 12/2019 |
| EP | 2997108 B1 | 2/2020 |
| EP | 3578207 A3 | 3/2020 |
| EP | 3623446 A1 | 3/2020 |
| EP | 3560066 B1 | 4/2020 |
| EP | 3411086 B1 | 7/2020 |
| EP | 3073971 B1 | 1/2021 |
| JP | H03218764 A | 9/1991 |
| JP | H11128325 A | 5/1999 |
| JP | H11230899 A | 8/1999 |
| JP | 2001332216 A | 11/2001 |
| JP | 2003159570 A | 6/2003 |
| JP | 2004128331 A | 4/2004 |
| JP | 2005216647 A | 8/2005 |
| JP | 2005218850 A | 8/2005 |
| JP | 2005323654 A | 11/2005 |
| JP | 2007220549 A | 8/2007 |
| JP | 2007289641 A | 11/2007 |
| JP | 2017059321 A | 3/2017 |
| JP | 2017213263 A | 12/2017 |
| JP | 2018019670 A | 2/2018 |
| JP | 2018114197 A | 7/2018 |
| JP | 2018114209 A | 7/2018 |
| JP | 2018146413 A | 9/2018 |
| JP | 2018177055 A | 11/2018 |
| JP | 6490318 B1 | 3/2019 |
| JP | 2019072411 A | 5/2019 |
| JP | 2019116991 A | 7/2019 |
| JP | 6558376 B2 | 8/2019 |
| JP | 6561881 B2 | 8/2019 |
| JP | 2019188127 A | 10/2019 |
| JP | 6607623 B1 | 11/2019 |
| JP | 2020000285 A | 1/2020 |
| JP | 666086162 B2 | 3/2020 |
| TW | M512405 U | 11/2015 |
| WO | 9607451 A2 | 3/1996 |
| WO | 0191810 A1 | 12/2001 |
| WO | 0242164 A2 | 5/2002 |
| WO | 02092138 A1 | 11/2002 |
| WO | 2019079976 A1 | 5/2019 |
| WO | 2019079983 A1 | 5/2019 |
| WO | 2019164810 A1 | 8/2019 |

OTHER PUBLICATIONS

Avago Technologies, "HSMF-C113 and HSMF-C115 Right Angle Tricolor Surface Mount ChipLEDs Data Sheet," Document No. AV02-0611EN, Apr. 9, 2010, 8 pages.

Cui Devices, "CFM-80 Series DC Axial Fan," Revision 1.05, Feb. 10, 2020, 7 pages.

Cypress Semiconductor, "CY8CKIT-059: PSoC® 5LP Prototyping Kit" Document No. 630-60242-01, Revision 3, Jun. 16, 2015, 3 pages.

Cypress Semiconductor, "CY8CKIT-059: PSoC® 5LP Prototyping Kit Guide," Document No. 001-96498, Revision G, Mar. 12, 2018, 48 pages.

Hirose Electric Co., Ltd, "LF10WBP-4S(31) Specification Sheet," Jun. 14, 2019, 1 page.

Hirose Electric Co., Ltd, "LF10WBR-4P Specification Sheet," Sep. 10, 2016, 1 page.

IDX, "DUO-C150 Compact 143Wh Li-ion V-Mount Battery Data Sheet," Jan. 2019, https://cdn.shopify.com/s/files/1/0282/9559/4123/files/DUO-C150_Datasheet_2.pdf, 2 pages.

Klaran, "Klaran® WD Series UVC LEDs Data Sheet," 2018, www.klaran.com, Crystal IS, Inc., 8 pages.

Linear Technology, "LT6118 Current Sense Amplifier, Reference and Comparator with POR," Document No. 6118f, 2014, www.linear.com/LT6118, 24 pages.

LITECH, "LITECH-180W Series Specification of Lithium Battery," Apr. 15, 2020, 7 pages.

LiTech, "Specification of LiTech Power Li-ion 12S2P 44.4V 6.4Ah Battery Pack," Model No. LP12S2P8A8AL01, Document No. DSE-A-1214-01, Version 0, approved Mar. 30, 2020, LiTech Power Co.,Ltd., 6 pages.

LiTech, "Specification of LiTech Power Li-ion 12S2P 44.4V 6.4Ah Battery Pack," Model No. LP12S2P8A8AL01, Document No. DSE-A-1214-01, Version 1, approved Mar. 30, 2020, LiTech Power Co.,Ltd., 6 pages.

Maxim Integrated, "MAX9611/MAX9612: High-Side, Current-Sense Amplifiers with 12-Bit ADC and OP Amp/Comparator," Dcoument No. 19-5543, Revision 5, Dec. 2019, 20 pages.

Molex, "Micro Fit (3.0) Right Angle SMT Clips Single Row / Tape and Reel," Document No. 3D-43650-004, Revision E1, Apr. 27, 2018, 1 page.

Molex, "Milligrid 2MM Pitch, SMT Vertical Shrouded Header," Document No. SD-87832-0001, Revision A12, Jul. 23, 2019, 13 pages.

Molex, "Picoblade 1.25 Header Assy Dip VT Tin Plating Type," Document No. 530470000-SD, Revision A, Oct. 15, 2019, 1 page.

Molex, "Pico-LOCK1.5 HDRASSY SGLRW R/A ETP H=2 for Circuit Size 4-8, 10,12," Document No. 5040500000-SD, Revision A, Feb. 18, 2019, 6 pages.

NXP Semiconductors, "MMA8451Q, 3-axis, 14-bit/8-bit digital accelerometer," Document No. MMA8451Q, Revision 10.3, Feb. 2017, 59 pages.

Omron Corporation, "D2MQSubminiature Basic Switch," available as early as Mar. 24, 2020 from https://omronfs.omron.com/en_US/ecb/products/pdf/en-d2mq.pdf, 4 pages.

Recom, "RCD-48 Series: Constant Current Buck LED Driver," Feb. 2017, www.recom-power.com, 4 pages.

SunLed, "3. 0mm×1.0 Right Angle SMD Chip LED Lamp," Part No. XZFBB56W-1, Document No. XDsB4251, Version3-Z, Mar. 28, 2016, 4 pages.

Texas Instruments, "LM75A Digital Temperature Sensor and Thermal Watchdog With Two-Wire Interface," Document No. SNOS808P, Jan. 2000, revised Dec. 2014, 30 pages.

Ivurth Elektronik, "3.00 MM Male Single Row Vertical Header," WERI Part No. 662 0xx 111 22, Sep. 10, 2014, 3 pages.

XP Power, "LED Driver LDU Series," Aug. 21, 2014, xppower.com, 4 pages.

(56) References Cited

OTHER PUBLICATIONS

U.S. Appl. No. 62/694,482.
U.S. Appl. No. 62/632,716.
U.S. Appl. No. 62/963,682.
U.S. Appl. No. 17/119,440.
International Patent Application No. PCT/US2020/066056.
Non-Final Office Action for U.S. Appl. No. 17/139,578, dated Feb. 22, 2021, 9 pages.
Notice of Allowance for U.S. Appl. No. 17/139,578, dated Mar. 24, 2021, 11 pages.

* cited by examiner

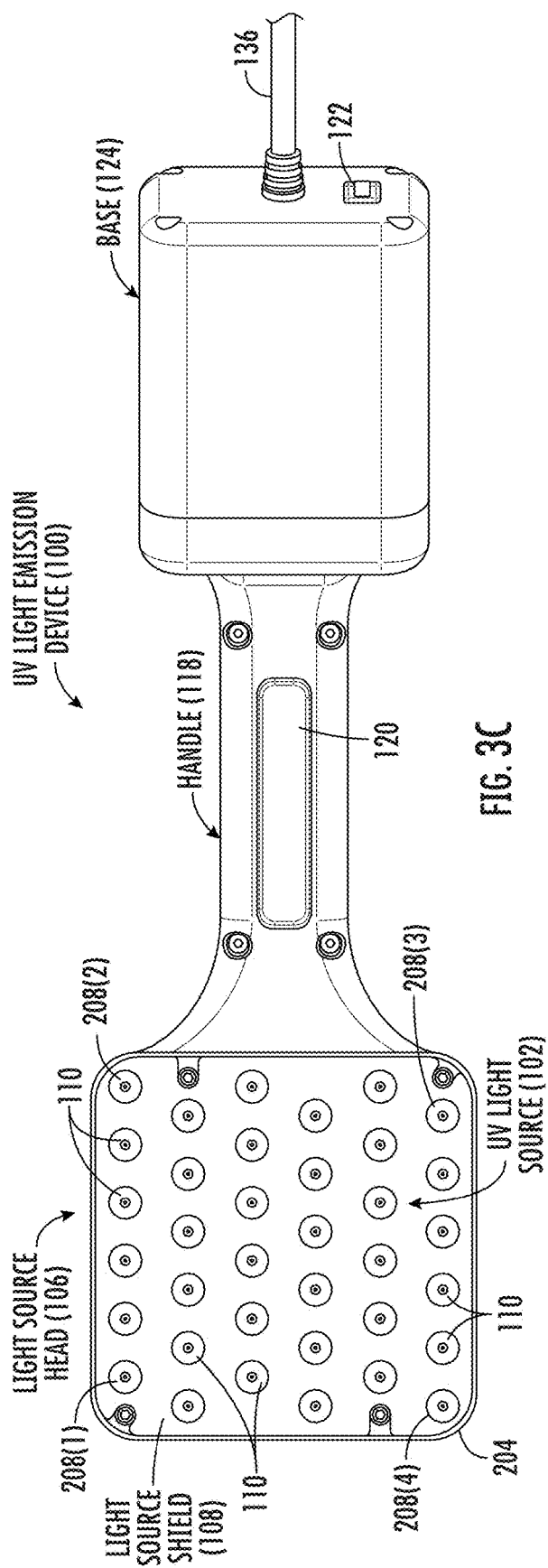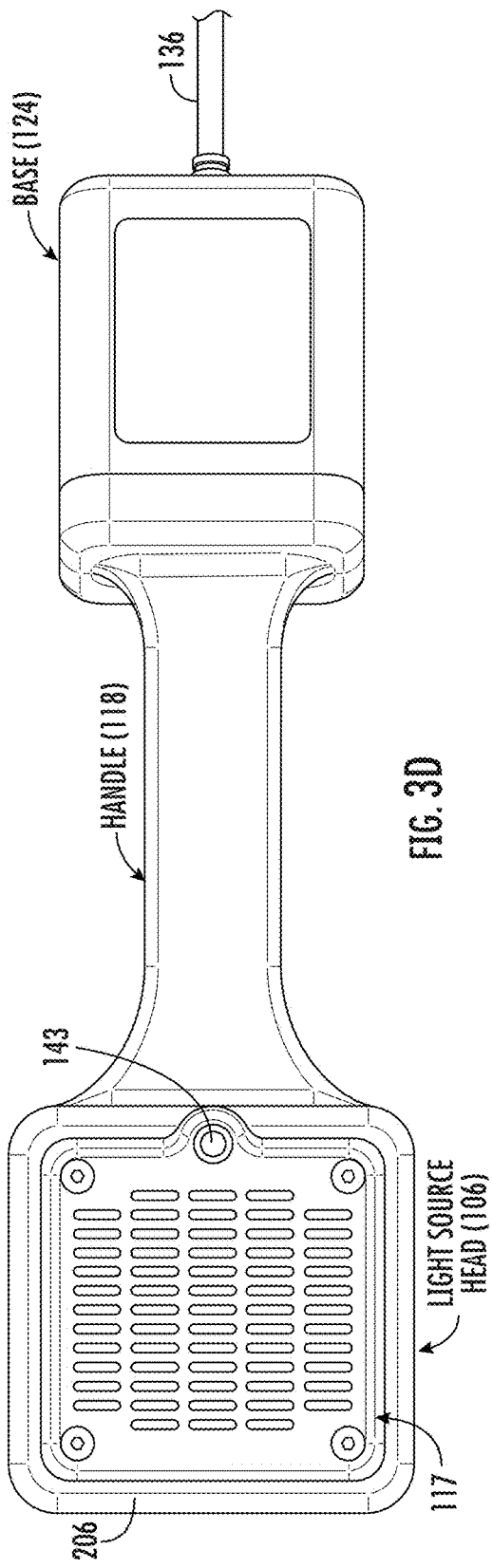

2200

| Address | Description |
|---|---|
| 40 | Error Count Temperature Sense IC High Byte |
| 41 | Error Count Temperature Sense IC Low Byte |
| 42 | Error Count FRAM IC High Byte |
| 43 | Error Count FRAM IC Low Byte |
| 44 | Error Count Fan High Byte |
| 45 | Error Count Fan Low Byte |
| 46 | Error Count Haptic IC High Byte |
| 47 | Error Count Haptic IC Low Byte |
| 48 | Error Count OverTemp LED Board High Byte |
| 49 | Error Count OverTemp LED Board Low Byte |
| 50 | Error Count Battery Low High Byte |
| 51 | Error Count Battery Low Low Byte |
| 52 | Error Count VLED High Byte |
| 53 | Error Count VLED Low Byte |
| 54 | Error Count Over Current High Byte |
| 55 | Error Count Over Current Low Byte |
| 56 | Error Count 12V Fault High Byte |
| 57 | Error Count 12V Fault Low Byte |
| 58 | Error Count Tilt High Byte |
| 59 | Error Count Tilt Low Byte |
| 60 | Error Count LED Undervolt High Byte |
| 61 | Error Count LED Undervolt Low Byte |
| 62 | Error Count LED Driver OverTemp High Byte |
| 63 | Error Count LED Driver OverTemp Low Byte |
| 64 | Error Count Dropped High Byte |
| 65 | Error Count Dropped Low Byte |
| 66 | Error Count Operator IMU Override High Byte |
| 67 | Error Count Operator IMU Override Low Byte |
| 68 | Accelerometer Peak X-Axis Float High Byte |
| 69 | Accelerometer Peak X-Axis Float Mid High Byte |
| 70 | Accelerometer Peak X-Axis Float Mid Low Byte |
| 71 | Accelerometer Peak X-Axis Float Low Byte |
| 72 | Accelerometer Peak Y-Axis Float High Byte |
| 73 | Accelerometer Peak Y-Axis Float Mid High Byte |
| 74 | Accelerometer Peak Y-Axis Float Mid Low Byte |
| 75 | Accelerometer Peak Y-Axis Float Low Byte |
| 76 | Accelerometer Peak Z-Axis Float High Byte |
| 77 | Accelerometer Peak Z-Axis Float Mid High Byte |
| 78 | Accelerometer Peak Z-Axis Float Mid Low Byte |
| 79 | Accelerometer Peak Z-Axis Float Low Byte |
| 80 | Voltage Limit Table CRC High Byte |
| 81 | Voltage Limit Table CRC Low Byte |
| 82 | Voltage Limit Low String 1 High Byte |
| 83 | Voltage Limit Low String 1 Mid High Byte |
| 84 | Voltage Limit Low String 1 Mid Low Byte |

| Address | Description |
|---|---|
| 85 | Voltage Limit Low String 1 Low Byte |
| 86 | Voltage Limit Low String 2 High Byte |
| 87 | Voltage Limit Low String 2 Mid High Byte |
| 88 | Voltage Limit Low String 2 Mid Low Byte |
| 89 | Voltage Limit Low String 2 Low Byte |
| 90 | Voltage Limit Low String 3 High Byte |
| 91 | Voltage Limit Low String 3 Mid High Byte |
| 92 | Voltage Limit Low String 3 Mid Low Byte |
| 93 | Voltage Limit Low String 3 Low Byte |
| 94 | Voltage Limit Low String 4 High Byte |
| 95 | Voltage Limit Low String 4 Mid High Byte |
| 96 | Voltage Limit Low String 4 Mid Low Byte |
| 97 | Voltage Limit Low String 4 Low Byte |
| 98 | Voltage Limit Low String 5 High Byte |
| 99 | Voltage Limit Low String 5 Mid High Byte |
| 100 | Voltage Limit Low String 5 Mid Low Byte |
| 101 | Voltage Limit Low String 5 Low Byte |
| 102 | Voltage Limit Low String 6 High Byte |
| 103 | Voltage Limit Low String 6 Mid High Byte |
| 104 | Voltage Limit Low String 6 Mid Low Byte |
| 105 | Voltage Limit Low String 6 Low Byte |
| 4096 | LED Derate Table CRC High Byte |
| 4097 | LED Derate Table CRC Low Byte |
| 4098 | LED Derate Table Data Start 50 Sequential Entries of LED_DERATE_TABLE_ENTRY |
| 16384 | Error Instance Count High Byte |
| 16385 | Error Instance Count Low Byte |
| 16386 | Error Instance Storage Start 5000 Sequential Entries of ERROR_LOG_ENTRY |

FIG. 22C

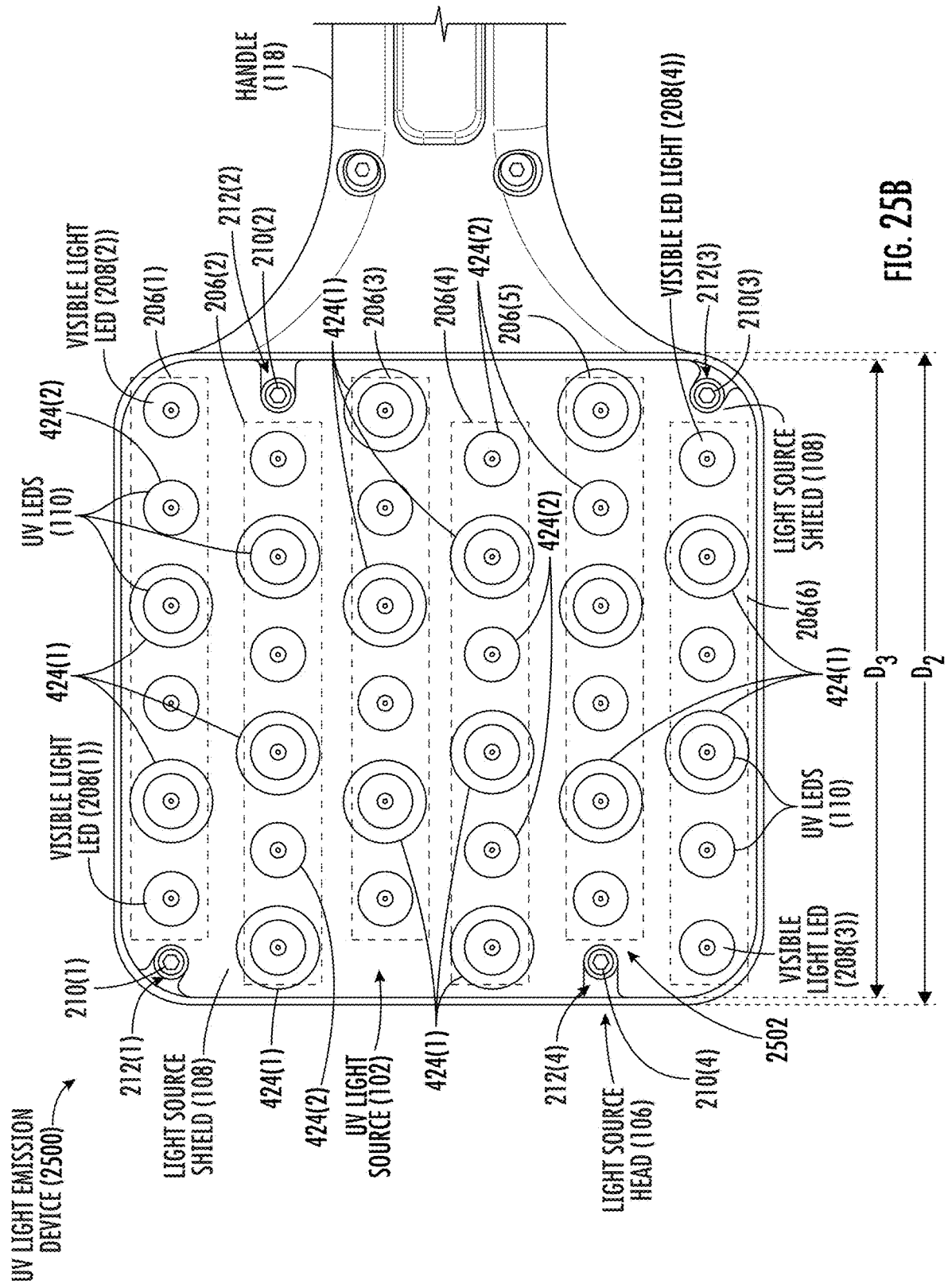

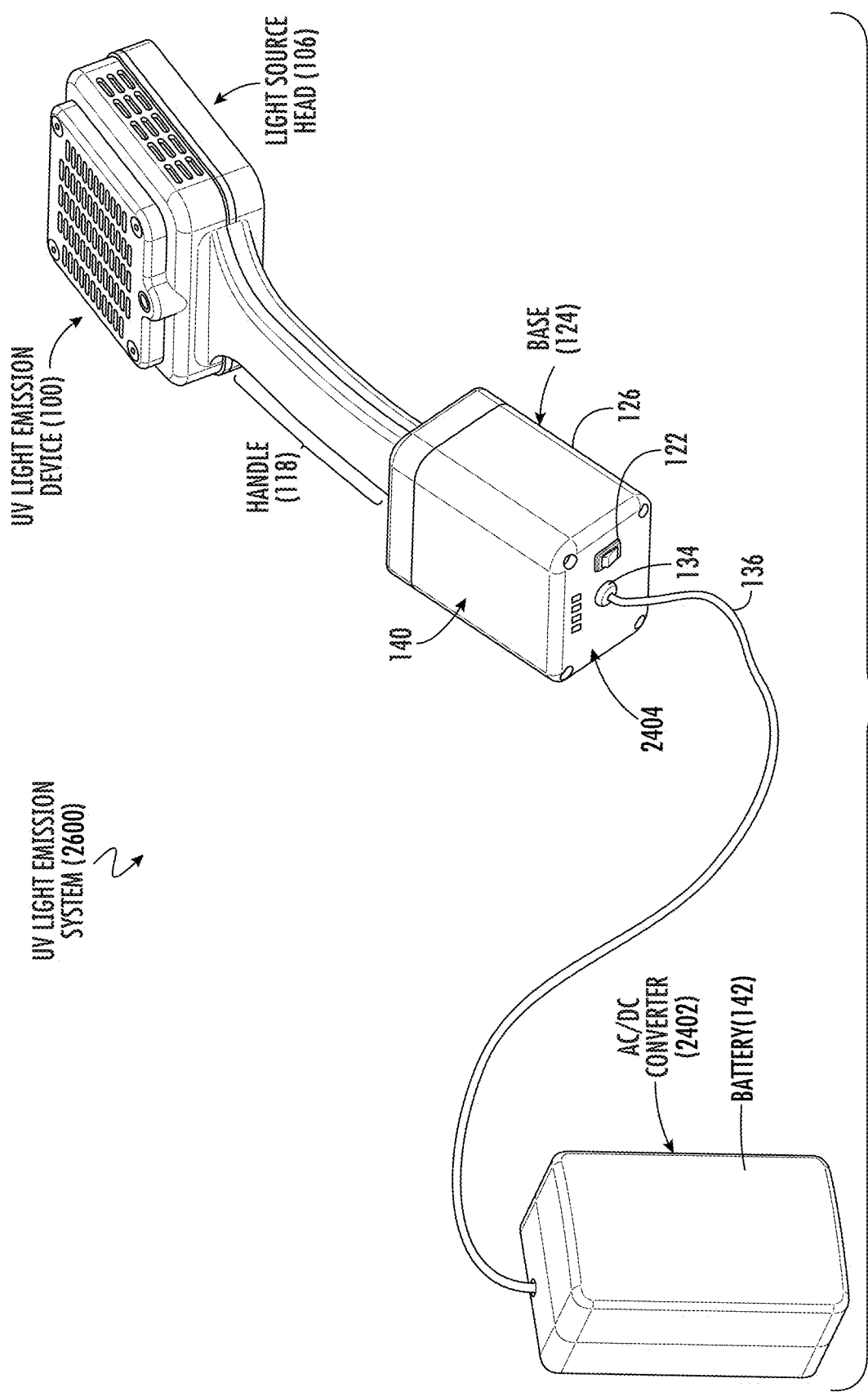

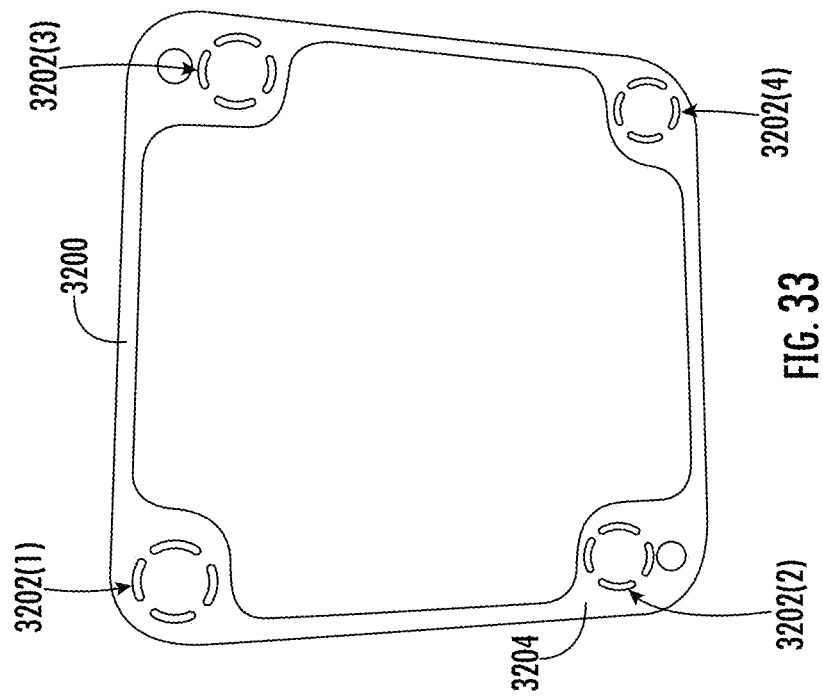
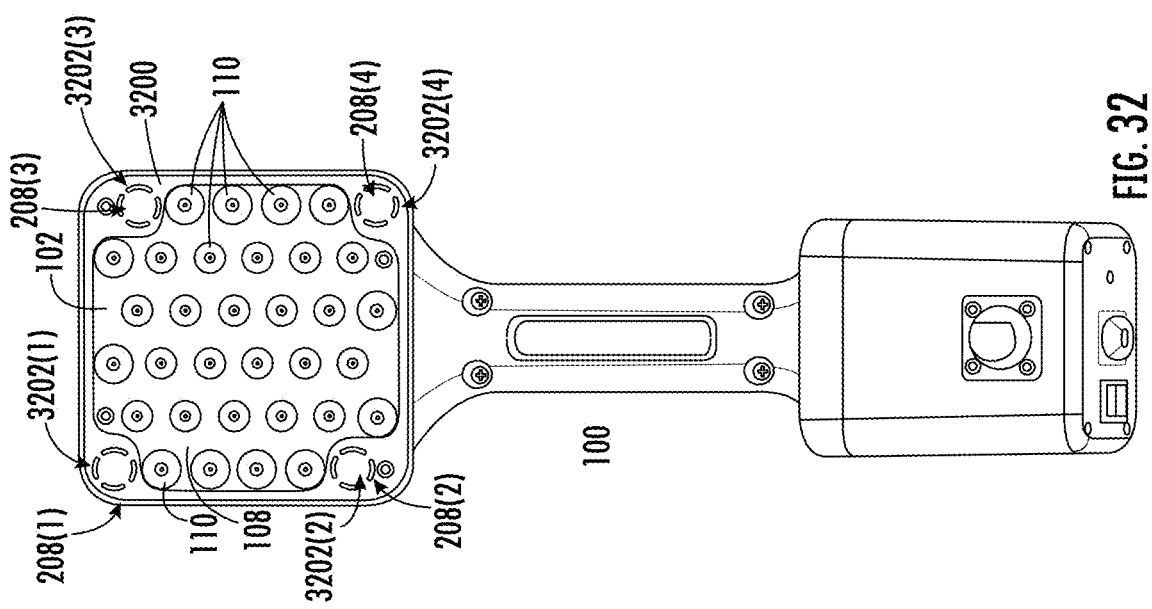
FIG. 33
FIG. 32

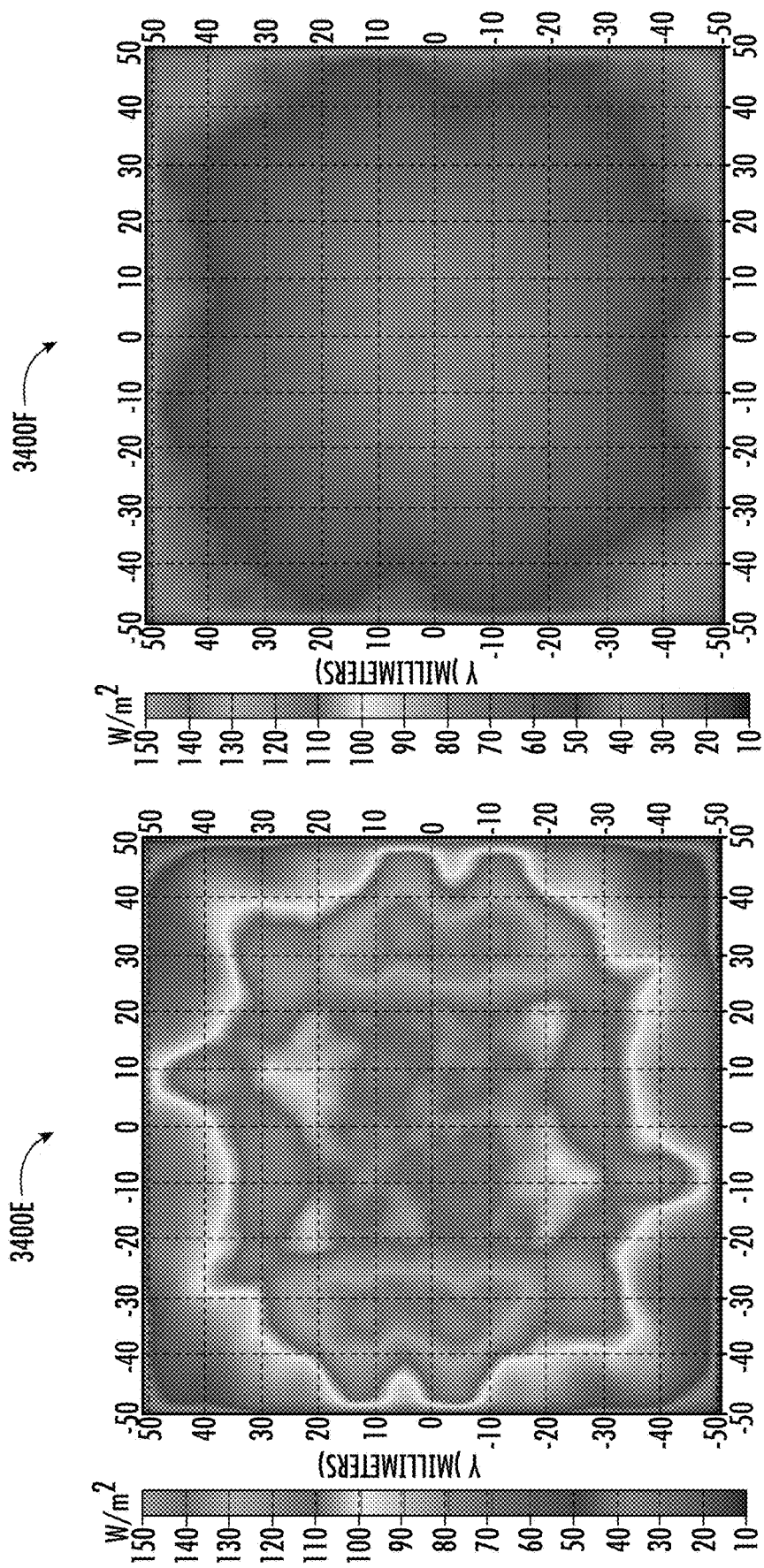

ULTRAVIOLET (UV) LIGHT EMISSION DEVICE, AND RELATED METHODS OF USE, PARTICULARLY SUITED FOR DECONTAMINATION

PRIORITY APPLICATIONS

The present application claims priority to U.S. Provisional Patent Application Ser. No. 63/019,231 entitled "ULTRAVIOLET (UV) LIGHT EMISSION DEVICE, AND RELATED METHODS OF USE, PARTICULARLY SUITED FOR DECONTAMINATION," filed on May 1, 2020, which is incorporated hereby by reference in its entirety.

The present application also claims priority to U.S. Provisional Patent Application Ser. No. 63/079,193 entitled "ULTRAVIOLET (UV) LIGHT EMISSION DEVICE, AND RELATED METHODS OF USE, PARTICULARLY SUITED FOR DECONTAMINATION," filed on Sep. 16, 2020, which is incorporated hereby by reference in its entirety.

FIELD OF THE DISCLOSURE

The technology of the disclosure relates to light-emitting devices, and more particularly to devices that emit ultraviolet (UV) light, particularly for use in inactivating and/or killing microorganisms, such as bacteria, viruses, spores, and other pathogens.

BACKGROUND

Pathogens, such as bacteria and viruses, are microorganisms that are present in everyday society. Pathogens are present in areas that humans encounter daily, such as bathrooms, living areas, door handles, public areas, etc. Some airborne pathogens are present in the air that humans breathe. Human beings can become infected with pathogens when they enter the human body as a host. The pathogens begin to multiply, which can result in bacterial infections and diseases that the human body must then fight off as part of its immune defense system response. Thus, it is important for humans to try to limit their exposure to these pathogens. Chemical disinfectants such as bleach, for example, can be used to inactivate or destroy microorganisms. For example, it may be important in hospital settings, in particular, to disinfect all surfaces in a patient's room or area so that the patient's risk of becoming infected with pathogens that are bacterial or viral is reduced. Chemical disinfectants commonly take the form of wipes that are infused with a chemical agent to apply the chemical disinfectant to inert surfaces. Chemical disinfectants can also be applied as a spray or mist in the air and on inert surfaces. However, it is not generally feasible to use chemical disinfectants to disinfect every possible surface that a human may come into contact with.

It is known that ultraviolet (UV) light can also damage the DNA of a microorganism, such as bacteria, viruses, and spores. For example, natural UV light from solar radiation can damage the DNA of a microorganism on surfaces, thus inactivating or killing the microorganism. However, UV light emitted by the sun is weak at the Earth's surface as the ozone layer of the atmosphere blocks most of the UV light. Thus, UV light emission devices that include a UV light source that emits UV light that can be directed to an intended area to inactivate or kill the microorganism present in the area have been designed as a disinfectant method. The UV light source of such UV light emission devices is designed to emit a desired wavelength or range of wavelengths of UV light to be able to expose microorganisms to such light to inactivate or kill the microorganisms. These UV light emission devices need to be designed to emit UV light with enough intensity (i.e., power transferred per unit area) that the UV light that reaches the ultimate surface or area to be disinfected is of sufficient intensity to be effective in inactivating or killing microorganisms of interest. The intensity of the UV light also affects how quickly an exposed microorganism is inactivated or killed. It may be important for business and other practical reasons to disinfect an area quickly, i.e., within minutes or seconds, for example.

For this reason, large UV light emission devices with high powered UV light sources can be deployed in areas to be disinfected. However, such UV light sources may not be safe for human exposure due to the high intensity of UV emitted light. Thus, these UV light emission devices may have to be used in areas that are closed off from humans until the disinfectant process is complete to avoid human exposure. Handheld UV light emission devices have also been designed as a convenient form factor to be used by humans to disinfect surfaces and other areas. However, handheld UV light emission devices can expose the human user to the UV light in an unsafe manner, especially if the intensity of the UV light source is sufficient to be effective in inactivating or killing microorganisms of interest quickly.

SUMMARY OF THE DISCLOSURE

Aspects disclosed herein include ultraviolet (UV) light emission devices and related methods of use. The UV light emission devices disclosed herein are particularly suited for use in disinfecting surfaces and air. The UV light emission devices disclosed herein can be provided in the form factor of a handheld device that is easily held and manipulated by a human user. The human user can manipulate the handheld UV light emission device to decontaminate surfaces, air, and other areas by orienting the handheld UV light emission device so that the UV light emitted from its light source is directed to the area of interest to be decontaminated.

In one exemplary aspect, a handheld light emission device is provided. The handheld light emission device includes a light source housing comprising an interior chamber and an opening to the interior chamber. The handheld light emission device also includes a UV light source disposed in the interior chamber of the light source housing, the UV light source comprising one or more UV lights each configured to emit UV light towards the opening of the light source housing. The handheld light emission device also includes one or more visible lights disposed in the interior chamber of the light source, and each configured to emit visible light towards the opening of the light source housing. The handheld light emission device also includes a handle comprising a first end and a second end opposite the first end, the first end of the handle coupled to the light source housing. The handheld light emission device also includes a base coupled to the second end of the handle. The handheld light emission device also includes an electrical control system disposed in the base, the electrical control system comprising a power rail configured to distribute a power signal, and at least one light driver circuit electrically coupled to the power rail and the UV light source. The base comprises a wiring assembly electrically coupled to the at least one light driver circuit and the UV light source. The at least one light driver circuit is configured to couple power from the power signal to the one or more UV lights over the wiring assembly in the UV light source to cause the one or more UV lights to emit UV light towards the opening of the light source housing. The at least one light driver circuit is also configured to couple power from the power signal to the one or more visible lights over the wiring assembly to the one or more visible lights to cause the one or more visible lights to emit visible light the opening of the light source housing.

In another exemplary aspect, a handheld light emission device is provided. The handheld light emission device includes a light source housing comprising an interior chamber and an opening to the interior chamber. The handheld light emission device also includes a UV light source disposed in the interior chamber of the light source housing, the UV light source comprising one or more UV lights each configured to emit UV light towards the opening of the light source housing. The handheld light emission device also includes one or more visible lights disposed in the interior chamber of the light source, and each configured to emit visible light towards the opening of the light source housing. The handheld light emission device also includes a handle comprising a first end and a second end opposite the first end, the first end of the handle coupled to the light source housing. The handheld light emission device also includes a base coupled to the second end of the handle. The handheld light emission device also includes an electrical control system disposed in the base, the electrical control system comprising a power rail configured to distribute a power signal, and at least one light driver circuit electrically coupled to the power rail and the UV light source. The base comprises a wiring assembly electrically coupled to the at least one light driver circuit and the UV light source. The at least one light driver circuit is configured to couple power from the power signal to the one or more UV lights over the wiring assembly in the UV light source to cause the one or more UV lights to emit UV light towards the opening of the light source housing. The at least one light driver circuit is also configured to couple power from the power signal to the one or more visible lights over the wiring assembly to the one or more visible lights to cause the one or more visible lights to emit visible light the opening of the light source housing. The opening of the light source housing comprises a planar opening disposed along a first plane of the light source housing. The one or more UV lights are each configured to emit UV light in a direction orthogonal to the plane of the planar opening. The one or more visible lights are each configured to emit UV light in the direction orthogonal to the plane of the planar opening. The one or more UV lights comprise one or more UV light-emitting devices (LEDs), each configured to emit UV light in at least one wavelength between 200-399 nanometers (nm).

In another exemplary aspect, a handheld light emission device is provided. The handheld light emission device includes a light source housing comprising an interior chamber and an opening to the interior chamber. The handheld light emission device also includes a UV light source disposed in the interior chamber of the light source housing, the UV light source comprising one or more UV lights each configured to emit UV light towards the opening of the light source housing. The handheld light emission device also includes one or more visible lights disposed in the interior chamber of the light source, and each configured to emit visible light towards the opening of the light source housing. The handheld light emission device also includes a handle comprising a first end and a second end opposite the first end, the first end of the handle coupled to the light source housing. The handheld light emission device also includes a base coupled to the second end of the handle. The handheld light emission device also includes an electrical control system disposed in the base, the electrical control system comprising a power rail configured to distribute a power signal, and at least one light driver circuit electrically coupled to the power rail and the UV light source. The base comprises a wiring assembly electrically coupled to the at least one light driver circuit and the UV light source. The at least one light driver circuit is configured to couple power from the power signal to the one or more UV lights over the wiring assembly in the UV light source to cause the one or more UV lights to emit UV light towards the opening of the light source housing. The at least one light driver circuit is also configured to couple power from the power signal to the one or more visible lights over the wiring assembly to the one or more visible lights to cause the one or more visible lights to emit visible light the opening of the light source housing. The one or more UV lights comprise one or more UV LEDs. The one or more visible lights comprise one or more visible LEDs. The electrical control system further comprises a power enable switch configured to distribute the power signal to the at least one light driver circuit in response to a power enable signal indicating a power enable state. The electrical control system also comprises a momentary switch configured to provide a trigger signal indicating an activation state in response to being activated. The electrical control system also comprises a controller circuit configured to receive the trigger signal from the switch and generate the power enable signal of a power enable state in response to the trigger signal indicating an activation state. The momentary switch is disposed in the handle and configured to be engaged in a closed position by a user when holding the handle to cause the secondary switch to provide the trigger signal.

In another exemplary aspect, a handheld light emission device is provided. The handheld light emission device includes a light source housing comprising an interior chamber and an opening to the interior chamber. The handheld light emission device also includes a UV light source disposed in the interior chamber of the light source housing, the UV light source comprising one or more UV lights each configured to emit UV light towards the opening of the light source housing. The handheld light emission device also includes one or more visible lights disposed in the interior chamber of the light source, and each configured to emit visible light towards the opening of the light source housing. The handheld light emission device also includes a handle comprising a first end and a second end opposite the first end, the first end of the handle coupled to the light source housing. The handheld light emission device also includes a base coupled to the second end of the handle. The handheld light emission device also includes an electrical control system disposed in the base, the electrical control system comprising a power rail configured to distribute a power signal, and at least one light driver circuit electrically coupled to the power rail and the UV light source. The base comprises a wiring assembly electrically coupled to the at least one light driver circuit and the UV light source. The at least one light driver circuit is configured to couple power from the power signal to the one or more UV lights over the wiring assembly in the UV light source to cause the one or more UV lights to emit UV light towards the opening of the light source housing. The at least one light driver circuit is also configured to couple power from the power signal to the one or more visible lights over the wiring assembly to the one or more visible lights to cause the one or more visible lights to emit visible light the opening of the light source housing. The electrical control system further comprises a power enable switch coupled to the power rail between an output node and the at least one light driver circuit. The power enable switch is configured to distribute the power signal from the output node to the at least one light driver circuit in response to a power enable signal indicating a power enable state. The power enable switch is also configured to not distribute the power signal from the output node to the at least one light driver circuit in response to a power enable signal indicating a power disable state. The electrical control system further comprises an inertial measurement (IMU) circuit configured to generate an accelerometer signal indicating an acceleration of the light source housing. The electrical control system further comprises a controller circuit configured to receive the accelerometer signal generated by the IMU circuit, determine if the accelerometer signal indicates an acceleration of the light source housing outside a predefined acceleration limit, and in response to determining the acceleration signal indicates an acceleration of the light source housing outside the predefined acceleration limit, generate the power enable signal of a power disable state.

BRIEF DESCRIPTION OF THE FIGURES

FIG. 3C is a bottom view of the UV light emission device in FIGS. 1A-1C;

FIG. 3D is a top view of the UV light emission device in FIGS. 1A-1C;

FIG. 22A-22C is a diagram of an exemplary status register that can be programmed and accessed in the UV light emission device to detect programming and record history information for the UV light emission device;

FIGS. 25A and 25B are schematic diagrams of an alternative UV light emission device similar to the UV light emission device in FIGS. 1A-1C, but with an alternative UV light source housing that allows air to be drawn into the UV light source housing and across the UV light source to expose the drawn-in air to the UV light emission;

FIG. 26 is a schematic diagram of an alternative UV light emission system that includes the UV light emission device and a power charging station configured to receive the UV light emission system and charge an integrated battery and/or to provide a wired interface connectivity for exchange of telemetry information stored in the UV light emission device;

FIG. 32 is a diagram of the UV light emission device in FIGS. 1A-1C with a mask disposed on the light source adjacent to the visible lights in the UV light source;

FIG. 33 is a diagram of a mask placed on the UV light source to cause visible light emitted from the visible light indicator on the surface to be patterned as shown in FIG. 31;

FIGS. 34A-34F are exemplary heat maps of UV light emitted by the UV light source of the UV light emission device in FIGS. 1A-1C as a function of distance from center and distance of the UV light source from a surface of interest.

DETAILED DESCRIPTION

Figure 1A:
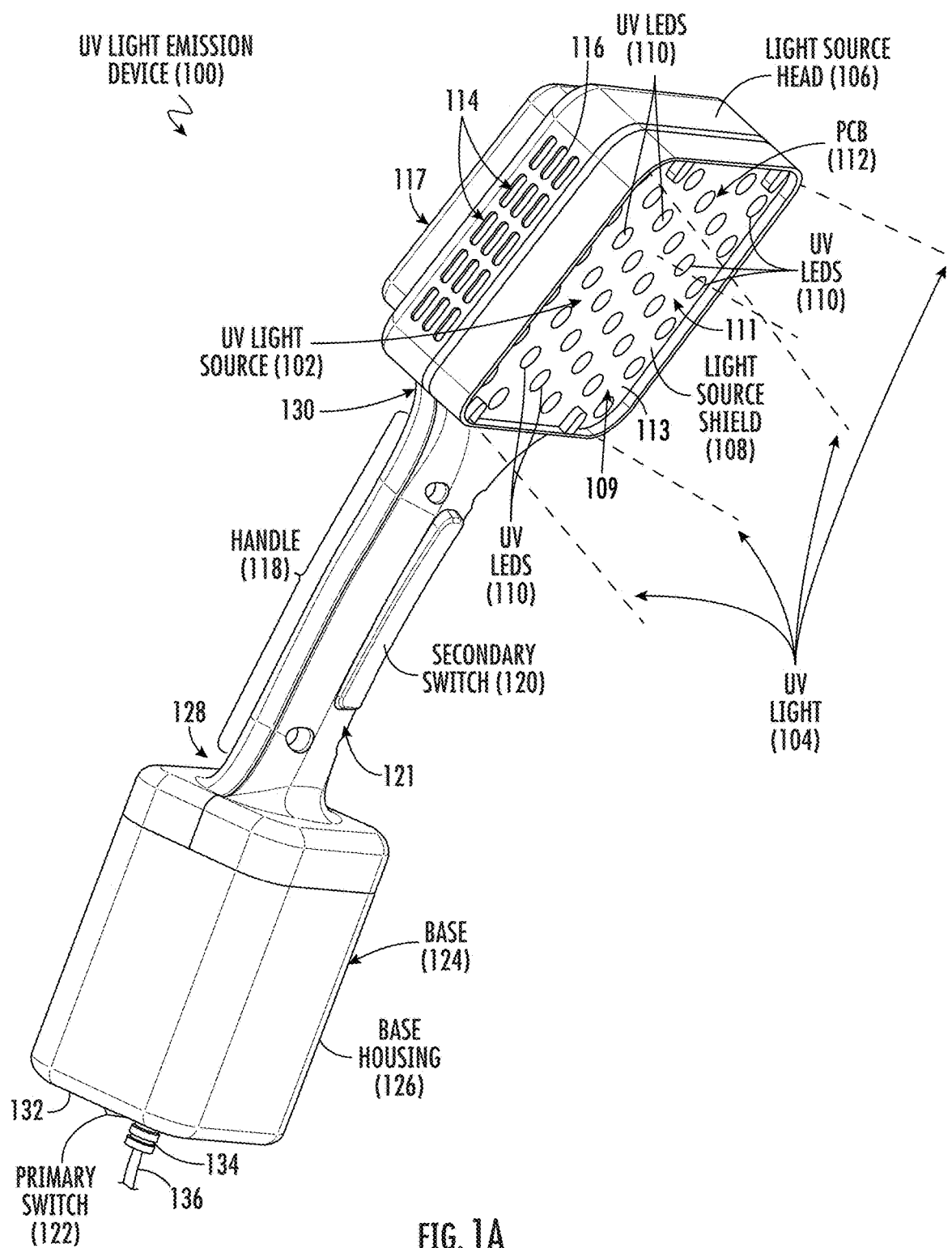
FIG. 1A is a front perspective view of an exemplary ultraviolet (UV) light emission device that includes a UV light source for UV light emission, wherein the UV light emission device is configured to be manipulated by a human user to be activated and oriented so that UV light emission from the UV light source can be directed to a surface or area of interest for decontamination.

With reference now to the drawing figures, several exemplary aspects of the present disclosure are described. The word "exemplary" is used herein to mean "serving as an example, instance, or illustration." Any aspect described herein as "exemplary" is not necessarily to be construed as preferred or advantageous over other aspects.

FIG. 1A is a front, perspective view of an exemplary ultraviolet (UV) light emission device 100 that includes a UV light source 102 that emits UV light 104. The UV light emission device 100 in FIG. 1A in this example is a handheld device that is configured to be manipulated by a human user to be activated and oriented so that emission of UV light 104 from the UV light source 102 can be directed to a surface or area of interest for decontamination. Certain wavelengths of UV light have been found effective in damaging the DNA of pathogens and, as a result, inactivating or killing such pathogens. As will be discussed in more detail below, the UV light emission device 100 in FIG. 1A includes a light source head 106 that is a housing that supports the UV light source 102 and provides supporting components to control emission of the UV light 104 from the UV light source 102. For example, the light source head 106 in this example could include an optional light source shield 108 that is disposed in front of an array of UV LEDs 110 configured to emit the UV light 104 as part of the UV light source 102. The UV LEDs 110 will each have a viewing angle that affects the angle of UV light emission from a normal plane, which in this example is the plane of the light source shield 108. The light source head 106 is designed to support the insertion and retention of the light source shield 108. The light source shield 108 is provided for safety reasons to avoid contact, including human contact, with the UV LEDs 110, to avoid skin burns due to the heat emanating from the UV LEDs 110 and/or to avoid damaging the UV LEDs 110. It may be important that the light source shield 108 be designed to allow at least a portion of the UV light 104 generated by the UV light source 102 to pass therethrough so that the UV light 104 can reach a desired surface or area of interest when the UV light emission device 100 is in use. For example, the light source shield 108 could be made of fused silica, quartz glass, or other UV translucent material, such as PCTFE (Polychlorotrifluoroethylene). The light source shield 108 may be manufactured to be shatterproof.

The light source shield 108 can be a solid member or could have openings. As another example, the light source shield 108 could include a patterned mesh, such as from a mesh metal or plastic material that has either openings or translucent sections to allow UV light 104 to pass through, but also reduces or prevents the ability for direct contact and/or damage to the UV LEDs 110. The mesh may be made from a metal material or alloys, such as stainless steel or aluminum material, as examples. An optional diffuser could be installed on or serve as the light source shield 108 to diffuse the UV light 104 emitted from the UV light source 102, but as the UV light 104 is not visible, a diffuser may not be desired or necessary. A filter coating 109 could also be disposed on the light source shield 108 to filter out certain wavelengths of the UV light 104 if desired. The light source shield 108 can include a first surface 111 disposed adjacent to and behind the UV light source 102 and a second surface 113 opposite the first surface 111. The filter coating 109 could be disposed on the first and/or second surfaces 111, 113 of the light source shield 108.

In addition, or in the alternative to employing the light source shield 108 to protect the UV LEDs 110 from contact for safety or other reasons, the UV LEDs 110 could be housed in reflectors that are sized to prevent direct human contact. This is discussed in more detail below with regard to FIGS. 4A and 4B. The openings of the reflectors 424 could be sized small enough to prevent a human finger from being able to be inserted therein and come in contact with the UV LEDs 110.

The UV light emission device 100 has been found to be effective at killing bacteria, viruses, and spores at a rate of 99.9% or higher. The UV light source 102 in the UV light emission device 100 is selected to be at a desired UV wavelength or range of wavelengths to damage or kill pathogens as a decontamination tool. For example, the UV light source 102 can be selected to emit UV light at a single or multiple UV wavelengths in the 200-399 nanometer (nm) wavelength range. For example, the UV light source 102 may be selected to emit UV light at a wavelength(s) between 260-270 nm. For example, the UV LEDs 110 may be the Klaran WD Series UVC LEDs, as a non-limiting example, that emits light at a wavelength(s) between 250-270 nm at an optical output power of either 60 milliWatts (mW) (Part No. KL265-50 W-SM-WD), 70 mW (Part No. KL265-50V-SM-WD), or 80 mW (Part No. KL265-50U-SM-WD). As another example, the UV light source 102 may be selected to emit UV light at peak wavelengths at 254 nm and/or 265 nm. As another example, the UV light source 102 may be selected to emit UV light at a wavelength(s) between 200-230 nm as Far-UVC light. For example, a Far-UV wavelength of 222 nm has been found to be effective in inactivating or killing pathogens and also be safe to human tissue. Thus, it may be possible to operate the UV light emission device 100 without the need to provide protection, such as masks, goggles, gloves, and/or other personal protective equipment (PPE) for a human user or human in the field of the UV light 104. As another example, the UV light source 102 may be selected to emit UV light at a wavelength of 207 nm.

The UV light emission device 100 could also be configured to change (e.g., upconvert) the wavelength frequency of UV light 104 emitted by the UV light source 102 to a higher energy/intensity level. For example, the UV light source 102, whether frequency-converted or not, may be configured to emit UV light 104 with an intensity of 5-100 milliWatts (mW) per square centimeter (cm$^2$) (mW/cm$^2$). For example, the UV light source 102 may be selected and configured to emit UV light 104 with an intensity of 10-60 mW/cm$^2$. As another example, the UV light source 102 may be selected and configured to emit the UV light 104 with an intensity of 20 mW/cm$^2$ for periods of up to one (1) second (sec.). For example, with the UV light 104 at an intensity of 20 mW/cm$^2$, the UV light emission device 100 could be swept over an area of interest that is at a height of five (5) cm above the surface and a rate of two (2) cm in length per second to expose the area of interest to the desired intensity and duration of the UV light 104 for decontamination. The UV light emission device 100 could be configured to emit the UV light 104 from the UV light source 102 for any amount of time desired by the user or for defined periods of time and to a desired intensity. For example, such defined periods of time could be 1-10 seconds and a time period specifically of one (1) second or less. The UV light emission device 100 could be configured to control the UV light source 102 to emit the UV light 104 as a steady-state light or to pulse the UV light source 102 to emit pulses of the UV light 104, such as at a pulse rate between 10-100 KiloHertz (kHz), for example. Controlling the pulse rate of the UV light 104 is another way to control the intensity of the UV light 104. The UV light emission device 100 could be configured to control the activation and deactivation of the UV light source 102 to control the pulse rate of the UV light 104 through a pulse-width modulated (PWM) signal to control the enabling and disabling of a light driver circuit, as an example.

Figure 1B:
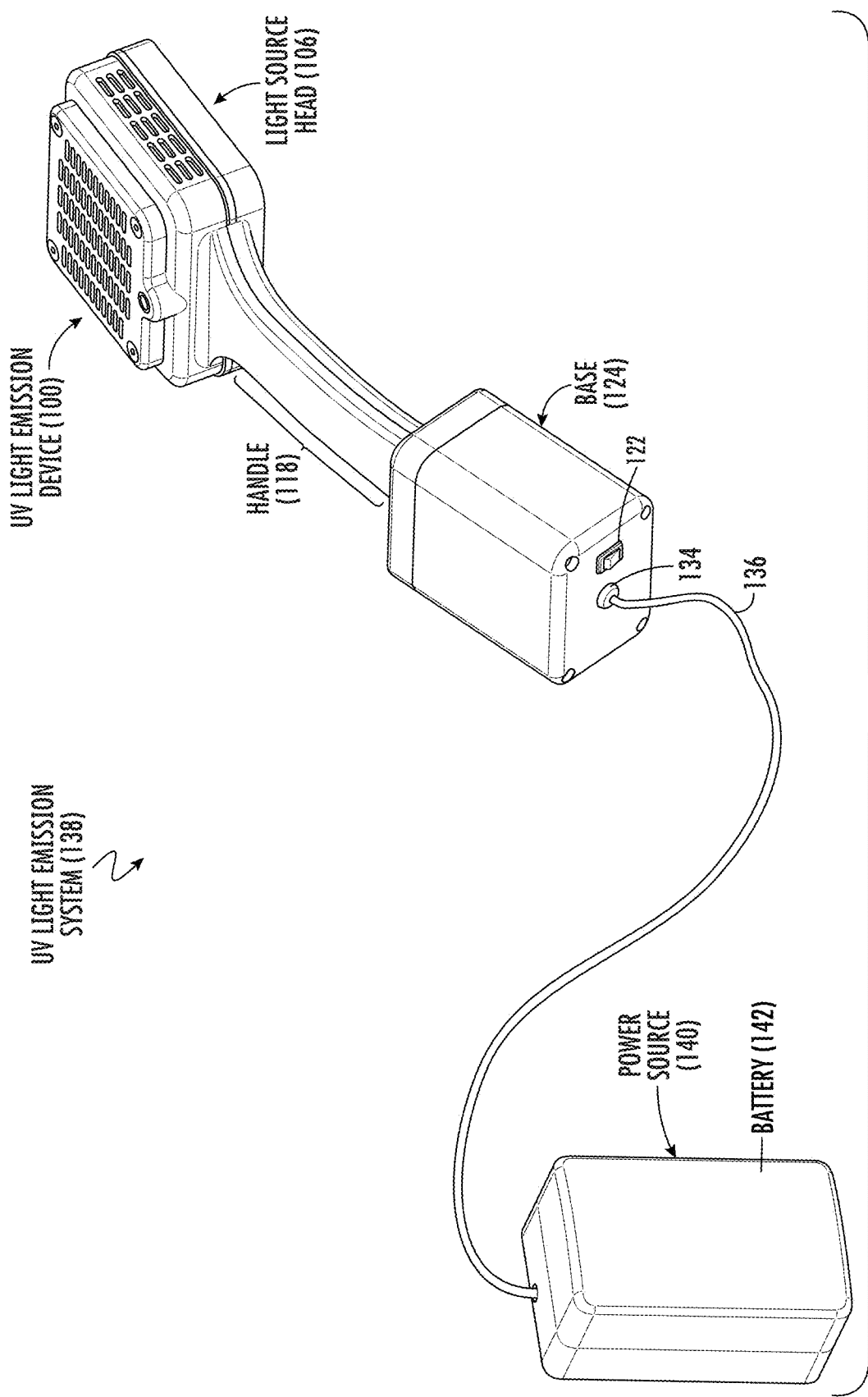
FIG. 1B is a perspective view of a UV light emission system that includes the UV light emission device in FIG. 1A and a power source to provide power to the UV light emission device for operation.
Figure 1C:
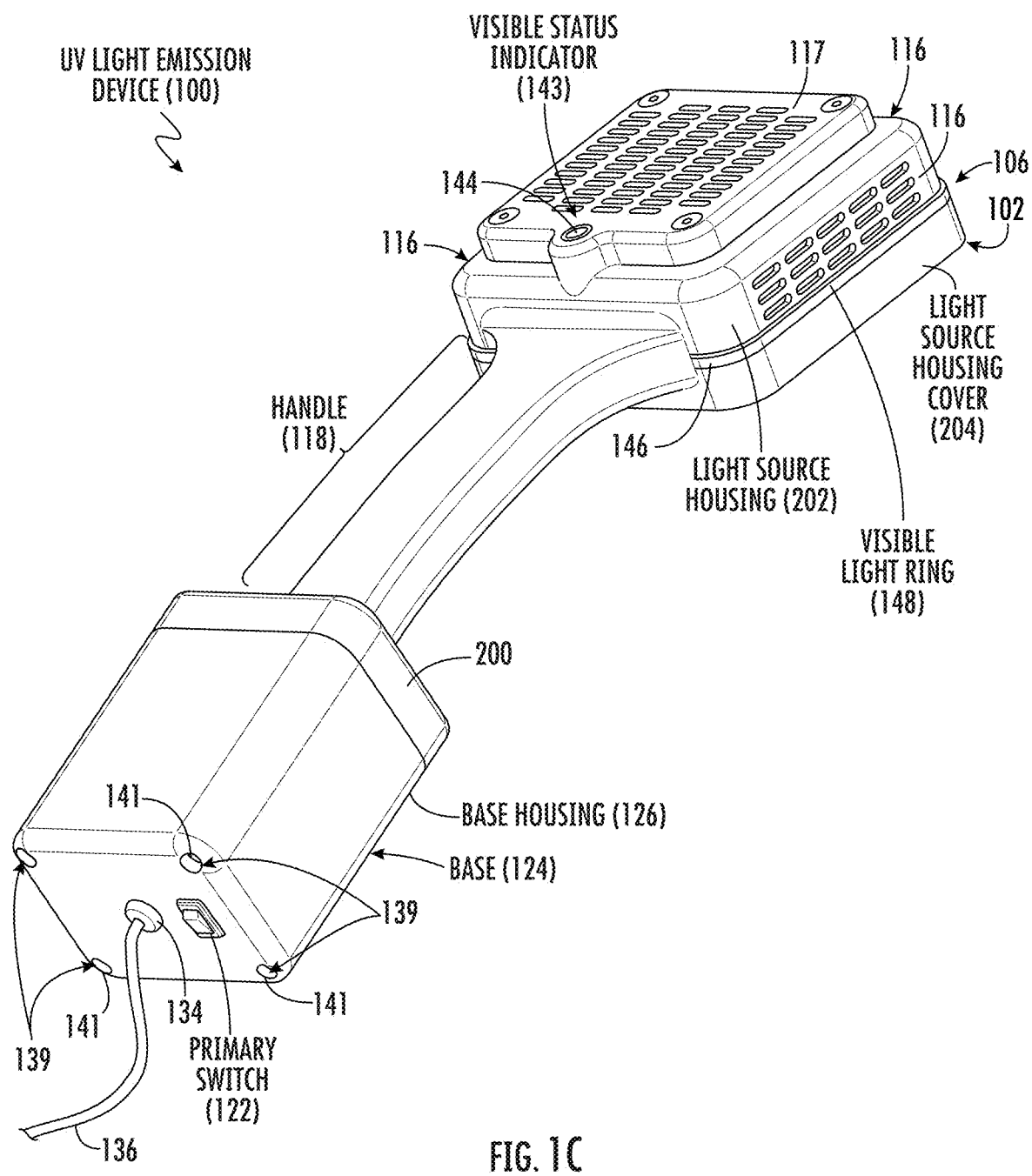
FIG. 1C is a close-up, rear perspective view of the UV light emission device in FIGS. 1A and 1B.

With continuing reference to FIG. 1A, as will be discussed in more detail below, the UV LEDs 110 are mounted on a printed circuit board (PCB) 112 that is installed inside the light source head 106. The light source head 106 also includes vent openings 114 on one or more of its sides 116 and rear 117, also shown in the rear perspective view of the UV light emission device 100 in FIG. 2A, to allow for the escape of heat generated inside the light source head 106 due to the heat generated from the UV LEDs 110 when activated (i.e., turned on). As will also be discussed in more detail below, the light source head 106 can support other components to support the operation of the UV light source 102, including a fan and heat sink for dissipation of heat generated by the UV LEDs 110, as an example. The light source head 106 can also be designed to support a PCB as part of the light source head 106 to support the UV LEDs 110 and other components, such as temperature sensors supporting operation and control functions. The light source head 106 in the UV light emission device 100 in FIGS. 1A-1C is square-shaped, but the light source head 106 could also be provided in other shapes, including circular-shaped, oval-shaped, or elliptical-shaped.

With continuing reference to FIG. 1A, the UV light emission device 100 also includes a handle 118 that is attached to the light source head 106. The handle 118 may be a separate component that is attached to the light source head 106 or formed as an integrated component with the light source head 106, such as that produced with a mold. The handle 118 supports a surface to allow a human user to engage the handle 118 with their hand to control and manipulate the orientation of the UV light 104 emitted from the UV light source 102. The user can lift the UV light emission device 100 by the handle 118 and manipulate the UV light source 102 through manipulation of the handle 118 to direct the UV light 104 emitted from the UV light source 102 to the surface or area desired to decontaminate such surface or area. For example, the UV light emission device 100 may be lightweight (e.g., 1.5 lbs. without integration of a battery or 3 lbs. with integration of a battery) to be easily handled and maneuvered by a human user. In this example, as shown in FIG. 1A, and as will be discussed in more detail below, the handle 118 includes a secondary switch 120 that is disposed on the underneath side 121 of the handle 118. The UV light emission device 100 is designed so that the UV light source 102 will not activate the UV LEDs 110 to emit UV light 104 unless the secondary switch 120 is depressed and activated to a closed state as a safety mechanism. FIG. 1A shows the secondary switch 120 is a non-activated state as not being depressed. The secondary switch 120 in this example is a momentary switch that acts as a trigger switch and returns to a non-depressed, non-activated, or open-state when a force is no longer applied to the secondary switch 120. In this manner, a user who grabs the handle 118 of the UV light emission device 100 to control it can squeeze the handle 118 to depress the secondary switch 120 to activate the secondary switch 120 such that it provides a trigger signal to activate the UV light source 102 to emit UV light 104. The secondary switch 120 could be a mechanical switch, or alternatively, a capacitive touch sensor switch, as an example. However, a capacitive touch sensor switch may not be desired if the UV light emission device 100 will be used by persons wearing gloves, for example, where the capacitance of the person does not transfer to the switch. When the user disengages the handle 118, the secondary switch 120 becomes non-depressed and thus non-activated such that it does not provide a trigger signal.

Thus, by providing the secondary switch 120 as a momentary switch, the UV light source 102 is only active when the secondary switch 120 is being actively depressed, such as by a user holding the handle 118 and depressing the secondary switch 120. When a user is no longer depressing the secondary switch 120, the secondary switch 120 becomes non-depressed and thus non-activated such that it does not provide a trigger signal to activate the UV light source 102. Thus, the secondary switch 120 can act as a safety measure to ensure that the UV light source 102 is not active when the secondary switch 120 is not being engaged. For example, if the user of the UV light emission device 100 lays the device down and releases the handle 118 such that the secondary switch 120 is not activated, the UV light source 102 will be deactivated. The secondary switch 120 as a momentary switch allows the user to control the ultimate on and off time of the UV LEDs 110.

Further, although not limiting and the UV light source 120 not being limited to the use of UV LEDs, the deployment of the secondary switch 120 as a momentary switch can also make more feasible the use of LEDs in the UV light source 120. LEDs are a semiconductor device. As soon as current flows to the LED, electrons flow through its P-N junction of a LED, and energy is released in the form of photons to emit light. The UV LEDs 110 of the UV light source 120 are able to essentially instantaneously emit UV light when current starts to flows under control of the secondary switch 120 when activated without having to wait for more significant elapsed time (e.g., 10-15 minutes) for a gas inside a bulb to "warm-up" to produce a fuller intensity light. The use of LEDs as the UV light source 102 allows a more instantaneous off and on of UV light emission, as controlled by the secondary switch 120 in this example, without having to employ other techniques for off and on employed by bulbs, such as pulse-width modulation (PWM). Also, in this example, the UV light emission device 100 includes a primary switch 122 that must be activated to a closed position for the UV light emission device 100 to be activated regardless of the state of the secondary switch 120. In this regard, a user cannot accidentally activate the UV light source 102 to emit the UV light 104 without depressing the secondary switch 120 on the handle 118 even if the primary switch 122 is activated. As will be discussed in more detail below, the primary switch 122 being activated couples a power source to an electronic control system and the UV light source 102 for operations. Thus, deactivating the primary switch 122 decouples power from the electronic control system and the UV light source 102 as a hard kill switch, such that the UV light emission device 100 will be completely non-operational regardless of the state of the secondary switch 120. The secondary switch 120 only controls activation and deactivation of the UV light source 102 as a secondary control mechanism.

With continuing reference to FIG. 1A, the UV light emission device 100 in this example also includes a base 124 that includes a base housing 126 that is attached to an end 128 of the handle 118 opposite an end 130 of the handle 118 attached to the light source head 106. The base 124, the handle 118, and the light source head 106 may all be made of hardened plastic material, as an example. The base housing 126 can be a separate component that is attached to the handle 118 or formed as an integrated component with the handle 118, such as that produced with a mold. As will be discussed in more detail below, in this example of the UV light emission device 100, the base housing 126 supports PCBs of the electronic control system and light source driver circuits (i.e., current drivers) to drive power to the UV LEDs 110 in the UV light source 102 for operation to emit the UV light 104. As discussed below, the electronic control system and light source driver circuits are located in the base 124 to separate them from the UV light source 102 that generates substantial heat. In this example, the base housing 126 is spatially separated from the light source head 106 by at least eight (8) inches through the intermediate handle 118 to spatially isolate the electronic control system from the UV light source 102. The base housing 126 can also be configured to support other components as desired, including sensors that may be employed to detect environmental and other conditions that are detected to affect the control and operation of the UV light emission device 100. The handle 118 can include an interior portion (not shown in FIG. 1A) that supports a wiring harness coupled between light source driver circuits in the base housing 126 and the UV light source 102. The wiring harness is connected to a PCB as part of the UV light source 102 in the light source head 106 to couple power and control signals from the light source driver circuits to the UV light source 102. The primary switch 122 is also supported in the base housing 126 and mounted on the bottom surface 132 of the base housing 126 for convenience.

As also shown in FIGS. 1A and 1B, a grommet 134 is also supported by the base housing 126 in this example and mounted on the bottom surface 132 of the base housing 126 to support an electrical cable 136 attached to the base housing 126 and extending into the base housing 126 for carrying power from an external power source to the light source driver circuits and electrical control system components in the base housing 126 for operation. FIG. 1B illustrates a UV light emission system 138 that includes the UV light emission device 100 and a power source 140 in the form of a battery 142 to provide power to the UV light emission device 100. The battery 142 is provided remote from the UV light emission device 100 in this example. Alternatively, the power source 140 could include an alternating current (AC) power interface and AC-DC power converter circuitry so that the power source could be power received directly through an AC power outlet without the need for a battery. As another example, the power source 140 could include both alternating current (AC) power interface and AC-DC power converter circuitry to charge the battery 142, and the UV light emission device 100 be portably used from power from the battery 142. As another example, the battery 142 could be integrated into the base 124 to avoid the need for attachment of the UV light emission device 100 through the electrical cable 136.

FIG. 1C is a close-up rear perspective view of the UV light emission device 100 in FIGS. 1A and 1B to illustrate additional detail. As shown in FIG. 1C, the base 124 is formed by the base housing 126 and a base attachment member 200 that is secured to the base housing 126 through fasteners 139, such as screws, that are received into respective orifices 141 in the base housing 126 and engage with internal female bosses/receivers in the base attachment member 200. The orifices 141 may be threaded to receive the fasteners 139, which may be self-tapping fasteners 139, for example. An interior chamber is formed in the base 124 between the base housing 126 and base attachment member 200. In this manner, the base housing 126 can be easily removed to access components, including the electrical control system and light source driver circuits, inside the base housing 126, such as for repair or troubleshooting. Also, as shown in FIG. 1C, the light source head 106 includes a light source housing 202 that is attached to a light source housing cover 204 to secure the UV light source 102. For example, the light source housing 202 and the light source housing cover 204 may be an approximately 4"×4" dimension to provide a large area for the embedded UV light source 102. An interior chamber is formed in the light source head 106 between the light source housing 202 and the light source housing cover 204. As discussed in more detail below, the components of the UV light source 102, including the UV LEDs 110, a PCB 112 in which the UV LEDs 110 are mounted, a fan, and heat sink are mounted inside the light source housing 202. The light source housing cover 204 may be made or surrounded on its outside from a softer material than the light source housing cover 204, such as rubber, silicone, polycarbonate, polyethylene material, a thermoplastic elastomer, and a thermoplastic urethane as examples, as a bumper to protect the light source shield 108, especially if the light source shield 108 is made from a delicate material, such as glass. In this manner, if the UV light emission device 100 is dropped, the light source housing cover 204 can absorb some of the impact from the collision.

With continuing reference to FIG. 1C, a visual status indicator 143, which is an LED 144 in this example, is mounted on the rear 117 of the light source housing 202 to provide a visual status of the UV light emission device 100 to a user. As will be discussed in more detail below, the light color and/or the emission pattern of the visual status indicator 143 can be controlled by the electronic control system of the UV light emission device 100 to provide information on operational and error modes of the UV light emission device 100 visually to the user. For example, the visual status indicator 143 can be controlled to emit different colors, such as red, green, and yellow, as well as emit light in different blink patterns. The visual status indicator 143 is preferentially mounted on the rear 117 of the light source housing 202 so that the visual status indicator 143 is in line of sight of a user as the user holds the handle 118 and directs the UV light 104 emitted from the UV light source 102 through the light source shield 108 away from the user towards a surface or area of interest.

With continuing reference to FIG. 1C, the UV light 104 emitted by the UV LEDs 110 is at a UV wavelength(s) that is not visible to the human eye. Thus, there is not a way for a user to detect that the UV light source 102 is operational and the UV LEDs 110 are emitting light by seeing the UV light 104 emanating from the UV light source 102. This could cause an unsafe condition if the user were to look in at the UV LEDs 110 wherein the UV light 104 reached the surface of the user's skin and/or cornea of their eyes, depending on the wavelength(s) of the UV light 104, the intensity of the UV light 104, and the duration of exposure. Thus, in this example, the light source head 106 also includes an additional visual status indicator 146 in the form of a visible light ring 148. The visible light ring 148 is made of a translucent material shaped in the form of a ring that fits and is retained between the light source housing 202 and the light source housing cover 204 when the light source housing cover 204 is secured to the light source housing 202. Visible light indicators or visible lights in the form of visible light LEDs (not shown) are located on a PCB that also supports the UV LEDs 110, in this example. The visible light LEDs are placed so that the light emitted from the visible light LEDs is directed towards the visible light ring 148 automatically when the UV light source 102 is operational. The visible light ring 148 acts as a light pipe, such that the visible light emitted by the visible light LEDs through the visible light ring 148 appear to light up or glow. In this example, the visible light indicators are electrically coupled to a light source driver circuit that receives power from the same main light power rail as the UV light source 102. Thus, if power is interrupted to the main light power rail as a safety condition, for example, the visible light ring 148 will not glow to indicate that the UV light source 102 is also non-operational. However, if power is coupled to the main light power rail, the visible light ring 148 will glow to indicate that the UV light source 102 is also receiving power and may be operational.

Alternatively or in addition, an optional mesh material installed over the light source shield 108 or providing the light source shield 108 could be coated with a phosphorous material that exhibits luminescence and illuminates when contacted by the UV light 104 for a period of time according to its decay rate. Thus, the light source shield 108 could also serve as a visual indicator to a user that the UV light source 102 is operational. This method may also be employed as a way to avoid further internal visible-light LEDs in the light source housing 202 to illuminate through the visible light ring 148, acting as a light pipe and/or to eliminate the visible light ring 148.

Figure 2:
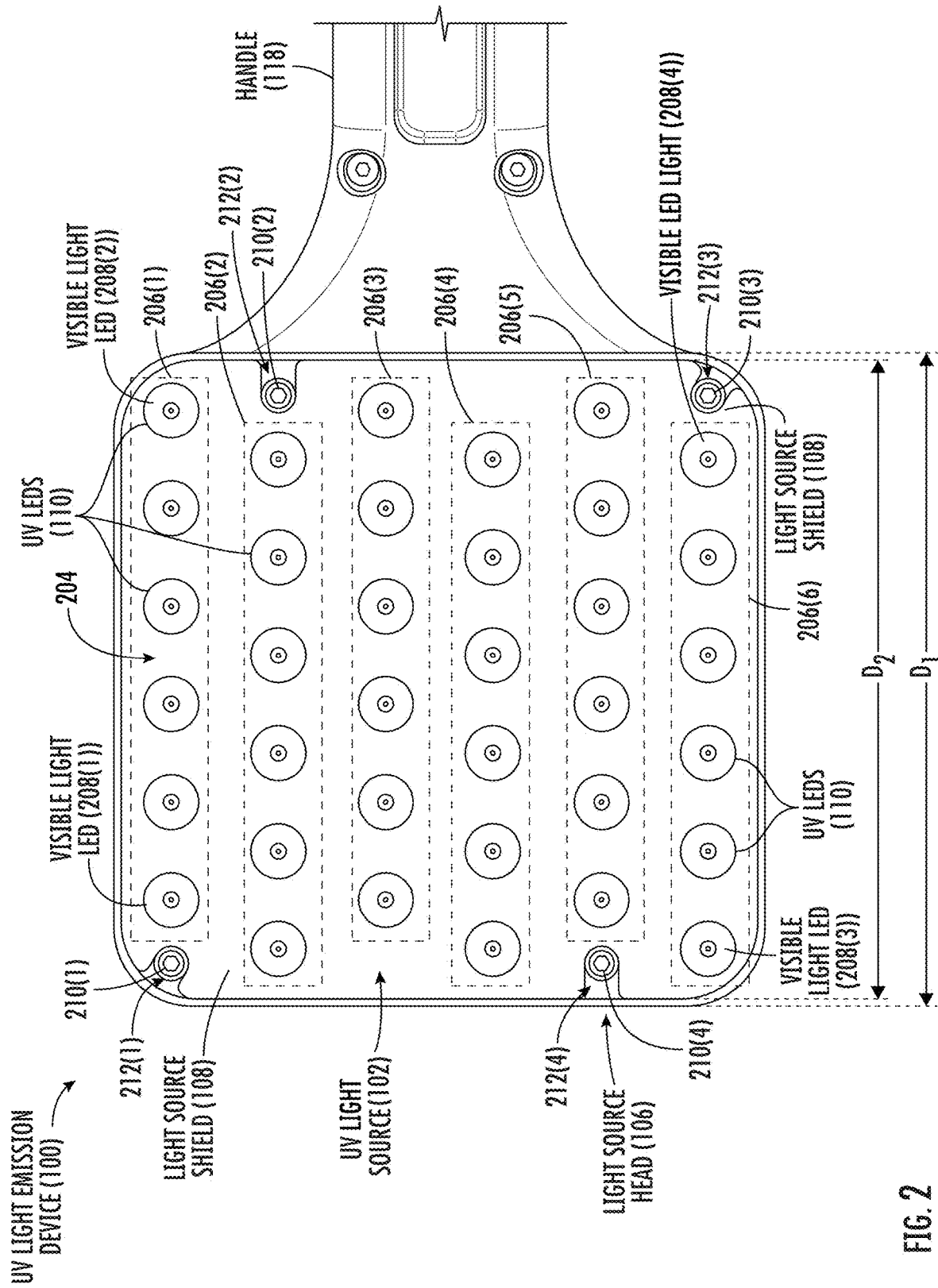
FIG. 2 is a bottom view of the UV light source of the UV light emission device in FIGS. 1A-1C.

FIG. 2 is a bottom view of the light source head 106 of the UV light emission device 100 in FIGS. 1A-1C to illustrate additional exemplary details of the UV light source 102 and the light source shield 108. As shown in FIG. 2, the UV light source 102 includes the UV LEDs 110 in this example, as previously discussed. The UV LEDs 110 are grouped in light strings that consist of either one LED or multiple LEDs electrically coupled together serially. In this example, there are six (6) light strings 206(1)-206(6) in the UV light source 102. A light string is defined as a circuit that can contain one light (e.g., a LED) or multiple lights (i.e., multiple LEDs) connected in series to each other. The grouping of a number of LEDs on a light string is a design choice and is dependent on the light source driver circuit selected and the amount of current needed to drive the LEDs according to their specifications to emit light of the desired intensity. The grouping of LEDs in light strings may also be desired to allow each light string 206(1)-206(6) to operate independently of the other light strings 206(1)-206(6) in case there is a failure in an LED in a given light string 206(1)-206(6) and/or its light source driver circuit.

With reference to FIG. 2, the UV light emission device 100 in this example also includes one or more visible lights in the light strings 206(1)-206(6) that are configured to emit light in the visible spectrum and at one or more wavelengths in the visible light spectrum (i.e., between 400-700 nanometers (nm)), which is safe to humans. For example, light strings 206(1) and 206(6) could each include two (2) visible lights 208(1)-208(2), and 208(3)-204(4), which can be in the form of visible light LEDs as an example. In this manner, when the light strings 206(1), 206(6) of the UV light source 102 are operational, current driving these light strings 206(1), 206(6) also automatically drives the visible lights 208(1)-208(4) in these light strings 206(1), 206(6) to emanate visible light. By automatic, it is meant that the UV light emission device 100 is configured to drive power to the visible lights 208(1)-208(4) to cause them to emit visible light when power is driven to the light strings 206(1), 206(6) to cause UV LEDs 110 to emit UV light in this example without further separate user activation or control. In this manner, the visible light emitted by the visible lights 208(1)-208(4) is visually perceptible to a user when the UV LEDs 110 are emitting UV light for the user's safety and to provide visual feedback to the user as discussed in more detail below. In other words, the user will know the UV LEDs 110 are emitting UV light that is not otherwise visible to the user when the visible lights 208(1)-208(4) are emitting visible light. For example, the visible lights 208(1)-208(4) may be configured to emit white light. For convenience, the visible lights 208(1)-208(4) can replace respective UV LEDs 110 that would otherwise be present in the UV light source 102. Thus, a user that is operating the UV light emission device 100 has indicators that are visibly perceptible in the form of the visible light emitted from the visible lights 208(1)-208(4) to also know that the UV light 104 is being emitted by the UV light source 102. In this example, as a non-limiting example, the visible lights 208(1)-208(4) are mounted in the UV light source 102 in the interior chamber of the light source housing 202 adjacent to the outside corners of the light source head 106 so that the visible light emitted from the UV light source 102 provides an approximate light border of where the UV light 104 may be emanating from the UV LEDs 110 when the UV light source 102 is activated. The visible light is emitted by visible lights 208(1)-208(4) in the direction of the UV light 104 emitted by the UV LEDs 110. The visible light emitted by the visible lights 208(1)-208(4) can intersect the UV light 104 emitted by the UV LEDs 110. In this manner, the user can determine by viewing the visible light emitted by the visible lights 208(1)-208(4), the direction and general area in which the UV light 104 is emitted by the UV LEDs 110. Alternatively, another visible light source other than the visible lights 208(1)-208(4) as LEDs may be employed, including but not limited to a laser that emits one or more laser beams, as an example. Alternatively, a single visible light could be mounted in the UV light source 102 in the center or center area of the light source head 106 so that the visible light emitted from the UV light source 102 is centered to the UV light 104 emanating from the UV LEDs 110 when the UV light source 102 is activated.

Also, in this example, a benefit of placing the visible lights 208(1)-208(4) in the series of light strings 206(1), 206(6) that also include UV LEDs 110 is to provide a safety mechanism. Current that reaches the UV LEDs 110 in the light strings 206(1), 206(6) will also reach the visible lights 208(1)-208(4) so that the visible lights 208(1)-208(4) will emit visible light when the UV light source 102 is emitting UV light 104. Also, as will be discussed in more detail below, the UV light emission device 100 is designed so that power can be decoupled from the UV light source 102 independent of power provided to the electronic control system that drives the visual status indicator 143 shown in FIG. 1C. Thus, the emission of light by the visual status indicator 143 in and of itself is not an absolute indicator of the presence or lack of presence of the UV light 104 emitted by the UV light source 102. However, as discussed above and in more detail below, the color and light pattern of the visual status indicator 143 can be controlled to indicate different operational modes and statuses to a user, which can include an operational status of the UV light source 102. In this instance, the visible lights 208(1)-208(4) are a secondary method of visually conveying to a user if the UV light source 102 is operational and emitting the UV light 104. The visual status indicator 143 can be a bi-color LED that is configured to emit different colors (e.g., green, red, and yellow colors) of light depending on a controlled operational mode.

With continuing reference to FIG. 2, the light source housing cover 204 includes female bosses/receivers (not shown) that are configured to receive fasteners 210(1)-210(4) to secure the light source shield 108 to the light source housing cover 204. The light source shield 108 includes openings 212(1)-212(4) that are configured to align with the female receivers internal to the light source housing cover 204 when the light source shield 108 is placed inside the light source housing cover 204. The light source housing cover 204 is designed to have an internal diameter $D_1$ that is slightly larger than the outer diameter $D_2$ of the light source shield 108 so that the light source shield 108 can fit inside the outer edges of the light source housing cover 204. Fasteners 210(1)-210(4) are inserted into the openings 212(1)-212(4) to secure the light source shield 108 to the light source head 106.

Figure 3A:
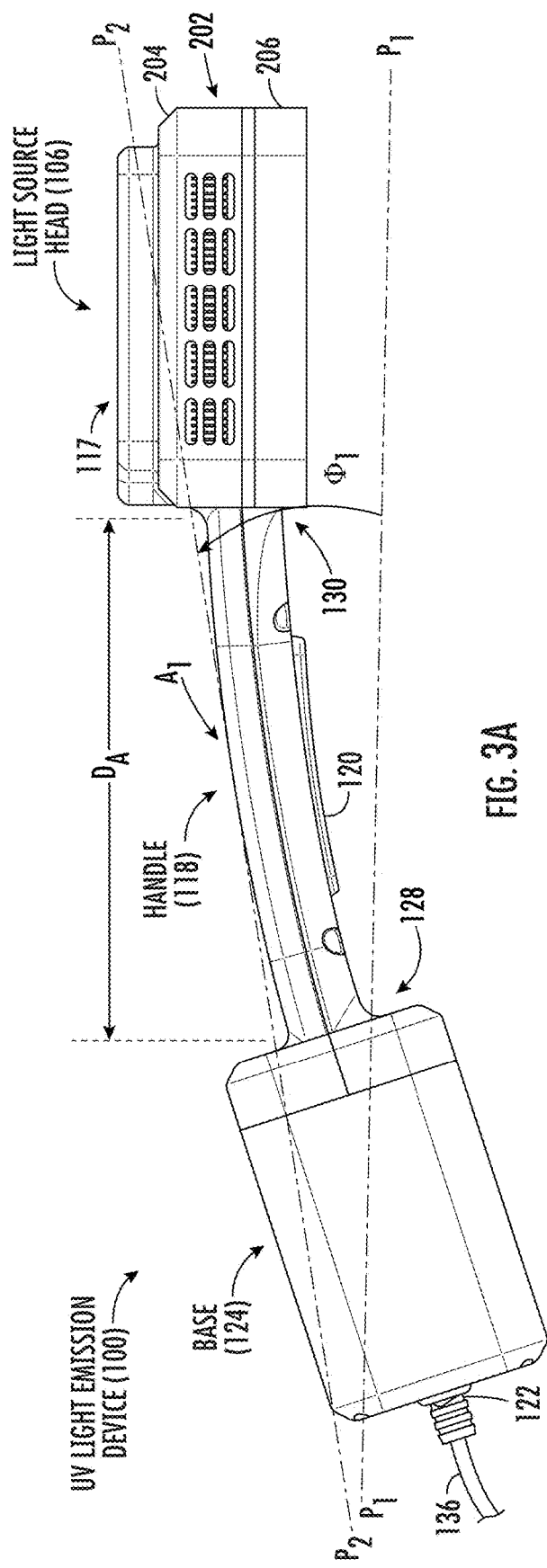
FIG. 3A is a first side view of the UV light emission device in FIGS. 1A-1C.
Figure 3B:
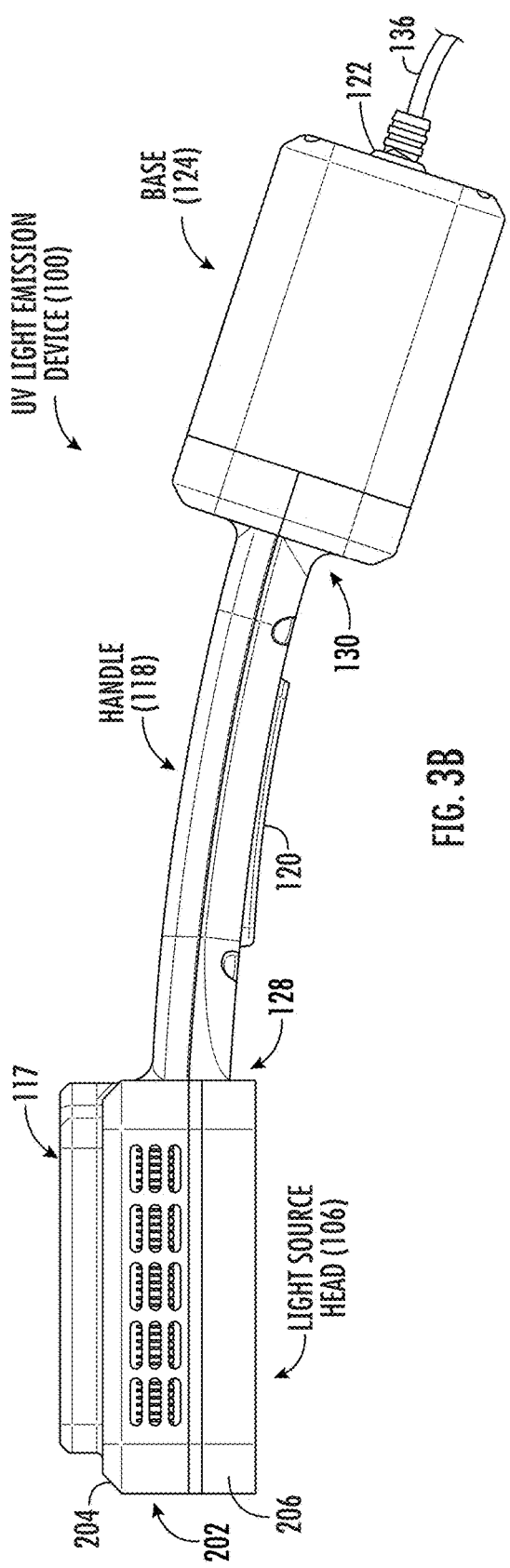
FIG. 3B is a second side view of the UV light emission device in FIGS. 1A-1C.
Figure 3E:
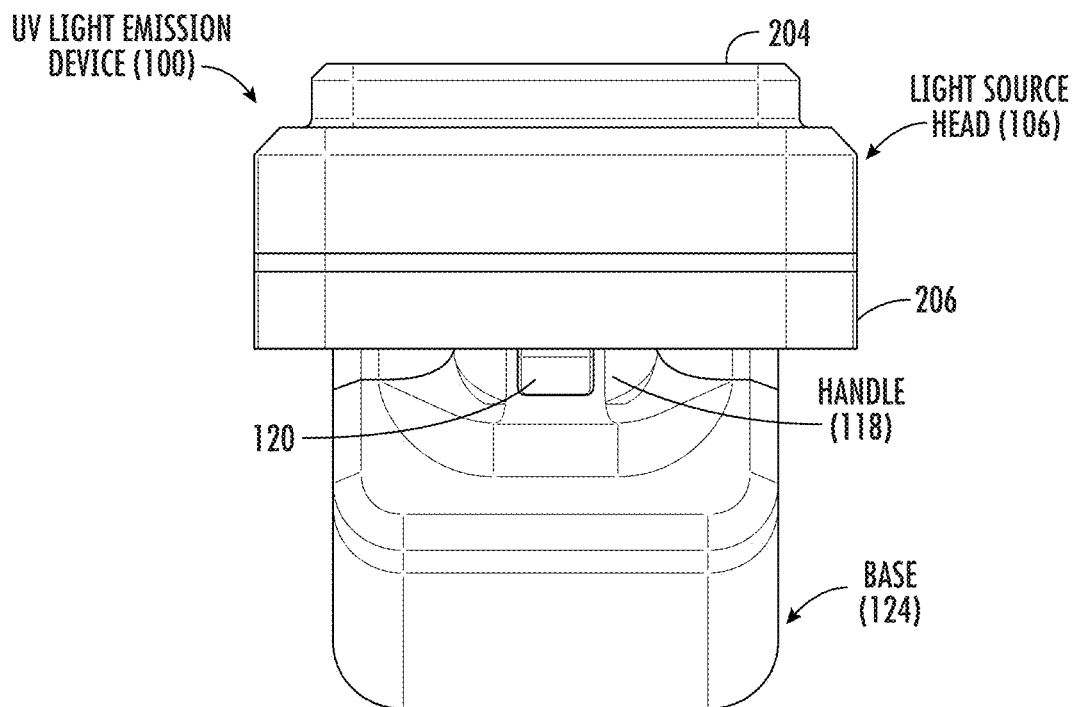
FIG. 3E is a front view of the UV light emission device in FIGS. 1A-1C.
Figure 3F:
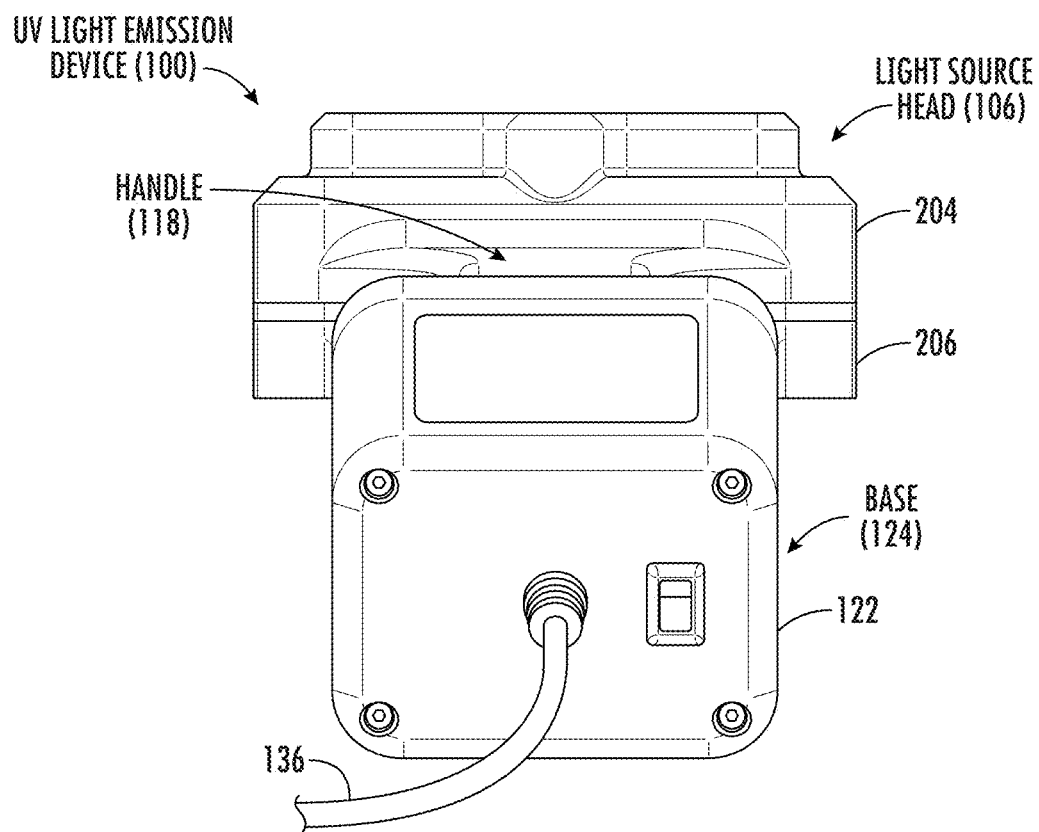
FIG. 3F is a rear view of the UV light emission device in FIGS. 1A-1C.

FIG. 3A is a first side view of the UV light emission device 100 in FIGS. 1A-1C with common elements discussed above labeled with common element numbers. As shown in FIG. 3A, the UV light emission device 100 is designed so that the plane $P_1$ of the opening # normal to the light source housing cover 204 and the UV light source 102 therein is at angle $\phi_1$ with respect to the tangential plane $P_2$ to the apex $A_1$ of the handle 118. The apex $A_1$ of the handle 118 may be located at half the distance DA between ends 128, 130 of the handle 118 as an example. In this manner, when a user is handling the UV light emission device 100 by the handle 118, the light source housing 202 and UV light source 102 will naturally be oriented in a parallel plane to plane $P_1$ with respect to the ground. Then angle $\phi_1$ between the first plane $P_1$ and the tangential plane $P_2$ can be between 1 and 45 degrees. FIG. 3B is a second side view of the UV light emission device in FIGS. 1A-1C with common elements discussed above labeled with common element numbers. FIG. 3C is a bottom view of the UV light emission device 100 in FIGS. 1A-1C with common elements discussed above labeled with common element numbers. FIG. 3D is a top view of the UV light emission device 100 in FIGS. 1A-1C with common elements discussed above labeled with common element numbers. FIG. 3E is a front view of the UV light emission device 100 in FIGS. 1A-1C with common elements discussed above labeled with common element numbers. FIG. 3F is a rear view of the UV light emission device 100 in FIGS. 1A-1C with common elements discussed above labeled with common element numbers.

Figure 4A:
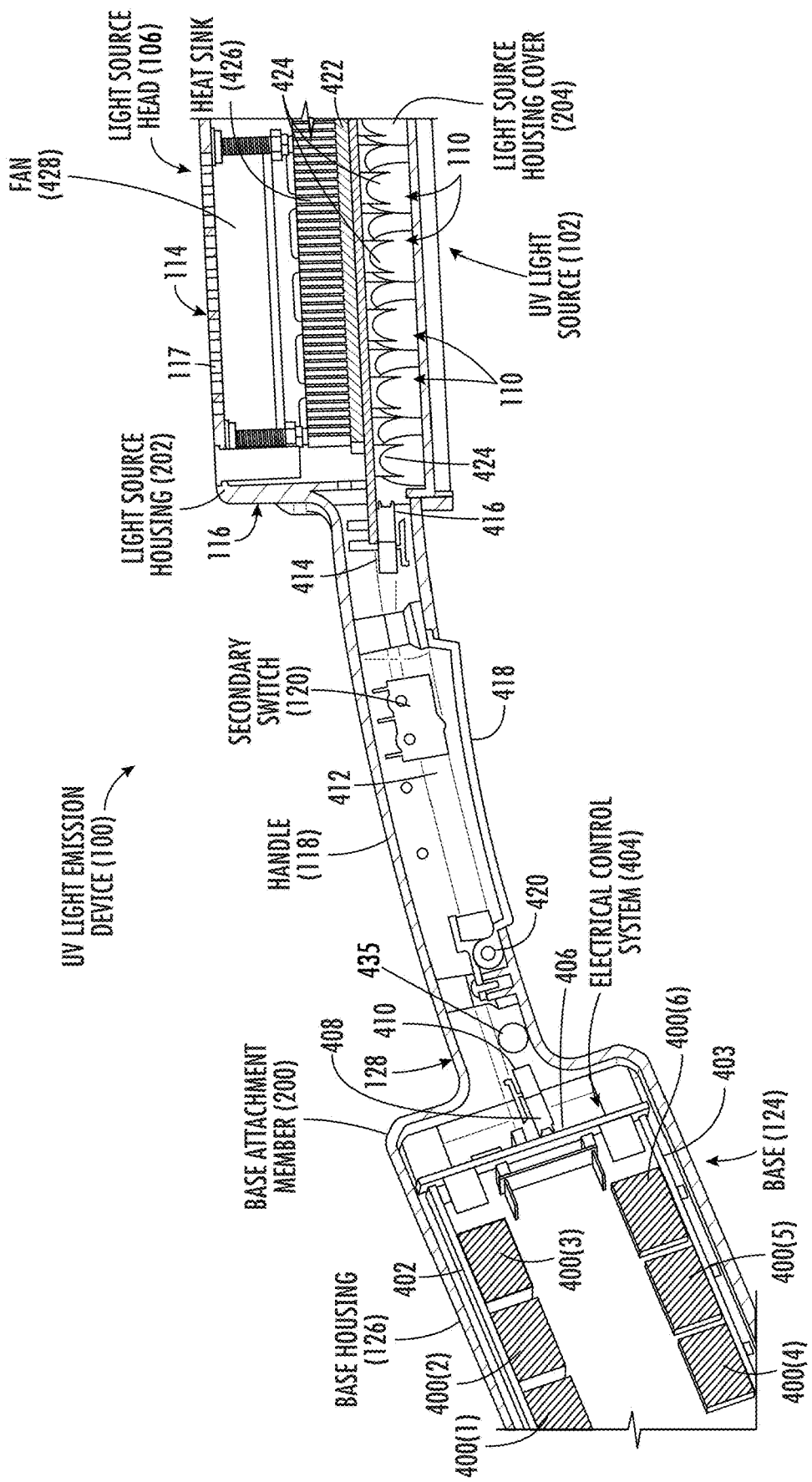
FIG. 4A is a side, cross-sectional view of the UV light emission device in FIGS. 1A-1C.
Figure 4B:
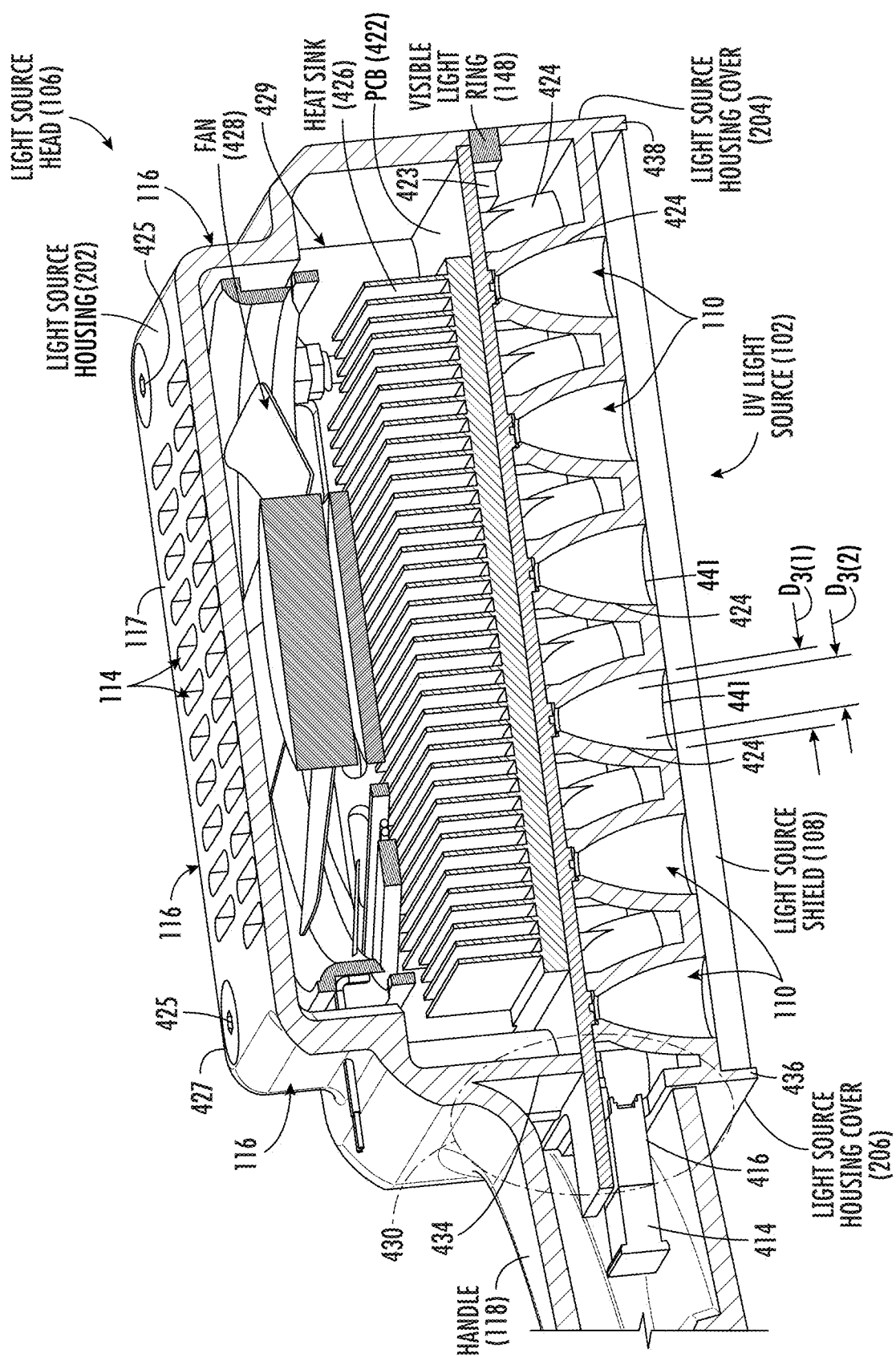
FIG. 4B is a close-up, side, cross-sectional view of a UV light source package area of the UV light emission device in FIGS. 1A-1C.
Figure 4C:
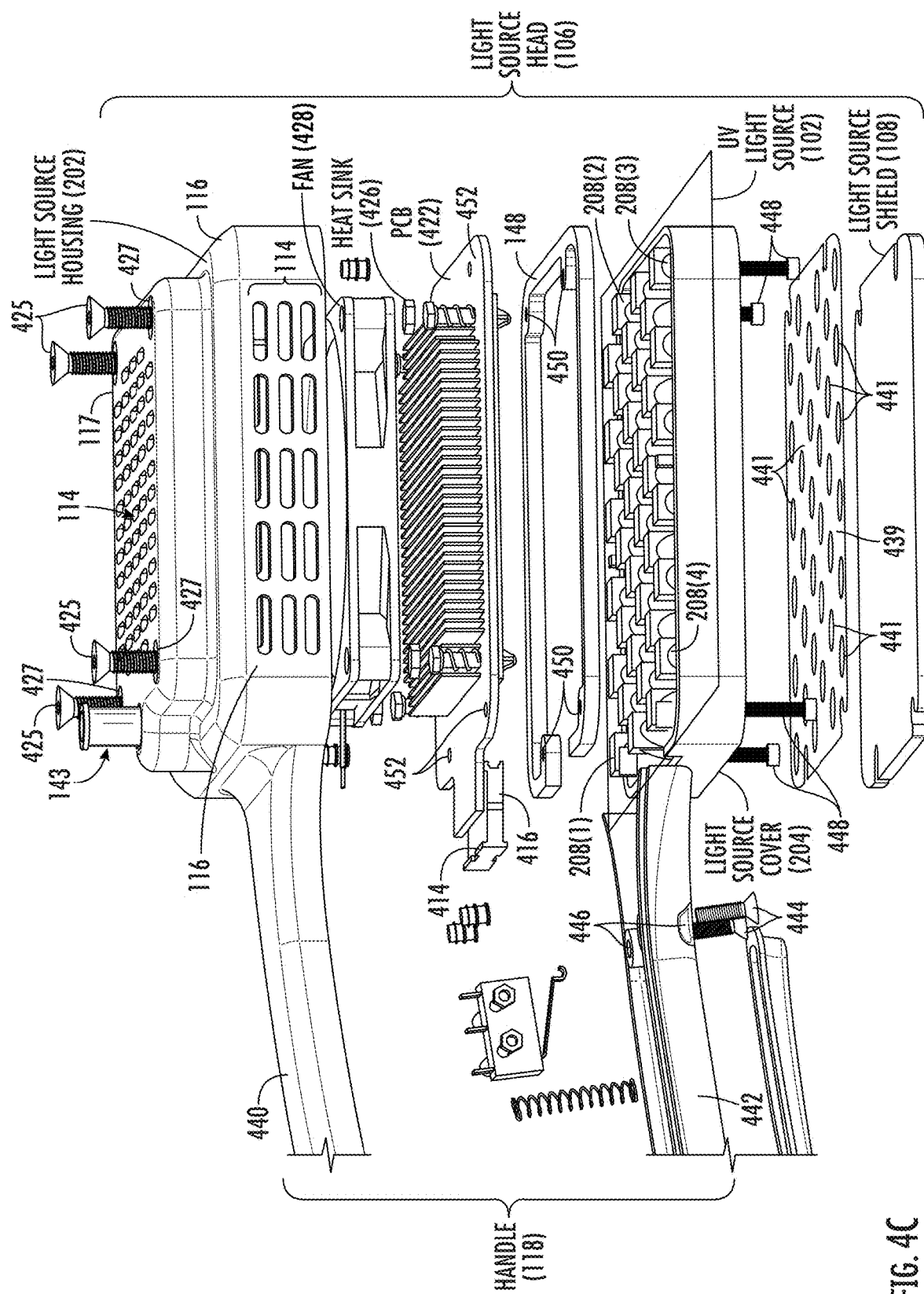
FIG. 4C is a side, exploded view of the UV light source package area of the UV light emission device in FIGS. 1A-1C.

To illustrate more exemplary detail of the UV light emission device 100 in FIGS. 1A-1C, FIGS. 4A-4D are provided. FIG. 4A is an overall side, cross-sectional view of the UV light emission device 100 in FIGS. 1A-1C. FIG. 4B is a close-up, side, cross-sectional view of the light source head 106 of the UV light emission device 100. FIG. 4C is a side perspective exploded cross-sectional view of the light source head 106 of the UV light emission device 100. FIG. 4D is an overall side, exploded view of the UV light emission device 100.

With reference to FIG. 4A, six (6) light driver circuits 400(1)-400(6) are installed in the base housing 126 of the base 124 to drive power to the UV light source 102 in the light source head 106. In this example, the light driver circuits 400(1)-400(6) are LED driver circuits to drive the UV LEDs 110 in the UV light source 102. In this example, the light driver circuits 400(1)-400(3) are mounted to a first light driver PCB 402 inside the base housing 126, and the light driver circuits 400(4)-400(6) are mounted to a second light driver PCB 403 opposite the first light driver PCB 402. As previously discussed, input power provided to the light driver circuits 400(1)-400(6) is sourced from the electrical cable 136 (see FIG. 1C). There are six (6) light driver circuits 400(1)-400(6) in this example because each light driver circuits 400(1)-400(6) drives power to one (1) light string 206(1)-206(6) among the six (6) light strings 206(1)-206(2) provided in the UV light source 102 (see FIG. 2). As will also be discussed in more detail below, current and voltage sensors (not shown) are also provided for the light driver circuits 400(1)-400(6) to sense current drawn from the light driver circuits 400(1)-400(6) and/or voltage across the driver circuits 400(1)-400(6) as a failure detection mechanism to determine if any of the light driver circuits 400(1)-400(6) have failed. The light driver circuits 400(1)-400(6) may not only be located in the base 124 apart from the UV light source 102 in the light source head 106 for packaging convenience but also to manage heat. This also creates balance by placing the electronic control system 404 and the light driver circuits 400(1)-400(6) in this example in the base 124 circuitry opposite the light source head 106. The center of gravity of the UV light emission device 100 is very close to the secondary switch 120, reducing wrist strain. The light driver circuits 400(1)-400(6) are configured to supply a large amount of current and generate heat. The UV light source 102 also generates heat. So, providing the light driver circuits 400(1)-400(6) in the base 124 apart from the light source head 106 may serve to improve heat dissipation rates and to more easily manage the temperature in the UV light source 102.

With continuing reference to FIG. 4A, an electrical control system 404 on an electrical control PCB 406 is also supported in the base housing 126. The electrical control system 404 is an electrical circuit. As will be discussed in more detail below, the electrical control system 404 includes a microprocessor that is configured to receive inputs from a number of sensors and other sources, including the secondary switch 120 on the handle 118, and control the activation of the light driver circuits 400(1)-400(6) to activate and deactivate the UV light source 102. As also shown in FIG. 4A, wiring connectors 408, 410 are provided inside the base 124 and extend inside the handle 118 to provide a wiring harness between the light driver circuits 400(1)-400(6), the electrical control system 404, and the UV light source 102. The wiring harness may include, for example, a ribbon cable 412 that is coupled to the wiring connector 410 and to another wiring connector 414 on the opposite end of the handle 118 adjacent to the light source head 106 that is connected to writing connector 416 coupled to the UV light source 102 to distribute power and other communications signals between the light driver circuits 400(1)-400(6) electrical control system 404.

With continuing reference to FIG. 4A, the secondary switch 120 is shown installed inside the handle 118 with a trigger 418 of the secondary switch 120 exposed from an opening in the body of the handle 118. The trigger 418 is attached to a spring-loaded hinge 420 that biases the trigger 418 outward to an open position. The trigger 418 of the secondary switch 120 is in electrical contact with the electrical control system 404. As will be discussed in more detail below, when the trigger 418 is not engaged such that the secondary switch 120 remains open such that a trigger signal cannot be provided, the electrical control system 404 disables the distribution of power from the power source received over the electrical cable 136 to the light driver circuits 400(1)-400(6) as a safety mechanism. When the trigger 418 is moved inward and engaged to close the secondary switch 120, the secondary switch 120 can provide a trigger signal in the electrical control system 404 that enables the distribution of power from the power source received over the electrical cable 136 to the light driver circuits 400(1)-400(6). For example, the secondary switch 120 may be the Omron D2MQ series Omron SS series (e.g., SS-01GL13) subminiature basic switch.

As discussed previously, by providing the secondary switch 120 as a momentary switch, the light driver circuits 400(1)-400(6) of the UV light source 102 are only active to generate current when the secondary switch 120 is being actively depressed, such as by a user holding the handle 118 and depressing the secondary switch 120. When a user is no longer depressing the secondary switch 120, the secondary switch 120 becomes non-depressed and thus non-activated such that it does not provide a trigger signal to activate the light driver circuits 400(1)-400(6). Thus, the secondary switch 120 can act as a safety measure to ensure that the UV light source 102 is not active when the secondary switch 120 is not being engaged. For example, if the user of the UV light emission device 100 lays the device down and releases the handle 118 such that the secondary switch 120 is not activated, the light driver circuits 400(1)-400(6) will be deactivated. The secondary switch 120 as a momentary switch allows the user to control the ultimate on and off time of the UV LEDs 110.

Further, although not limiting and the UV light source 102 not being limited to use of UV LEDs, the deployment of the secondary switch 120 as a momentary switch can also make more feasible the use of LEDs in the UV light source 102. LEDs are a semiconductor device. As soon as current flows to the LED, electrons flow through its P-N junction of a LED, and energy is released in the form of photons to emit light. The UV LEDs 110 of the UV light source 102 are able to essentially instantaneously emit UV light when current starts to flows under control of the secondary switch 120 when activated without having to wait for more significant elapsed time (e.g., 10-15 minutes) for a gas inside a bulb to "warm-up" to produce a fuller intensity light. The use of LEDs as the UV light source 102 allows a more instantaneous off and on of UV light emission, as controlled by the secondary switch 120 in this example, without having to employ other techniques for off and on employed by bulbs, such as pulse-width modulation (PWM).

With continuing reference to FIG. 4A, a cross-sectional view of the light source head 106 of the UV light emission device 100 is shown. FIG. 4B illustrates a close-up, cross-sectional view of the light source head 106 of the UV light emission device 100 shown in FIG. 4A to provide additional detail. FIG. 4C illustrates a side perspective exploded cross-sectional view of the light source head 106 of the UV light emission device 100 shown in FIGS. 4A and 4B. As shown in FIGS. 4A-4C, the UV light source 102 installed in the light source head 106 includes a light source PCB 422 in which the UV LEDs 110 and visible lights 208(1)-208(4) are mounted, as previously discussed in FIG. 2 above. Visible light indicators 423 (i.e., visible lights), which may be LEDs, are also mounted on the perimeter of the light source PCB 422 adjacent to the visible light ring 148 and driven by a light driver circuit 400(1)-400(6) to emit light to the visible light ring 148 that is then propagated through the visible light ring 148 when the UV light source 102 has activated an additional indicator of such. Thus, in this example, because the visible light indicators 423 are driven by a light driver circuit 400(1)-400(6) that also drives the UV LEDs 110 in the UV light source 102, the visible light indicators 423 are activated automatically in response to the light driver circuits 400(1)-400(6) driving the UV LEDs 110 in the UV light source 102. In this manner, the visible light emitted by the visual light indicators 143 via the visible light ring 148 is visually perceptible to a user when the UV LEDs 110 are emitting UV light for the user's safety. In other words, the user will know the UV LEDs 110 are emitting UV light that is not otherwise visible to the user when the visible light ring 148 is illuminated by visible light from the visual light indicators 143. The UV LEDs 110 and visible lights 208(1)-208(4) are mounted in parabolic reflectors 424 that may be reflectors of a metal material and that reflect and direct their emitted light in a ten (10) degree cone in this example.

A heat sink 426 is mounted on the backside of the light source PCB 422 for the UV light source 102 to dissipate heat generated from operation. A fan 428 is mounted inside the light source head 106 above the heat sink 426 to draw heat away from the heat sink 426 and the light source PCB 422 for the UV light source 102 and to direct such heat through the vent openings 114 in the rear 117 of the light source housing 202 for heat dissipation. Alternatively, the fan 428 could be controlled to draw air through the openings 114 in the rear 117 of the light source housing 202 and exhausting it through the openings 114 in the side(s) 116 of the light source housing 202 for heat dissipation. As discussed in more detail below, the fan 428 is electronically controlled by the electrical control system 404 to variably control the speed of the fan 428 based on sensed temperature in the UV light source 102 to provide sufficient heat dissipation. In another embodiment, the fan 428 can be eliminated using passive heat dissipation. This may be possible when UV light source 102 is efficient enough to not need additional airflow for heat dissipation.

In addition, since visible LEDs such as the visible light indicators 423 and UV LEDs, such as UV LEDs 110, have different optical efficiencies, where visible LEDs are generally more optically efficient, the circuit could be modified to shunt some of the currents around the white LED to reduce its brightness with a resistor. The brightness of the visible LED could also be reduced with a simple filter inserted in the individual reflector cells.

A fan 428 is mounted inside the light source head 106 above the heat sink 426 to draw heat away from the heat sink 426 and the light source PCB 422 for the UV light source 102 and to direct such heat through the vent openings 114 in the rear 117 of the light source housing 202 for heat dissipation. Alternatively, as discussed above, the fan 428 mounted inside the light source head 106 above the heat sink 426 could pull air through the openings 114 in the rear 117 of the light source head 106. Pulled air could be exhausted through the openings 114 in the side 116 to carry heat generated from the light source PCB 422 in the UV light source 102 away from the UV light source 102. As discussed in more detail below, the fan 428 is electronically controlled by the electrical control system 404 to variably control the speed of the fan 428 based on sense temperature in the UV light source 102 to provide sufficient heat dissipation. The fan 428 is mounted inside the light source housing 202 through fasteners 425 that are extended through openings 427 in the rear 117 of the light source housing 202. The interior chamber 429 created by the light source housing 202 also provides additional spaces that can further facilitate the dissipation of heat. Note that the interface area 430 between the handle 118 and the light source housing 202 is a closed-off space by the presence of the light source PCB 422 and internal walls 432, 434 of the light source housing 202 and light source housing cover 204.

Also, as shown in FIG. 4A, the UV light emission device 100 includes a haptic feedback device 435 in the handle 118 that is coupled to the electrical control system 404. As discussed in more detail below, the electrical control system 404 is configured to activate the haptic feedback device 435 to apply a vibratory force to the handle 118 under certain conditions and operational modes of the UV light emission device 100. The vibratory force will be felt by a human user who is holding the handle 118 to control and manipulate the UV light emission device 100 in its normal, operational use. For example, the haptic feedback device 435 can be configured to be controlled by a haptic motor driver (shown in FIG. 5 below) in the electrical control system 404 to spin to cause the haptic feedback device 435 to exert a vibratory force to the handle 118. The electrical control system 404 could cause activate the haptic feedback device 435 to create different sequences of vibratory force as different indicators or instructions to a human user of the UV light emission device 100, such as various error conditions.

FIG. 4B also shows the raised outer edges 436, 438 of the light source housing cover 204 that then create an internal compartment for the light source shield 108 to be inserted and fit inside to be mounted to the light source housing cover 204 in front of the direction of emission of light from the UV light source 102. An optional screen 439 (e.g., metal screen) can also be provided and fit between the light source shield 108 and the light source housing cover 204 to further protect the UV light source 102 and/or to provide a sacrificial surface. The optional screen 439 includes openings 441 that align with the UV LEDs 110 in the UV light source 102. An adhesive or tape (e.g., a double-sided tape) can be used to secure the light source shield 108 to the optional screen 439. Thus, for example, if the light source shield 108 is made of glass and it breaks, the glass shield will remain in place and attached to the optional screen 439 for safety reasons.

Also, as discussed earlier, in addition, or alternatively to providing the light source shield 108, the parabolic reflectors 424 could be provided to have an opening or aperture 441 of diameter $D_{3(1)}$ as shown in FIG. 4B. The light from the respective UV LEDs 110 and visible light 208(1)-208(4) is emitted towards the respective aperture 441 of the parabolic reflectors 424. The diameter $D_3$ of the apertures 441 of the parabolic reflectors 424 can be sized to be smaller than the diameter of a typical, smaller sized human finger. For example, the diameter $D_3$ of the aperture 441 could be 0.5 inches or smaller. This would prevent a human from being able to put their finger or other appendages inside the opening 441 of the parabolic reflectors 424 in direct contact with the UV LEDs 110 and/or the visible light 208(1)-208(4) for safety reasons. This may allow a separate light shield, like light source shield 108, to not be used or required to provide the desired safety of preventing direct human contact with the UV LEDs 110 and visible light 208(1)-208(4).

Note that the diameter of the parabolic reflectors 424 decreases from the aperture 441 back to where the actual position of the UV LEDs 110 or visible light 208(1)-208(4) is disposed within the parabolic reflectors 424. Thus, even if the diameter $D_{3(1)}$ of the aperture 441 has a large enough opening to receive a human finger or other parts, the reducing internal diameter of the parabolic reflectors 424 may still prevent a human finger or other parts from reaching and contacting the UV LEDs 110 or visible light 208(1)-208(4) within the parabolic reflectors 424. For example, as shown in FIG. 4B, the diameter $D_{3(2)}$ of the parabolic reflectors 424 is less than the diameter $D_3$ of their apertures 441. The diameter $D_{3(2)}$ of the parabolic reflectors 424 still located a distance away from the UV LEDs 110 or visible light 208(1)-208(4) is disposed within the parabolic reflectors 424 may also be small enough to prevent human finger or other parts from reaching and contacting the surface of the UV LEDs 110 or visible light 208(1)-208(4).

As further shown in FIG. 4C, the handle 118 is comprised of two handle members 440, 442 that come together in clamshell-like fashion and are fitted together by fasteners 444 through openings in the handle member 442 to be secured to the handle member 440. As previously discussed, the two handle members 440, 442 have internal openings such that an interior chamber is formed inside the handle 118 when assembled for the ribbon cable 412 (see FIG. 4A) of the wiring harness and secondary switch 120. Similarly, as shown in FIG. 4C, the light source housing cover 204 is secured to the light source housing 202 through fasteners 448 that are inserted into openings in the light source housing cover 204. The fasteners 448 can be extended through openings 450 in the visible light ring 148 and openings 452 in the light source PCB 422 and into openings in the light source housing 202 to secure the light source housing cover 204 to the light source housing 202.

Figure 5:
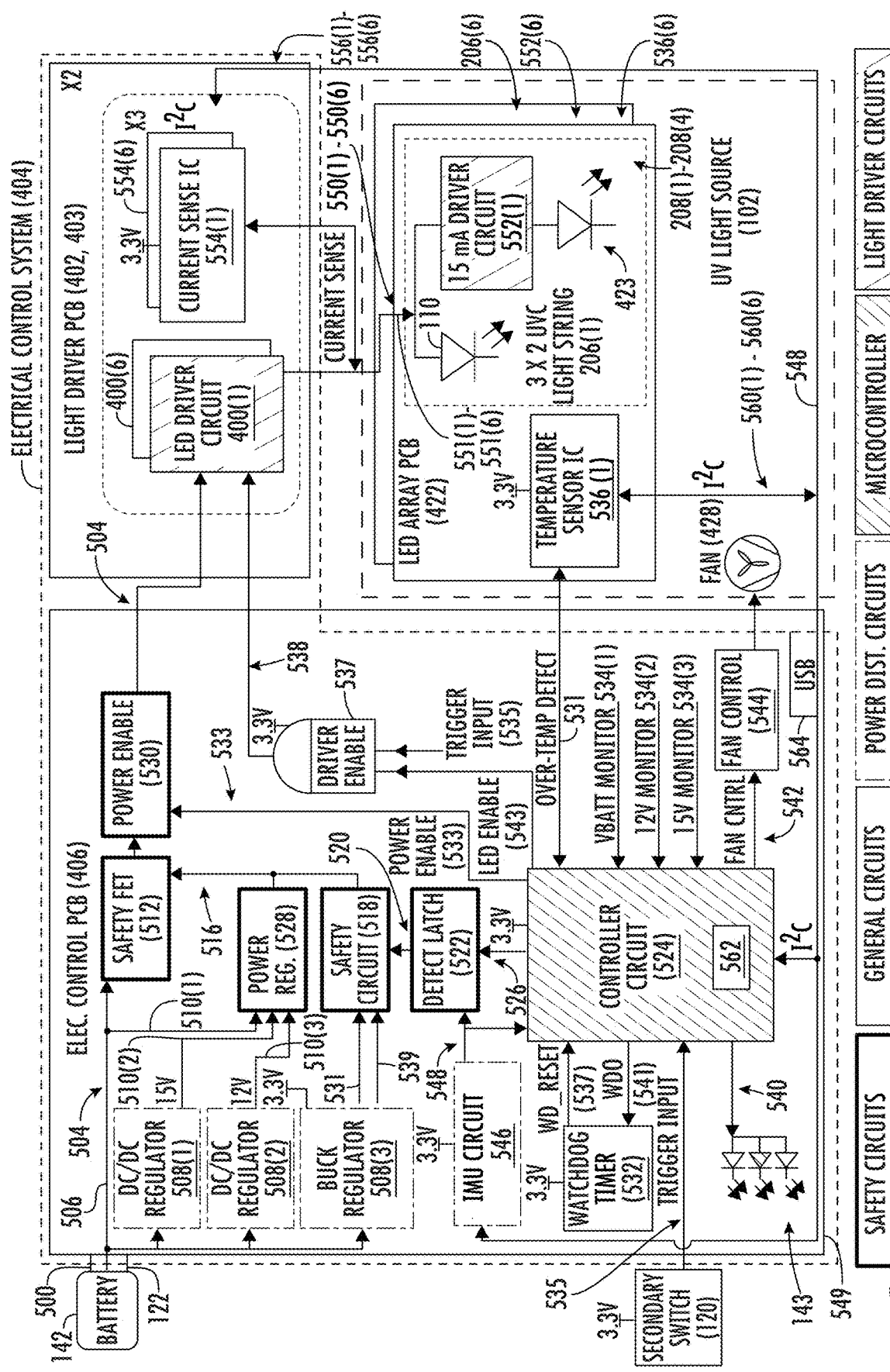
FIG. 5 is a schematic diagram of an exemplary electrical control system that can be included in the UV light emission device in FIGS. 1A-1C.

As discussed above, the UV light emission device 100 includes an electrical control system 404 that is on one or more PCBs and housed in the base housing 126 to control the overall electronic control of the UV light emission device 100. In this regard, FIG. 5 is a schematic diagram of the exemplary electrical control system 404 in the UV light emission device 100 in FIGS. 1A-1C. As will be discussed below, the electrical control system 404 includes safety circuits, power distribution circuits for controlling the distribution of power to the light driver circuits 400(1)-400(6) and the UV light source 102, and other general circuits. As shown in FIG. 5, the electrical control system 404 includes an external power interface 500 that is configured to be coupled to the electrical cable 136 that is electrically coupled to a battery 142 as a power source (e.g., 44.4 Volts (V)). As previously discussed, the battery 142 may be external to the UV light emission device 100 or alternatively integrated within the UV light emission device 100. A power signal 504 generated by the battery 142 is electrically received by an input power rail 506 controlled by inline primary switch 122 (see FIGS. 1A-1C) into three (3) DC-DC regulator circuits 508(1)-508(3) to provide different voltage levels to different voltage rails 510(1)-510(3) since different circuits in the electrical control system are specified for different operation voltages, which in this example are 15V, 12V, and 3.3V, respectively. For example, the battery 142 may be a rechargeable Lithium-Ion battery rated at 44.4V, 6.4 Ah manufactured by LiTech. As another example, the battery 142 may be a 14.4 VDC nominal 143 W/hr. battery manufactured by IDX. The electrical control system 404 may also have battery overload and reserve battery protection circuits. The input power rail 506 is also coupled to a safety switch 512, which may be a field-effect-transistor (FET). The safety switch 512 is configured to pass the power signal 504 to a power enable circuit 530 (e.g., a power switch) in response to a power safety signal 516 generated by a safety circuit 518, indicating either a power safe or power unsafe state independent of any software-controlled device, such as a microprocessor controller circuit as discussed below, as a failsafe mechanism. The safety circuit 518 is configured to receive a power signal 520 indicating an enable or disable state from a detect latch 522 that is controlled by a controller circuit 524, which is a microcontroller in this example, to latch a latch reset signal 526 as either a power safe or power unsafe state. As will be discussed below, the controller circuit 524 is configured to set the detect latch 522 to a power safe state when it is determined that it is safe to distribute power in the UV light emission device 100 to the light driver circuits 400(1)-400(6) to distribute power to the UV light source 102. When it is desired to discontinue power distribution to the light driver circuits 400(1)-400(6), the controller circuit 524 is configured to generate the latch reset signal 526 to a latch reset state as a power unsafe state. The detect latch 522 is configured to default to a power unsafe state on power-up of the electrical control system 404.

As also shown in FIG. 5, the safety switch 512 is also controlled based on a power regulator circuit 528 that is configured to pull the power safety signal 516 to ground or a power rail voltage to indicate either the power safe or power unsafe state to control the safety switch 512. Thus, if there are any voltage irregularities on the input power rail 506 or from the DC-DC regulator circuits 508(1)-508(3), the power regulator circuit 528 is configured to generate the power safety signal 516 in a power unsafe state to disable the safety switch 512 and interrupt power distribution from the input power rail 506 to a power enable circuit 530 as a safety measure. Note that the safety circuit 518 and the power regulator circuit 528 are configured to generate the power safety signal 516 irrespective of whether the controller circuit 524 is operational as a safety measure, and in case the controller circuit 524 discontinues to operate properly. This is because it is desired in this example to detect fault conditions with regard to any voltage irregularities on the input power rail 506 or from the DC-DC regulator circuits 508(1)-508(3) when power is first turned on to the UV light emission device 100, and before the controller circuit 524 starts up and becomes operational as a hardware circuit-only safety feature.

The safety circuit 518 in this example also receives an analog over-temperature signal 531, and a watchdog reset signal 539 as additional mechanisms to cause the safety circuit 518 to generate the power safety signal 516 in a power unsafe state to disable the safety switch 512 from distributing the power signal 504, even if the controller circuit 524 is not operational. For example, the controller circuit 524 includes a watchdog timer circuit 532 that is configured to be updated periodically by the controller circuit 524 from an output signal 541, and if it is not, the watchdog timer circuit 532 times out and generates a watchdog reset signal 539 to restart the controller circuit 524. The watchdog reset signal 539 is also provided to the safety circuit 518 to cause the safety circuit 518 to generate the power safety signal 516 in a power unsafe state to disable the safety switch 512 from distributing the power signal 504 when the controller circuit 524 becomes or is non-operational, and until the controller circuit 524 is successfully rebooted and operational. The safety circuit 518 is also configured to generate the power safety signal 516 in a power unsafe state to disable the safety switch 512 from distributing the power signal 504 when an overall temperature condition at the UV light source 102 is detected via the analog over-temperature signal 531 generated by the temperature sensor circuit 536 described below.

It is also desired for the controller circuit 524 to also be able to control enabling and disabling of power distribution of the power signal 504. For example, the controller circuit 524 includes a trigger signal 535 from the secondary switch 120 that indicates a power enable state (e.g., a logic '1' value) when the secondary switch 120 is engaged and a power disable state (e.g., a logic '0' value) when the secondary switch 120 is not engaged. As discussed above, the secondary switch 120 is configured to be engaged by a user when using the UV light emission device 100 to control when the UV light source 102 is activated or de-activated. In this regard, the power enable switch 530 is provided, which may be a FET. The power enable switch 530 is coupled between the safety switch 512 and the light driver circuits 400(1)-400(6) to control power distribution to the light driver circuits 400(1)-400(6). The power enable switch 530 is under the sole control of the controller circuit 524 to provide another mechanism to control power distribution of the power signal 504 to the light driver circuits 400(1)-400(6) driving the UV light source 102. In this manner, as discussed in more detail below, a software algorithm executed in software or firmware by the controller circuit 524 can control the enabling and disabling of power distribution of the power signal 504 to the light driver circuits 400(1)-400(6) based on a number of conditions detected by input signals. In this regard, the controller circuit 524 is configured to generate a power enable signal 533 to the power enable switch 530 of a power enable or power disable state. For example, the controller circuit 524 is configured to receive power input signals 534(1)-534(3) that can be coupled to the voltage rails 510(1)-510(3) to detect if the DC-DC regulator circuits 508(1)-508(2) are distributing their expected voltages in addition to the power regulator circuit 528 that does not involve the controller circuit 524. In response to the power enable signal 533 being a power enable state, the power enable switch 530 is configured to distribute the received power signal 504 to the light driver circuits 400(1)-400(6).

With continuing reference to FIG. 5, a driver enable circuit 537 is also provided that controls a driver enable signal 538 in either a driver enable state or driver disable state. The driver enable signal 538 is coupled to the light driver circuits 400(1)-400(4) to control the activation or deactivation of the light driver circuits 400(1)-400(4). If the driver enable signal 538 is in a power disable state, the light driver circuits 400(1)-400(4) will be disabled and not drive power to the UV light source 102 regardless of whether or not the power enable switch 530 distributes the power signal 504 to the light driver circuits 400(1)-400(4). The driver enable circuit 537 is coupled to a light enable signal 543 generated by the controller circuit 524 and a trigger signal 535, which must both indicate a power enable state for the driver enable circuit 537 to generate the driver enable signal 538 (DRIVER ENABLE) of a power enable state to enable the light driver circuits 400(1)-400(4).

With continuing reference to FIG. 5, the controller circuit 524 is also configured to generate a visual feedback signal 540 to the visual status indicator 143 (see FIG. 1C) to control the operational mode, color, and pulse pattern of light emitted by the visual status indicator 143. The controller circuit 524 is also configured to generate a fan control signal 542 to a fan control switch 544 to control operation of the fan 428 in the UV light source 102 to dissipate heat generated by the UV light source 102. The controller circuit 524 can pulse-width-modulate the fan control signal 542 provided to the fan control switch 544 to control the speed of the fan 428. The electrical control system 404 also includes an inertial measurement unit (IMU) circuit 546 that includes an accelerometer circuit. The IMU is configured to generate an accelerometer or orientation signal 548 to the detect latch 522 and the controller circuit 524. For example, the IMU circuit 546 may be the MMA84511Q digital accelerometer by NXP Semiconductors. The IMU circuit 546 may be programmed over a communication bus 549 (e.g., an I²C communications bus) to generate the accelerometer or orientation signal 548 based on the UV light emission device 100 exceeding a given acceleration and/or angle or orientation as a safety feature. For example, the accelerometer or orientation signal 548 may indicate an initialize state, a test ok state indicating a current is sensed in a test state, an ok state indicating current is sensed in an operational state, or an error state. For example, the accelerometer or orientation signal 548 may be in an error state if the UV light emission device 100 is dropped or rotated by a user beyond a programmed allowable angle based on acceleration or orientation of the UV light emission device 100. If the accelerometer or orientation signal 548 is in an error state, this causes the detect latch 522 to register the error condition to cause the controller circuit 524 to disable the power enable switch 530 to discontinue distribution of the power signal 504 to the light driver circuits 400(1)-400(4).

Figure 6:
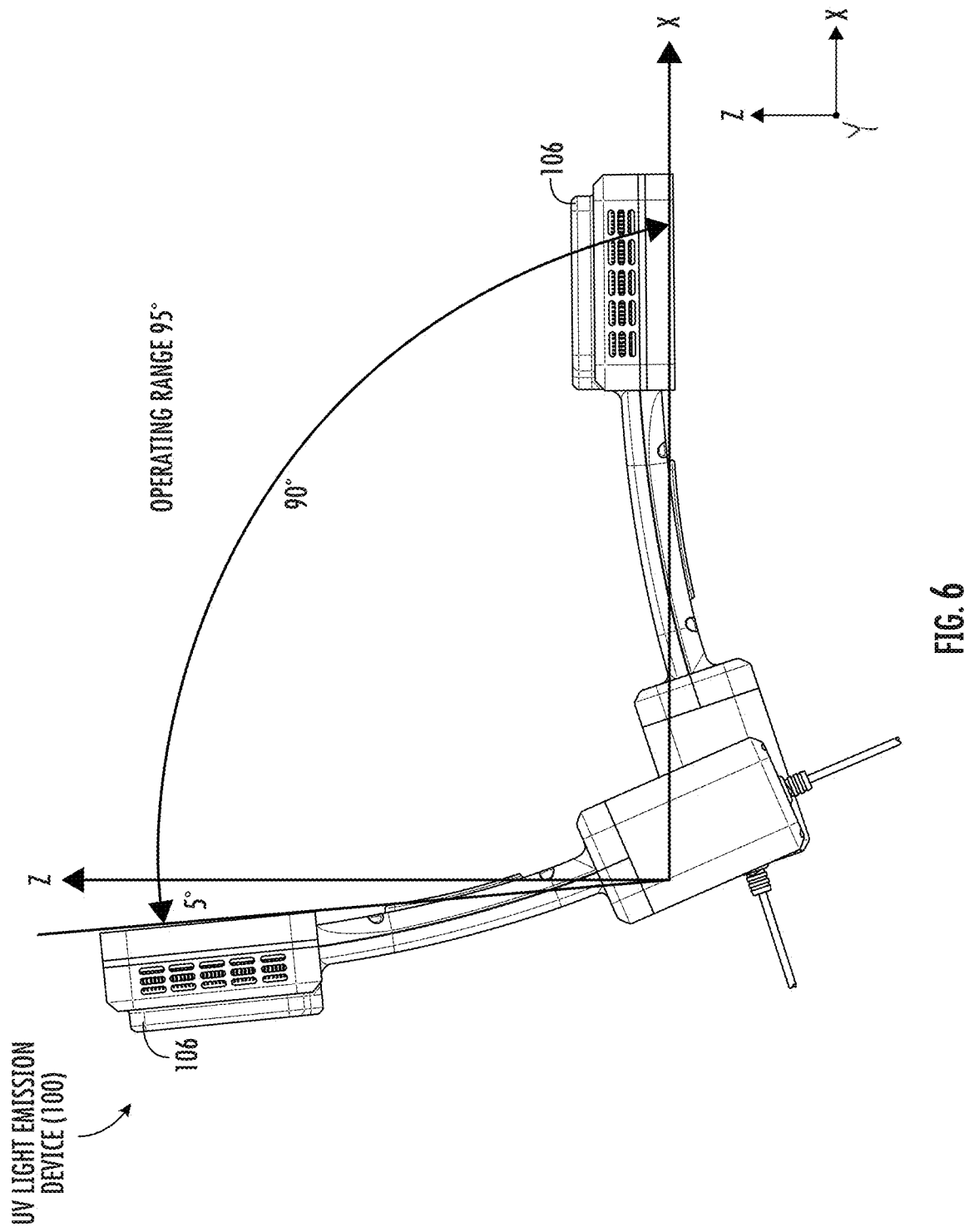
FIG. 6 is a diagram illustrating operational control of the UV light source in the UV light emission device in FIGS. 1A-1C based on orientation of the UV light emission device.

The IMU circuit 546 can also be configured to generate an acceleration (or force) signal 548 to indicate the amount of g-force imposed on the UV light emission device 100 as a drop detect safety feature, for example. If the g-force on the UV light emission device 100 is detected by the electronic control system 404 to exceed a defined force threshold level, the detect latch 522 can be activated to register this error condition and inform the controller circuit 524. The controller circuit 524 can disable the UV light emission device 100 if desired, for example. This detected error condition in the detect latch 522 could cause the controller circuit 524 to disable the power enable switch 530 to discontinue distribution of the power signal 504 to the light driver circuits 400(1)-400(4) so that light is not emitted from the UV light source 102. In one example, the IMU circuit 546 is configured to generate the force signal 547 to cause the detect latch 522 to register the drop detection error if the g-force measured exceeds 7G. 7G of force was found to be the equivalent of an approximate two (2) foot drop of the UV light emission device 100. For example, FIG. 6 is a diagram illustrating control of operation of the UV light emission device 100 in FIGS. 1A-1C based on orientation of the UV light emission device 100 detected by the IMU circuit 546 in the electrical control system 404 in FIG. 5. As shown in FIG. 6, the UV light emission device 100 is shown moving in an X-Z plane, where Z is a height direction from the ground and X is a horizontal direction parallel to the ground. In this example, the IMU circuit 546 detects the angular orientation, which is shown as the light source head 106 between 0 and 90 degrees. In this example, the controller circuit 524 is configured to continue to generate the power enable signal 533 in a power enable state if the IMU circuit 546 detects the angular orientation, which is shown as the light source head 106 between 0 and 90 degrees. When the controller circuit 524 detects that the angular orientation of the UV light emission device 100 is more than five (5) degrees beyond its permitted angular range of 0 to 90 degrees (or 95 degrees from the Z plane parallel to ground), in this example, the controller circuit 524 is configured to generate the power enable signal 533 in a power disable state to disable the power enable switch 530 to disable power distribution of the power signal 504 to the light driver circuits 400(1)-400(4), as shown in FIG. 5.

With reference back to FIG. 5, the electrical control system 404 also includes the light driver circuits 400(1)-400(6). As previously discussed, in this example, the light driver circuits 400(1)-400(3) are provided on a first light driver PCB 402, and the light driver circuits 400(4)-400(6) are provided on a second light driver PCB 403 (see also, FIG. 2). The light driver circuits 400(1)-400(6) are configured to generate current signals 550(1)-550(6) on current outputs 551(1)-551(6) to respective light strings 206(1)-206(6) and a driver circuit 552(1)-552(6) that drives the visible light indicators 423 configured to emit light to the visible light ring 148. In this example, the respective light strings 206(1)-206(6) and visible light indicators 423 are coupled to the same node that is coupled to the respective current outputs 551(1)-551(6) so that it is guaranteed that the visible light indicators 423 will receive current 553 if the respective light strings 206(1)-206(6) receive current 553 for safety reasons. For example, the visible status indicators 143 may be the SunLED right angle SMD chip LED, Part XZFBB56 W-1. In this manner, the user will be able to visibly detect light emanating from the visible light ring 148 when the light strings 206(1)-206(6) are emitting the UV light 104. As a safety mechanism, a current sense circuit 554(1)-554(6) is provided for each light driver circuit 400(1)-400(6) to sense the current signals 550(1)-550(6) generated on the current outputs 551(1)-551(6) by the light driver circuits 400(1)-400(6). The current sense circuits 554(1)-554(6) are each configured to generate current sense signals 556(1)-556(6) on the communication bus 549 to be received by the controller circuit 524 to determine if the light driver circuits 400(1)-400(6) are operational as a diagnostic feature. For example, if a LED in the light string 206(1)-206(6) has failed, causing an open circuit, this can be detected by the lack of current in the current sense signals 550(1)-550(6). This will cause the overall current in the current signal 550(1)-550(6) to change. For example, the current sense signals 556(1)-556(2) may indicate an initialize state, a test ok state indicating a current is sensed in a test state, an ok state indicating current is sensed in an operational state, or an error state. For example, the controller circuit 524 can be configured to determine if the current signal 550(1)-550(6) changed in current based on the received the current sense signals 556(1)-556(6) on the communication bus 549. The controller circuit 524 can be configured to detect an open circuit if the current drops by more than a defined threshold amount of current.

In certain embodiments, the controller circuit 524 is configured to cause a respective LED driver circuit 400(1)-400(6) to automatically compensate for an open circuit in the UV LEDs 110 and visible lights 208(1)-208(4) in a respective light string 206(1)-206(6) of the UV light source 102. As discussed above with regard to FIG. 7, each light string 206(1)-206(6) has three (3) LEDs, which either all UV LEDs 100 or a combination of the UV LEDs 110 and visible light indicator 208, connected in series with another series-connected three (3) LEDs 110, 208 of all UV LEDs 100 or a combination of the UV LEDs 110. The light strings 206(1)-206(6) are connected in parallel. If UV LEDs 100 or a visible light indicator 208 in a three (3) LED, series-connected string incurs an open circuit, the controller circuit 524 can detect this condition by the current drop as discussed above. The current/voltage sense ICs 854(1)-854(6) and/or the controller circuit 524 can be configured to automatically compensates for the loss of a three (3) LED series-connected string that has an open circuit light string 206(1)-206(6) by increasing (e.g., doubling) the current signals 550(1)-550(6) the parallel three (3) series connected LED string in the same light string 206(1)-206(6) to maintain the same output energy in a given light string 206(1)-206(6). Each parallel LED string in the light string 206(1)-206(6) has a constant current source. Thus, normally, 50% of the current in current signals 550(1)-550(6) will flow in each parallel LED string. If one of parallel LED strings becomes open circuited, then 100% of the current of a respective current signal 550(1)-550(6) from a respective LED driver circuit 400(1)-406(6) will flow in the other remaining parallel LED strings in a given light string 206(1)-206(6). The optical output power emitted by a parallel LED string is directly proportional to current in the respective current signal 550(1)-550(6) so the optical output of the remaining parallel LED string in a given light string 206(1)-206(6) will compensate for the open-circuited parallel LED string. If parallel LED strings in a given light string 206(1)-206(6) have an open circuit, an error condition would be generated by the controller circuit 524.

Temperature sensor circuits 558(1)-558(6) are also provided in the UV light source 102 and are associated with each light string 206(1)-206(6) to detect temperature of the light strings 206(1)-206(6) based on their emitted light as driven by the current signals 550(1)-550(6) from the light driver circuits 400(1)-400(6). The temperature sensor circuits 558(1)-558(6) are configured to generate temperature detect signals 560(1)-560(6) on the communication bus 549 to be received by the controller circuit 524 to detect over-temperature conditions in the UV light source 102. For example, the temperature detect signals 560(1)-560(6) may indicate an initialize state, a test ok state indicating a current and voltage is sensed in a test state, an ok state indicating current and voltage is sensed in an operational state, or an error state. The controller circuit 524 is configured to control the power enable switch 530 to discontinue power distribution to the light driver circuits 400(1)-400(6) in response to detecting an over-temperature condition. Also, the temperature detect signals 560(1)-560(6) may be provided to the safety circuit 518 to allow the safety circuit 518 to disable the safety switch 512 to disable power distribution independent of the controller circuit 524 being operational. The temperature sensor circuits 536(1) may be configured for the temperature threshold to be set or programmed.

It is also noted that memory may be provided in the electrical control system 404 in FIG. 5 to record conditions present. For example, the memory may be a non-volatile memory (NVM). For example, the controller circuit 524 may include an NVM 562 on-chip that can be used to record data that can later be accessed. For example, a USB port 564 may be provided in the electrical control system 404 that can be interfaced with the controller circuit 524 to access the data in the NVM 562. The electrical control system 404 could also include a Wi-Fi or Bluetooth interface for transfer of data. An Ethernet port could also be provided in addition or in lieu of the USB port 564. This is discussed in more detail below.

Figure 7:
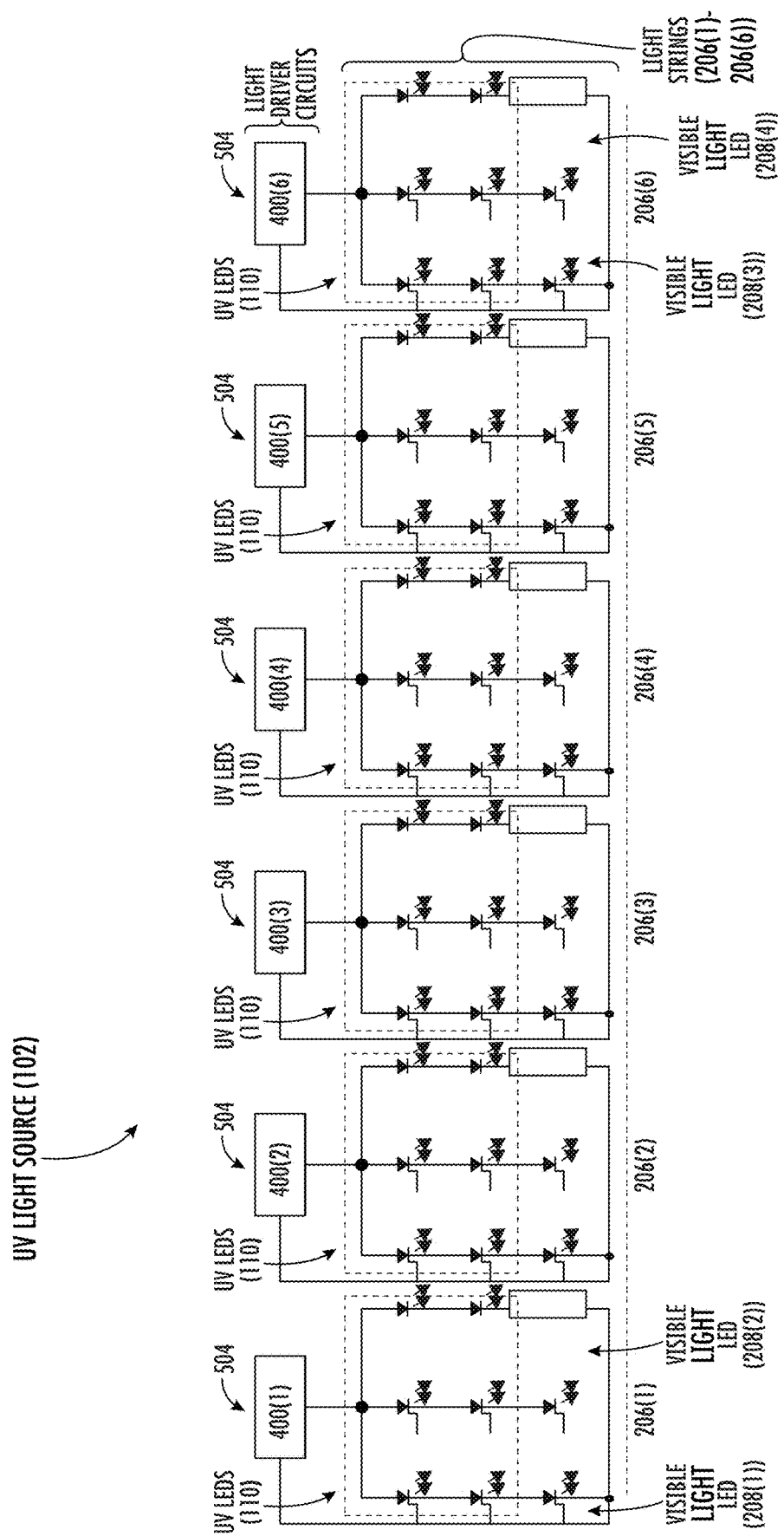
FIG. 7 is an electrical diagram of light-emitting devices of the UV light source of the UV light emission device in FIGS. 1A-1C.

FIG. 7 is an electrical diagram of the light strings 206(1)-206(6) in the UV light source 102 in the UV light emission device 100 in FIGS. 1A-1C compatible with the mechanical diagram of the UV light source 102 in FIG. 2. As shown in FIG. 6, each light string 206(1)-206(6) in this example has six (6) LEDs. Light string 206(1) and 206(6) include four UV LEDs 110 and the two (2) visible lights 208(1)-208(2), 208(3)-208(4), respectively, as previously described in FIG. 2. Each light string 206(1)-206(6) is driven by its respective light driver circuit 400(1)-400(6), as previously discussed. As also previously discussed, the light strings 206(1) and 206(6) that include visible lights 208(1)-208(2), 208(3)-208(4) are coupled together in series so that if the UV LEDs 110 in such light strings 206(1), 206(6) receive power to emit light, the visible lights 208(1)-208(2), 208(3)-208(4) will also receive current to emit light as an indicator to the user of the UV light emission device 100 as a safety feature.

Figure 8:
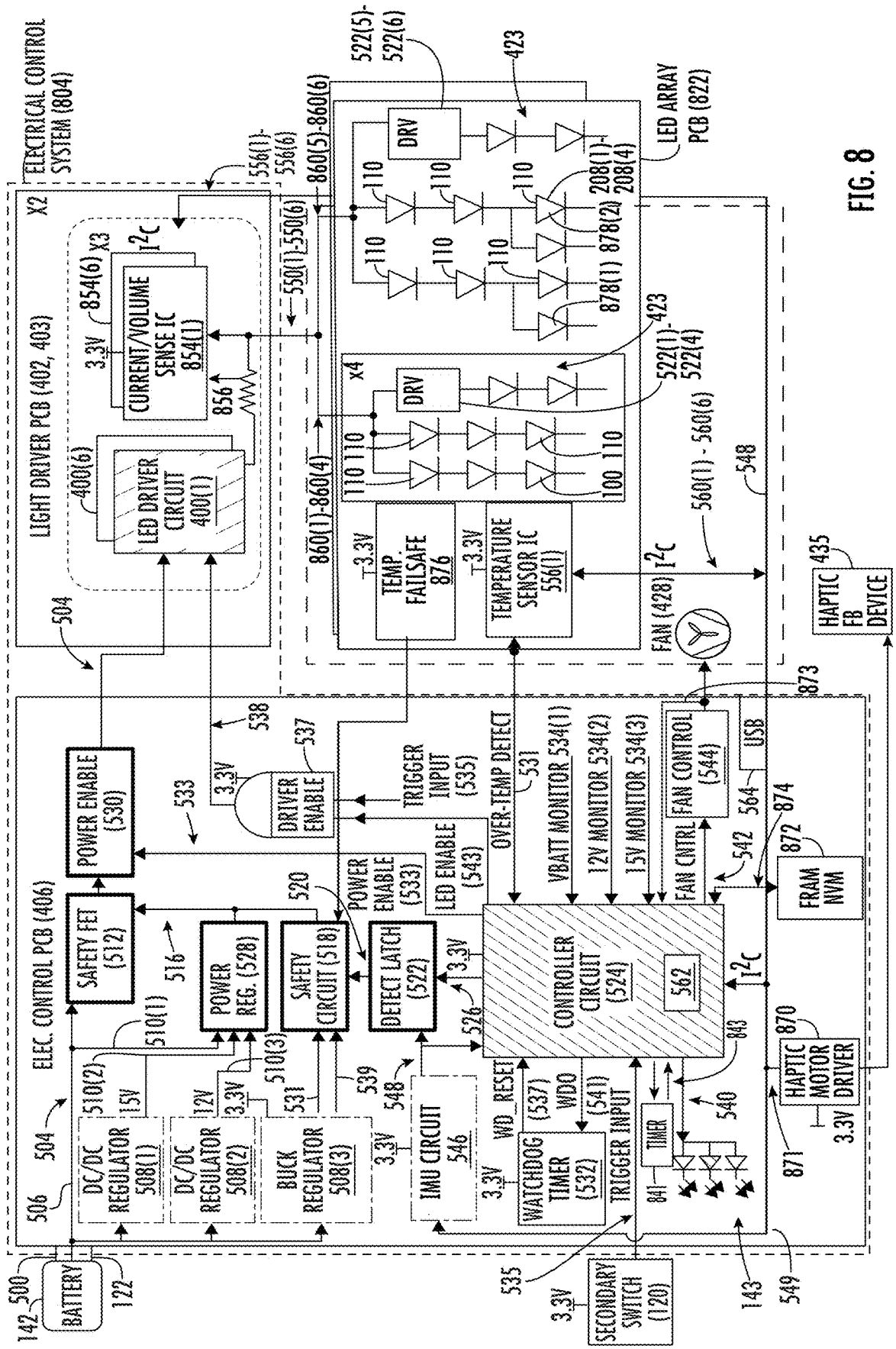
FIG. 8 is a schematic diagram of another exemplary electrical control system that can be included in the UV light emission device in FIGS. 1A-1C.

FIG. 8 is a schematic diagram of another exemplary electrical control system 804 that can be included in the UV light emission device 100 in FIGS. 1A-1C. Shared common components between the electrical control system 804 in FIG. 8 and the electrical control system 404 in FIG. 4 are shown with common element numbers between FIGS. 4 and 8. These common components will not be re-described in FIG. 8.

With reference to FIG. 8, in this example, the electrical control system 804 includes the haptic motor driver 870. A haptic motor driver 870 is coupled to the communication bus 549. As discussed in more detail below, the controller circuit 524 is configured to issue a haptic enable signal 871 to the haptic motor driver 870 to activate the haptic motor driver 870 and to control the spin of the haptic motor driver 870 as desired. The haptic motor driver 870 is coupled to the haptic feedback device 435 outside of the electronic control system 804 and disposed in the UV light emission device 100, as shown in FIG. 4A.

With continuing reference to FIG. 8, in this example, the electronic control system 804 also includes the ability of the controller circuit 524 to control a timer circuit 841, The controller circuit 524 can initiate a timer circuit 841 to increment a counter based on a clock signal. The timer circuit 841 can issue a timer signal 843 to provide a count value of the timer to the controller circuit 524 to maintain one or more counters. For example, the controller circuit 524 can be configured to use the timer signal 843 from the timer circuit 841 to accumulate a total time (e.g., hours) of usage of the UV light source 102 is activated to track its operational age. The total accumulated time representing the operational age of the UV light source 102 can be stored in FRAM NVM 872 and/or NVM 562. The controller circuit 524 could be configured to deactivate the LED driver circuits 406(1)-406(6) and not allow the UV light emission device 100 to be reactivated after the operational age of the UV light source 102 exceeds a defined threshold. An error condition can be generated in this instance by the controller circuit 524 and recorded in a status register in the FRAM NVM 872 and/or the NVM 562. The controller circuit 524 can also use the timer circuit 841 to maintain other counters that can be used for tracking time of tasks and for timeout purposes.

With continuing reference to FIG. 8, in this example, the electronic control system 804 also includes a FRAM NVM 872. The FRAM NVM 872 is located off-chip from the controller circuit 524. The FRAM NVM 872 is coupled to the controller circuit 524 via an interface bus 874. As discussed in more detail below, the FRAM NVM 872 is provided to store data for the UV light emission device 100, such as its serial number, date of last service, usage time, and error codes, etc. This serial number and date of last service can be stored in the FRAM NVM 872 at manufacture or service. The controller circuit 524 is configured to store usage time and error codes in the FRAM NVM 872 at run time. The data in the FRAM NVM 872 can be accessed remotely through the USB port 564, for example.

With continuing reference to FIG. 8, in this example, the fan 428 of the electronic control system 804 can include the ability to generate a tachometer feedback signal 873 that can be provided to the controller circuit 524. The controller circuit 524 can detect the speed of the fan 428 based on the information in the tachometer feedback signal 873 to verify and variably control the fan 428 speed in a closed-loop manner.

With continuing reference to FIG. 8, in this example, the electronic control system 804 includes an LED array PCB 822 that has differences from the LED array PCB 422 in the electronic control system 404 in FIG. 5. In this regard, the LED array PCB 822 also includes a temperature failsafe circuit 876 that is configured to generate a signal to the safety circuit 518 if the detected temperature is outside a desired temperature range. This is because it may be desired to disable the UV light source 102 and/or UV light emission device 100 if its temperature exceeds a temperature outside a designated temperature range for safety reasons. The safety circuit 518 can disable the safety FET 512 in response to a detected temperature by the temperature failsafe circuit 876 outside the desired temperature range.

With continuing reference to FIG. 8, in this example, the LED array PCB 822 of the electronic control system 804 includes the driver circuits 552(1)-552(6) to drive the light strings 206(1)-206(6) as in the electronic control system 404 in FIG. 5. However, in this example, two of the light strings 206(5), 206(6) each include two additional current sources 878(1), 878(2) coupled in parallel to respective visible light indicator 208(1)-208(4), which were previously described. The additional current sources 878(1), 878(2) draw some of the current driven from the respective driver circuits 552(5), 552(6) to the visible light indicator 208(1)-208(4) in the light strings 206(5), 206(6) to regulate or limit their brightness. This is done because, in this example, the current driven to the UV LEDs 110 is also driven to the visible light indicator 208(1)-208(4) as being coupled in series. However, the amount of current desired to be driven to the UV LEDs 110 may be more current than desired to be driven to the visible light indicator 208(1)-208(4). For example, it may be desired to drive more current to the UV LEDs 110 for effective decontamination, whereas that same current level may cause the visible brightness of the visible lights 208(1)-208(4) to be greater than desired. For example, the additional current sources 878(1), 878(2) could be resistors.

With continuing reference to FIG. 8, in this example, the light driver PCBs 402, 403 in the electronic control system 804 are also configured with current/voltage sense circuits 854(1)-854(6) for each respective light string 206(1)-206(6). This is opposed to only including current sense circuits 554(1)-554(6) like in the electronic controls system 404 in FIG. 5. In this manner, as discussed in more detail below, the current/voltage sense circuits 854(1)-854(6) can also detect voltage driven to the respective light strings 206(1)-206(6) to detect a short circuit in the light strings 206(1)-206(6). A current sense resistor 856 is provided between the current/voltage sense circuits 854(1)-854(6) and the light strings 206(1)-206(6). If, for example, a UV LED 110 fails in its light string 206(1)-206(6), creating a short circuit in its respective light string 206(1)-206(6), this failure may not be detectable by the human eye, because the UV LED 110 emits UV light in the non-visible UV spectrum. Current sensing is not used to detect a short circuit in the light strings 206(1)-206(6) because the current signals 550(1)-550(6) driven by the LED driver circuits 400(1)-406(2) to the light strings 206(1)-206(6) does not change. However, a short circuit in a UV LED 110 or visible light indicator 208(1)-208(4) will cause a voltage drop in its light string 206(1)-206(6) that can be detected by sensing voltage. This is because the same voltage is applied in parallel to each of the light strings 206(1)-206(6). Thus, a short circuit in one of the light strings 206(1)-206(6) will present a different resistance in that light string 206(1)-206(6) versus the other light strings 206(1)-206(6), thus cause a different voltage divide across its UV LED 110 and/or visible light indicator 208(1)-208(4).

As discussed above, the electronic control systems 404, 804 in FIGS. 5 and 8 are configured to detect a short circuit in a LED 110, 208 in a light string 206(1)-206(6) of the UV light source 102. The current/voltage sense circuits 854(1)-

854(6) are configured to detect a sensed voltage signal 860(1)-860(6) in its respective light string 206(1)-206(6) to detect a short circuit in a light string 206(1)-206(6). This is because a short circuit in a UV LED 110 or visible light indicator 208(1)-208(4) in a given light string 206(1)-206(6) will cause a voltage drop in its respective light string 206(1)-206(6) that can be detected by sensing voltage. This is because the same voltage is applied in parallel to each of the light strings 206(1)-206(6). Thus, a short circuit in one of the light strings 206(1)-206(6) will present a different resistance in that light string 206(1)-206(6) versus the other light strings 206(1)-206(6). However, process and temperature variations can cause the normal voltage drop across the UV LEDs 110 and/or visible light indicator 208(1)-208(4) in a given light string 206(1)-206(6) to vary without a short circuit. Thus, when a current/voltage sense circuit 854(1)-854(6) detects a voltage at a given light string 206(1)-206(6), it is difficult to determine if the change in voltage in a given light string 206(1)-206(6) is normal or the result of a short circuit in the respective light string 206(1)-206(6).

In this regard, in examples disclosed herein, to compensate for a variation in voltage drop across UV LED 110 and/or visible light indicator 208(1)-208(4) in a given light string 206(1)-206(6) due to process and/or temperature variations, the controller circuit 524 in the electronic control system 404, 804 in FIGS. 5 and 8 can be configured to compensate for variability in voltage drop across UV LED 110 and/or visible light indicator 208(1)-208(4) in a given light string 206(1)-206(6) for detecting a short circuit. In this regard, the current/voltage sense circuits 854(1)-854(6) can be configured to measure the voltage at each light string 206(1)-206(6) at manufacture time as a baseline voltage. The measured baseline voltages for each light string 206(1)-206(6) can be stored in a voltage limit table in the NVM 562 and/or FRAM NVM 872. During operation, the controller circuit 524 can then read in the measured baseline voltages from the voltage limit table for each light string 206(1)-206(6) from NVM 562 and/or FRAM NVM 872 and set a threshold voltage value as a percentage change of such measured baseline voltages for detecting a short circuit. Thus, during normal operation of the UV light emission device 100, if the controller circuit 524 determines based on the sensed voltages for the light strings 206(1)-206(6) by the respective current/voltage sense circuits 854(1)-854(6) that the sense voltages deviate beyond the threshold voltage levels calibrated for the respective light strings 206(1)-206(6), the controller circuit 524 can generate a short circuit error and inform the user through an error state as shown in FIG. 9 for example and/or through the haptic feedback device 435.

Figure 9:
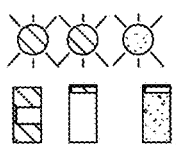
FIG. 9 is a diagram of operational states according to execution of a state machine in the UV light emission device in FIGS. 1A-1C that can be executed by the controller circuit in the electrical control system in FIG. 5 or 8, for example.

Now that the exemplary mechanical, electrical, and optical features and components of the exemplary UV light emission device 100 in FIGS. 1A-1C have been discussed, exemplary operational aspects of the UV light emission device 100 are now discussed in more detail with regard to FIG. 9. FIG. 9 is a diagram of the state machine that can be executed by the controller circuit 524 in the electrical control system 404 in FIG. 5 and/or the electrical control system 804 in FIG. 8 and implemented by other components that are not controlled by the controller circuit 524 to control the operation of the UV light emission device 100. In FIG. 9, states are indicated under the "State" column and include "Power On," "Power-On Self-Test (POST)," "MONITOR," "RECOVERABLE ERROR," "BATTERY LOW," and "LATCHED ERROR" states. The "Power On," "POST," "MONITOR," "RECOVERABLE ERROR," and "BATTERY LOW" states also have sub-states. The conditions of the communication bus 549 inputs, the failsafe inputs, and the controller circuit 524 outputs are shown with their respective signal names and labels in reference to FIGS. 5 and 8 (for features that are provided by the additional components in FIG. 8). A '0' indicates an error condition present for an input or a disable state for an output. A '1' indicates no error condition for an input or an enable state for an output. An 'X' indicates a don't care (i.e., no concern) condition. An "OK" condition indicates an ok status where no error condition is present. An "INIT" condition indicates that the device for the stated input is in an initialization phase. A "Control" condition for the fan 428 indicates that the controller circuit 524 is controlling the speed of the fan 428 through the fan control signal 542 according to the temperature from the temperature detect signals 560(1)-560(6). Note that for signals that are replicated for different light strings 206(1)-206(6) and light driver circuits 400(1)-400(6), any error in any of these signals is indicated as a '0' condition in the state machine.

With reference to FIG. 9, when the primary switch 122 (FIG. 1A-1C) of the UV light emission device 100 is activated by a user, the UV light emission device 100 is in a "Power On" state as indicated in the "State" column. The state of the trigger signal 535 of the secondary switch 120 (Trigger) is a don't care condition (X). The power enable signal 533, the light enable signal 543, and fan control signal 542 are in a disable state automatically upon initialization as indicated by a '0' in the "Power On" state to disable the UV light source 102 and since the controller circuit 524 is not yet operational in the "Power On" state. The current sense signals 556(1)-556(2), the temperature detect signals 560(1)-560(6), and the accelerometer or orientation signal 548 are in an initialization (INIT) state for testing. The fail-safe inputs of power input signals 534(1)-534(3), the analog over-temperature signal 531, the watchdog reset signal 537, the force signal 547, and the timeout signal 843 are treated as don't care situations (X) in the "Power On" state, because the latch reset signal 526 is initially set to a power unsafe state (logic state '1') to disable the safety switch 512 from distributing the power signal 504 as shown in FIGS. 5 and 8. The power enable signal 533 is set to a power disable state (logic '0') to prevent distribution of the power signal 504 to the light driver circuits 400(1)-400(6) for operation in this state. The visual status indicator 143 will be pulsed between red, yellow, and green colors to indicate the "Power On" state visually to the user. The trigger signal 535 of the secondary switch 120 indicates a '1' value in the +Trigger substate of the "Power On" state when the secondary switch 120 is engaged.

The controller circuit 524 will next transition to the "POST" state if the current sense signals 556(1)-556(2), the temperature sensor circuits 558(1)-558(6), and accelerometer or orientation signal 548 indicate a TEST_OK status meaning that their respective current sense circuits 554(1)-554(6), temperature detection circuits, and the IMU circuit 546 are detected as operational. The fan control signal 542 is controlled as indicated by the "Control" state to activate the fan 428 after the "Power On" state.

With continuing reference to FIG. 9, in the "POST" state, the controller circuit 524 determines if the UV light emission device 100 has any errors or failures on the voltage rails 510(1)-510(3) or if the temperature exceeds a designed threshold temperature in the UV light source 102. The controller circuit 524 receives and analyzes the power input signals 534(1)-534(3) and the analog over-temperature signal 531. If the controller circuit 524 determines if the power input signals 534(1)-534(3) indicate the voltage rails 510

(1)-510(3) have their expected voltages from the DC-DC regulator circuits 508(1)-508(2) as indicated by a logic '1' state and if the analog over-temperature signal 531 generated by the temperature sensor circuit 536 indicates a temperature below the preset temperature threshold as indicated by the logic '1' state, the controller circuit 524 enters a "Post-OK" sub-state of the "POST" state. The latch reset signal 526 is set to a power save condition (logic '0') to allow the power enable switch 530 to enable distribution of the power signal 504 to the light driver circuits 400(1)-400(6). However, the power enable signal 533 is set to a power disable state (logic '0') to prevent distribution of the power signal 504 to the light driver circuits 400(1)-400(6) for operation in this state. In the "Post-OK" sub-state, the visual status indicator 143 will be solid green in colors to indicate the "Post-OK" sub-state visually to the user that no errors have yet been detected, and the controller circuit 524 will enter the "MONITOR" state for normal operation. The controller circuit 524 activates the haptic motor driver 870 to activate the haptic feedback device 435 to the user if the user engages the secondary switch 120.

However, if the controller circuit 524 determines if the power input signals 534(2)-534(3) indicate the voltage rails 510(2)-510(3) have their expected voltages from the DC-DC regulator circuits 508(2)-508(3) as indicated by a logic '1' state, and if the analog over-temperature signal 531 generated by the temperature sensor circuit 536 determines the power input signal 534(1) for voltage rail 510(1) is lower than expected in the "POST" state, this is an indication of the battery 142 having a low charge. In response, the controller circuit 524 enters the "Battery Low" sub-state of the "POST" state. In the "Battery low" sub-state of the "POST" state, the visual status indicator 143 will pulse in a pattern of off-red-red states to indicate the "Post OK" sub-state visually, thus indicating the low battery condition to the user. The latch reset signal 526 is still set to a power safe condition (logic '0') to allow the power enable switch 530 to enable distribution of the power signal 504 to the light driver circuits 400(1)-400(6) for operation. However, the power enable signal 533 is set to a power disable state (logic '0') to prevent distribution of the power signal 504 to the light driver circuits 400(1)-400(6) for operation in this state. The controller circuit 524 then enters the "BATTERY LOW" state and remains in this state until the UV light emission device 100 is powered down by switching off the primary switch 122 and repowering the UV light emission device 100 to start up in the "Power On" state. If the battery 142 is not changed or recharged, the UV light emission device 100 will enter the "BATTERY LOW" state again after power-up.

If, in the "Post-OK" sub-state of the "POST" state, the controller circuit 524 determines that a power input signal 534(2)-534(3) indicates its voltage rail 510(2)-510(3) does not have the expected voltages from the DC-DC regulator circuits 508(2)-508(3), or the analog over-temperature signal 531 generated by the temperature sensor circuit 536 is above its defined threshold limit, as indicated by the "ERROR" condition in the "Post error" rows in FIG. 9, this is an indication of a failsafe error condition in which the UV light source 102 of the UV light emission device 100 should not be allowed to operate. In response, the power enable signal 533 is set to a power disable state (logic '0') to prevent distribution of the power signal 504 to the light driver circuits 400(1)-400(6) for operation in this state, and the controller circuit 524 enters a "LATCHED ERROR" state. The controller circuit 524 activates the haptic motor driver 870 to activate the haptic feedback device 435 to the user to indicate the error condition if the secondary switch 120 is engaged by the user as shown in the "error+trig" substate of the "POST" state. In the "LATCHED ERROR" state, the visual status indicator 143 will pulse in pattern of red-off-red states to indicate the "LATCHED ERROR" state. The controller circuit 524 remains in the "LATCHED ERROR" state until the UV light emission device 100 is powered down by switching off the primary switch 122 and repowering the UV light emission device 100 to start up in the "Power On" state.

In the "MONITOR" state, the UV light emission device 100 is ready to be operational to distribute power to the UV light source 102 to emit the UV light 104. This is shown in the "Monitor (ready)" sub-state in FIG. 8, where all signals indicate no error conditions, except that the trigger signal 535 of the secondary switch 120 (Trigger) indicates that the secondary switch 120 is not engaged by a user. Thus, the controller circuit 524 still sets the power enable signal 533 to a power disable state (logic '0') to prevent distribution of the power signal 504 to the light driver circuits 400(1)-400(6) for operation in this state. The latch reset signal 526 was previously latched in a power safe condition (logic '0') to allow the power enable switch 530 to enable distribution of the power signal 504 to the light driver circuits 400(1)-400(6) for operation once the power enable signal 533 is set to a power enable state (logic '1'). In the "Monitor (ready)" sub-state of the "MONITOR" state, the visual status indicator 143 will be generated in a pattern of solid green in color to indicate the "ready" sub-state visually to the user.

Once the trigger signal 535 of the secondary switch 120 (Trigger) indicates that the secondary switch 120 is engaged by a user, the controller circuit 524 enters the "Monitor (trigger+OK)" sub-state of the "MONITOR" state. The power enable signal 533 is set to a power enable state (logic '1') to enable the safety switch 512 to distribute the power signal 504 to the light driver circuits 400(1)-400(6) for operation. The light enable signal 543 is also set to a power enable state (logic '1') to allow the power enable switch 530 to distribute the power signal 504 to the light driver circuits 400(1)-400(6) for operation in this state. In the "Monitor (trigger+OK)" sub-state of the "MONITOR" state, the visual status indicator 143 will be generated in a pattern of solid green in color to visually indicate the operation "ok" status to the user. The UV light emission device 100 will remain in the "MONITOR" state in the "Monitor (trigger+OK)" sub-state or the "Monitor (ready)" sub-state until an error occurs or until the UV light emission device 100 is turned off by the primary switch 122.

The UV light emission device 100 will go into the "MONITOR" state in the "Monitor (trigger+OK+timeout)" sub-state if the UV light emission device 100 has been activated by the secondary switch 120 for too long such that a time out has occurred. In the "Battery low" sub-state of the "POST" state, the visual status indicator 143 will pulse in a pattern of yellow, yellow, off states in this example to indicate to the user to release the secondary switch 120. The controller circuit 524 activates the haptic motor driver 870 to activate the haptic feedback device 435 to the user if the user engages the secondary switch 120.

In the "MONITOR" state, if the controller circuit 524 detects through a timer circuit 841 that the secondary switch 120 has been engaged continuously for more than a defined period of time (e.g., 5 minutes), the controller circuit 524 will enter the "Monitor (trigger+OK+ON-Time)" sub-state. For example, this may be an indication that the secondary switch 120 is being engaged accidentally without an intent by a user to engage, or it may be desired to only allow emission of UV light 104 for a defined period of time without a further disengagement and reengagement of the secondary switch 120 to prevent battery run down. The power enable signal 533 is set to a power disable state (logic '1') to disable the safety switch 512 to halt distribution of the power signal 504 to the light driver circuits 400(1)-400(6) for operation. The light enable signal 543 is also set to a power disable state (logic '1') to disable the power enable switch 530 distributing the power signal 504 to the light driver circuits 400(1)-400(6). The controller circuit 524 will go to the "MONITOR (ready)" sub-state, which will then require a release of the secondary switch 120 and a reengagement of the secondary switch 120 to enter into the "RECOVERABLE ERROR" state to be able to recover once the secondary switch 120 is released and activated again to reactivate the UV light source 102.

In the "MONITOR" state, if the accelerometer or orientation signal 548 generated by the IMU circuit 546 indicates an acceleration or tilt condition that is outside the programmed operational range of the UV light emission device 100, the controller circuit 524 will enter the "Monitor (trigger+tilt)" sub-state. The power enable signal 533 is set to a power disable state (logic '1') to disable the safety switch 512 to halt distribution of the power signal 504 to the light driver circuits 400(1)-400(6) for operation. The light enable signal 543 is also set to a power disable state (logic '1') to disable the power enable switch 530 distributing the power signal 504 to the light driver circuits 400(1)-400(6). The visual status indicator 143 will be generated in a pattern of green-off-green color to indicate the operation "ok" status, but tilt orientation visually to indicate to the user. The controller circuit 524 then goes into the "RECOVERABLE ERROR" state either in the "RECOVERABLE ERROR (trigger)" sub-state (if the secondary switch 120 is engaged) or "RECOVERABLE ERROR (trigger released)" sub-state (when the secondary switch 120 is released). The controller circuit 524 will go to the "RECOVERABLE ERROR (trigger released)" sub-state once the secondary switch 120 is released and no other errors are present. The visual status indicator 143 is also caused to emit a mostly yellow color state followed by a short off state in this example to signify the recoverable error to the user in the "RECOVERABLE ERROR" state. The controller circuit 524 will go to the "MONITOR (ready)" sub-state thereafter if no other errors are present to allow the user to reengage the secondary switch 120 to cause the UV light 104 to be emitted as discussed for this sub-state as discussed above.

Also, while in the "MONITOR" state, if the controller circuit 524 determines that the power input signal 534(1) for voltage rail 510(1) is lower than expected in the "POST" state, this is an indication of the battery 142 having a low charge. In response, the controller circuit 524 enters the "Monitor (battery low+OK)" sub-state of the "MONITOR" state. The power enable signal 533 is set to a power disable state (logic '1') to disable the safety switch 512 to halt distribution of the power signal 504 to the light driver circuits 400(1)-400(6) for operation. The light enable signal 543 is also set to a power disable state (logic '1') to disable the power enable switch 530 distributing the power signal 504 to the light driver circuits 400(1)-400(6). The visual status indicator 143 will be generated in a pattern of off-off-red in color to indicate to the user that the battery is low. The controller circuit 524 activates the haptic motor driver 870 to activate the haptic feedback device 435 to the user if the user is engaging the secondary switch 120 in the "battery low+OK+Trig" substate of the "MONITOR" state. The controller circuit 524 then goes into the "BATTERY LOW" state and will remain in the "BATTERY LOW" state until the UV light emission device 100 is turned off by primary switch 122 and repowered to go back into the "Power On" state. If the battery 142 is not changed, the UV light emission device 100 will enter the "BATTERY LOW" state again after powering up. The visual status indicator 143 is also caused to emit a mostly off state followed by a short red color emission in this example to signify the battery low error to the user in the "BATTERY LOW" state.

Also, while in the "MONITOR" state, if the controller circuit 524 determines that any other error has occurred based on the failsafe inputs or the communication bus 549 inputs as previously described in regard to FIG. 5 or 8, the controller circuit 524 enters the "Monitor (error or Dropped)" sub-state of the "MONITOR" state. The power enable signal 533 is set to a power disable state (logic '1') to disable the safety switch 512 to halt distribution of the power signal 504 to the light driver circuits 400(1)-400(6) for operation. The light enable signal 543 is also set to a power disable state (logic '1') to disable the power enable switch 530 distributing the power signal 504 to the light driver circuits 400(1)-400(6). The visual status indicator 143 will be generated in a pattern of red-off-red in color to indicate the operation "ok" status, to indicate to the user that the battery is low. The controller circuit 524 activates the haptic motor driver 870 to activate the haptic feedback device 435 to the user if the user is engaging the secondary switch 120 in the "error or Dropped+Trig" substate of the "MONITOR" state.

The controller circuit 524 will go into the "LATCHED ERROR" state and will remain in the "LATCHED ERROR" state until the UV light emission device 100 is turned off by primary switch 122 and repowered to go back into the "Power On" state. A power cycle is required in this example to reset the UV light emission device 100 for the UV light source 102 to be able to be operational again. The visual status indicator 143 is also caused to emit three (3) rapid red color states followed by three (3) slow flashing red color states in this example to signify the latched error to the user in the "LATCHED ERROR" state.

Figure 10:
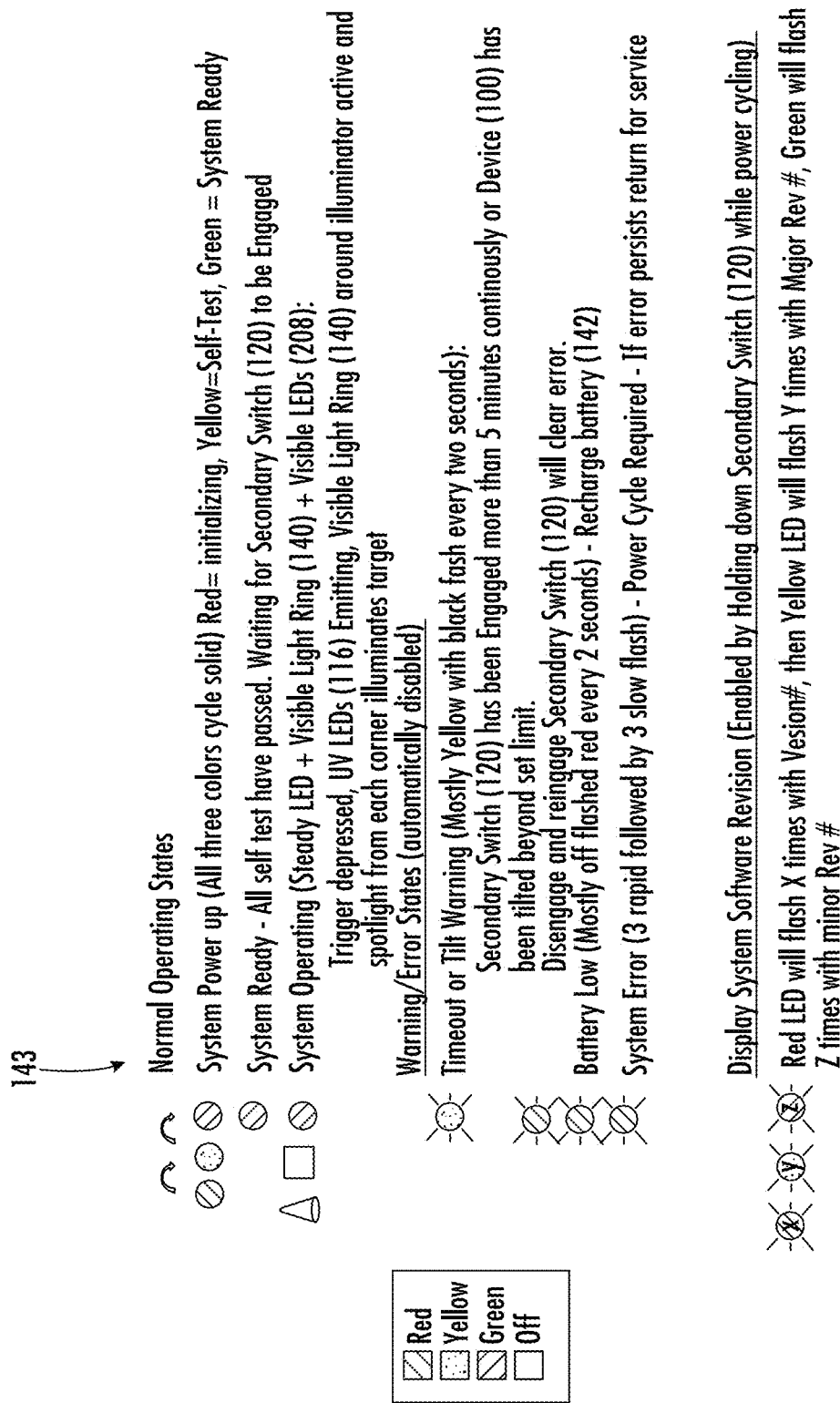
FIG. 10 is a diagram of light patterns and colors controlled to be emitted by the visual status indicator of the UV light emission device in FIGS. 1A-1C based on the operating states and errors of the UV light emission device according to the operational states in FIG. 9.

FIG. 10 illustrates the illumination modes of the visual status indicator 143 by the controller circuit 524 in FIGS. 4 and 8 for normal operating states of "POWER ON," "POST," and "MONITOR" in FIG. 9. FIG. 10 also illustrates the illumination modes of the visual status indicator 143 by the controller circuit 524 in FIGS. 5 and 8 for error operating states of "TILT ERROR, "BATTERY LOW," and "LATCHED ERROR" in FIG. 9. FIG. 10 illustrates the illumination modes of the visual status indicator 143 by the controller circuit 524 in FIGS. 4 and 8 to be able to indicate the software revision number of the software executed by the controller circuit 524.

As discussed above, the electrical control system 404 in FIGS. 5 and 8 may include memory accessible to the controller circuit 524 to record conditions and history of events for the UV light emission device 100. For example, the controller circuit 524 may include the NVM 562 on-chip and FRAM NVM 872 (FIG. 8) that can be used to record data that can later be accessed. As shown in FIG. 8, in this example, the controller circuit 524 is configured to update counters in the NVM 562 for a defined number of events. These events are a drop of the UV light emission device 100 as indicated by the acceleration signal 547, tilt of the UV light emission device 100 as indicated by the accelerometer or orientation signal 548, current sense errors as indicated by the current sense circuits 554(1)-554(6), power supply errors as indicated by the power input signals 534(1)-534(3), communication bus 549 errors, power enable errors as indicated by the power enable signal 533 being generated in a power disable state, temperature errors as indicated by the temperature detect signals 560(1)-560(6), the recoverable errors as indicated by the accelerometer or orientation signal 548, and total accumulated minutes of use. FIG. 8 shows this data that can be recorded by the controller circuit 524 in the NVM 562 and the byte format of such. This recorded data can be accessed through a communication port provided to the controller circuit 524 and can be accessed by an external device via a coupling to the communication port. The NVM 562 can also include a circular buffer that is used to record error codes that are generated by the controller circuit 524 based on detected errors.

Now that exemplary components and states of the UV light emission device 100 have been described, exemplary hardware circuits and processes for the operation of the UV light emission device 100 that can include the electronic control system 404 in FIG. 5 or the electronic control system 804 in FIG. 8, for example, will now be described below.

Figure 11:
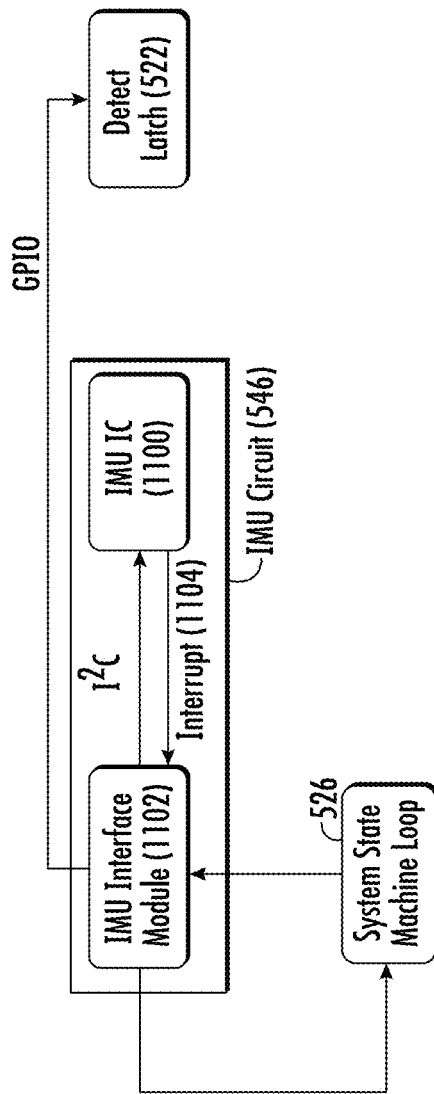
FIG. 11 is a diagram illustrating the IMU circuit operation in the UV light emission device in the electronic control systems in FIGS. 5 and 8.

FIG. 11 is a diagram illustrating the IMU circuit 546 operation in the UV light emission device in the electronic control systems 404, 804 in FIGS. 5 and 8. An IMU integrated circuit (IC) 1100 in the IMU circuit 546 is initialized by the controller circuit 524 through an IMU interface module 1102 coupled to the communications bus 549 with programming in the power-on state with the threshold force to be detected for drop detection of the UV light emission device 100. The IMU IC 1100 is configured to issue an interrupt 1104 in response to detecting a g-force exceeding the threshold force. In response to the interrupt 1104, the detect latch 522 is enabled to disable the light emission from the UV light source 102 of the UV light emission device 100 as previously described. The interrupt 1104 is also communicated to the controller circuit 524 through an IMU interface module 1102 coupled to the communication bus 549. The controller circuit 524 can react in response to the interrupt 1200 based on the operational state in FIG. 9.

Figure 12:
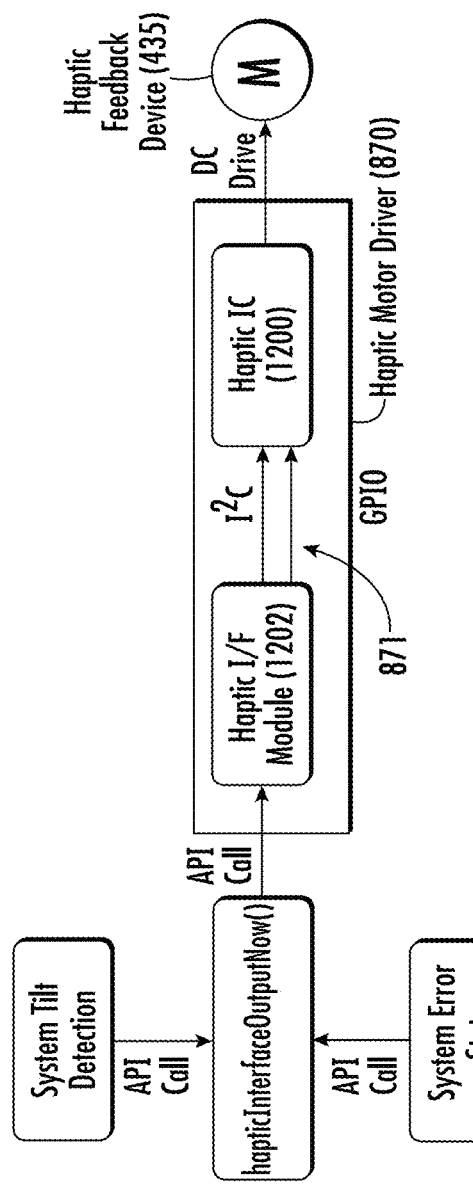
FIG. 12 is a hardware diagram of the haptic feedback device in electronic control systems in FIGS. 5 and 8 of the UV light emission device.

FIG. 12 is a diagram illustrating the haptic motor driver 870 and haptic feedback device 435 in the UV light emission device 100 in the electronic control systems in FIGS. 5 and 8. A haptic integrated circuit (IC) 1200 in the haptic motor driver 870 controls the haptic feedback device 435. The haptic IC 1200 is coupled to a haptic interface module 1202 to communicate commands from the controller circuit 524 to the haptic motor driver 870 to control the haptic feedback device 435. As discussed in the operational state in FIG. 9, the controller circuit 524 is configured to activate the haptic motor driver 870 in response to tilt detection or another error state.

Figure 13A:
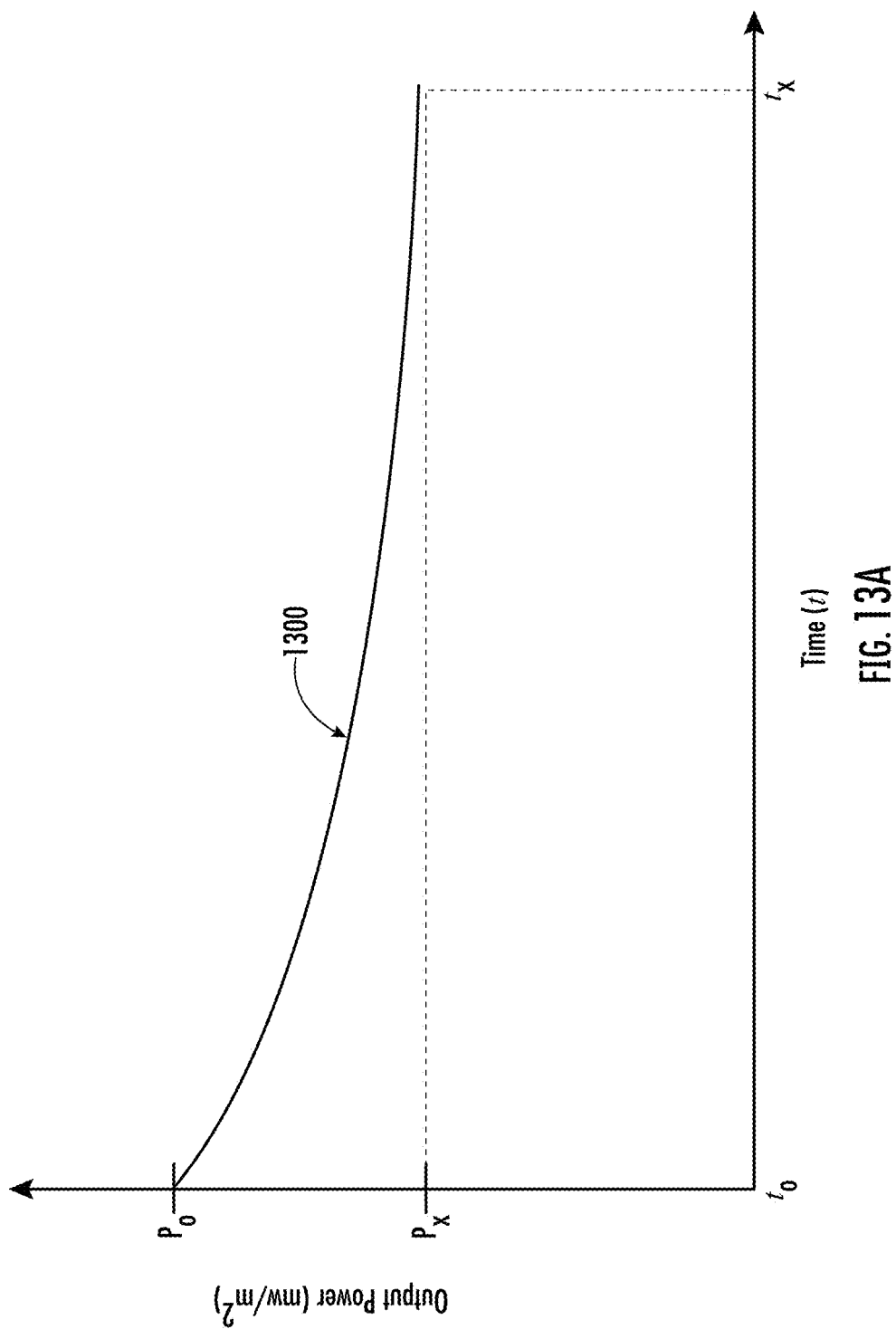
FIG. 13A is a graph illustrating an exemplary degradation in output power of a UV LED over time.

The controller circuit 524 in the electronic control systems 404, 804 in FIG. 5 and FIG. 8 can also be configured to dynamically adjust the power in the current signals 550(1)-550(6) overtime to compensate for the loss in optical performance of the UV LEDs 110 in the light strings 206(1)-206( ) in the UV light source. For example, FIG. 13A illustrates a graph that shows an exemplary power output of UV LEDs 110 from an initial time $t_0$ to a designated time tx (e.g., 5000 hours of operation) for a given fixed amount of current in current signals 550(1)-550(6). As shown in the curve 1300 in FIG. 13A, the power output of UV LEDs 110 degrades over time even though the current level in current signals 550(1)-550(6) remains the same. For example, the output power of a UV LED 110 at time t0 for a given current level may be 14.5 mW/m$^2$, but the output power of a UV LED 110 may degrade to 12 mW/m$^2$ at time tx. It may be desired for the output power of the UV LEDs 110 to not degrade over time.

Figure 13B:
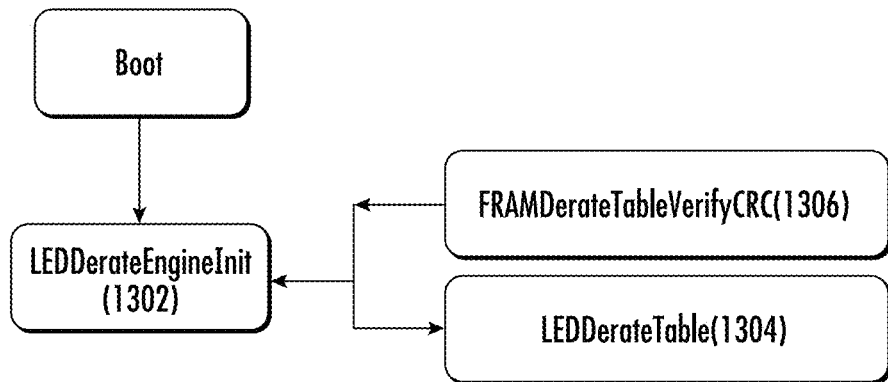
FIGS. 13B and 13C are diagrams of the light source derate operation in the UV light emission device in the electronic control systems in FIGS. 5 and 8.
Figure 13C:
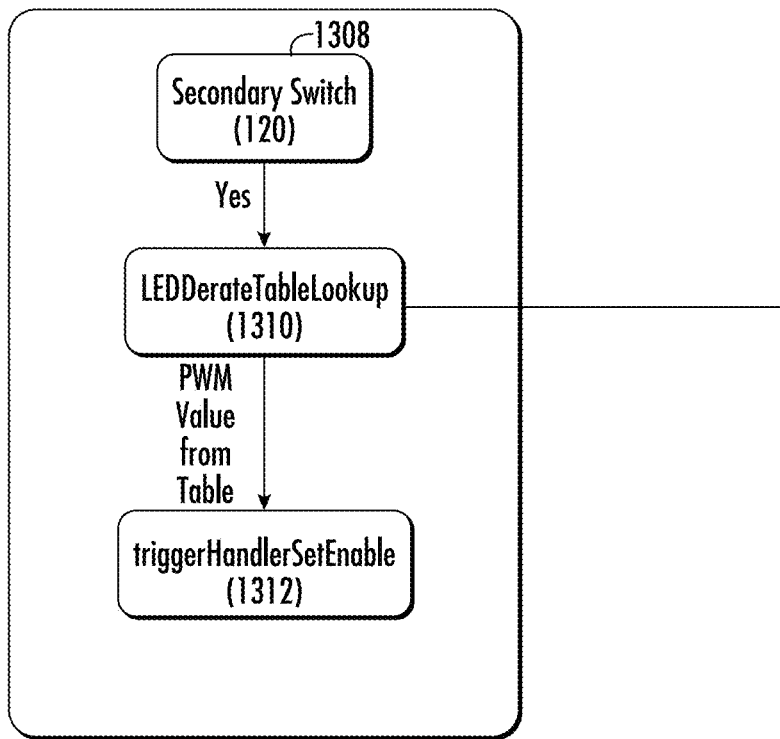

Thus, in an example, the controller circuit 524 may be configured to cause the LED driver circuits 400(1)-406(6) in the UV light source 102 to increasing generate a higher level of current in current signals 550(1)-550(2) over time as the output power of the UV LEDs 110 is known to degrade. In this regard, FIG. 13B illustrates a diagram of the controller circuit 524 operation to compensate for the degradation in output power of the UV LEDs 110 over time. In this regard, at power-on of the UV light emission device 100 and as part of the boot-up operation of the controller circuit 524, the controller circuit 524 executes a LED derate engine 1302 that loads in a LED derate table circuit 1304 from NVM 562 and/or the FRAM NVM 872. The values in LED derate table circuit 1304 can be checked for a parity error checking function 1306. The LED derate table 1304 defines values to allow the controller circuit 524 to predict the light intensity degradation of the UV LEDs 110 over an accumulated usage time. For example, the LED derate table circuit 1304 can be based on empirical data programmed into a look-up table as LED derate values or a formula representing a function for calculated expected light intensity as a function of accumulated usage time. The LED derate table circuit 1304 is used by the controller circuit 524 to set the current level for the LED driver circuits 406(1)-406(6) to generate in the current signals 550(1)-550(6). When the controller circuit 524 enters into a state 1308, as shown in FIG. 13C, in response to the activation of the secondary switch 120 such that the LED driver circuits 406(1)-406(6) are enabled to cause the UV LEDs 110 to emit UV light 104, the controller circuit 524 can consult the LED derate table circuit 1304 to obtain LED derate values based on the accumulated UV LED 110 usage to set the current level for the LED driver circuits 406(1)-406(6) to generate in the current signals 550(1)-550(6).

In one example, the current level of the current signals 550(1)-550(6) can be monitored and controlled based on the sensed current signals 556(1)-556(6) by the current-voltage sense circuits 854(1)-854(6). In another example, the controller circuit 524 can configure the LED driver circuits 406(1)-406(6) to adjust the average current of the current signals 550(1)-550(6) in an open-loop control based on controlling the duty cycle of pulse-width modulated (PWM) of the current signals 550(1)-550(6). If a digital current potentiometer is used to control the current levels of the current signals 550(1)-550(6), the digital current potentiometer can be adjusted for the new current level according to the LED derate table circuit 1304. If PWM is used to control the average current of the current signals 550(1)-550(6), the LED driver circuits 406(1)-406(1) can be controlled to generate the desired average current of current signals 550(1)-550(6), by the controller circuit 524 enabling and disabling the power signal 504 as a PWM signal 1312 according to the determined duty cycle based on the LED derate table circuit 1304.

Figure 14:
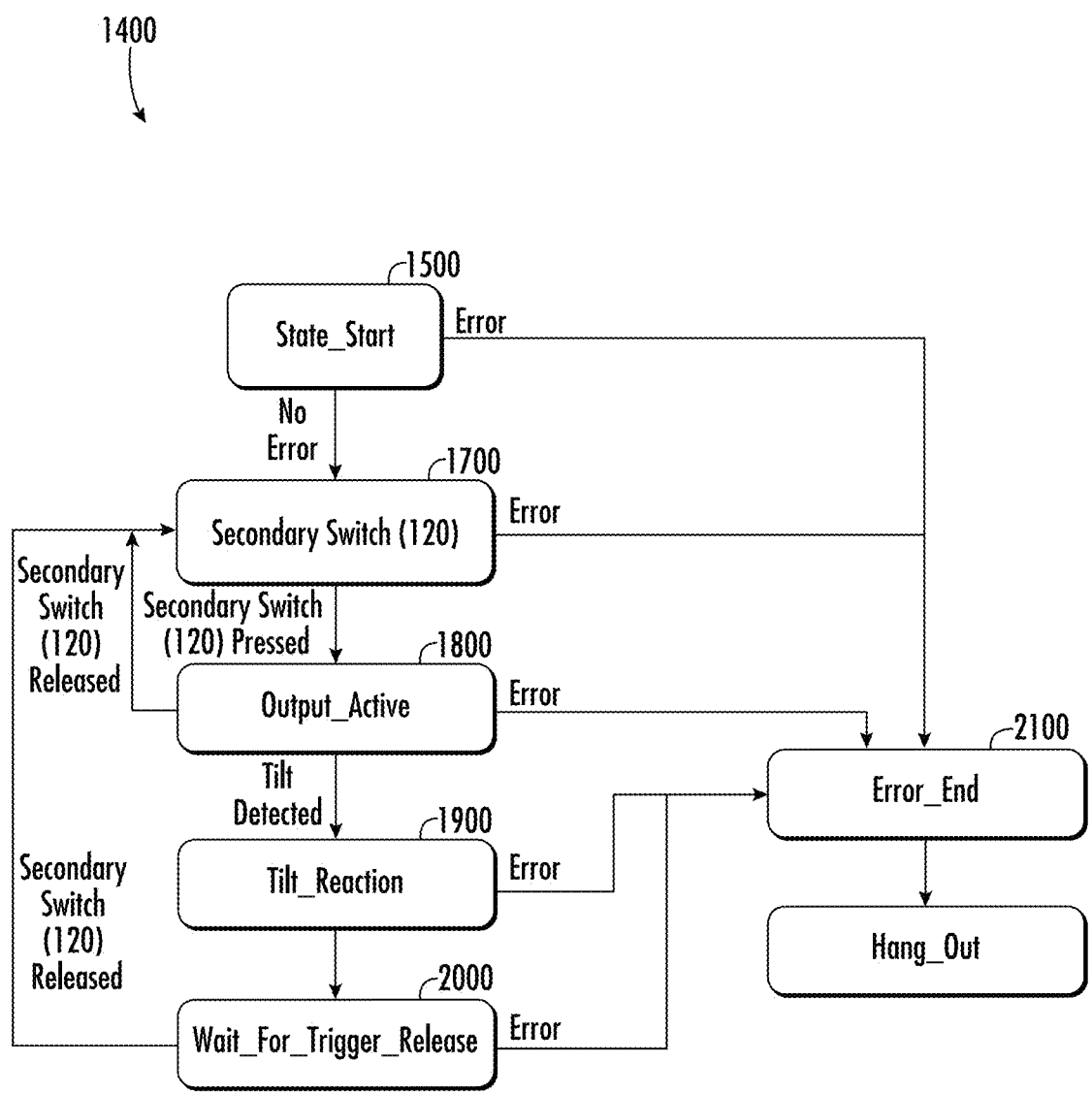
FIG. 14 is a flowchart illustrating an exemplary overall control process for the UV emission device 100 in FIGS. 1A-1C as controlled by the controller circuit in FIGS. 5 and 8.
Figure 15:
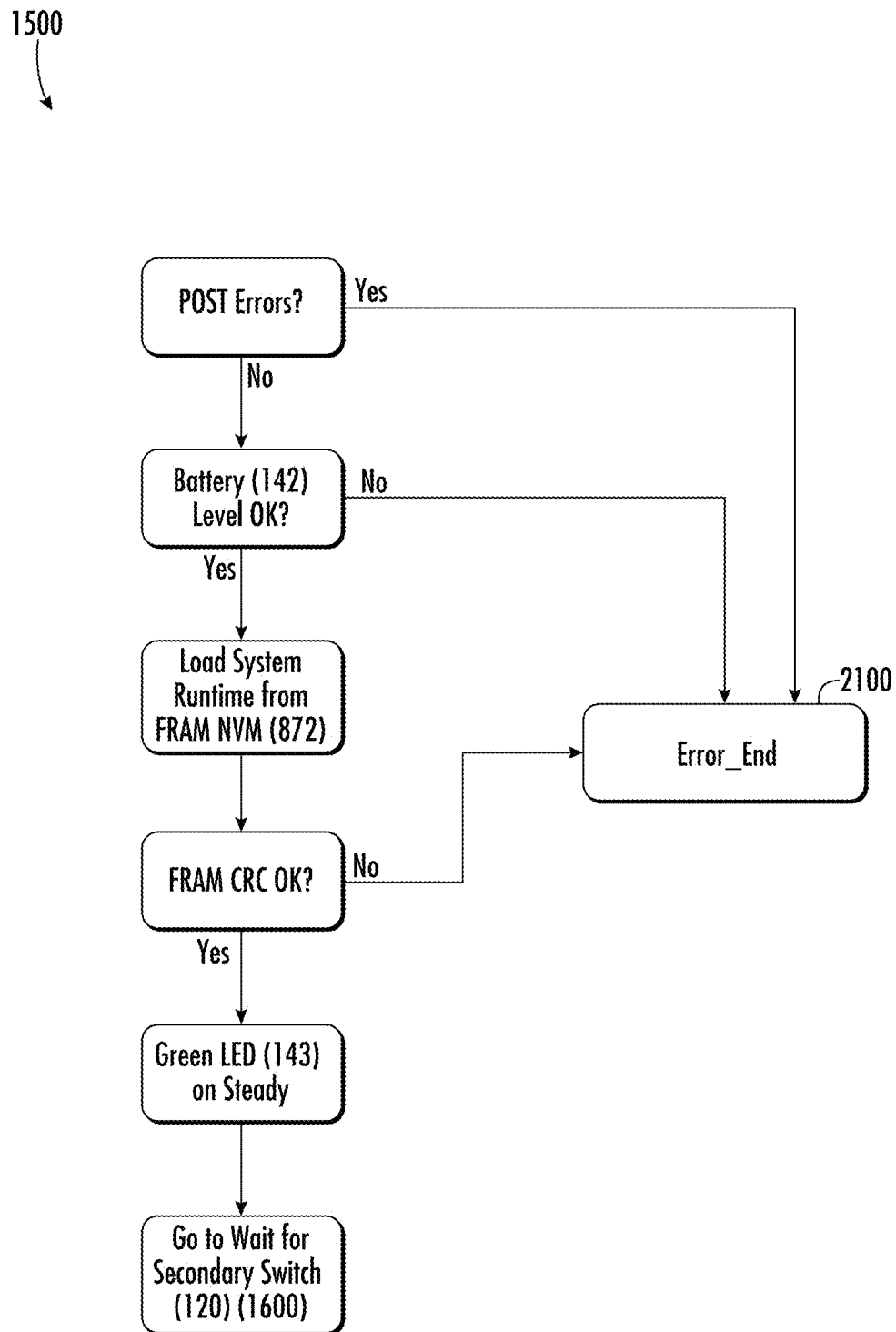
FIG. 15 is a flowchart illustrating an exemplary process for power-on and power-on self-test (POST) states in the overall control process in FIG. 14.

FIG. 14 is a flowchart illustrating an exemplary overall control process 1400 for controlling the overall operation of the UV emission device 100 in FIGS. 1A-1C as controlled by the controller circuit 524 in FIGS. 5 and 8. The process 1400 in FIG. 14 is executed by the controller circuit 524 when powered up/on and booted-up in response to the primary switch 122 being activated. As shown in FIG. 14, the controller circuit 524 executes a system start-up process for the power-on and POST states in the operational state in FIG. 9. The exemplary system start-up process 1500 is shown in FIG. 15 and described below. After the system start-up process 1500, the controller circuit 524 executes a process 1600 in FIG. 16, described below, to wait for the secondary switch 120 to be activated by the user before entering an output active process 1700 in FIG. 17, described below in the MONITOR state discussed in FIG. 9. The controller circuit 524 remains ready and/or in an operational state in the MONITOR state with the UV light source 102 activated subject to activation of the secondary switch 120, until an error occurs or the UV light emission device 100 is powered down by deactivation of the primary switch 122. If an error is detected in the processes 1500-1800, the controller circuit 524 enters into an error state 1402 as discussed in the operational state in FIG. 9 and then waits until the UV light emission device 100 is reactivated according to the error state. The controller circuit 524 is configured to perform a tilt reaction process 1800 in FIG. 18, discussed below, in response to detection of a tilt beyond a tilt threshold or force beyond a force threshold of the UV light emission device 100 from the MONITOR state in process 1700. If tilt or force error occurs, the UV light source 102 is disabled the controller circuit 524 waits for the secondary switch 120 to be released in process 1900 in FIG. 19, discussed below. The UV light source 102 is reactivated by the controller circuit 524 in response to the secondary switch 120 being reactivated.

FIG. 15 is a flowchart illustrating an exemplary process 1500 for power-on and power-on self-test (POST) states in the overall control process in FIG. 14.

Figure 16A:
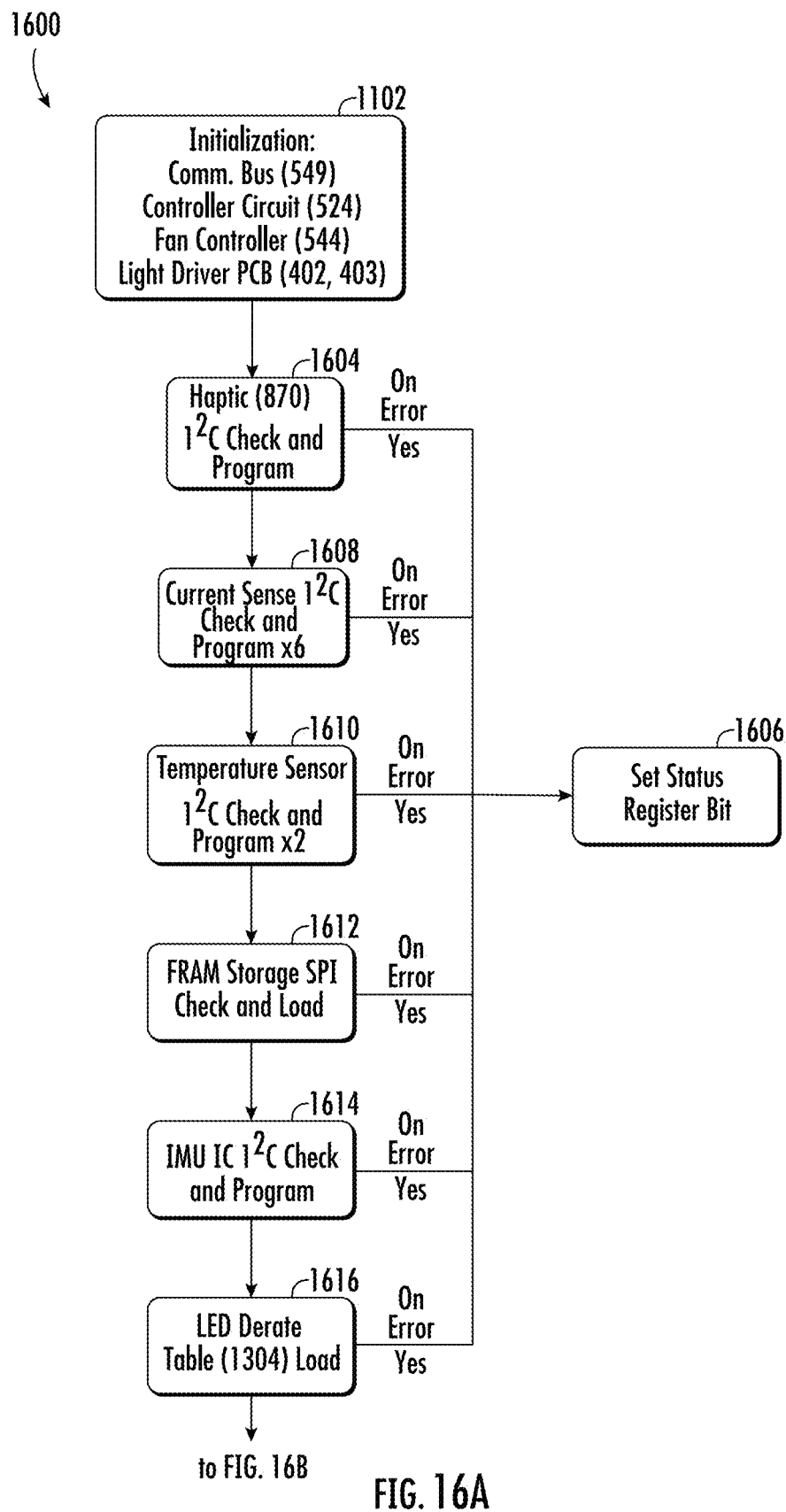
FIGS. 16A and 16B is a flowchart illustrating an exemplary process for error detection in the power-up self-test (POST) state of the UV light emission device.

FIG. 16A is a flowchart illustrating an exemplary process 1600 for a power-on and POST of the UV light emission device 100 in FIGS. 1A-1C that can be performed by the controller circuit 524 in FIGS. 5 and 8. When the primary switch 122 is turned on, power is applied to the electronic control system 404, 804, and its controller circuit 524 in the power-on state as previously discussed in FIG. 9. The controller circuit 404, 804 then goes to the POST state, as discussed in FIG. 9, to initialize the UV light emission device 100. In the power-on state, the communication bus 549, the controller circuit 524, the fan controller 544, and light driver PCB 402, 403 are powered on (block 1602 in FIG. 16A). The controller circuit 404, 804 programs and checks the haptic motor driver 870 via the communication bus 549 (block 1604 in FIG. 16A). If an error occurs, the controller circuit 404, 804 sets an error state in a status bit designated for the haptic motor driver 870 in the NVM 562 and/or FRAM 872 and handles the error condition according to the operational state in FIG. 9 (block 1606 in FIG. 16A). The controller circuit 404, 804 checks the current sense signals 556(1)-556(2) to determine if current is flowing to the light driver PCB 402, 403 (block 1608 in FIG. 16A). If an error occurs, the controller circuit 404, 804 sets an error state in a status bit designated for the current sense in the NVM 562 and/or FRAM 872 and handles the error condition according to the operational state in FIG. 9 (block 1606 in FIG. 16A). The controller circuit 404, 804 checks the analog over-temperature signal 531 for the temperature sensor 536 (block 1610 in FIG. 16A). If an error occurs, the controller circuit 404, 804 sets an error state in a status bit designated for the temperature sense in the NVM 562 and/or FRAM 872 and handles the error condition according to the operational state in FIG. 9 (block 1606 in FIG. 16A). The controller circuit 404, 804 checks the FRAM 872 to determine if it is operational by writing and reading a bit to the FRAM 872 and verifying (block 1612 in FIG. 16A). If an error occurs, the controller circuit 404, 804 sets an error state in a status bit designated for the FRAM 872 in the NVM 562 and handles the error condition according to the operational state in FIG. 9 (block 1606 in FIG. 16A). The controller circuit 404, 804 checks the IMU circuit 546 to determine if it is operational (block 1614 in FIG. 16A). If an error occurs, the controller circuit 404, 804 sets an error state in a status bit designated for the IMU circuit 546 in the NVM 562 and/or FRAM 872 and handles the error condition according to the operational states in FIG. 9 (block 1606 in FIG. 16A). The controller circuit 404, 804 loads the LED derate table circuit (described in more detail below) into the NVM 562 and/or FRAM 872 (block 1616 in FIG. 16A). If an error occurs, the controller circuit 404, 804 sets an error state in a status bit designated for the LED derate table circuit in the NVM 562 and/or FRAM 872 and handles the error condition according to the operational states in FIG. 9 (block 1606 in FIG. 16A).

Figure 16B:
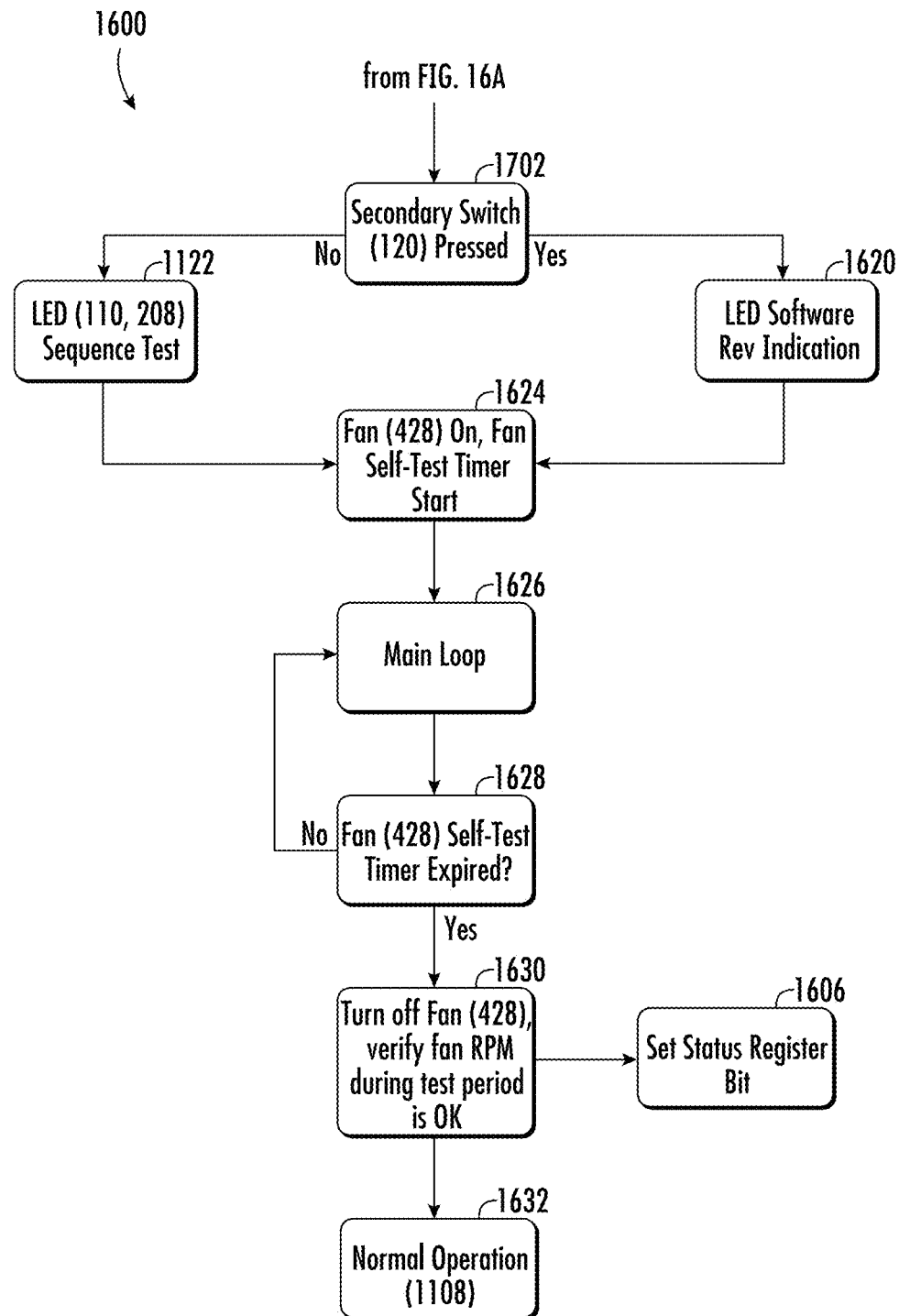

Thereafter, the controller circuit 404, 804 determines if the user has depressed the secondary switch 120 (block 1618 in FIG. 16B). The controller circuit 404, 804 is configured to display the software revision number through a sequence of the visual status indicator 143, as shown in FIG. 10 in this example, if the user depressed the secondary switch 120 at power-on (block 1620 in FIG. 16B). If the user has not depressed the secondary switch 120, the controller circuit 404, 804 initiates a LED sequence test for the UV LEDs 160 and visible light indicator 208(1)-208(4) (block 1622 in FIG. 16B). The controller circuit 404, 804 then does a fan 428 self-test by turning on and off the fan 428 via the fan controller 544 (block 1624 in FIG. 16B). The controller circuit 404, 804 then enters a loop (block 1626 in FIG. 16B) where it is determined if a timer for the fan-self test has expired based on whether the tachometer feedback signal 873 indicates rotation of the fan 428 within the timeout period (block 1628 in FIG. 16B). If the fan 428 is operational, the controller circuit 404, 804 turns off the fan 428 and verifies the revolutions per minute (RPM) of the fan 428 according to the RPM setting to the fan controller 544 and the RPMs detected from the tachometer feedback signal 873 (block 1630 in FIG. 16B). If an error is detected, the controller circuit 404, 804 sets an error state in a status bit designated for the fan 428 in the NVM 562 and/or FRAM 872 and handles the error condition according to the operational state in FIG. 9 (block 1606 in FIG. 16A). Otherwise, the controller circuit 404, 804 proceeds to the MONITOR state in FIG. 9 for normal operation (block 1632 in FIG. 16B).

Figure 17:
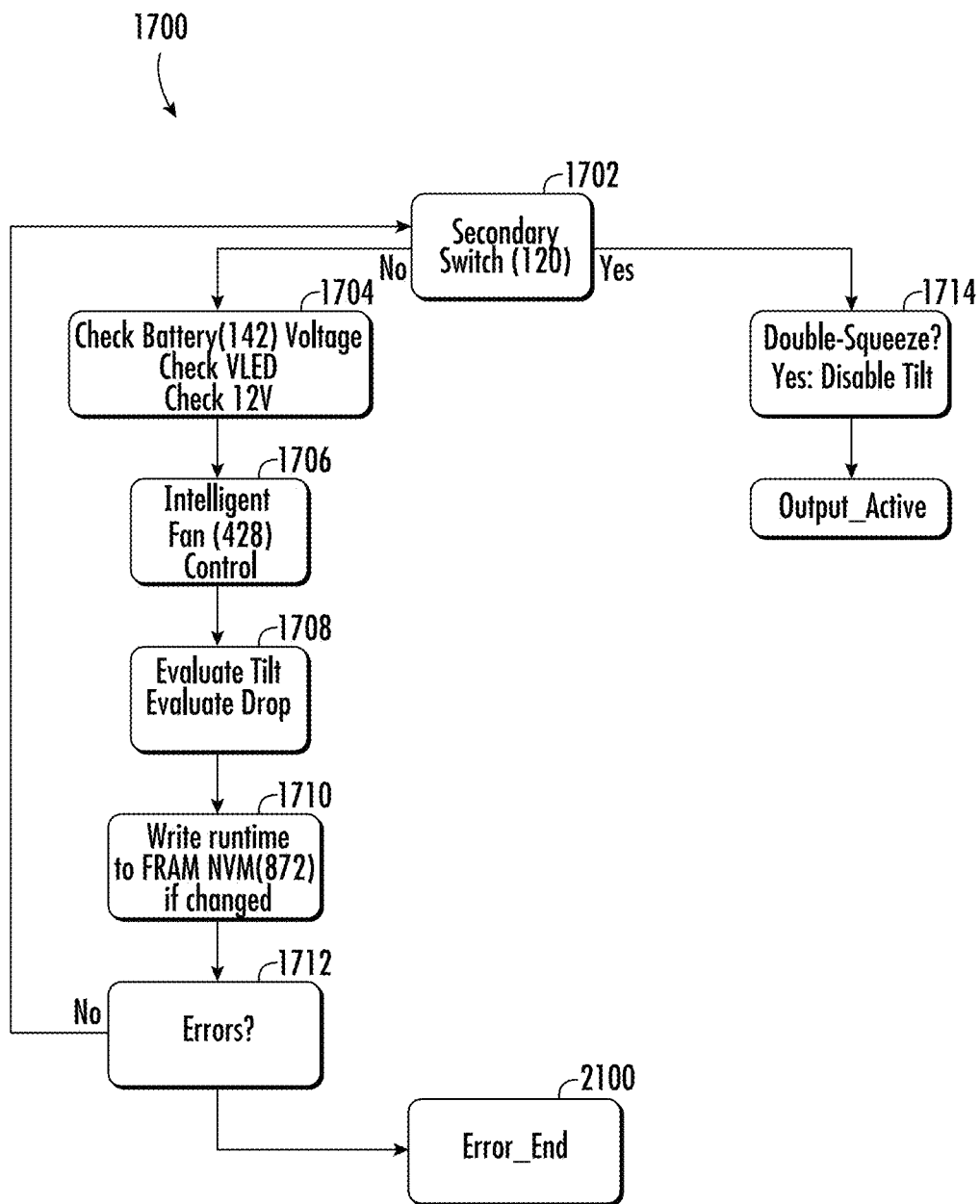
FIG. 17 is a flowchart illustrating an exemplary process performed by the UV light emission device while waiting for the secondary switch of the UV light emission device activated by the user to start light emission operation.

FIG. 17 is a flowchart illustrating an exemplary process 1700 for operation of the UV light emission device 100 while waiting for the secondary switch 120 of the UV light emission device 100 to be activated by the user to start operation. In this regard, while the secondary switch 120 of the UV light emission device 100 is not activated (block 1702 in FIG. 17), the controller circuit 524 performs a series of checks and evaluations. The controller circuit 524 determines if the battery 142 voltage is above a defined voltage threshold (block 1704 in FIG. 7). The controller circuit 524 determines if the fan controller 544 is operational to control the fan 428 (block 1706 in FIG. 7). The controller circuit 524 determines if the UV light emission device 100 has been tilted beyond the programmed tilt orientation based on the accelerometer or orientation signal 548 or if it has been dropped according to the force signal 547 (block 1708 in FIG. 7). The controller circuit 524 writes any errors detected to a status register in the NVM 562 or FRAM NVM 872 to log the error (block 1710 in FIG. 7). If any errors were detected (block 1712 in FIG. 7), the controller circuit 524 enters into an error state and performs the process 2100 in FIG. 21, discussed below. If not, the controller circuit 524 continues to perform the checks in blocks 1704-1712 until the secondary switch 120 is activated. If no errors are detected, and the secondary switch 120 is activated (block 1702 in FIG. 17), the controller circuit 524 executes a process 1800 for an operational state in FIG. 18. In this example, if the controller circuit 524 detects that the secondary switch 120 was activated twice, the tilt detection feature is disabled in the controller circuit 524 (block 1714 in FIG. 7).

Figure 18:
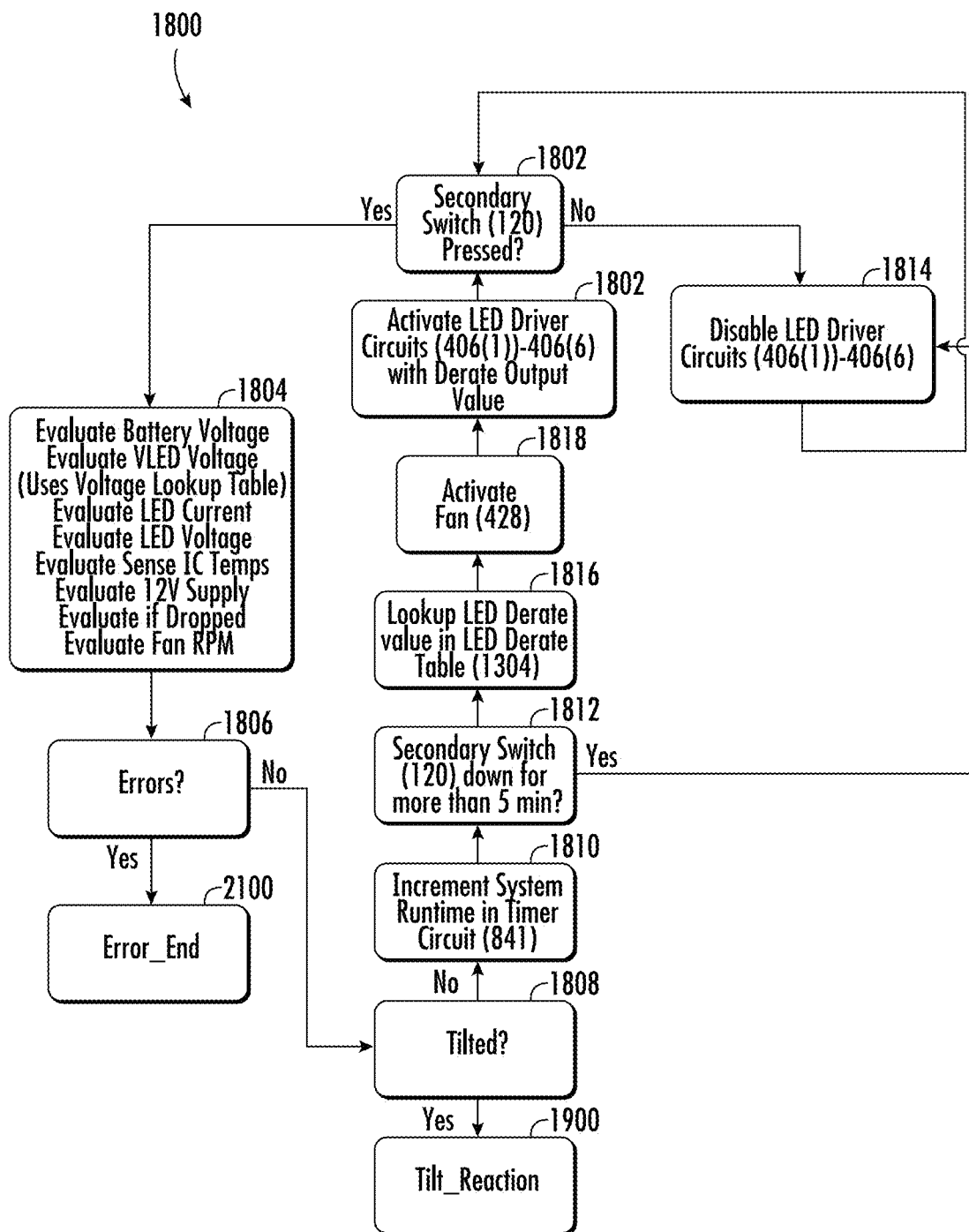
FIG. 18 is a flowchart illustrating an exemplary process for an operational state of the UV light emission device in response to the secondary switch of the UV light emission device being activated.

FIG. 18 is a flowchart illustrating an exemplary process 1800 for an operational state of the UV light emission device 100 in response to the secondary switch 120 of the UV light emission device 100 being activated in the process 1700 in FIG. 17 (block 1802 in FIG. 18). In response to detection of activation of the secondary switch 120, the controller circuit 524 performs a series of evaluations (block 1805 in FIG. 18) to check for errors according to the operational states in FIG. 9. If an error is detected (block 1806 in FIG. 8), the controller circuit 524 enters into an error state and performs the process 2100 in FIG. 21, discussed below. If an error is not detected and a tilt outside a threshold tilt range is not detected (block 1808 in FIG. 8), the controller circuit 524 increments a runtime counter (block 1810 in FIG. 8) and determines if the secondary switch 120 has been engaged for more than a predetermined amount of time (e.g., 5 minutes) (block 1812 in FIG. 8). If so, the controller circuit 524 disables the LED driver circuits 406(1)-406(6) (block 1814 in FIG. 8) and goes back to block 1802 to check to wait for reactivation of the secondary switch 120. This is to ensure that the LED driver circuits 406(1)-406(6) are not continuously activated for more than a defined period of time. If the secondary switch 120 has not been engaged for more than a predetermined amount of time (block 1812 in FIG. 18), the controller circuit 524 looks up a LED derate value in the LED derate table circuit 1304 to controlling the current of the current signals 550(1)-550(6) generated by the LED driver circuits 406(1)-406(6) to the light strings 206(1)-206(6) of the UV light source (block 1814 in FIG. 18). The controller circuit 524 activates the fan controller 544 to activate the fan 428 (block 1816 in FIG. 18). The controller circuit 524 then activates the LED driver circuits 406(1)-406(6) to cause the current signals 550(1)-550(6) to be generated by the LED driver circuits 406(1)-406(6) to the light strings 206(1)-206(6) at a current level controlled based on the read LED derate value from the LED derate table circuit 1304 in block 1816. The controller circuit 524 then determines if the secondary switch 120 will continue to be activated, and if not, disables the LED driver circuits 406(1)-406(6) until the secondary switch 120 is reactivated (block 1802 in FIG. 18).

Figure 19:
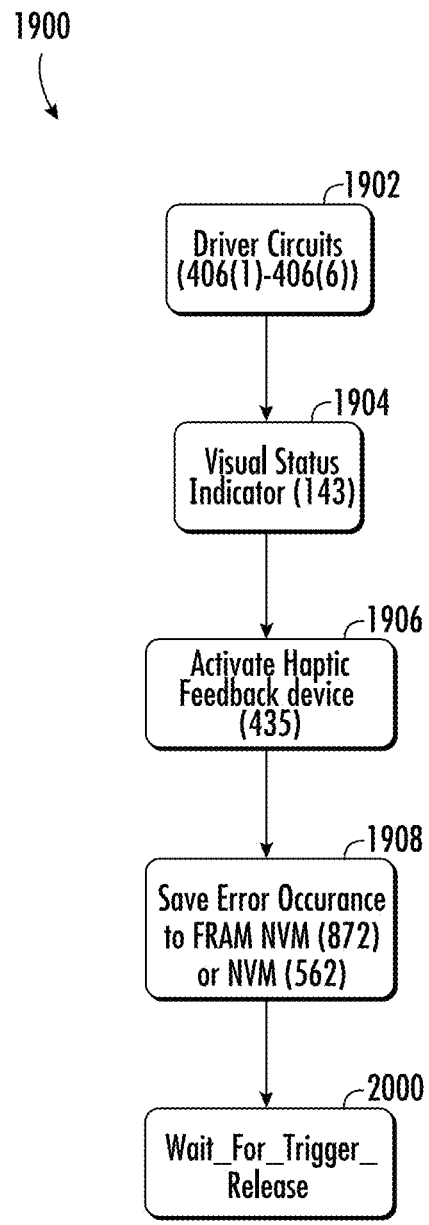
FIG. 19 is a flowchart illustrating an exemplary process in response to a tilt detection of the UV light emission device.

FIG. 19 is a flowchart illustrating an exemplary tilt reaction process 1900 in response to a detected tilt of the UV light emission device 100. The process 1900 in FIG. 19 can be executed in response to a tilt detection in the overall operation process 1400 in FIG. 14. With reference to FIG. 19, in response to the controller circuit 524 detecting a tilt, the controller circuit 524 deactivates the LED driver circuits 406(1)-406(6) of the UV light source 102 (block 1902 in FIG. 19). The controller circuit 524 then sets the visual status indicator 143 to a fast flashing green color state as also set forth in the operational state in FIG. 9 (block 1904 in FIG. 19). The controller circuit 524 then activates the haptic feedback device 435 to signify the error condition through physical feedback to the user (block 1906 in FIG. 19). The controller circuit 524 then saves the error condition to the status register in the NVM 562 and/or the FRAM NVM 872 (block 1906 in FIG. 19) and goes a wait for secondary switch 120 release and re-activation process 200 in FIG. 20. This is because for a tilt error, the controller circuit 524 is configured to allow the LED light drivers 406(1)-406(6) 100 to be reactivated to activate the light strings 206(1)-206(6) when the secondary switch 120 release and re-activated.

Figure 20:
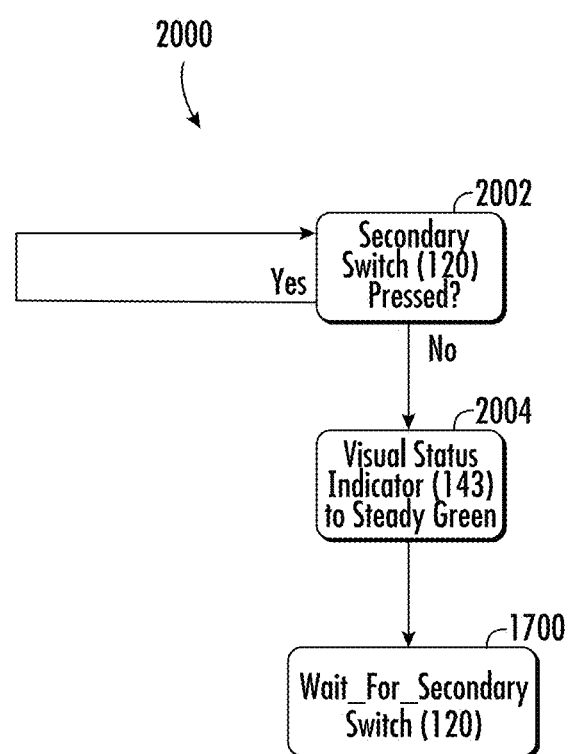
FIG. 20 is a flowchart illustrating an exemplary process of waiting for the secondary switch of the UV light emission device to be released after tilt detection.

FIG. 20 is a flowchart illustrating an exemplary process 2000 of waiting for the secondary switch 120 of the UV light emission device 100 to be released. The process 200 includes the controller circuit 524 detecting when the secondary switch 120 has been deactivated (block 2002 in FIG. 20). When the controller circuit 524 detects the secondary switch 120 has been deactivated, the controller circuit 524 sets the visual status indicator 143 to a sold, steady green color state as shown in the state diagram in FIG. 19 (block 2004 in FIG. 20), and goes back to the wait for secondary switch 120 to be activated process 1700 in FIG. 17.

Figure 21:
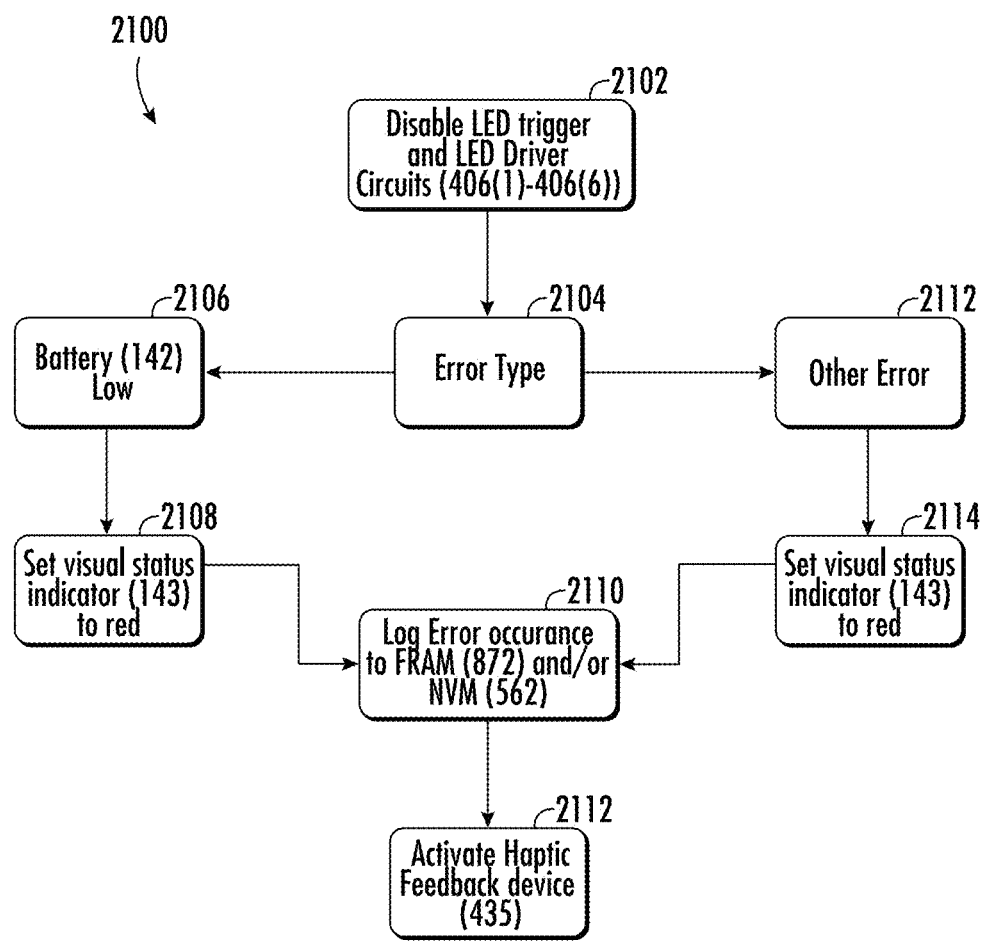
FIG. 21 is a flowchart illustrating an exemplary process of handling error detection in the UV light emission device.

FIG. 21 is a flowchart illustrating an exemplary process 2100 of handling error detection in the UV light emission device 100. When an error is detected, the controller circuit 524 disables the LED driver circuits 406(1)-406(6) so that light is not emitted from the UV LEDs 110 and visible lights 208(1)-208(4) in the UV light source 102 (block 2102 in FIG. 21). The controller circuit 524 then determines if the error detected is a battery 142 low error (block 2104 in FIG. 21). If so, the controller circuit 524 enters the BATTERY LOW state as discussed in FIG. 9 (block 2106 in FIG. 19) and sets the visual status indicator 143 to a slow red flashing state (block 2108 in FIG. 19). The controller circuit 524 then logs the battery 142 low error in the status register in the NVM 562 and/or the FRAM NVM 872 (block 2110 in FIG. 19). The controller circuit 524 then activates the haptic feedback device 435 (block 2112 in FIG. 19). If the error is other than a battery 142 low error (block 2112 in FIG. 19), the controller circuit 524 sets the visual status indicator 143 to a three (3) short and three (3) long red flashing state (block 2114 in FIG. 19), then logs the error in the status register in the NVM 562 and/or the FRAM NVM 872 (block 2110). The controller circuit 524 then waits until the UV light emission device 100 is reactivated to recover from the error, which may require the secondary switch 120 to be reactivated and/or a power cycle by deactivating and reactivating the primary switch 122.

Figure 22A:
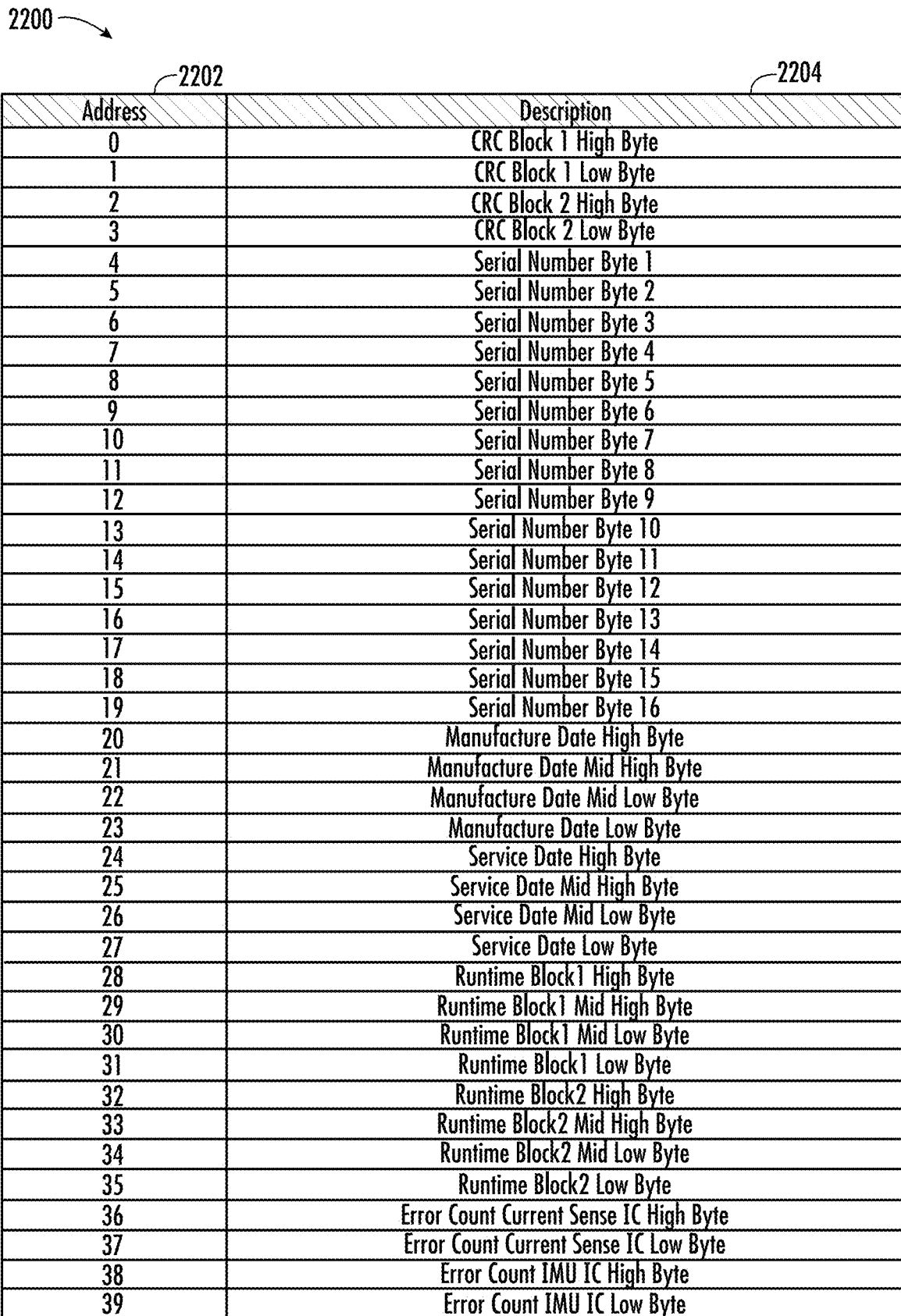

FIG. 22A-22C is a diagram of an exemplary status register 2200 that can be programmed and access in the NVM 562 and/or the FRAM NVM 872 to detect programming and register history information, including errors, for the UV light emission device 100. The status register 2200 is indexable by an address 2202, as shown in FIGS. 22A-22C. At each address 2202, the status register 2200 contains a block (e.g., a byte, word, etc.) of memory space to allow a status to be written. The memory space at each address 2202 is dedicated to a specific type of data, as shown in the written description column 2204 in FIGS. 22A-22C.

Figure 23:
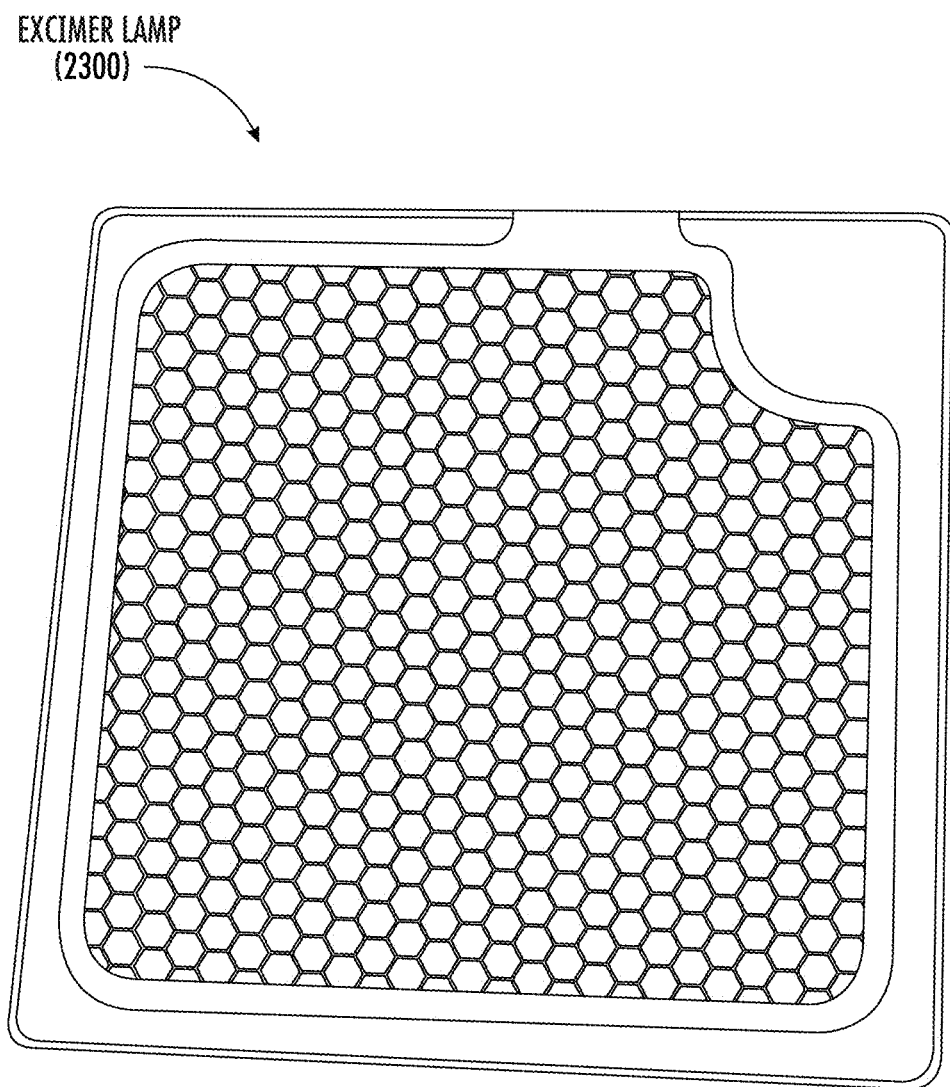
FIG. 23 is a diagram of an alternative UV light source in the form of an excimer UV lamp that can be employed in the UV light emission device in FIGS. 1A-1C.

UV light sources other than the UV LEDs 110 described above can also be employed in the UV light emission device 100 in FIGS. 1A-1C to emit the UV light 104. In this regard, FIG. 23 is a diagram of an alternative UV light source in the form of a planar excimer UV lamp 2300 that can be employed in the UV light emission device 100 in FIGS. 1A-1C. For example, the excimer UV lamp 2300 could be a Krypton-containing or Krypton-Chlorine (KrCl) light source with a peak emission at 222 nm wavelength as an example. For example, the excimer UV lamp 2300 could be the high-power ultraviolet (UV) and vacuum ultraviolet (VUV) lamps with micro-cavity plasma arrays disclosed in U.S. Patent Application No. 2019/0214244 A1 incorporated herein by references in its entirety. FIG. 10 is a schematic diagram of an alternative electrical control system 2404 that can be employed in the UV light emission device in FIGS. 1A-1C employing the excimer UV lamp 2300 in FIG. 23. Common elements between the electrical control system 404 in FIG. 10 and the electrical control system 404 in FIG. 5 are shown with common element numbers between FIGS. 5 and 24 and will not be re-described.

Figure 24:
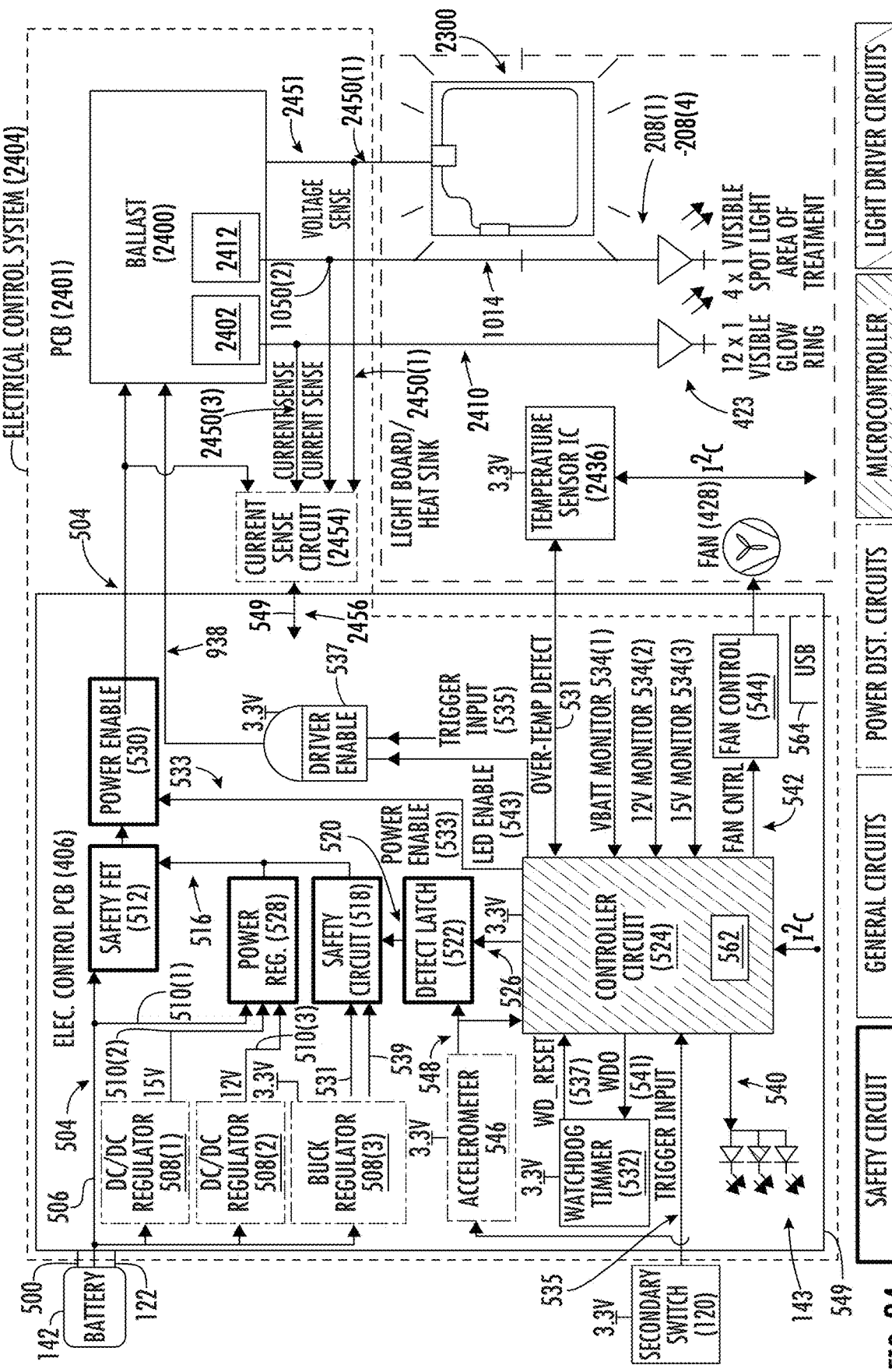
FIG. 24 is a schematic diagram of an alternative electrical control system that can be employed in the UV light emission device in FIGS. 1A-1C employing the excimer UV lamp in FIG. 23.

As shown in FIG. 24, the power signal 504 distributed by the power enable switch 530 is coupled to a ballast 2400. The ballast 2400 is configured to generate a voltage signal 2450(1) to power the excimer UV lamp 900. The ballast 2400 is mounted to PCB 2401. The ballast 2400 also includes a LED light driver 2402 to generate a current signal 2410 to the visible light indicators 423 that emit light into the visible light ring 148. The ballast 2400 also includes a LED light driver 2412 to generate a current signal 2414 to the visible lights 208(1)-208(4) that provide a visible light source indicating when the UV light 244 is being emitted from the excimer UV lamp 900. A current sense circuit 2454 is also provided on the PCB 2401 and is configured to sense the current signals 2410, 2414 and voltage signals 2450(1)-2450(3) generated by the ballast 2400 and its LED light drivers 2402, 242412 to detect error conditions similar to the detection of the current signals 550(1)-550(6) in the electrical control system 404 in FIG. 5. The current sense circuit 2454 is configured to generate a current sense signal 2456 on the communication bus 549 to indicate to the controller circuit 524 if an error condition is present in the current signals 2410, 2414 and respective voltage signals 2450(1)-2450(3) such that the ballast 2400 or the LED light drivers 2402, 2412 are malfunctioning or not operating properly. Note that the electronic control system 804 in FIG. 8 could also include the planar excimer UV lamp 2300.

Figure 25A:
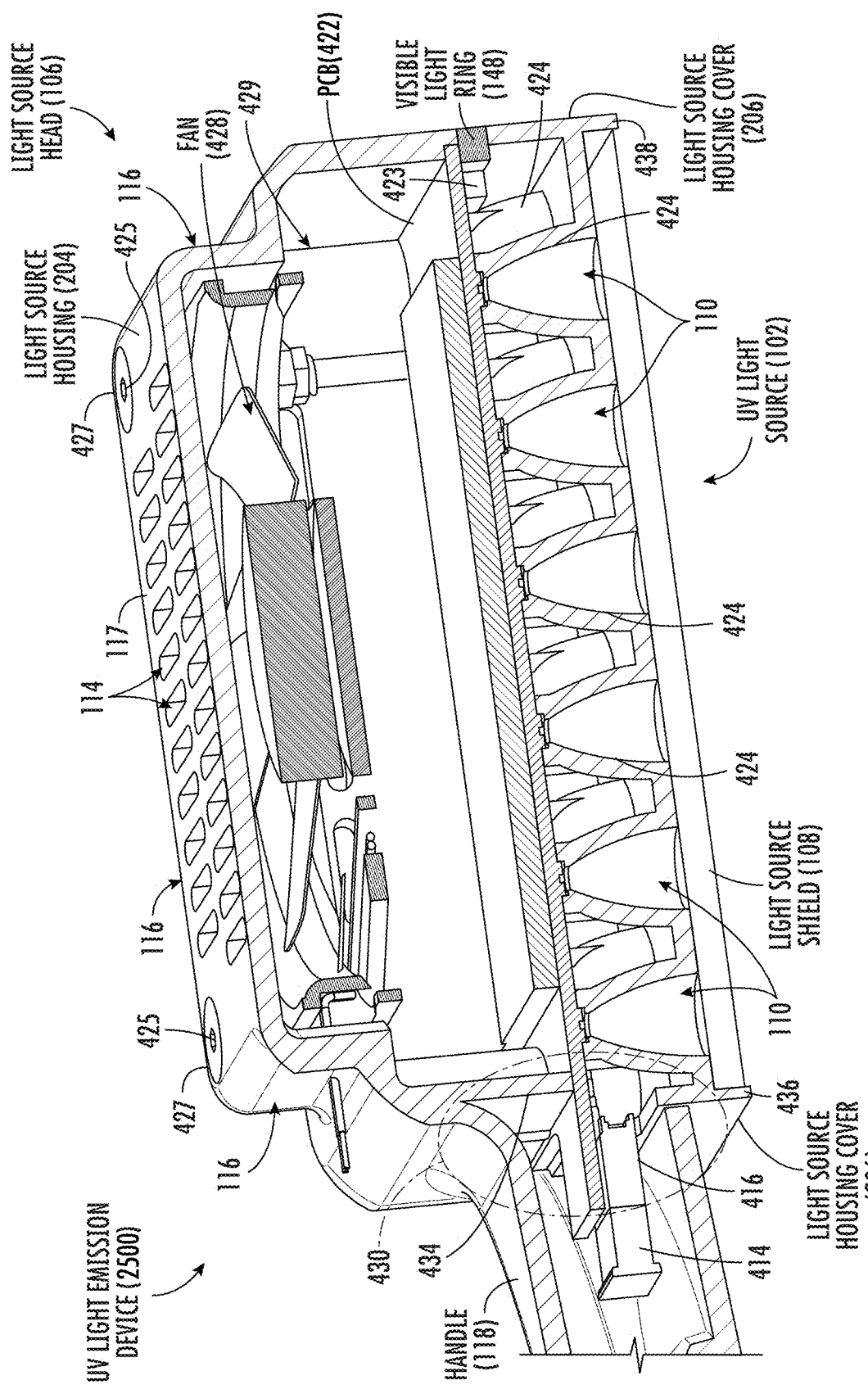

FIGS. 25A and 25B are schematic diagrams of an alternative UV light emission device 2500 similar to the UV light emission device 100 in FIGS. 1A-1C, but that allows air to be drawn into the light source housing 202 and across the UV light source 102 to expose the drawn-in air to the UV light emission. FIG. 25A is a close-up, side, cross-sectional view of the light source head 106 of the UV light emission device 2500. FIG. 25B is a bottom view of the UV light source 102 of the UV light emission device 2500 in FIG. 25A. Common elements between the UV light emission device 2500 in FIGS. 25A and 25B and the UV light emission device 100 in FIGS. 4B and 2, respectively, are shown with common element numbers and not re-described.

With reference to FIG. 25A, the UV light emission device 2500 includes a light source head 106 that includes a light source housing 202 that is attached to the light source housing cover 204 to secure the UV light source 102. The fan 428 is mounted inside the light source head 106 to draw heat away from the light source PCB 422 for the UV light source 102 and to direct such heat through the vent openings 114 in the rear 117 of the light source housing 202 for heat dissipation. However, as shown in FIG. 25B, the light source shield 108 includes openings 2502. The heat sink 426 is removed or rearranged so that there is fluid communication between the fan 428 and the openings 2502. Thus, when the fan 428 draws air from the UV light source 102, the suction generated by the fan 428 also draws air through the openings 2502 and past the UV light source 102 to decontaminate the drawn-in air. The air is then exposed on the opposite side of the fan 428 through the vent openings 114 in the rear 117 of the light source housing 202. The vent openings 114 on the sides of the light source housing 202 may be present or may be removed fully or partially to cause the drawn-in air to pass across the UV light source 102. Alternatively, as discussed above, the fan 428 mounted inside the light source head 106 above the heat sink 426 could pull air through the openings 114 in the rear 117 of the light source head 106, exhausting such air through the openings 114 in the side 116 to carry heat generated from the light source PCB 422 for the UV light source 102 away from the UV light source 102.

FIG. 25B also illustrates an alternative light source housing 202 that has UV LEDs 110 in different sized parabolic reflectors 424(1), 424(2). These larger and smaller parabolic reflectors 424(1), 424(2) cause the UV light emitted by the UV LEDs 110 to be reflected and shaped differently to provide narrower and broader UV beam angles, respectively. Providing the smaller parabolic reflectors 424(2) to provide a broader UV beam angle of UV light emitted by the UV LEDs 110 may provide a more uniform UV light emission on a target of interest. Providing the larger parabolic reflectors 424(1) to provide a narrower UV beam angle of UV light to be emitted by the UV LEDs 110 may contain the emitted UV light within a desired target area on a target of interest, such as the 4"×4" target surface.

FIG. 26 is a schematic diagram of an alternative UV light emission system 2600 that includes the UV light emission device 100 in FIGS. 1A-1C but provides the battery 142 as integrated with the base 124 to allow more portability. The UV light emission system 2600 can still be connected to a power source as an AC-to-DC converter 2602 for wall outlet power and for battery 142 charging. Also, the electrical leads 2604 are exposed from the base housing 126 to allow the UV light emission device 100 to be placed in a docking station or cradle for charging, data transmission, and/or secure storage. The electrical leads 2604 include leads for power and ground, but also include leads that can be electrically coupled to the USB port 264, the communication bus 549 or other interface of the electrical control systems 404, 804 in FIGS. 5 and 8, for example, to communicate with the UV light emission device 100 and to extract the data stored in the NVM 262. Alternatively, the battery 142 could be inductively charged through the base housing 126 without the need for electrical leads 2604.

Other light sources for generating UV light not described above could also be employed in the UV light emission device 100, including a microplasma UV lamp, a laser UV light source, an OLED UV light source, and a chemiluminescence UV light source, as non-limiting examples. The circuit boards discussed herein may be clad with a metal such as aluminum for further heat dissipation.

The UV light emission device 100 can be configured so that the base housing 126 is compatible with a battery 142 is a v-mount battery in this example to standardize the mounting system, electrical connectors, and voltage output. This type of battery 142 can be found in power photography and videography equipment. The battery 142 provides a 14.4 VDC nominal output and comes in a variety of capacities. Using a standard battery offers many benefits. For example, the battery 142 may be the IDX Duo-C150 (143 Wh battery)

Figure 27A:
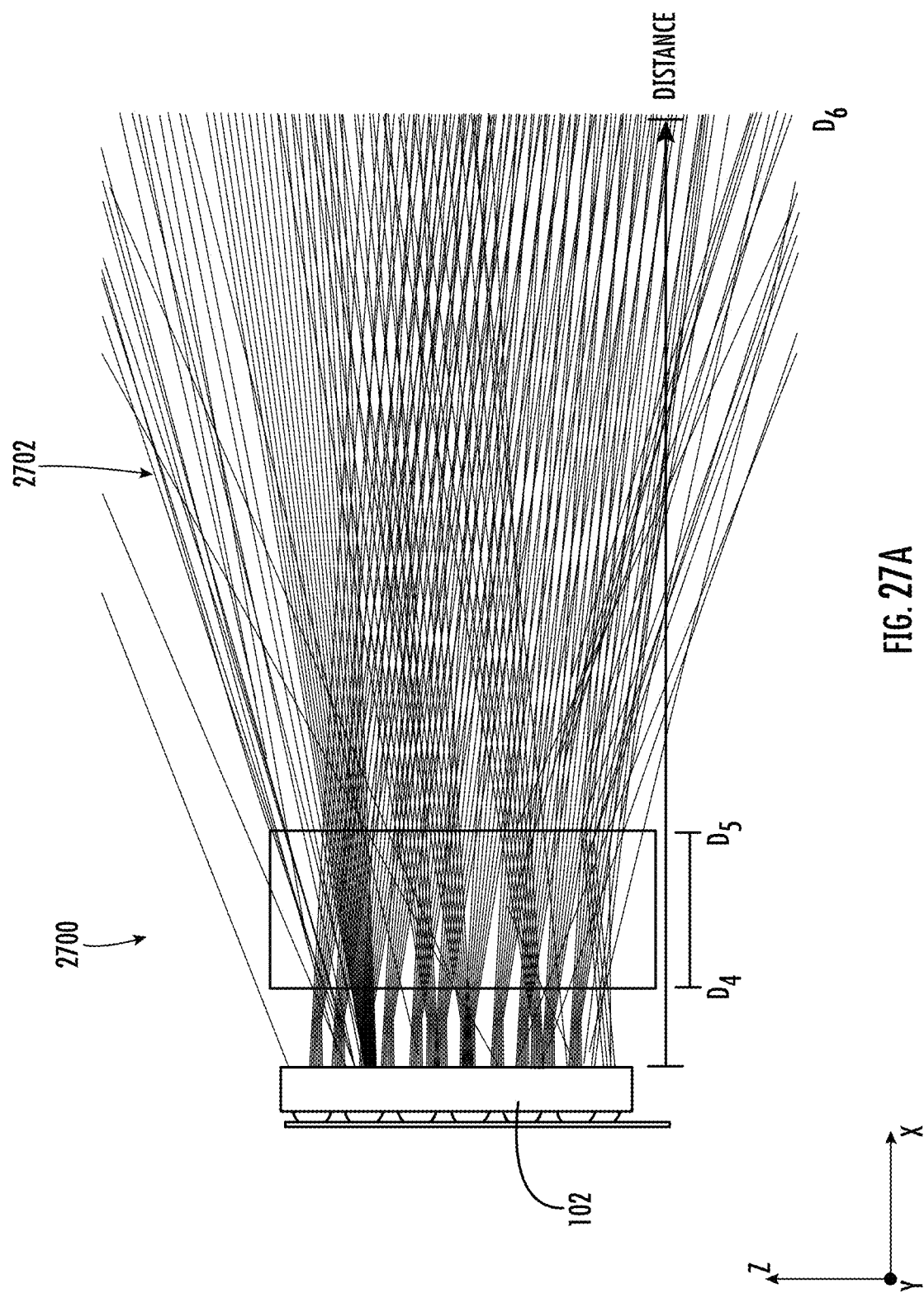
FIGS. 27A and 27B illustrate exemplary depths of focus of UV light emitted from the UV light source of the UV light emission device in FIGS. 1A-1C as a function of distance from the UV light source.
Figure 27B:
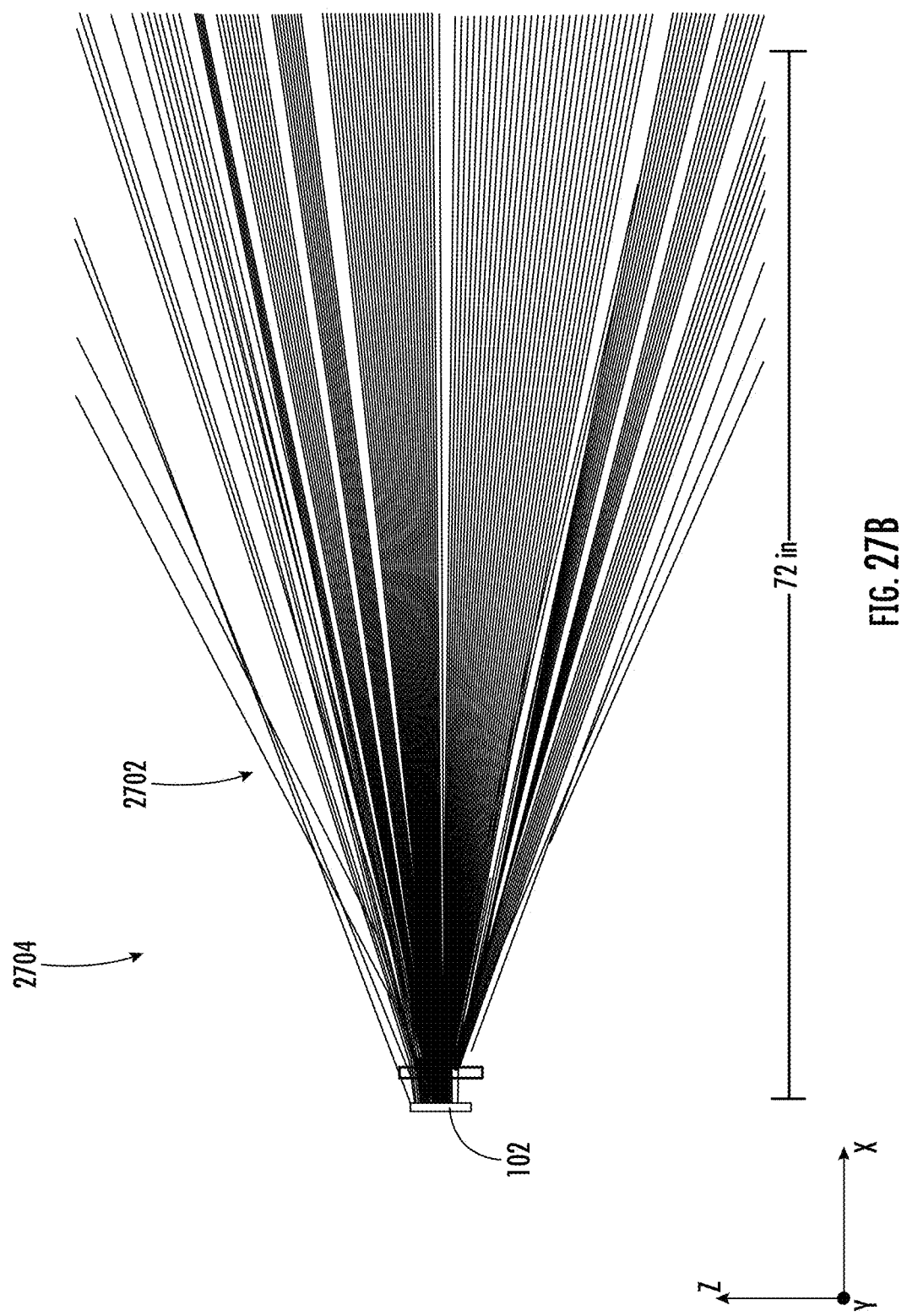
Figure 28:
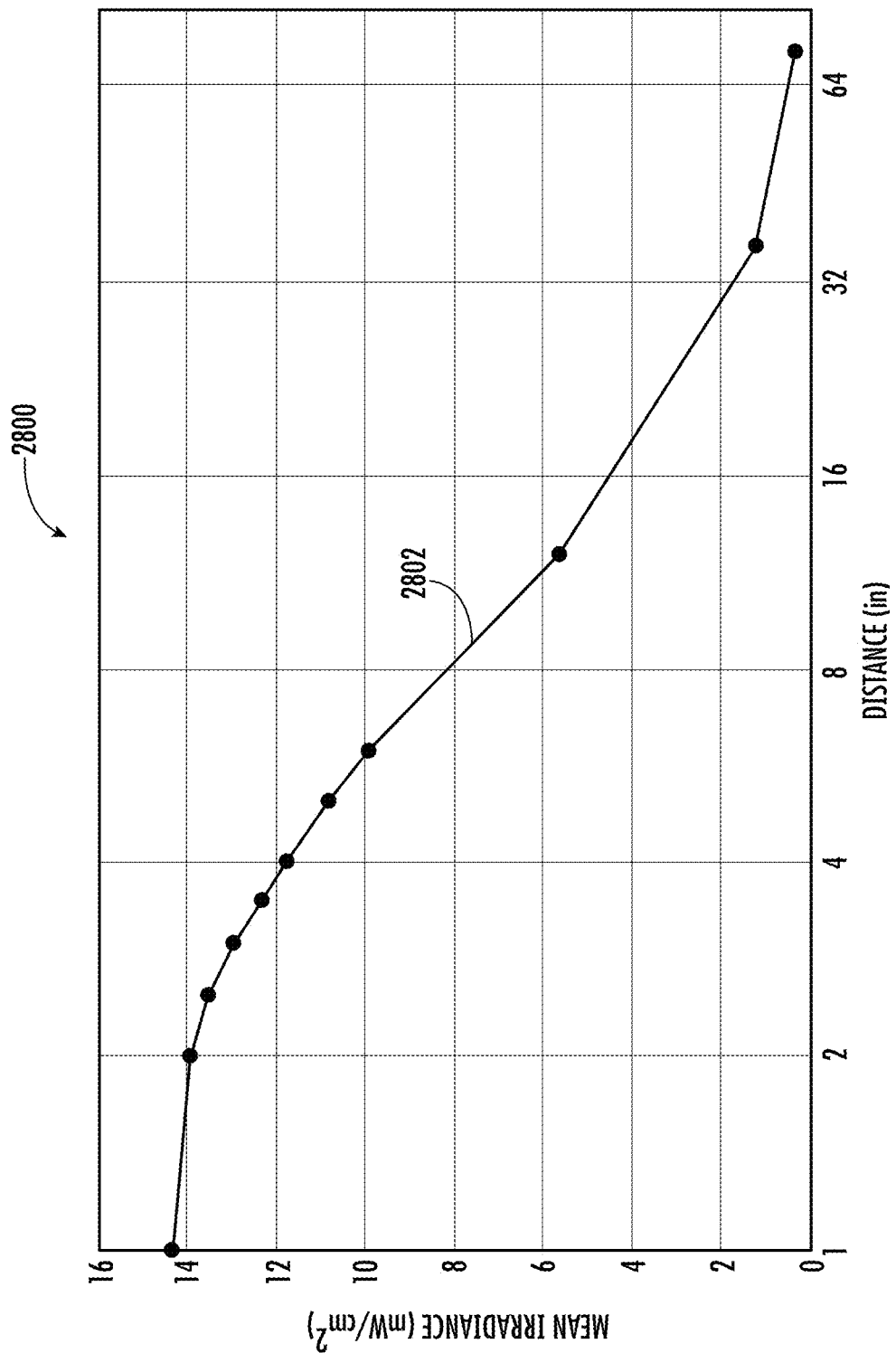
FIG. 28 is a graph illustrating an exemplary relationship between mean irradiance of UV light emitted from the UV light source of the UV light emission device in FIGS. 1A-1C on a surface of interest and distance of the surface from the UV light source.

The depth of focus of the light emitted by the UV LEDs 110 in the UV light source 102 of the UV light emission device 100 determines the output power as a function of emission range. It may be desired to control depth of focus of the light emitted by the UV LEDs 110 to control the output power as a function of emission range so that a user could direct the UV light source 102 towards a given surface to expose that surface to the UV light 104 without the UV light source 102 actually having to come into contact with such surface. For example, FIG. 27A is a diagram of depth of focus 2700 of UV light 2702 emitted from the UV LEDs 110 of the UV light source 102 of the UV light emission device 100 as a function of distance from the UV light source 102. As shown therein, as the UV light 2702 travels a further distance in the X-axis direction, the UV light spreads out a further distance in the Z-axis, thus causes a loss of intensity of the UV light 2702. For example, the depth of focus of the UV light 2702 is shown at distance $D_4$, which is one (1) inch in this example, distance $D_5$, which in three (3) inches in this example, and distance $D_6$, which is twelve (12) inches in this example. Thus, the intensity of the UV light 2702 emitted from the UV LED 110 on a surface of distance $D_6$ away from the UV light source 102 will be less than the intensity of the UV light 2702 emitted from the UV LED 110 on a surface of distance $D_5$ away from the UV light source 102. The intensity of the UV light 2702 emitted from the UV LED 110 on a surface of distance $D_5$ away from the UV light source 102 will be less than the intensity of the UV light 2702 emitted from the UV LED 110 on a surface of distance $D_4$ away from the UV light source 102. FIG. 27B is a diagram that illustrates the depth of focus 2704 of the UV light 2702 emitted from the UV LEDs 110 of the UV light source 102 up to a much further distance $D_7$, which may be 72 inches. FIG. 28 illustrates a graph 2800 illustrating mean irradiance 2802 of the UV light source 102 in $mW/cm^2$ as a function of distance in inches (in). As shown therein, the irradiance 2802 reduces substantially linearly to distance from 2 inches to 32 inches as an example. Thus, controlling the power of the UV lights 110 in the UV light source 102 is a way to control the irradiance to achieve the desired optical output power at a given distance of the UV light source 102 from a surface.

Figure 29:
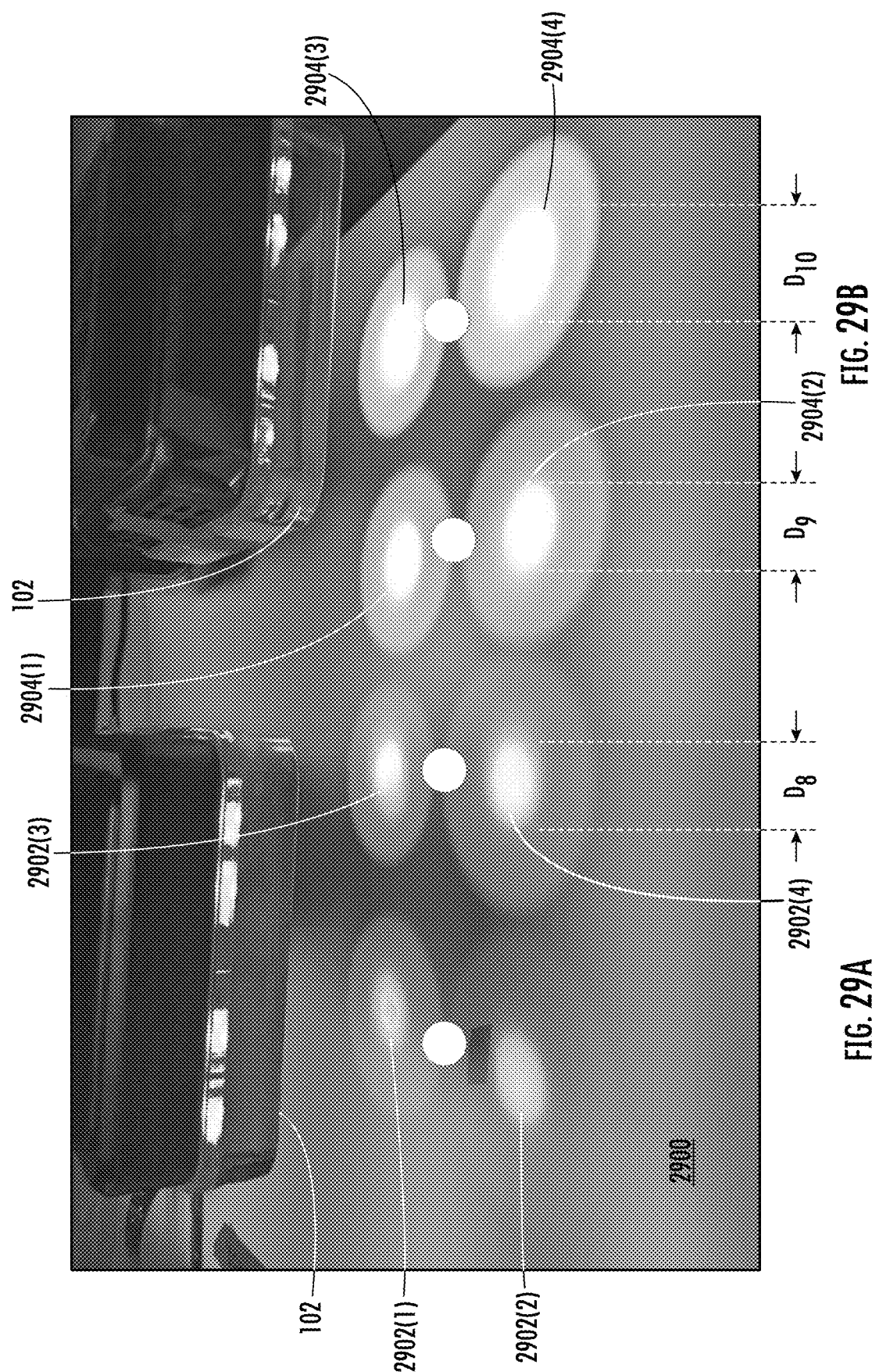
FIGS. 29A and 29B illustrate exemplary spotlights formed on a surface as a result of orienting the UV light source of the UV light emission device in FIGS. 1A-1C towards a surface at different distances and the visible UV lights of the UV light source emitting visible light onto the surface.

It was found that the visible light emitted from the visible lights 208(1)-208(4) in the UV light source 102 can provide a visual feedback to a user directing the UV light source 102 toward a surface to emit UV light from the UV LEDs 110 towards that surface. The visible light from the visible lights 208(1)-208(4) appears on the surface that the UV light from the UV LEDs 110 is emitted, as shown in FIGS. 29A and 29B. As shown in FIGS. 29A and 29B, the UV light source 102 is placed above a surface 2900 at a greater distance in FIG. 29B than in FIG. 29A. Thus, the spotlights 2902(1)-2902(4) formed on the surface 2900 from visible light emission from the visible lights 208(1)-208(4) in FIG. 29A have a smaller visible light beam spread of smaller diameter $D_8$ than the visible light beam spread (diameter) of spotlights 2904(1)-2904(4) formed on the surface 2900 from visible light emission from the visible lights 208(1)-208(4) in FIG. 29B. Thus, if a correlation can be found between the visible light beam spread diameter and/or orientation of spotlights on a surface 2900 resulting from visible light being emitted by the visible lights 208(1)-208(4) of the UV light source 102 and the desired power of the UV light at the surface for decontamination, the spotlights on a surface 2900 resulting from visible light being emitted by the visible lights 208 (1)-208(4) of the UV light source 102 can be used as a visual indicator to a user of the UV light emission device 100 on the recommended distance to hold the UV light source 102 away from a surface to be decontaminated.

Figure 30:
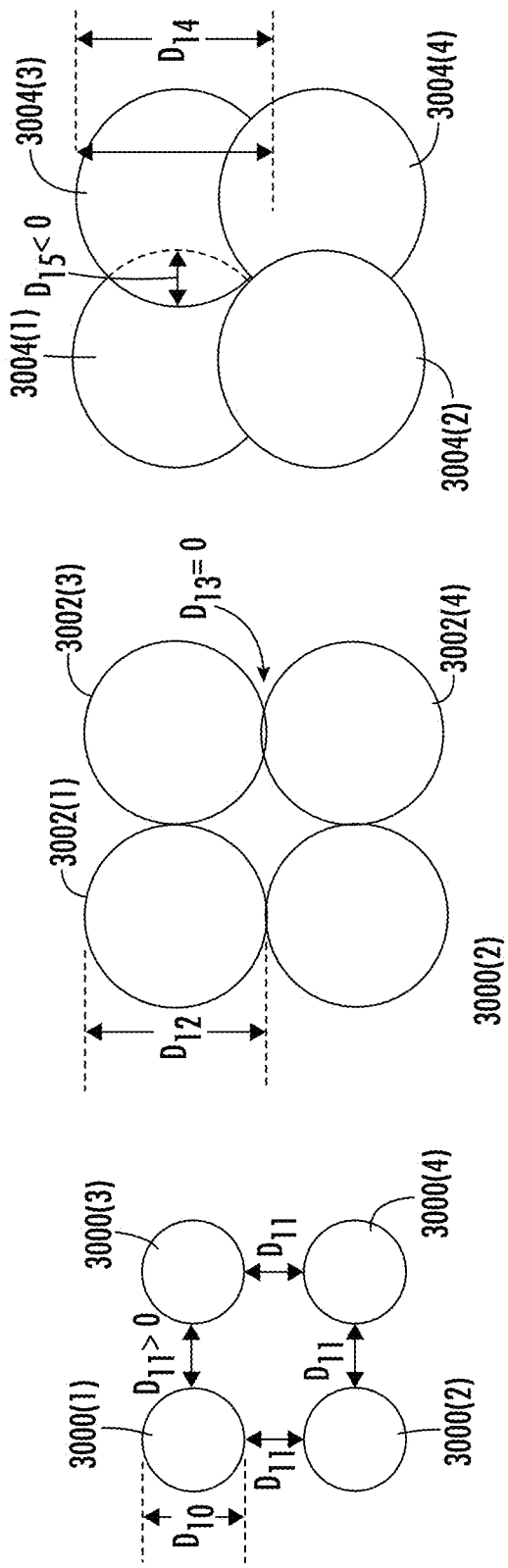
FIGS. 30A-30C illustrate exemplary spotlights patterns on a surface as a result of orienting the UV light source of the UV light emission device in FIGS. 1A-1C towards a surface at different distances, and the visible UV lights of the UV light source emitting visible light onto the surface.

It was found by an example experimentation that for a distance of one (1) inch between the UV light source 102 of the UV light emission device 100 and the surface 2900, the power of the UV light at the surface 2900 was 16.78 $mW/cm^2$. FIG. 30A shows the visible light beam spread diameter of the spotlights 3000(1)-3000(4) on a surface from the visible light emitted by the visible lights 208(1)-208(4) of the UV light source 102 when placed one (1) inch away from the surface. As shown in FIG. 30A, at a distance of one (1) inch, the spotlights 3000(1)-3000(4) have a visible light beam spread diameter of $D_{10}$ and are located a distance $D_{11}$ from each other. The distance $D_{11}$ is greater than 0, meaning there is a gap distance between adjacent spotlights 3000(1)-3000(4). It was also found by experimentation that for a distance of 2.5 inches between the UV light source 102 and the surface 2900, the power of the UV light at the surface 2900 was 15.8 $mW/cm^2$. FIG. 30B shows the visible light beam spread diameter of the spotlights 3002(1)-3002(4) on a surface from the visible light emitted by the visible lights 208(1)-208(4) of the UV light source 102 when placed 2.5 inches away from the surface. As shown in FIG. 30B, at a distance of 2.5 inches, the spotlights 3000(1)-3000(4) have a visible light beam spread diameter of $D_{12}$ and are located a distance $D_{13}$ from each other of zero (0), meaning there is no gap distance and the spotlights 3002(1)-3002(4) either barely touch, are extremely close, and touch each other or almost touch each other to the human visual eye. It was also found by experimentation that for a distance of 3.5 inches between the UV light source 102 and the surface 2900, the power of the UV light at the surface 2900 was 16.6 $mW/cm^2$. As shown in FIG. 30C, at a distance of 3.5 inches, the spotlights 3004(1)-3004(4) have a visible light beam spread diameter of $D_{14}$ and are located a distance $D_{15}$ from each in an overlapping manner, or a negative distance as compared to the spotlights 3000(1)-300(4) in FIG. 30A.

Figure 31:
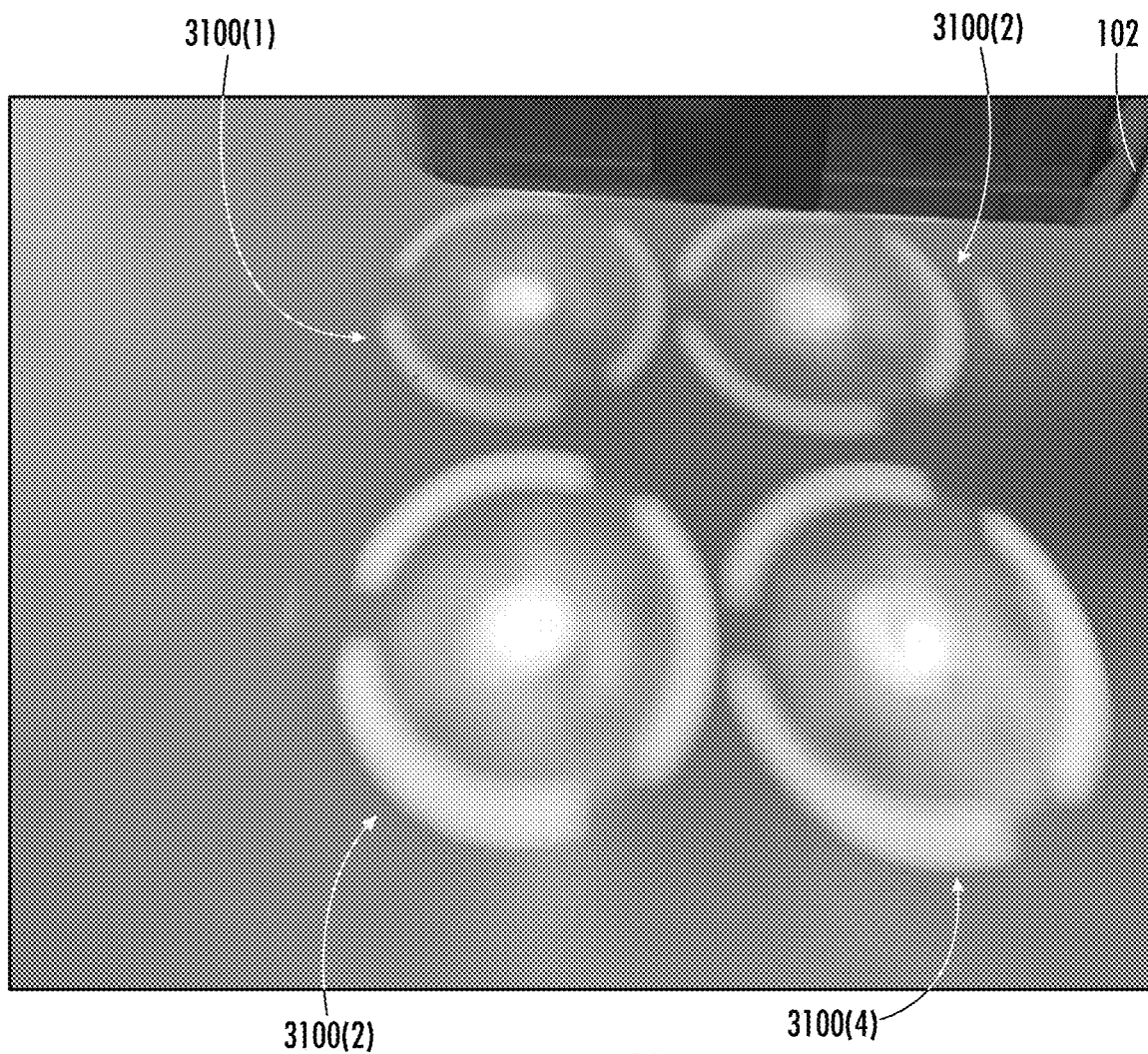
FIG. 31 is a diagram of exemplary, alternative patterned spotlights on a surface as a result of providing a mask on the UV light source with patterned openings adjacent to the visible lights and orienting the UV light source of the UV light emission device in FIGS. 1A-1C towards a surface at different distances, and the visible UV lights of the UV light source emitting visible light on the surface.
Figure 34B:
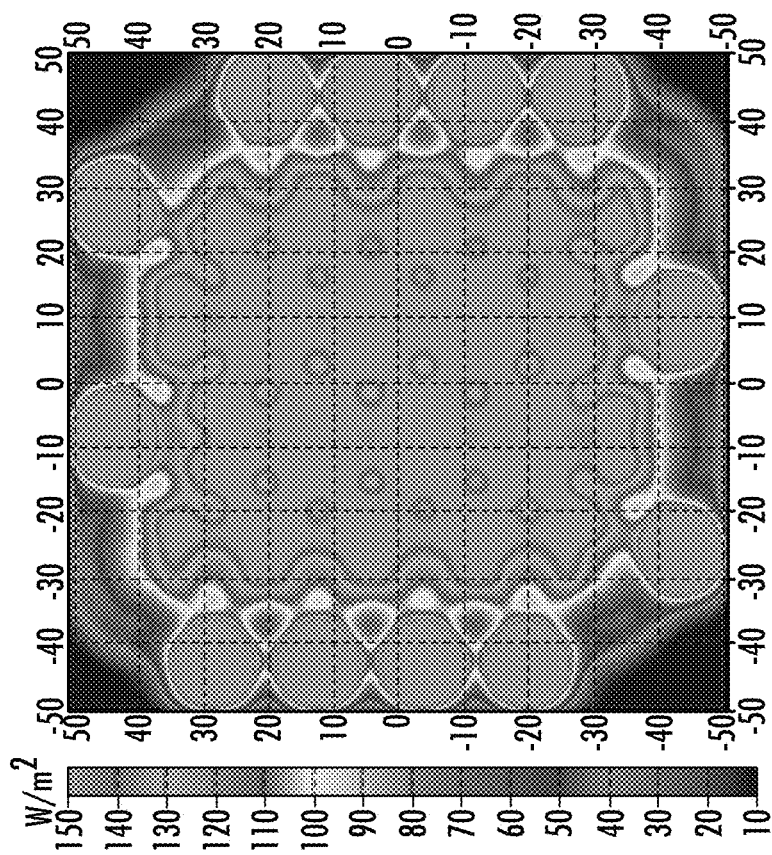
Figure 34A:
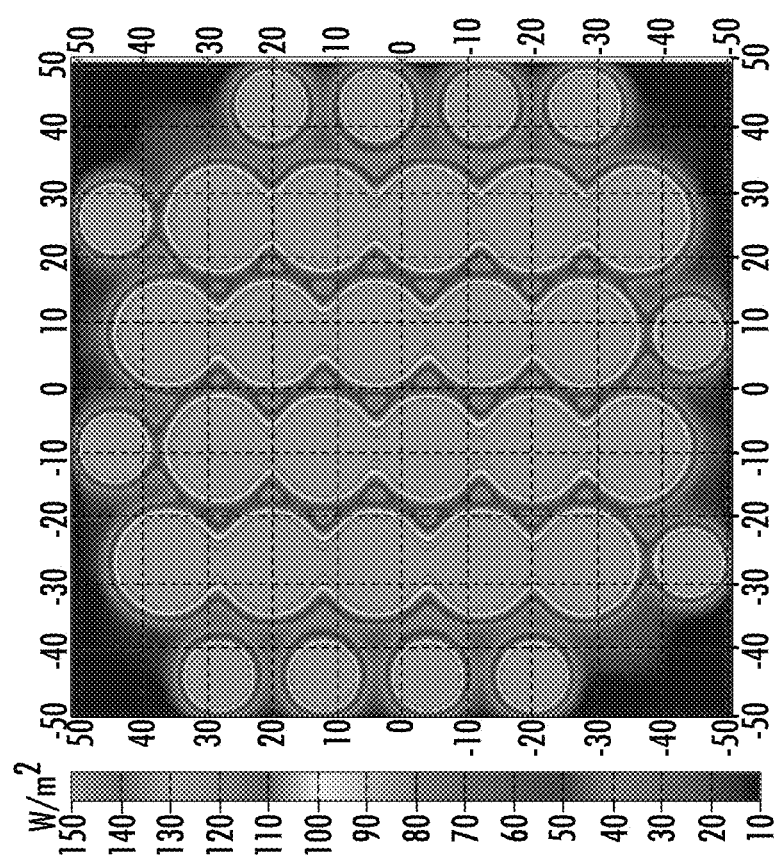
Figure 34D:
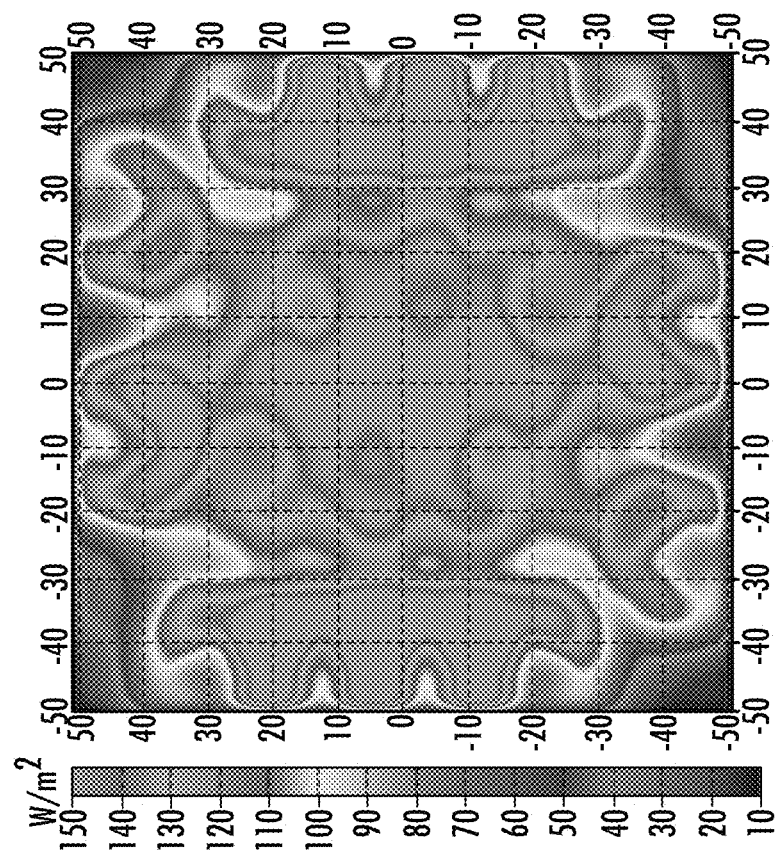
Figure 34C:
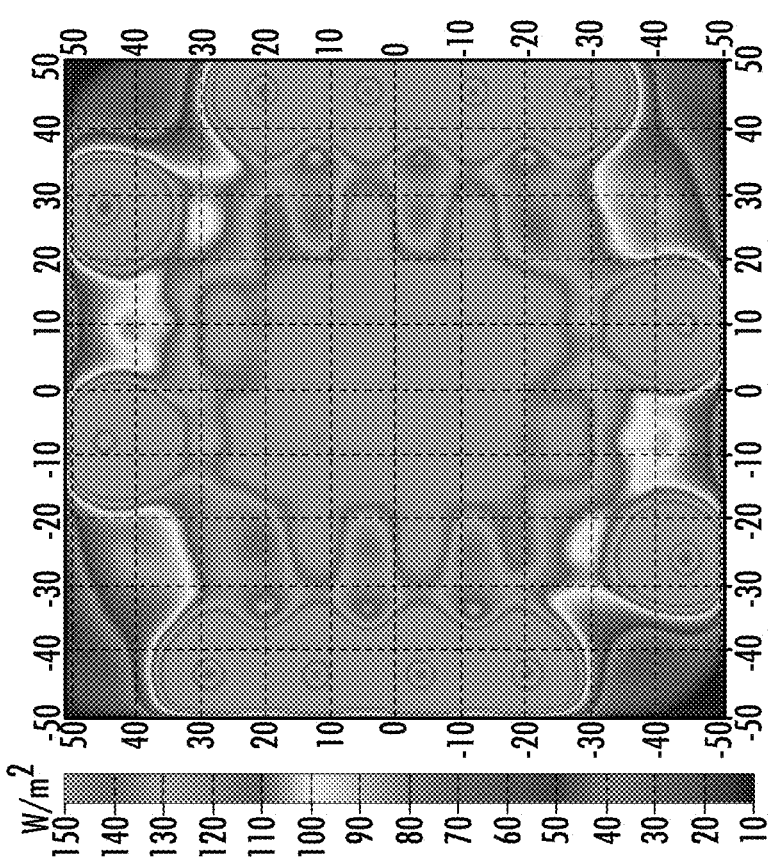

The visual feedback from spotlights formed on a surface as a result of the visible light emitted from the visible lights 208(1)-208(4) not only provides an indication to the user that the UV light source 102 is activated and operational but also allows the user to instantly determine that they are holding the UV light source 102 of the UV light emission device 100 at the prescribed distance from the surface to achieve the desired light power of the UV light 104 emitted from the UV LEDs 110 on the surface. For instance, if the user is instructed to hold the UV light emission device 100 so that the spotlights formed on a surface as a result of the visible light emitted from the visible lights 208(1)-208(4) are just touching each other as shown in FIG. 30B, this can be used as an indirect instruction for the user to hold the UV light source 102 2.5 inches from a surface of interest to achieve the desired UV light power and intensity at the surface of interest. As shown in FIGS. 29A and 29B, the visible light beam spread size (i.e., diameter) of the spotlights formed on a surface as a result of directing the UV light source of the UV light emission device 100 towards the surface and the visible lights 208(1)-208(4) emitting visible light may not be consistent. Variables such as ambient light and the angle of orientation of the UV light source 102 with respect to a surface of interest, and the topography of the surface, affect the formation of the spotlights on the surface of interest. Thus, this may cause a user to hold the UV light source 102 at a distance from a surface of interest that is not desired or ideal for the desired light power and intensity according to the depth of focus of the UV LEDs 110. In this regard, as shown in FIG. 31, the spotlights 3100(1)-3100(4) emitted by the visible lights 208(1)-208(4) of the UV light source 102 can be manipulated to a desired pattern to provide a more easily discernable spotlight to a user. The pattern shown in FIG. 31 is a rectangular-shaped pattern (e.g., a square-shaped pattern) that forms a rectangle when drawing imaginary lines between the center areas of the light beams on the target of interest from the visible light emitted by the visible lights 208(1)-208(4). The pattern can be any shape pattern depending on the number of visible lights 208 and the orientation of the visible lights 208 in the light source housing 202. In this example, the pattern shown in FIG. 31 is polygonal-shaped (e.g., with four (4) sides). The pattern could be circular-shaped. Only one visible light 208 could be included with the circular-shaped cone of light on the target of interest from the visible light emitted by the visible light 208 is circular shaped. The distance between the visible light 208 and the target of interest affects the shape and diameter of the cone of light. In this example, the UV LEDs 110 are arranged in the light source housing 202 such that their emitted UV light is contained within the shaped pattern formed by drawing imaginary lines between the beams of light on the target of interest emitted by the visible lights 208(1)-208(4) depending on the type of visible lights 208(1)-208(4), their distance from the target of interest, and the type and shape of their reflectors 424.

FIG. 32 is a diagram of the mask 3200 placed on the UV light source 102 that includes patterned sections 3202(1)-3202(4) to cause visible light emitted from the visible lights 208(1)-208(4) on a surface to be patterned as shown in FIG. 31. The visible light emitted from the visible lights 208(1)-208(4) is emitted through the respective patterned sections 3202(1)-3202(4) of the mask 3200. This may control the visible light beam spread of the visible light to be of a higher resolution to be more easily visible by a user and for a user to more easily visibly detect the perimeter of the visible light beam spread of the visible lights 208(1)-208(4). FIG. 33 illustrates the mask 3200 in a closer view. For example, the mask 3200 can be formed from a laser cut think stainless steel sheet 3204 to be able to fit over the top the UV light source shield 108 as an example.

The use of the mask 3200 also affects the brightness of the visible light emitted by the visible lights 208(1)-208(4). The patterned sections 3202(1)-3202(4) can be designed to control the desired brightness of the visible light emitted by the visible lights 208(1)-208(4). This may be important to achieve a desired light intensity of UV light 104 emitted by the UV light source 102, that is not visible to the human eye, without causing the visible lights 208(1)-208(4) to emit visible light at a brightness that is deemed too bright and/or undesirable for a user. As discussed above, certain light driver circuits 400(1)-400(6) are configured to drive a current in the same light string 206(1)-206(6) that has both UV LEDs 100 and a visible light 208(1)-208(4). Thus, the same amount of current drive to the UV LEDs 100 in such a light string 206(1)-206(6) is also driven to the visible light 208(1)-208(4) in the same light string 206(1)-206(6). It may not be possible or desired to drive less current to the visible light 208(1)-208(4), especially if LEDs, without affecting and/or shutting off the operation of the visible light 208(1)-208(4). There may be a threshold current (e.g., 250 mA) necessary to achieve an on state with visible LEDs. Thus, in this example, to drive the desired amount of current to the UV LEDs 110 to achieve the desired light intensity for efficacy, this amount of current driven to the visible light(s) 208(1)-208(4) in the same light string 206(1)-206(6) may be too bright. The visible lights 208(1)-208(4) may be more efficient than the UV LEDs 110 in terms of conversion of current to light power. Thus, by placing the patterned sections 3202(1)-3202(4) of the mask 3200 in the light path of the visible light(s) 208(1)-208(4), the visible light emitted from the visible light(s) 208(1)-208(4) is attenuated or blocked. The patterned sections 3202(1)-3202(4) of the mask 3200 may be arranged to block the center area of the light path of the visible light(s) 208(1)-208(4) to block the more light intense areas of the visible light emitted by the visible light(s) 208(1)-208(4). Visible light emitted by the visible light(s) 208(1)-208(4) may leak around the solid portions of the patterned sections 3202(1)-3202(4). Alternatively, a filter could be placed on the light source housing 202 to filter all light emitted from the visible lights 208(1)-208(4), but this attenuates the entire cone of light emitted from the visible lights 208(1)-208(4). The patterned sections 3202(1)-3202(4) of the mask 3200 allow the selective filtering of visible light emitted by the visible lights 208(1)-208(4). It may also be desired to purposefully control the uniformity of the UV light emitted from the UV LEDs 110 to provide a uniform intensity of UV light 104 on a surface of interest from the UV light emission device 100. The design of the parabolic reflectors 424 of the UV light source 102, as shown in FIGS. 4A and 4B, affects the uniformity of the UV light 104 emitted from the UV LEDs 110 of the UV light source 102. In this regard, experiments were conducted to explore the uniformity of the intensity of UV light 104 at various distances from the parabolic reflectors 424 on a surface of interest. FIGS. 34A-34F illustrate various heat maps 3400A-3400F that show two-dimensional power distribution (distance in mm from center vs. $W/m^2$) of UV light 104 emitted by the UV light source 102 across a 4"×4" area at varying distances from the parabolic reflectors 424 at distances of 1 inch, 2 inches, 3 inches, 4 inches, 6 inches, and 12 inches, respectively. Light from a point source decreases as the square of the distance. A doubling of distance would cause the light power of the UV light 104 to decrease by a factor of 4. The parabolic reflectors 424 collimate the UV light 1 in the nearfield, which extends the range of usable distance. If the UV light 104 were not collimated, the output power of the UV light 104 at 2" would be 25% of the output power of UV light 104 at 1". The average power of the UV light 104 in the heat map 3400A in FIG. 34A was 143.58 $W/m^2$. The average power of the UV light 104 in the heat map 3400B in FIG. 34B was 139.41 $W/m^2$. The average power of the UV light 104 in the heat map 3400C in FIG. 34C was 129.56 $W/m^2$. The average power of the UV light 104 in the heat map 3400D in FIG. 34D was 117.75 $W/m^2$. The average power of the UV light 104 in the heat map 3400E in FIG. 34E was 99.08 $W/m^2$. The average power of the UV light 104 in the heat map 3400F in FIG. 34F was 56.46 $W/m^2$.

Figure 35:
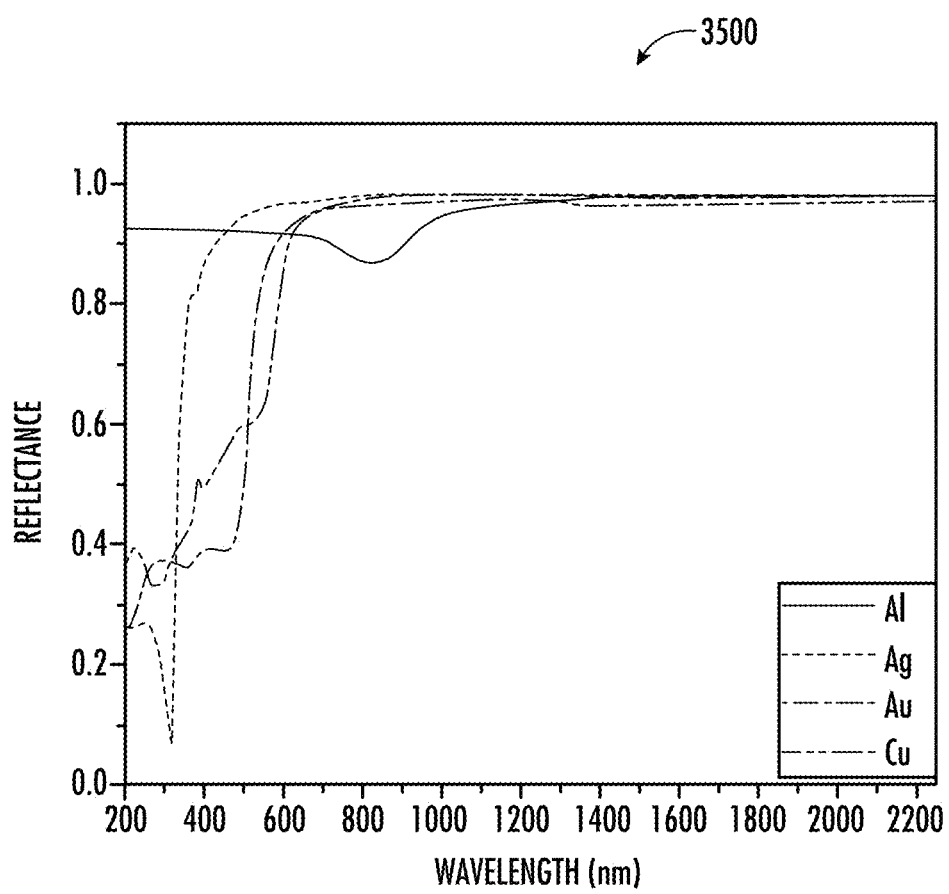
FIG. 35 is a graph illustrating an exemplary reflectance versus wavelength of different common metals.

The reflectivity of light off of various materials has long been characterized. Aluminum is known to have a high reflectivity compare to other metals, for example. For example, as shown in the graph 3500 in FIG. 35, it is shown that not all metallic reflectors respond the same as the short wavelengths. The graph in FIG. 35 plots reflectance vs. wavelength in nm for aluminum (Al), silver (Ag), gold (Au), and copper (Cu). Note that silver, gold, and copper have very low reflectance as the wavelength drops below 600 nm. At a UV light of 270 nm emitted from the UV light source 102 as an example, note that graph 3500 shows that only aluminum exhibits decent reflectivity at >90% at this wavelength. For this reason, reflectors made for lower wavelengths (220-300 nm) are often made from aluminum. Unfortunately, aluminum may also oxidize and quickly corrodes such that it will lose its reflective properties unless protected.

In this regard, in an example, the parabolic reflectors 424 in the UV light source 102 of the UV light emission device 100 may be coated with a thick protective coasting by adding a thin coat of $SiO_2$ (glass) to the surface of parabolic reflectors 424. The parabolic reflectors 424 uses a planetary system and crucible to deposit aluminum onto a plastic substrate and then apply a thin coat of $SiO_2$ (glass). In this fashion, reflectivity measurement of >70% at a UV light wavelength of 270 nm has been observed. For example, the protective coating could be formed on the parabolic reflectors 424 by electron beam deposition process (E-Beam). Source materials in the coating chamber can either be vaporized using heating or electron-beam bombardment of powder or granular dielectric or metallic substances. The subsequent vapor condenses upon the optical surfaces, and via precision computer control of heating, vacuum levels, substrate location, and rotation during the deposition process, result in conformal optical coatings of pre-specified optical thicknesses.

Figure 36:
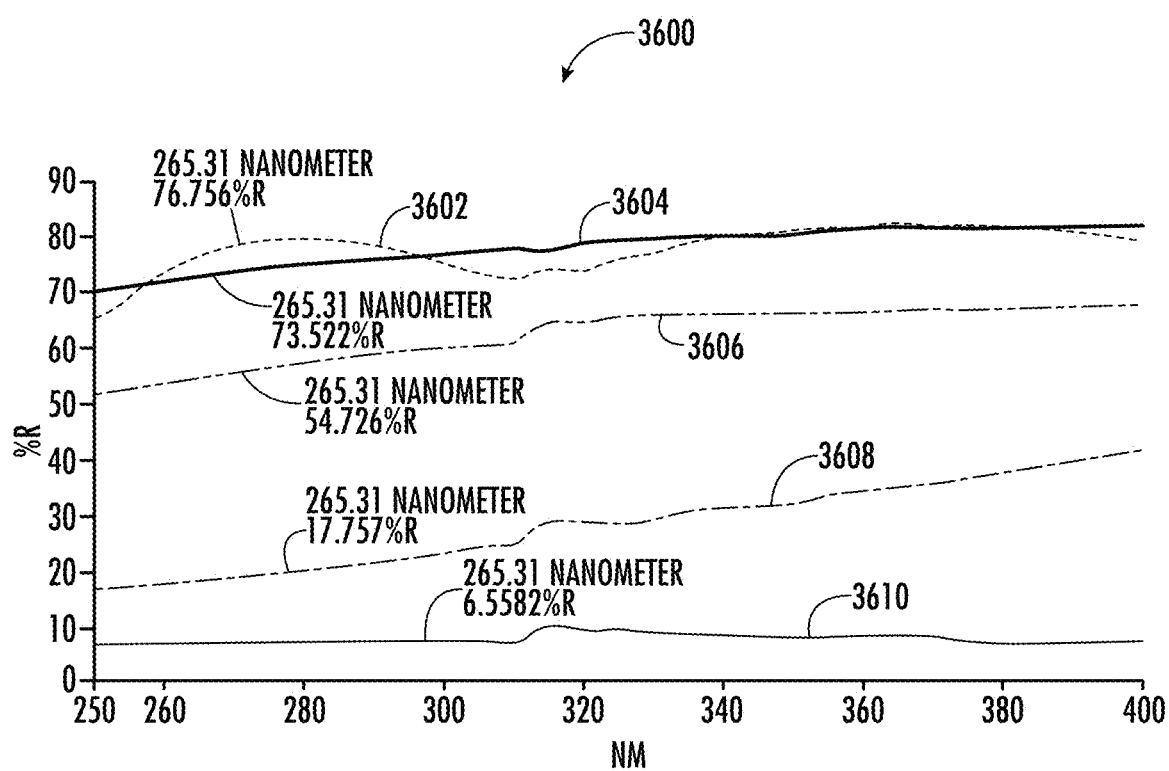
FIG. 36 is a graph illustrating an exemplary reflectance versus wavelength of different coatings on parabolic reflectors of the UV light source in the UV light emission device in FIGS. 1A-1C.

FIG. 36 is a graph 3600 that shows percentage reflectance of the SiO$_2$ (glass) 3602 as compared to other coatings 3604, 3606, 3608, 3610, 3612. Curve 3610 illustrates the reflectance of the plastic parabolic reflector 424 with no coating. Curve 3608 illustrates the reflectance of the parabolic reflector 424 coated with aluminum. Curves 3606, 3604 illustrate reflectances of the parabolic reflector 424 of other sample coatings. Curve 3602 illustrates the reflectance of the plastic parabolic reflector 424 with SiO$_2$ (glass).

FIG. 37A-37D illustrate an alternative UV light emission device 3700 similar to FIGS. 1A-1C but with a power connector 3702 and a mounting structure 3706 on the base housing 124. Common elements between the UV light emission device 3700 in FIGS. 37A-37D and the UV light emission device 100 in FIGS. 1A-1C are shown with common element numbers. The previous description of the UV light emission device 100 in FIGS. 1A-36 is applicable to the UV light emission device 3700. The power connector 3702 is a male connector used to connect the UV light emission device 3700 to a battery. A cable 132 is fitted with a female cable connector 3704 that can be secured to connector 3702. The power connector 3702 is connector made by Hirose Electric Co., part no. LF10WBP-4s(31), and the cable connector 3704 is also made by Hirose Electric Co., part LF10WBR-4P. FIGS. 37A-37D also illustrate a mounting structure 3706 that is fitted to the base housing 124. The mounting structure 3706 is a circular metal member that is configured to be received in a receiver in a belt clip 3800 shown in FIGS. 38A-38C to hold the support the base member 124 of the UV light emission device 3700 on a user's belt clip.

Figure 37A:
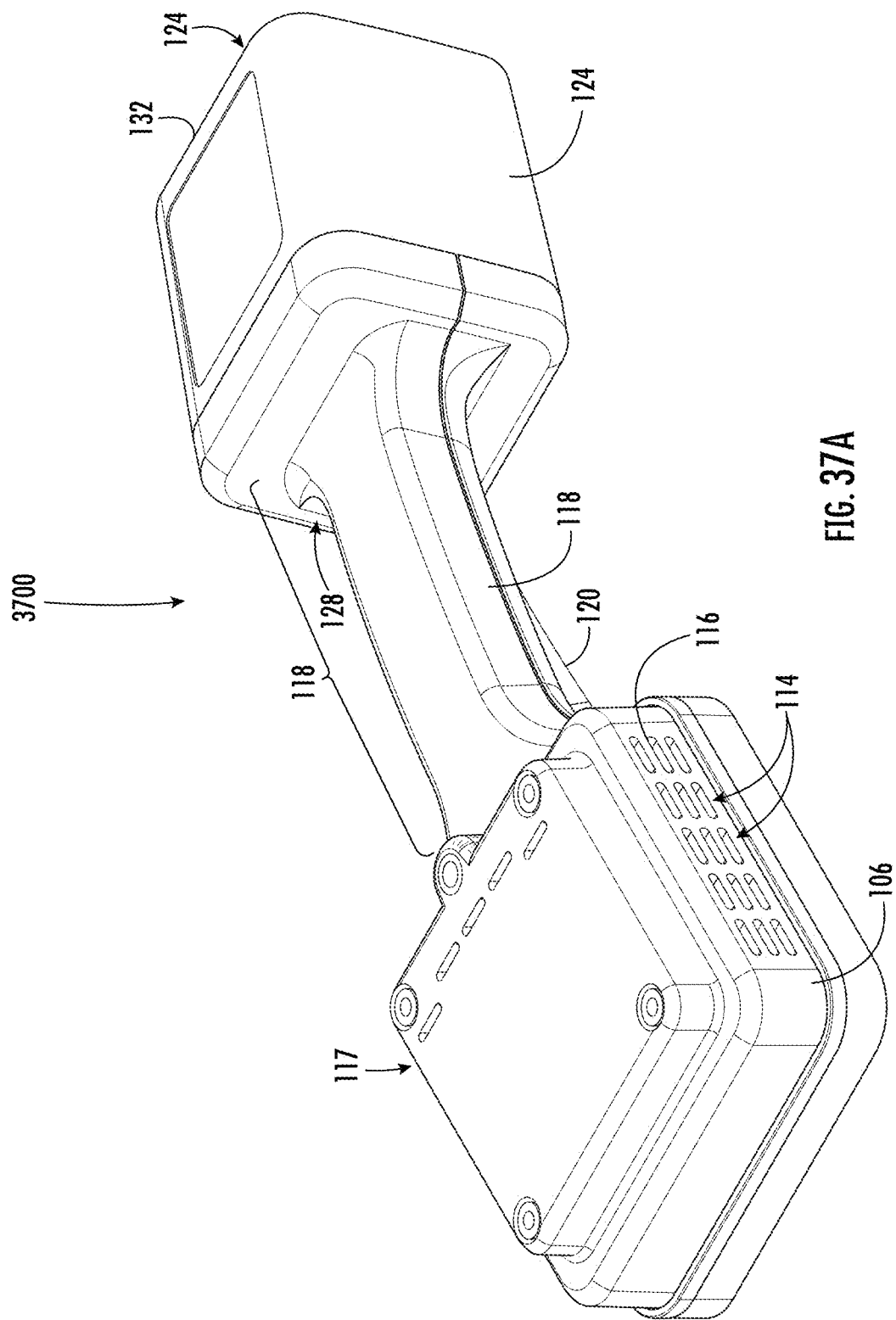
FIGS. 37A-37D illustrate an alternative UV light emission device similar to FIGS. 1A-1C, but with a power connector and a mounting structure on the base.
Figure 37B:
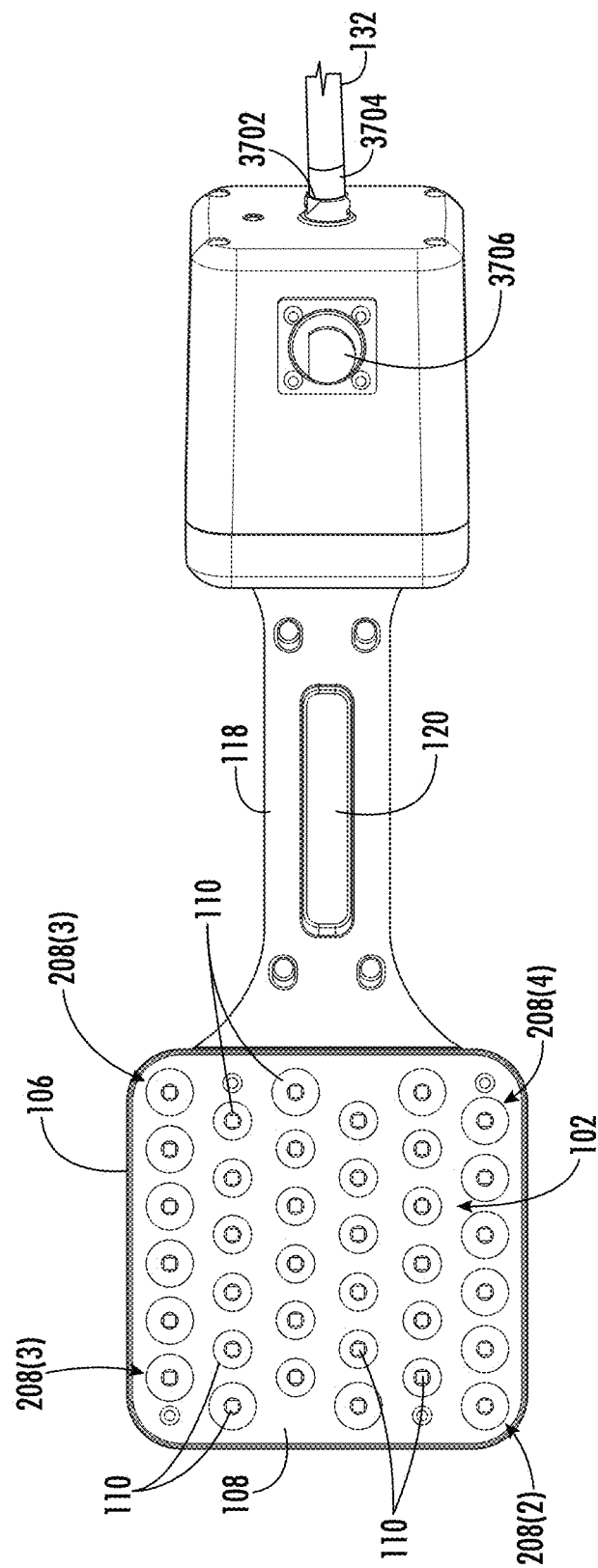
Figure 37C:
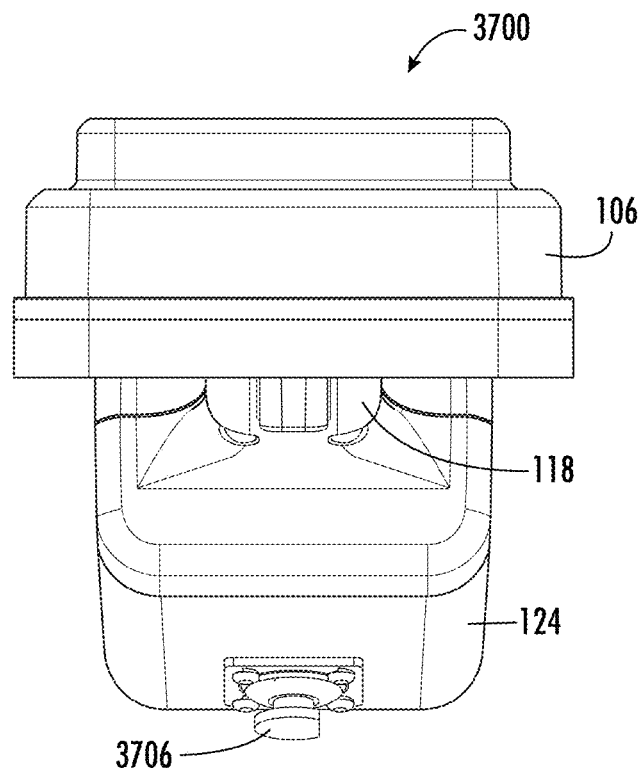
Figure 37D:
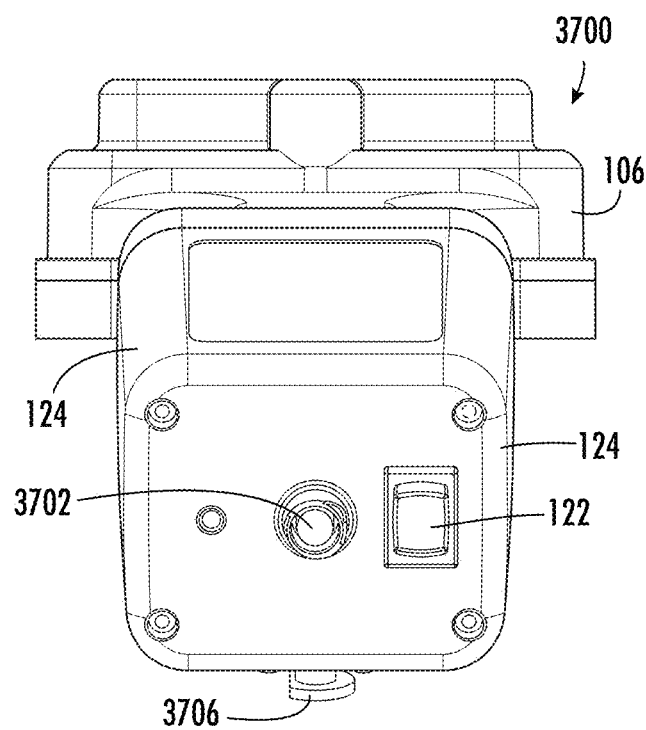
Figure 38C:
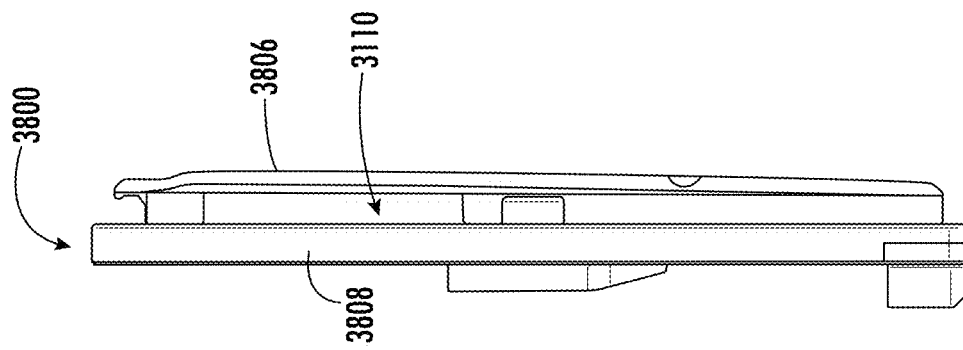
FIGS. 38A-38C are respective perspective, front and side views, respectively, of belt clip that is configured to receive the mounting structure on the base of the UV light emission device in FIGS. 37A-37C to mount the UV light emission device to a user's belt.
Figure 38B:
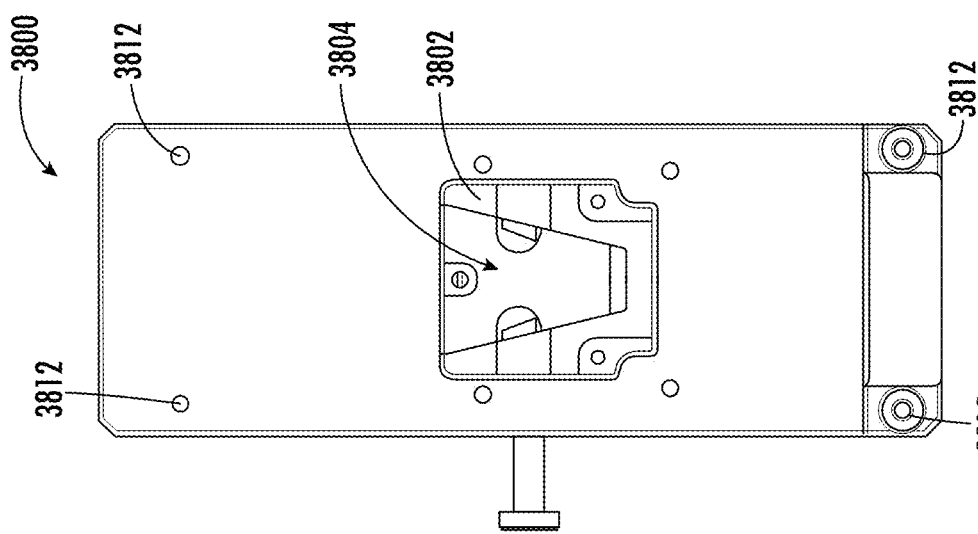
Figure 38A:
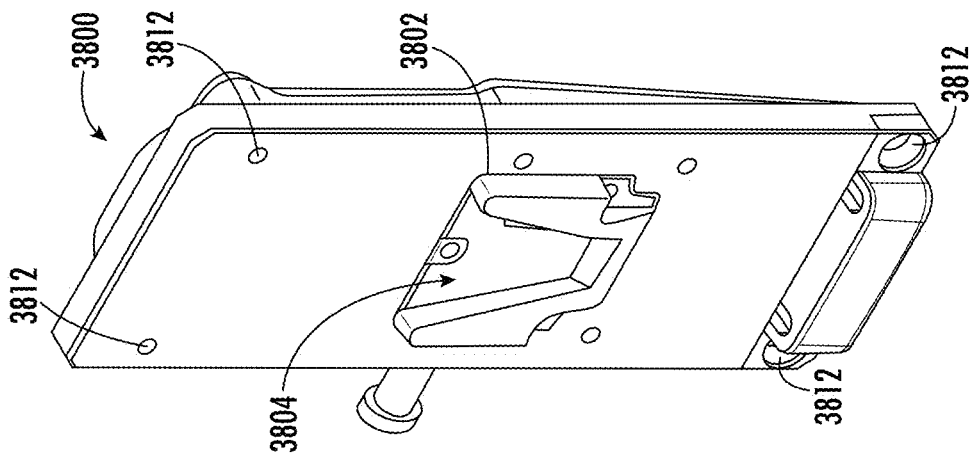

In this regard, FIG. 38A-38C are respective perspective, front and side views, respectively, of belt clip 3800 that is configured to receive the mounting structure 3706 on the base housing 124 of the UV light emission device 3700 in FIGS. 37A-37C to mount the UV light emission device 3700 to a user's belt. As shown in FIG. 38A-38C, the mounting structure 3706 includes a V-shaped receiver 3804 that is configured to receive and secure the mounting structure 3706. As shown in the side view of the belt clip 3800 in FIG. 38C, the belt clip 3800 includes a front member 3808 and a back member 3806 attached to each other and disposed in substantially parallel planes with a slot 3110 formed therebetween to be able to receive a user's belt. In this manner, the belt clip 3800 can be secured to a user's belt. The mounting structure 3706 on the base housing 124 of the UV light emission device 3700 in FIGS. 37A-37C is received in the receiver 3804 wherein the handle 118 and light source housing 106 can rotate and swivel downward due to gravity such that the UV light emission device 3700 hangs down from the belt clip 3800 by the base member 124 and its mounting structure 3706 secured in the receiver 3804. The mounting structure 3706 being circular in shape allows it to easily rotate within the receiver 3804. The belt clip 3800 can also include orifices 3812 to be able to mount the belt clip 3800 to a wall or other surface to support the UV light emission device 3700 in different manners than on a user's belt.

Figure 39:
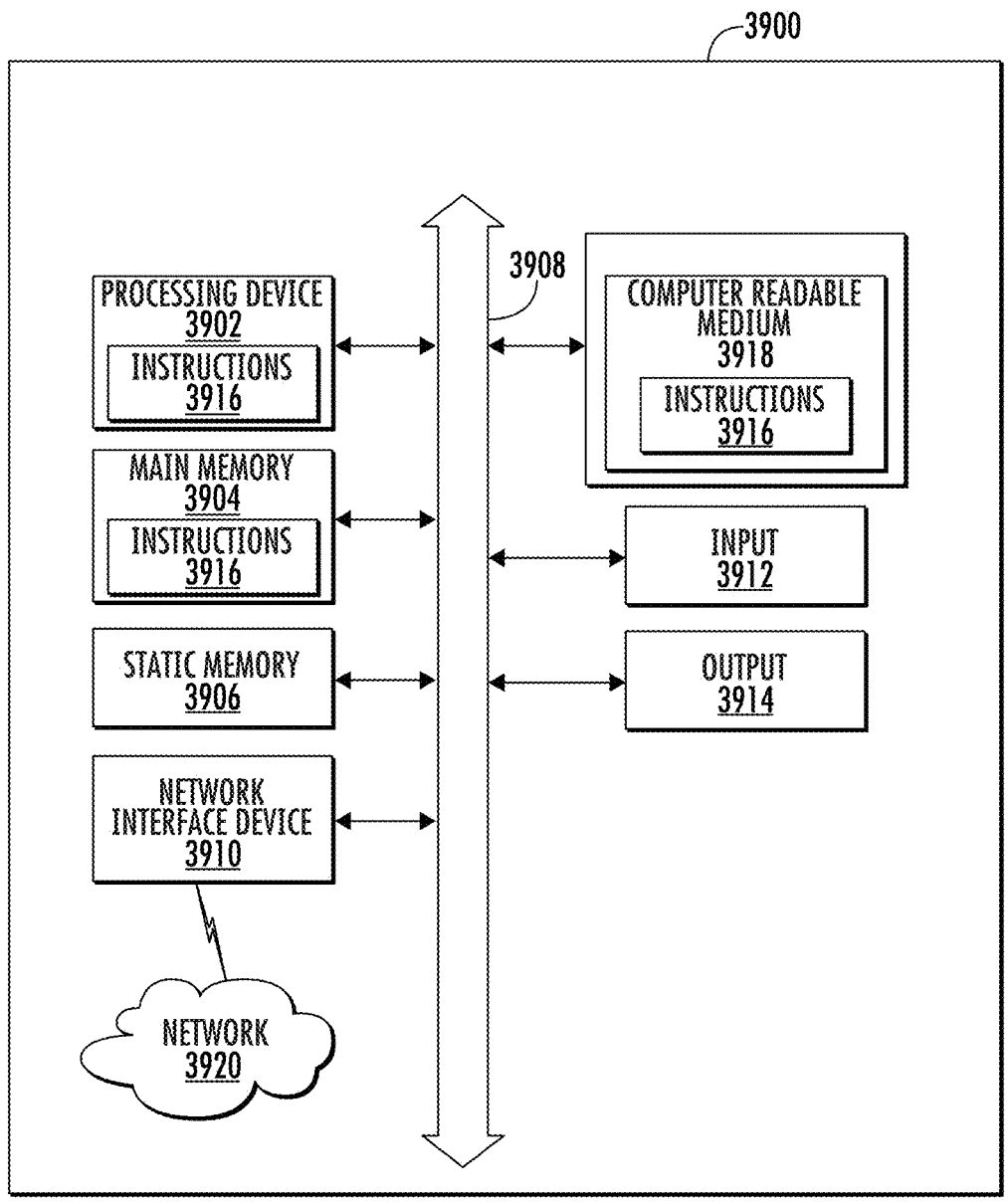
FIG. 39 a schematic diagram of a representation of an exemplary computer system, wherein the exemplary computer system is configured to control the operation of a UV light emission device, including but not limited to the UV light emission devices disclosed herein.

The UV light emission devices and charging bases disclosed herein can include a computer system 3900, such as shown in FIG. 39, to control the operation of a UV light emission device, including but not limited to the UV light emission devices disclosed herein. For example, the computer system 3900 may be the controller circuit 524 in the electrical control systems 404, 804, 1004 in FIGS. 5, 8, and 10. With reference to FIG. 39, the computer system 3900 includes a set of instructions for causing the multi-operator radio node component(s) to provide its designed functionality and their circuits discussed above. The multi-operator radio node component(s) may be connected (e.g., networked) to other machines in a LAN, an intranet, an extranet, or the Internet. The multi-operator radio node component(s) may operate in a client-server network environment or as a peer machine in a peer-to-peer (or distributed) network environment. While only a single device is illustrated, the term "device" shall also be taken to include any collection of devices that individually or jointly execute a set (or multiple sets) of instructions to perform any one or more of the methodologies discussed herein. The multi-operator radio node component(s) may be a circuit or circuits included in an electronic board card, such as a printed circuit board (PCB) as an example, a server, a personal computer, a desktop computer, a laptop computer, a personal digital assistant (PDA), a computing pad, a mobile device, or any other device, and may represent, for example, a server, edge computer, or a user's computer. The exemplary computer system 3900 in this embodiment includes a processing circuit or processing device 3902, a main memory 3904 (e.g., read-only memory (ROM), flash memory, dynamic random access memory (DRAM) such as synchronous DRAM (SDRAM), etc.), and a static memory 3906 (e.g., flash memory, static random access memory (SRAM), etc.), which may communicate with each other via a data bus 3908. Alternatively, the processing device 3902 may be connected to the main memory 3904 and/or static memory 3906 directly or via some other means of connectivity. The processing device 3902 may be a controller, and the main memory 3904 or static memory 3906 may be any type of memory.

The processing device 3902 represents one or more general-purpose processing circuits such as a microprocessor, central processing unit, or the like. More particularly, the processing device 3902 may be a complex instruction set computing (CISC) microprocessor, a reduced instruction set computing (RISC) microprocessor, a very long instruction word (VLIW) microprocessor, a processor implementing other instruction sets, or processors implementing a combination of instruction sets. The processing device 3902 is configured to execute processing logic in instructions 3916 for performing the operations and steps discussed herein.

The computer system 3900 may further include a network interface device 3910. The computer system 3900 also may or may not include an input 3912 to receive input and selections to be communicated to the computer system 3900 when executing instructions. The computer system 3900 also may or may not include an output 3914, including but not limited to a display, a video display unit (e.g., a liquid crystal display (LCD) or a cathode ray tube (CRT)), an alphanumeric input device (e.g., a keyboard), and/or a cursor control device (e.g., a mouse).

The computer system 3900 may or may not include a data storage device that includes instructions 3916 stored in a computer-readable medium 3918. The instructions 3916 may also reside, completely or at least partially, within the main memory 3904 and/or within the processing device 3902 during execution thereof by the computer system 3900, the main memory 3904, and the processing device 3902 also constituting computer-readable medium. The instructions 3916 may further be transmitted or received over a network 3920 via the network interface device 3910.

While the computer-readable medium 3918 is shown in an exemplary embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the processing circuit and that cause the processing circuit to perform any one or more of the methodologies of the embodiments disclosed herein. The term "computer-readable medium" shall accordingly be taken to include, but not be limited to, solid-state memories, optical and magnetic medium, and carrier wave signals.

The embodiments disclosed herein include various steps. The steps of the embodiments disclosed herein may be performed by hardware components or may be embodied in machine-executable instructions, which may be used to cause a general-purpose or special-purpose processor programmed with the instructions to perform the steps. Alternatively, the steps may be performed by a combination of hardware and software.

The embodiments disclosed herein may be provided as a computer program product, or software, that may include a machine-readable medium (or a computer-readable medium) having stored thereon instructions, which may be used to program a computer system (or other electronic devices) to perform a process according to the embodiments disclosed herein. A machine-readable medium includes any mechanism for storing or transmitting information in a form readable by a machine (e.g., a computer). For example, a machine-readable medium includes a machine-readable storage medium (e.g., read-only memory ("ROM"), random access memory ("RAM"), magnetic disk storage medium, optical storage medium, flash memory devices, etc.).

The various illustrative logical blocks, modules, and circuits described in connection with the embodiments disclosed herein may be implemented or performed with a processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A controller may be a processor. A processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The embodiments disclosed herein may be embodied in hardware and in instructions that are stored in hardware and may reside, for example, in Random Access Memory (RAM), flash memory, Read-Only Memory (ROM), Electrically Programmable ROM (EPROM), Electrically Erasable Programmable ROM (EEPROM), registers, a hard disk, a removable disk, a CD-ROM, or any other form of computer-readable medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

Unless otherwise expressly stated, it is in no way intended that any method set forth herein be construed as requiring that its steps be performed in a specific order. Accordingly, where a method claim does not actually recite an order to be followed by its steps, or it is not otherwise specifically stated in the claims or descriptions that the steps are to be limited to a specific order, it is no way intended that any particular order be inferred. It will be apparent to those skilled in the art that various modifications and variations can be made without departing from the spirit or scope of the invention. Since modifications combinations, sub-combinations, and variations of the disclosed embodiments incorporating the spirit and substance of the invention may occur to persons skilled in the art, the invention should be construed to include everything within the scope of the appended claims and their equivalents It is also noted that the operational steps described in any of the exemplary aspects herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary aspects may be combined. It is to be understood that the operational steps illustrated in the flowchart diagrams may be subject to numerous different modifications as will be readily apparent to one of skill in the art. Those of skill in the art will also understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A handheld light emission device for decontamination of a surface, air, or area, comprising:
    a light source housing comprising an interior chamber and an opening to the interior chamber; and
    a UV light source disposed in the interior chamber of the light source housing, the UV light source comprising one or more UV lights each configured to emit UV light towards the opening of the light source housing;
    one or more visible lights disposed in the interior chamber of the light source and each configured to emit visible light towards the opening of the light source housing;
    a handle comprising a first end and a second end opposite the first end, the first end of the handle coupled to the light source housing;

a base coupled to the second end of the handle;
an electrical control system disposed in the base, the electrical control system comprising:
  a power rail configured to distribute a power signal; and
  at least one light driver circuit electrically coupled to the power rail and the UV light source;
the base comprising a wiring assembly electrically coupled to the at least one light driver circuit and the UV light source; and
the at least one light driver circuit configured to:
  couple power from the power signal to the one or more UV lights over the wiring assembly in the UV light source to cause the one or more UV lights to emit UV light towards the opening of the light source housing; and
  couple power from the power signal to the one or more visible lights over the wiring assembly to the one or more visible lights to cause the one or more visible lights to emit visible light the opening of the light source housing.

2. The handheld light emission device of claim 1, wherein the opening of the light source housing comprises a planar opening disposed along a first plane of the light source housing;
  the one or more UV lights are each configured to emit UV light in a direction orthogonal the first plane of the planar opening; and
  the one or more visible lights are each configured to emit UV light in a direction orthogonal the first plane of the planar opening.

3. The handheld light emission device of claim 1, wherein the one or more light driver circuits are configured to couple power from the power signal to the one or more UV lights and the one or more visible lights such that the one or more visible lights only receive the power when the one or more UV lights receive power.

4. The handheld light emission device of claim 1, wherein the one or more visible lights are configured to emit white light.

5. The handheld light emission device of claim 1, wherein:
  the one or more UV lights comprise one or more UV light-emitting diodes (LEDs);
  the one or more visible lights comprise one or more visible LEDs; and
  the electrical control system further comprises:
  a power enable switch configured to distribute the power signal to the at least one light driver circuit in response to a power enable signal indicating a power enable state;
  a momentary switch configured to provide a trigger signal indicating an activation state in response to being activated; and
  a controller circuit configured to:
    receive the trigger signal from the momentary switch; and
    generate the power enable signal of a power enable state in response to the trigger signal indicating an activation state.

6. The handheld light emission device of claim 5, wherein the momentary switch is disposed in the handle and configured to be engaged in a closed position by a user when holding the handle to cause the secondary switch to provide the trigger signal.

7. The handheld light emission device of claim 1, wherein the one or more UV lights comprise one or more UV light-emitting devices (LEDs), each configured to emit UV light in at least one wavelength between 200-399 nanometers (nm).

8. The handheld light emission device of claim 1, wherein the one or more UV lights comprise one or more UV light-emitting devices (LEDs), each configured to emit UV light in at least one wavelength between 250-280 nanometers (nm).

9. The handheld light emission device of claim 1, wherein the one or more UV lights comprise one or more UV light-emitting devices (LEDs), each configured to emit UV light in at least one wavelength between 200-230 nanometers (nm).

10. The handheld light emission device of claim 1, wherein the light source housing is spatially separated from the base by at least eight (8) inches.

11. The handheld light emission device of claim 1, further comprising:
  a visible light source comprising one or more visible lights each configured to emit visible light; and
  wherein:
    the light source housing further comprises a visible light ring disposed around a peripheral edge of the light source housing and having at least one translucent side exposed from the light source housing, the visible light ring configured to receive the visible light emitted by the visible light source and to propagate the received visible light through the at least one translucent side; and
    the at least one light driver circuit is further coupled to the visible light source, the at least one light driver circuit configured to couple power from the power signal to the one or more visible lights to cause the one or more visible lights to emit visible light toward the at least one translucent side of the visible light ring.

12. The handheld light emission device of claim 1, wherein:
  the opening of the light source housing comprises a planar opening disposed along a first plane of the light source housing such that the one or more UV lights of the UV light source are configured to emit UV light in a direction orthogonal to the plane of the planar opening; and
  the handle coupled to the light source housing having a tangential plane that is non-parallel to the first plane at an angle.

13. The handheld light emission device of claim 1, wherein an angle between the first plane and the tangential plane are between 1 and 45 degrees.

14. The handheld light emission device of claim 1, wherein the electrical control system further comprises:
  a primary switch comprising an input node coupled to the power rail and an output node, the primary switch coupled in series to the power rail, the primary switch configured to be activated to couple the power signal on the input node to the output node, and configured to be deactivated to disconnect the power signal from the output node;
  a power enable switch coupled to the power rail between the output node and the at least one light driver circuit, the power enable switch configured to distribute the power signal from the output node to the at least one light driver circuit in response to a power enable signal indicating a power enable state;

a secondary switch configured to provide a trigger signal indicating an activation state in response to being activated; and
a controller circuit configured to:
receive the trigger signal from the secondary switch; and
generate the power enable signal of a power enable state in response to the trigger signal indicating an activation state.

15. The handheld light emission device of claim 14, wherein the secondary switch is disposed in the handle and configured to be engaged in a closed position by a user when holding the handle to cause the secondary switch to provide the trigger signal.

16. The handheld light emission device of claim 14, wherein the secondary switch is a momentary switch that is configured to return to an open position when not engaged by the user such that the secondary switch does not provide the trigger signal.

17. The handheld light emission device of claim 14, further comprising a haptic feedback device,
the controller circuit further configured to activate the haptic feedback device to generate a haptic.

18. The handheld light emission device of claim 1, wherein:
the electrical control system further comprises:
a power enable switch coupled to the power rail between an output node and the at least one light driver circuit;
the power enable switch configured to distribute the power signal from the output node to the at least one light driver circuit in response to a power enable signal indicating a power enable state; and
the power enable switch configured to not distribute the power signal from the output node to the at least one light driver circuit in response to a power enable signal indicating a power disable state;
an inertial measurement (IMU) circuit configured to generate an accelerometer signal indicating an acceleration of the light source housing; and
a controller circuit configured to:
receive the accelerometer signal generated by the IMU circuit;
determine if the accelerometer signal indicates an acceleration of the light source housing outside a predefined acceleration limit; and
in response to determining the acceleration signal indicates an acceleration of the light source housing outside the predefined acceleration limit, generate the power enable signal of a power disable state.

19. The handheld light emission device of claim 1, wherein:
the opening of the light source housing comprises a planar opening disposed along a first plane of the light source housing such that the one or more UV lights of the UV light source are configured to emit UV light in a direction orthogonal the plane of the planar opening; and
the electrical control system further comprises:
a power enable switch coupled to the power rail between an output node and the at least one light driver circuit;
the power enable switch configured to distribute the power signal from the output node to the at least one light driver circuit in response to a power enable signal indicating a power enable state; and
the power enable switch configured to not distribute the power signal from the output node to the at least one light driver circuit in response to a power enable signal indicating a power disable state;
an inertial measurement (IMU) circuit configured to generate an orientation signal indicating an orientation of the light source housing relative to a plane of the planar opening being parallel to the ground;
a controller circuit configured to:
receive the orientation signal generated by the IMU circuit;
determine if the orientation signal indicates an orientation of the light source housing outside a predefined orientation limit; and
in response to determining the orientation signal indicates an orientation of the light source housing outside the predefined orientation limit, generate the power enable signal of a power disable state.

20. The handheld light emission device of claim 19, wherein the predefined orientation limit is the planar surface of the UV light source being oriented in a plane between 90-95 degrees from the ground.

21. The handheld light emission device of claim 19, wherein the controller circuit is configured to generate the power enable signal of a power enable state in response to determining the orientation signal, indicates an orientation of the light source housing within the predefined orientation limit.

22. The handheld light emission device of claim 1, wherein:
the electrical control system further comprises:
a safety switch coupled to the power rail between the output node and the at least one light driver circuit;
the safety switch configured to distribute the power signal from an output node to the at least one light driver circuit in response to a power safety signal indicating a power safe state; and
the safety switch configured to not distribute the power signal from the output node to the at least one light driver circuit in response to a power safety signal indicating a power unsafe state; and
a safety circuit configured to generate the power safety signal.

23. The handheld light emission device of claim 22, wherein:
the electrical control system further comprises:
a power regulator circuit coupled to the power rail and the safety circuit, the power regulator circuit configured to:
detect a voltage of a voltage signal based on the power signal; and
generate a signal indicating if the voltage signal is within an expected voltage range; and
the safety circuit configured to:
receive the signal indicating if the voltage signal is within an expected voltage range; and
in response to receiving the signal indicating the voltage signal is outside of the expected voltage range, generate the power safety signal indicating a power unsafe state.

24. The handheld light emission device of claim 22, wherein:
the electrical control system further comprises:
a temperature sensor disposed in the light source housing adjacent to the UV light source; and the temperature sensor configured to:
sense a temperature in an area of the UV light source; and
generate a temperature signal indicative of the sensed temperature in the area of the UV light source; and
the safety circuit configured to:
receive the temperature signal indicative of the sensed temperature in the area of the UV light source;
determine if the temperature signal indicates the sensed temperature is outside a predetermined temperature range for the UV light source; and
in response to determining the temperature signal indicates the sensed temperature is outside the predetermined temperature range for the UV light source, generate the power safety signal indicating a power unsafe state.

25. The handheld light emission device of claim 1, wherein:
the electrical control system further comprises:
a power enable switch coupled to the power rail between an output node and the at least one light driver circuit;
the power enable switch configured to distribute the power signal from the output node to the at least one light driver circuit in response to a power enable signal indicating a power enable state;
a safety switch configured to not distribute the power signal from the output node to the at least one light driver circuit in response to a power enable signal indicating a power disable state; and
a controller circuit configured to generate the power enable signal.

26. The handheld light emission device of claim 25, wherein:
the electrical control system further comprises:
a temperature sensor disposed in the light source housing adjacent to the UV light source;
the temperature sensor configured to:
sense a temperature in an area of the UV light source; and
generate a temperature signal indicative of the sensed temperature in the area of the UV light source;
the controller circuit further configured to:
receive the temperature signal indicative of the sensed temperature in the area of the UV light source;
determine the temperature in the area of the UV light source based on the received temperature signal;
determine if the temperature determined in the area of the UV light is outside a predetermined temperature range for the UV light source; and
in response to determining the temperature signal indicates the sensed temperature outside is the predetermined temperature range for the UV light source, generate the power enable signal indicating a power disable state.

27. The handheld light emission device of claim 1, further comprising a circular-shaped mounting structure attached to the base, the mounting structure configured to be received in a receiver to support the handheld light emission device, wherein the circular-shaped mounting structure is configured to swivel about the receiver to allow the handheld light emission device to swivel about the receiver.

28. A handheld light emission device for decontamination of a surface, air, or area, comprising:
a light source housing comprising an interior chamber and an opening to the interior chamber; and
a UV light source disposed in the interior chamber of the light source housing, the UV light source comprising one or more UV lights each configured to emit UV light towards the opening of the light source housing;
one or more visible lights disposed in the interior chamber of the light source and each configured to emit visible light towards the opening of the light source housing;
a handle comprising a first end and a second end opposite the first end, the first end of the handle coupled to the light source housing;
a base coupled to the second end of the handle;
an electrical control system disposed in the base, the electrical control system comprising:
a power rail configured to distribute a power signal; and
at least one light driver circuit electrically coupled to the power rail and the UV light source;
the base comprising a wiring assembly electrically coupled to the at least one light driver circuit and the UV light source; and
the at least one light driver circuit configured to:
couple power from the power signal to the one or more UV lights over the wiring assembly in the UV light source to cause the one or more UV lights to emit UV light towards the opening of the light source housing; and
couple power from the power signal to the one or more visible lights over the wiring assembly to the one or more visible lights to cause the one or more visible lights to emit visible light the opening of the light source housing;
the opening of the light source housing comprises a planar opening disposed along a first plane of the light source housing;
the one or more UV lights are each configured to emit UV light in a direction orthogonal the plane of the planar opening;
the one or more visible lights are each configured to emit UV light in the direction orthogonal the plane of the planar opening; and
the one or more UV lights comprise one or more UV light-emitting devices (LEDs), each configured to emit UV light in at least one wavelength between 200-399 nanometers (nm).

29. A handheld light emission device for decontamination of a surface, air, or area, comprising:
a light source housing comprising an interior chamber and an opening to the interior chamber; and
a UV light source disposed in the interior chamber of the light source housing, the UV light source comprising one or more UV lights each configured to emit UV light towards the opening of the light source housing;
one or more visible lights disposed in the interior chamber of the light source and each configured to emit visible light towards the opening of the light source housing;
a handle comprising a first end and a second end opposite the first end, the first end of the handle coupled to the light source housing;
a base coupled to the second end of the handle;
an electrical control system disposed in the base, the electrical control system comprising:
a power rail configured to distribute a power signal; and
at least one light driver circuit electrically coupled to the power rail and the UV light source;

the base comprising a wiring assembly electrically coupled to the at least one light driver circuit and the UV light source; and the at least one light driver circuit configured to:
couple power from the power signal to the one or more UV lights over the wiring assembly in the UV light source to cause the one or more UV lights to emit UV light towards the opening of the light source housing; and
couple power from the power signal to the one or more visible lights over the wiring assembly to the one or more visible lights to cause the one or more visible lights to emit visible light the opening of the light source housing;

the one or more UV lights comprise one or more UV light-emitting diodes (LEDs);

the one or more visible lights comprise one or more visible LEDs; and the electrical control system further comprises:
a power enable switch configured to distribute the power signal to the at least one light driver circuit in response to a power enable signal indicating a power enable state;
a momentary switch configured to provide a trigger signal indicating an activation state in response to being activated; and
a controller circuit configured to:
receive the trigger signal from the switch; and
generate the power enable signal of a power enable state in response to the trigger signal indicating an activation state; and
the momentary switch is disposed in the handle and configured to be engaged in a closed position by a user when holding the handle to cause the secondary switch to provide the trigger signal.

30. A handheld light emission device for decontamination of a surface, air, or area, comprising:
a light source housing comprising an interior chamber and an opening to the interior chamber; and
a UV light source disposed in the interior chamber of the light source housing, the UV light source comprising one or more UV lights each configured to emit UV light towards the opening of the light source housing;
one or more visible lights disposed in the interior chamber of the UV light source and each configured to emit visible light towards the opening of the light source housing;
a handle comprising a first end and a second end opposite the first end, the first end of the handle coupled to the light source housing;
a base coupled to the second end of the handle;
an electrical control system disposed in the base, the electrical control system comprising:
a power rail configured to distribute a power signal; and
at least one light driver circuit electrically coupled to the power rail and the UV light source;

the base comprising a wiring assembly electrically coupled to the at least one light driver circuit and the UV light source; and the at least one light driver circuit configured to:
couple power from the power signal to the one or more UV lights over the wiring assembly in the UV light source to cause the one or more UV lights to emit UV light towards the opening of the light source housing; and
couple power from the power signal to the one or more visible lights over the wiring assembly to the one or more visible lights to cause the one or more visible lights to emit visible light the opening of the light source housing;

the opening of the light source housing comprises a planar opening disposed along a first plane of the light source housing such that the one or more UV lights of the UV light source are configured to emit UV light in a direction orthogonal the plane of the planar opening;

the handle coupled to the light source housing having a tangential plane that is non-parallel to the first plane at an angle;

the electrical control system further comprises:
a power enable switch coupled to the power rail between an output node and the at least one light driver circuit;
the power enable switch configured to distribute the power signal from the output node to the at least one light driver circuit in response to a power enable signal indicating a power enable state; and
the power enable switch configured to not distribute the power signal from the output node to the at least one light driver circuit in response to a power enable signal indicating a power disable state;
an inertial measurement (IMU) circuit configured to generate an accelerometer signal indicating an acceleration of the light source housing; and
a controller circuit configured to:
receive the accelerometer signal generated by the IMU circuit;
determine if the accelerometer signal indicates an acceleration of the light source housing outside a predefined acceleration limit; and
in response to determining the acceleration signal indicates an acceleration of the light source housing outside the predefined acceleration limit, generate the power enable signal of a power disable state.

* * * * *